(12) United States Patent
Coelingh Bennink et al.

(10) Patent No.: US 11,819,542 B2
(45) Date of Patent: Nov. 21, 2023

(54) IMMUNOTHERAPEUTIC METHOD FOR TREATING LUNG CANCER BY ADMINISTERING A POLYPEPTIDE COMPRISING AN EPITOPE OF HZP3

(71) Applicant: Pantarhei Bioscience B.V., Zeist (NL)

(72) Inventors: Herman Jan Tijmen Coelingh Bennink, Zeist (NL); Nafis Ahmed Rahman, Turku (FI)

(73) Assignee: Pantarhei Bioscience B.V., Zeist (NL)

(*) Notice: Subject to any disclaimer, the term of this patent is extended or adjusted under 35 U.S.C. 154(b) by 489 days.

(21) Appl. No.: 16/760,457

(22) PCT Filed: Oct. 31, 2018

(86) PCT No.: PCT/EP2018/079802
§ 371 (c)(1),
(2) Date: Apr. 30, 2020

(87) PCT Pub. No.: WO2019/086507
PCT Pub. Date: May 9, 2019

(65) Prior Publication Data
US 2020/0276291 A1 Sep. 3, 2020

(30) Foreign Application Priority Data
Oct. 31, 2017 (EP) .................................. 17199441

(51) Int. Cl.
| | | |
|---|---|---|
| *A61K 39/00* | (2006.01) |
| *A61K 38/17* | (2006.01) |
| *A61P 35/00* | (2006.01) |
| *A61P 35/04* | (2006.01) |
| *A61K 39/39* | (2006.01) |
| *A61K 35/15* | (2015.01) |
| *A61K 38/08* | (2019.01) |
| *C07K 14/705* | (2006.01) |
| *A61K 47/68* | (2017.01) |
| *A61K 35/17* | (2015.01) |
| *A61K 39/395* | (2006.01) |
| *A61K 51/00* | (2006.01) |

(52) U.S. Cl.
CPC ...... *A61K 39/001114* (2018.08); *A61K 35/15* (2013.01); *A61K 38/08* (2013.01); *A61K 38/177* (2013.01); *A61K 38/1774* (2013.01); *A61K 39/001111* (2018.08); *A61K 39/39* (2013.01); *A61P 35/00* (2018.01); *A61P 35/04* (2018.01); *A61K 35/17* (2013.01); *A61K 39/3955* (2013.01); *A61K 47/68* (2017.08); *A61K 51/00* (2013.01); *A61K 2039/5154* (2013.01); *A61K 2039/5158* (2013.01); *A61K 2039/53* (2013.01); *C07K 14/705* (2013.01); *C07K 14/70503* (2013.01)

(58) Field of Classification Search
CPC .......... C07K 14/70503; A61K 38/1774; A61K 39/001111; A61K 38/08; A61P 35/00; A61P 35/04
See application file for complete search history.

(56) References Cited

FOREIGN PATENT DOCUMENTS

| WO | WO2012/026820 A2 | 3/2012 |
| WO | WO2017/097699 A1 | 6/2017 |

OTHER PUBLICATIONS

Rahman N A et al: A novel treatment strategy for ovarian cancer based on immunization against zona pellucida protein (ZP) 3, The FASEB Journal, vol. 26, No. 1, Jan. 1, 2012, pp. 324-333, Federati0n of American S0cieties f0r Experimental Biology, United States.
Anonymous: "ZP3", The Human Protein Atlas Aug. 17, 2017. Retrieved from the Internet: URL:https://www.proteinatlas.org/ENSG00000188372-ZP3/pathology.
Rhim, Sung Hee, et al. "Autoimmune disease of the ovary induced by a ZP3 peptide from the mouse zona pellucida." The Journal of clinical investigation 89.1 (1992): 28-35.
Gupta, Satish K., and Vidisha Minhas. "Wildlife population management: are contraceptive vaccines a feasible proposition." Front Biosci (Schol Ed) 9.9 (2017): 357-74.
Mask, Tracy A., et al. "Serum antibody immunoreactivity to equine zona protein after SpayVac vaccination." Theriogenology 84.2 (2015): 261-267.
Shrestha, Abhinav, et al. "Canine zona pellucida glycoprotein-3: up-scaled production, immunization strategy and its outcome on fertility." Vaccine 33.1 (2015): 133-140.
Harris, Jeffrey D., et al. "Expression and purification of recombinant human zona pellucida proteins." Protein expression and purification 16.2 (1999): 298-307.
Martinez, M. L., and J. D. Harris. "Effectiveness of zona pellucida protein ZPB as an immunocontraceptive antigen." Reproduction 120.1 (2000): 19-32.

(Continued)

*Primary Examiner* — Zachary C Howard
(74) *Attorney, Agent, or Firm* — N.V. Nederlandsch Octrooibureau

(57) ABSTRACT

The present invention relates to treatment and diagnosis of lung cancer and metastases thereof. More specifically, the invention relates to such therapeutic use of antigen sources providing immunogenic polypeptides comprising at least an immunogenic portion of a cancer cell associated protein, which preferably is a zona pellucida (ZP) protein, especially a ZP3 protein or the extracellular domain thereof, whereby the antigen source induces a cellular immune response against the lung cancer cells. The antigen source can be a proteinaceous composition comprising such immunogenic ZP polypeptide, a nucleic acid encoding the immunogenic ZP polypeptide, or a cell expressing or presenting the immunogenic ZP polypeptide. In addition, the invention relates to the therapeutic use of a T cell comprising a T cell receptor that binds an MHC-peptide complex, wherein the peptide is a peptide from the immunogenic ZP polypeptide. The invention further relates to the therapeutic and/or diagnostic use of antibodies that specifically binds to the immunogenic ZP polypeptide.

12 Claims, 6 Drawing Sheets
Specification includes a Sequence Listing.

(56) References Cited

OTHER PUBLICATIONS

Govind, Chhabi K., Neelu Srivastava, and Satish K. Gupta. "Evaluation of the immunocontraceptive potential of *Escherichia coli* expressed recombinant non-human primate zona pellucida glycoproteins in homologous animal model." Vaccine 21.1-2 (2002): 78-88.

Paterson, Margaret, et al. "Evaluation of the contraceptive potential of recombinant human ZP3 and human ZP3 peptides in a primate model: their safety and efficacy." American Journal of Reproductive Immunology 40.3 (1998): 198-209.

Srivastava, N., et al. "Evaluation of the immunocontraceptive potential of *Escherichia coli*-expressed recombinant dog ZP2 and ZP3 in a homologous animal model." Reproduction—Cambridge—123.6 (2002): 847-857.

*Fig. 4*

| | |
|---|---|
| hZP3 30-78 | GGASHPETSVQPVLVECQEATLMVSKDLFGTGKLTRAADLTLGPEAC |
| hZP3 76-101 | EACEPLVSMDTEDVRFEVGLHECGN |
| hZP3 99-141 | CGNSMQVTDDALVYSTFLDDPRPVGNLSIVRTNRAEPIECR |
| hZP3 138-187 | IECRYPRQGNVSSQAILPTWLPFRTTVFSEKLTFSLRLMEENWNAEKRS |
| hZP3 185-225 | KRSPTFHLGDAAHLQAEIHTGSHVPLRLFVDHCVATPTPDQ |
| hZP3 224-267 | DQNASPYHTIVDFHGCLVDGLTDASSAFKVPRPGPDTLQFTVDV |
| hZP3 257-290 | GPDTLQFTVDVFHANDSRNMYITCHLKVTLAE |
| hZP3 298-317 | KACSFSKPSNSWFPVEGPAD |
| hZP3 331-357 | SHSRRQPHVMSQWSRSASRNRRHVTEE |
| hZP3 358-383 | ADVTVGPLFLDRRGDHEVEQWALPS |

IMMUNOTHERAPEUTIC METHOD FOR TREATING LUNG CANCER BY ADMINISTERING A POLYPEPTIDE COMPRISING AN EPITOPE OF HZP3

FIELD OF THE INVENTION

The present invention relates to treatment and diagnosis of lung cancer and metastases thereof. More specifically, the invention relates to antigen sources providing at least an immunogenic portion of a cancer cell associated protein, which preferably is a zona pellucida (ZP) protein, especially a ZP3 protein. Such antigen sources may be used in vaccines and pharmaceutical compositions for therapeutic and prophylactic treatment of primary and/or recurring lung cancer and metastases thereof.

BACKGROUND OF THE INVENTION

Lung cancer refers to cancers originating from lung tissue, which can arise in any part of the lung, although the vast majority (approximately 90%-95%) of lung cancers are carcinomas-malignancies that arise from epithelial cells. There are two main types of lung carcinoma, categorized by histopathological analysis to: non-small cell (80.4%) and small cell (16.8%) lung carcinoma. Cancers also can arise from the pleura (called mesotheliomas) or rarely from supporting tissues within the lungs, for example, the blood vessels. The major causes of any cancer include non-genetic factors such as exposure to carcinogens (e.g. tobacco smoke, asbestos, arsenic, particulate matter), ionizing radiation, and viral infection. Epidemiological studies have shown that genetic factors may contribute to the risk of developing lung cancer.

Lung cancer is one of the most common cancers. In 2007, lung cancer accounted for approximately 15% of all cancer diagnoses and 28% of all cancer deaths. It is the fourth most diagnosed cancer in men and women, but it is the number one cause of death from cancer each year in both men and women. Most cases of lung cancer are diagnosed at an advanced stage, conferring a poor prognosis. Lung cancer is highly lethal, with a 5-year patient survival rate of only 14% being observed in the United States. Treatment for lung cancer depends on the cancer's specific cell type, on metastases, and the patient's performance status. Common treatments include (combinations of) surgery, chemotherapy (e.g. cisplatin, carboplatin, gemcitabine, paclitaxel, docetaxel, etoposide, vinorelbine, topotecan, irinotecan), radiation therapy, immunotherapy (e.g. atezolizumab, nivolumab, pembrolizumab) and 'targeted therapies' (e.g. Gefitinib, Erlotinib, bevacizumab). A number of 'targeted agents' are at the early stages of clinical development, such as cyclooxygenase-2 inhibitors, the apoptosis promoter exisulind, proteasome inhibitors, bexarotene, and the epidermal growth factor receptor inhibitor cetuximab.

Small cell lung carcinoma is treated primarily with radiation and chemotherapy with cisplatin or etoposide, sometimes in combination with carboplatin, gemcitabine, paclitaxel, vinorelbine, topotecan or irinotecan. Surgery has no demonstrable influence on survival in small cell lung carcinoma. In extensive-stage small cell lung cancer celecoxib may be combined with etoposide for improved outcomes.

Non-small cell lung carcinoma (NSCLC) is any type of epithelial lung cancer other than small cell lung carcinoma (SCLC). NSCLC accounts for about 85% of all lung cancers. As a class, NSCLCs are relatively insensitive to chemotherapy, compared to SCLC. When possible, they are primarily treated by surgical resection with curative intent, although chemotherapy is increasingly being used both pre-operatively (neoadjuvant chemotherapy) and post-operatively (adjuvant chemotherapy). Currently, first-line treatment of NSCLC involves surgery and chemotherapy with cisplatin or carboplatin, often in combination with gemcitabine, paclitaxel, docetaxel, etoposide or vinorelbine. Surgery is usually only an option in NSCLC limited to one lung, up to stage IIIA. If surgery is no longer an option primary chemotherapy is given.

While the existing therapies provide some benefit in the management of lung cancer, prospects are still generally poor and it is still absolutely essential to find treatment modalities that are more effective and less toxic. The identification of novel therapeutic targets for lung cancer treatment is a crucial step in the realization of this objective.

Advances in molecular medicine have increased the interest in tumor-specific antigens that could serve as targets for various immunotherapeutic or small molecule strategies.

To serve as a suitable target for immunotherapeutic cancer strategies, such antigens should be highly expressed in cancer tissues and ideally not in normal tissues. Expression in tissues that are dispensable for life, however, may be acceptable.

The concept of treating ZP expressing tumors by active immunization has been described in the art before. For instance, Rahman et al. (A novel treatment strategy for ovarian cancer based on immunization with zona pellucida protein (ZP) 3. FASEB J. 2012 January; 26(1):324-33) proofs the principle of treating malignant ovarian tumors in transgenic mice by eliciting humoral and cellular vaccination against ZP3 proteins and ZP3 expressing cells, respectively. Furthermore, active immunization with ZP proteins is common practice in large wild animals as method for sterilization, which demonstrates its feasibility and safety (see e.g. Gupta and Minhas, Frontiers In Bioscience, 2017, Scholar, 9, 357-374, www.bioscience.org; Mask et al., 2015, Theriogenology; 84(2):261-267). Numerous studies were conducted, wherein reduction in fertility was associated with antibody titers (Shresta et al., 2015, Vaccine 33, 133-140; Harris et al., 1999, Protein Expr Purif; 16(2):298-307; Martinez and Harris, 2000, J Reprod Fertil.; 120(1):19-32). Additional degenerative ovarian pathologies were described for immunization with recombinant ZP3 and ZP4, in particular (e.g. Govind et al., 2002, Vaccine 21, 78-88; Paterson et al., 1998, Am J Reprod Immunol 40, 198-209; and Srivastava et al., 2002, Reproduction 123, 847-857). In a study of ovarian autoimmune disease, the investigators demonstrated that oophoritis (ovarian tissue damage) can be induced in mice through eliciting a ZP3 specific CD4$^+$ T cell response by vaccination with a 15-amino acid ZP3 polypeptide, containing an MHC class II binding epitope (Rhim et al., 1992, J. Clin. Invest. 89, 28-35). Expression of ZP protein in lung cancer has however not been reported.

It is an object of the present invention to provide novel immunotherapeutic strategies for the treatment of and/or recurring lung cancer and metastases thereof.

SUMMARY OF THE INVENTION

The present inventors have surprisingly found that the zona pellucida (ZP) proteins, especially the zona pellucida 3 protein (ZP3) is expressed in lung cancer cells and constitutes a suitable target for immunotherapeutic strategies in the treatment of lung cancer and metastases thereof, as well as in the diagnosis thereof.

ZP3 is normally found in females in the so-called 'zona pellucida' that forms an extracellular matrix surrounding the oocyte. This zona pellucida induces acrosome reaction on sperm, determines the species specificity for fertilization and prevents polyspermy in mammals. The zona pellucida contains four major glycoproteins, ZP1, ZP2, ZP3 and ZP4. For convenience we shall refer herein to zona pellucida or ZP "proteins", which term will be understood to include both glycosylated and non-glycosylated forms of the zona pellucida proteins, unless specifically indicated otherwise.

The present invention resides in the finding that the lung cancer cells can display significant expression of a ZP protein, to such extent that immunotherapeutic strategies, such as e.g. passive immunization, active immunization and targeted therapy using immunoconjugates can be applied, to result in at least one of i) reduced growth or size of primary tumors, ii) reduced growth or size of metastases originating therefrom, iii) eradication of tumors, and iv) increased survival.

The present strategy is equally suitable for preventing metastasis of a lung cancer as well as for preventing the recurrence of lung cancer in previously treated subjects. It is therefore understood that the terms "lung cancer cell" and "ZP expressing lung cancer cell" also include such cells derived from lung cancer cells as they may occur in other parts of the body than lungs, e.g. as a result of metastasis.

Example 4 herein describes a pre-clinical study in humanised HLA-A2 transgenic mice with hZP3-expressing tumors. Vaccination of these transgenic mice with hZP3 polypeptide (aa 1-383) and with hZP3 HLA-A2-restricted T cell epitopes induced CD8$^+$ T cells. Furthermore, no increase in tumor size was observed, whereas tumor size increased in control mice treated with PBS.

Expression of ZP protein in lung cancer cells has never been established before. There is thus no indication in the prior art that lung cancer cells can in fact be targeted by ZP based immunotherapy. The present invention therefore provides for the first time, methods of treating lung cancer in a subject, targeting ZP protein as a tumor specific antigen. As will be understood by those skilled in the art on the basis of the present disclosure, such therapies include passive immunization, active immunization as well as targeted therapies using immunoconjugates.

These and other aspects of the present invention will be described in more detail hereafter.

DETAILED DESCRIPTION OF THE INVENTION

A first aspect of the present invention relates to a method for therapeutic and/or prophylactic treatment or diagnosis of primary and/or recurring lung cancer and of metastases thereof in a subject in need thereof, wherein the method comprises the administration to said subject of at least one of:
  a source of an immunogenic polypeptide capable of eliciting a cellular or humoral immune response against a human Zona Pellucida protein (hZP), preferably hZP3 or hZP3(23-350);
  a T cell comprising a T cell receptor that binds an MHC-peptide complex, wherein the peptide is a peptide from an hZP, preferably from hZP3 or hZP3(23-350);
  an antibody or fragment thereof that specifically binds to an hZP, preferably to hZP3 or hZP3(23-350); and a genetic construct comprising a nucleic acid sequence encoding said polypeptide or antibody, wherein the genetic construct is configured to be delivered and expressed in a human.

The term 'lung cancer', as used herein, refers both to primary and/or recurring lung cancers as well as metastases thereof that may have settled anywhere in the body. Preferably, the present method is a method for treating cancers originating from the epithelial cells, which cancers are collectively also referred to as carcinomas. More in particular, the invention concerns the treatment of NSCLC, which includes adenocarcinomas, squamous cell carcinomas and large cell carcinomas, as well as metastases thereof.

Typically, for the purpose of the present invention, the term 'lung cancer' refers to malignant diseases or conditions and can be used interchangeably with certain other terms like '(malignant) lung tumor' and '(malignant) neoplastic disease'. Typically, for the purpose of the present invention, the term 'lung cancer' does not encompass benign neoplasm and/or benign tumors. Nevertheless, the present invention, in its broadest sense, may also encompass treatment of subjects suffering from such benign conditions in order to prevent progression into or development of malignancies (lung cancer). Lung cancer can be staged by using the American Joint Committee on Cancer TNM (Tumor, Node, Metastases) classification, as follows:

Stage I: The tumor is found only in one lung and has not spread to any lymph nodes.
  Stage II: The tumor has spread to lymph nodes that are contained within the surrounding lung.
  Stage IIIa: The tumor has spread to the lymph nodes outside of the lung, to those of the tracheal area, including the chest wall and diaphragm on the same side as the cancer started.
  Stage IIIb: The tumor has spread to the lymph nodes on the opposite lung or in the neck.
  Stage IV: The tumor has spread to other parts of the lungs or distantly throughout the body.

The above TNM staging system is not often used for patients with SCLC, because most cases have suspected or definite metastatic disease at the time of diagnosis. Survival in these patients usually is unaffected by minor differences in the extent of tumor involvement. Instead, most experts use a simple, two-stage system created by the Veterans Administration Lung Cancer Study Group. This system defines SCLC as being of "limited" or "extensive" stage. The present method produces significant response rates in all stages and the invention thus, in its broadest sense, concerns treatment of lung cancer of any one of the above stages.

The method according to the invention may constitute the primary treatment or be applied as adjunctive therapy prior to, during or following treatment of patients using any other method of treatment, including for example:
  surgery;
  radiation therapy;
  chemotherapy, e.g. using platinum based drugs such as cisplatin and carboplatin; nucleoside analogues such as gemcitabine, taxanes such as paclitaxel and docetaxel; topoisomerase I inhibitors such as topotecan and irinotecan; topoisomerase II inhibitors such as etoposide; and anti-mitotic drugs such as vinorelbine;
  'targeted therapy', e.g. using EGFR inhibitors such as Gefitinib; tyrosine kinase inhibitors such as Erlotinib; VEGF-A inhibitors such as bevacizumab; cyclo-oxygenase-2 inhibitors; inhibitors of cyclic guanosine monophosphate phosphodiesterase such as exisulind;

proteasome inhibitors; RXR agonists such as bexarotene; and EGFR inhibitors such as cetuximab;
an immunomodulating therapy, e.g. as described below; and
Combinations thereof.

The method of the invention is preferably combined with an immunomodulating therapy. It is particularly preferred that when the method of the invention comprises the administration of a source of an immunogenic polypeptide capable of eliciting a cellular or humoral immune response against hZP that such method is combined with an immunomodulating therapy. Immunomodulating therapies that can be combined with the method of the invention can be selected from one or more of:

using a checkpoint inhibitor, such as e.g. an antibody against PD1, PDL1, CTLA4, TIM-3 and/or LAG-3;
using an antibody targeting selected TNF receptor family members, such as e.g. an antibody against CD40, 4-1 BB, CD137, OX-40/CD134 and/or CD27;
using an immunosuppressive cytokine such as e.g. IL-10, TGF-β and/or IL-6;
using a γC cytokine such as e.g. IL-7, IL-15, and IL-21 and/r IL-2, as these cytokines have the capacity to expand antigen-experienced T cells;
using a TLR agonist such as e.g. described by Kaczanowska et al. (J Leukoc Biol. 2013 June; 93(6): 847-863) and/or a TLR ligand as described hereinbelow;
using an agonist of invariant natural killer T (iNKT) cells, such as e.g. a synthetic iNKT agonist described by Cerundolo et al. (Curr Opin Immunol. 2010; 22(3):417-24).

The invention provides methods which are suitably employed for treatment of primary lung cancer, recurrent lung cancer and metastases thereof, which is considered herein to constitute 'therapeutic treatment' or 'curative treatment', as well as for preventing metastases and/or recurrence of lung cancer optionally after or in combination with other methods of treatment, such as described before, which is considered herein to constitute 'prophylactic treatment'.

For the methods of the invention, the subject to be treated is preferably a human and may be a male or female. When the subject to be treated is a (premenopausal) female the clinical efficacy of the method can be monitored by monitoring autoimmunity against ovarian tissue. E.g. blood hormone levels can then be used as a biomarker for clinical efficacy and substitute the clinical endpoint (PFS, OS) to shorten read-out timelines.

The present invention is based on the finding of expression of ZP proteins by the cancerous cell which presents various options for immunotherapeutic strategies. Nevertheless, as different tumors may have different or altered patterns of gene expression, certain lung cancers not expressing ZP proteins to any significant extent might occur as well, as will be understood by the skilled person. Hence, typically, the invention concerns treatment of lung cancer or metastases thereof, expressing ZP proteins, preferably ZP3.

The naming of the ZP glycoprotein components has been rather inconsistent over the years, employing several criteria, including apparent molecular weight, protein sequence length and sequence identity comparison, which has resulted in a confused nomenclature. Harris et al. [(1994) DNA seq. 96:829-834] proposed a uniform system of nomenclature in which ZP genes were named in order of length of their encoded protein sequence from longest to shortest. Since, under those criteria the mouse ZP genes fell in the order ZP2, then ZP1 and then ZP3, a new system was introduced wherein ZP2 became ZPA, ZP1 became ZPB and ZP3 became ZPC. More recently Hughes et al [(1999) BBA-Gene Structure and Expression 1447:303-306], amongst others, reported that the true human orthologue of the known mouse ZP1 gene is not ZPB, but that there is a distinct human ZP1 gene. It is now generally accepted that there are four distinct (human) ZP glycoprotein families ZP1, ZP2, ZP3 and ZPB [cf. Lefievre et al (2004) Hum. Reprod. 19:1580-1586]. The ZPB glycoprotein according to this nomenclature is now also referred to as ZP4. This nomenclature is for example applied in the Uniprot/SWISSprot, ensEMBL, BLAST (NCBI), SOURCE, SMART, STRING, PSORT2, CDART, UniGene and SOSUI databases, all implemented in the Bioinformatic Harvester (harvester.embl.de).

In accordance with this the terms ZP1, ZP2, ZP3 and ZP4 are employed herein to denote the four ZP glycoprotein families, wherein ZP2, ZP3 and ZP4 correspond to ZPA, ZPC and ZPB, respectively, according to the nomenclature proposed by Harris et al. More in particular, the terms hZP1, hZP2, hZP3 and hZP4 as used herein refer to the proteins having polypeptide backbones listed in SEQ ID NO. 1, SEQ ID NO. 2, SEQ ID NO. 3 and SEQ ID NO. 4, respectively, and allelic variants thereof.

In accordance with the invention, the ZP protein is typically a ZP3 protein.

Allelic variants of the ZP sequences that can occur in nature are also encompassed by the respective terms ZP and hZP. Allelic variants include in particular variants resulting from single nucleotide polymorphisms (SNPs). SNPs may fall within coding sequences of genes, non-coding regions of genes, or in the intergenic regions between genes. SNPs within a coding sequence will not necessarily change the amino acid sequence of the protein that is produced. An SNP in which both forms lead to the same polypeptide sequence is termed synonymous (sometimes called a silent mutation) —if a different polypeptide sequence is produced they are nonsynonymous. For a variant to be considered an SNP, it must occur in at least 1% of the population. In the context of the present invention 'allelic variants' may also include polypeptide sequence variants resulting from (nonsynonymous) mutations, i.e. polypeptide variants resulting from point mutations, insertions, deletions, etc. occurring in less than 1% of the population.

Thus, in accordance with the present invention the terms hZP1, hZP2, hZP3 and hZP4 include ZP proteins which differ from SEQ ID NO. 1, SEQ ID NO. 2, SEQ ID NO. 3 and SEQ ID NO. 4, respectively, by minor sequence modifications. Such modifications include, but are not limited to: changes in one or a few amino acids, including deletions (e.g., a truncated version of the peptide) insertions and/or substitutions.

An 'allelic variant' is herein understood to have at least 90%, preferably at least 95%, more preferably at least 97%, still more preferably at least 98%, still more preferably at least 99%, still more preferably at least 99.5% and most preferably at least 99.9% amino acid sequence identity with any of SEQ ID NO. 1, SEQ ID NO. 2, SEQ ID NO. 3 and SEQ ID NO. 4.

Each of the ZP proteins comprises a signal peptide to direct it into a secretory pathway, a zona domain and a transmembrane domain near the carboxyl terminus followed by a short cytoplasmic tail. In embodiments of the invention that comprises the administration of an antibody or fragment thereof that specifically binds to hZP, the antibodies or fragments thereof are preferably directed against ZP extracellular domain. In embodiments of the invention that concern active immunization a source of an immunogenic polypeptide capable of eliciting a cellular immune response against an hZP, in principle any part of the hZP that comprises a class I MHC- and/or class II MHC-restricted T cell epitope can be used.

The amino acid sequence of hZP3 nascent protein contains a N-terminal signal peptide sequence protein (amino acid positions 1-22 in SEQ ID NO: 3), a conserved "ZP extracellular domain" (amino acid positions 23-350 in SEQ ID NO: 3), and a pro-peptide (amino acid positions 351-424 in SEQ ID NO: 3), consisting of a consensus furin cleavage site (CFCS; amino acid positions 351-352 in SEQ ID NO: 3), a polymerization-blocking external hydrophobic patch (EHP), and a C-terminal transmembrane domain (amino acid positions 353-424 in SEQ ID NO: 3). The hZP3 signal peptide is cleaved off during translation and cleavage at the CFCS separates the mature hZP3 extracellular domain protein (consisting of amino acid positions 23-350 in SEQ ID NO: 3) from the EHP, allowing it to incorporate into nascent ZP filaments. Hence, the amino acid backbone of mature hZP3 extracellular domain has the amino acid sequence consisting of amino acid positions 23-350 in SEQ ID NO: 3 of hZP3. This extracellular domain fragment is denominated herein as hZP3(23-350) (SEQ ID NO: 5).

In a preferred embodiment the present invention relates to a method for treatment of lung cancer and metastases thereof in a subject by active immunization. The method of active immunization preferably comprises administering a source of an immunogenic polypeptide capable of eliciting a cellular immune response against an hZP3 or against cells expressing (any part of) an hZP3 and/or a humoral immune response against an hZP3 or an hZP3(23-350).

The source of the immunogenic polypeptide can be a proteinaceous source, a nucleic acid or a combination thereof. The proteinaceous source can e.g. be a composition comprising one or more peptides, polypeptides or proteins that act as immunogen. Alternatively the source of the immunogenic polypeptide can be a nucleic acid molecule encoding one or more immunogenic peptides, polypeptides or proteins, which nucleic acid molecule, when administered to the subject to be treated expresses the immunogenic peptides, polypeptides or proteins. The nucleic acid molecule can be a DNA, cDNA RNA, mRNA, a variant thereof, a fragment thereof, or a combination thereof, as e.g. described in WO2014/165291 and WO2013/087083. The source of the immunogenic polypeptide can further be a cell, preferably a live cell, that expresses the immunogenic polypeptide or presents an epitope of the immunogenic polypeptide. Preferably, the cell is a microbial, more preferably a bacterium such as e.g. a live-attenuated Listeria monocytogenes, as e.g. described in WO2015/164121. Alternatively, the cellular source of the immunogenic polypeptide of the invention is an autologous or allogeneic dendritic cell that presents at least one epitope of the immunogenic polypeptide in an HLA molecule on its surfaces.

In a preferred embodiment the immunogenic polypeptide comprises a contiguous amino acid sequence selected from the amino acid sequence of an hZP protein, which contiguous amino acid sequence preferably comprises at least one of a class I MHC- and a class II MHC-restricted T cell epitope. More preferably, the immunogenic polypeptide comprises a contiguous amino acid sequence selected from the amino acid sequence of the hZP3 protein (i.e. SEQ ID NO: 3) which contiguous amino acid sequence preferably comprises at least one of a class I MHC- and a class II MHC-restricted T cell epitope, e.g. selected from Tables 2, 3 and 5, respectively. More preferably, the contiguous amino acid sequence comprises at least one of a class I MHC- and a class II MHC-restricted T cell epitope with a low percentile rank (see Moutaftsi et al., Nat Biotechnol. 2006 July; 24(7):817-9; and Kotturi et al., J Virol. 2007 May; 81(10): 4928-40). A class I MHC-restricted T cell epitope with a low percentile rank preferably is an epitope with a percentile rank that is not higher than 1.00, 0.80, 0.40, 0.30, 0.20, 0.15, 0.10 or 0.05 (see e.g. Tables 2 and 5). A class II MHC-restricted T cell epitope with a low percentile rank preferably is an epitope with a percentile rank that is not higher than 2.50, 2.40, 2.05, 2.00, 1.80, 1.60, 1.40, 1.20, 1.10, 1.00, 0.90, 0.70, 0.60, 0.50, 0.40, 0.20. 0.15, 0.10, 0.05 or 0.02. Preferably, the contiguous amino acid sequence is selected from an amino acid sequence from the group of amino acid sequences from proteolytic hZP3 fragments consisting of the sequence of the N-terminal signal peptide (positions 1-22 in SEQ ID NO: 3), the sequence of the mature extracellular domain (positions 23-350 in SEQ ID NO: 3, i.e. SEQ ID NO: 5), and the sequence of the propeptide (amino acid positions 351-424 in SEQ ID NO: 3). Examples of such contiguous amino acid sequences are given in FIG. 4 and combinations of such contiguous amino acid sequences are listed in Table 4.

The contiguous amino acid sequence from an hZP(3) protein as comprised within the immunogenic polypeptide, preferably comprises an immunologically active (sequence) fragment of the hZP(3) protein. The term "immunologically active fragments thereof" will generally be understood in the art to refer to a fragment of a hZP(3) protein antigen comprising at least an epitope, which means that the immunogenic polypeptide at least comprises 4, 5, 6, 7 or 8 contiguous amino acids from the sequence of the hZP(3) protein antigen. According to the present invention the fragment comprises at least an MHC class I or MHC class II binding peptide presented by such MHC molecule to the immune system. An 'immunologically active fragment' according to this invention comprises at least 7, 8, 9, 10, 11, 12, 13, 14, 15, 16 or 17 contiguous amino acids from the sequence of the ZP protein antigen or homologue or analogue thereof. While the majority of the MHC binding peptides are of a length of 9 amino acids, longer peptides can be accommodated by the bulging of their central portion (Guo et al., 1992, Nature; 360(6402):364-366; Speir et al., 2001, Immunity; 14(1):81-92), resulting in binding peptides of length 8 to 15 (Schumacher et al., 1991, Nature; 350 (6320):703-706). Examples of MHC class I binding peptides in the sequence of hZP3 are given in Tables 2 and 5. Peptides binding to class II proteins are not constrained in size (Nelson et al., 1999, Rev Immunogenet; 1(1):47-59; Yassai et al., 2002, J Immunol; 168(3):1281-1285) and can vary from 11 to 30 amino acids long (Rammensee 1995, Immunogenetics; 41(4):178-228) possibly even whole proteins. The binding motif however is about 9 amino acids long. MHC class II can accommodate much longer peptides than MHC class I because the ends of the MHC II binding groove are open, hence an epitope (binding into the groove) may be flanked by additional stretches of amino acids on either end. Examples of MHC class II binding peptides in the sequence of hZP3 are given in Table 3. Still more preferably the fragment comprises both a Cytotoxic T Lymphocyte (CTL) and a Helper T Lymphocyte (HTL) epitope. Most preferably however, the fragment is a peptide that requires processing by an antigen presenting cell, i.e. the fragment has a length of at least about 18 amino acids, which 18 amino acids are not necessarily a contiguous sequence from the hZP(3) protein antigen.

The length of a contiguous amino acid sequence from an hZP(3) protein as comprised within the immunogenic polypeptide or the length of the immunogenic polypeptide itself, therefore preferably is at least 18, 19, 20, 21, 22, 25, 27, 30, 33 or 35 amino acids and preferably no more than 100, 80, 60, 50, 45, 40, 35, 33 or 30 amino acids. Preferably the length of a contiguous amino acid sequence from an hZP(3) protein as comprised within the immunogenic polypeptide, or the length of the immunogenic polypeptide itself, is 19-50 or 19-45, more preferably 25-40 amino acids, even more preferably 25-35 and most preferably 25-30 amino acids. From the view point of manufacturability an immunogenic polypeptide with a length of around 25 amino acids is optimal, while still long enough to contain multiple epitopes and force presentation via Antigen Presenting Cells. Suitable examples of such immunogenic polypeptides comprising contiguous amino acid sequence from the hZP3 protein and each comprising one or more MHC class I and/or MHC class II binding peptide are presented in FIG. 4.

The terms "homologues thereof", as used herein refer to polypeptides which differ from the naturally occurring polypeptide by minor modifications, but which maintain the basic polypeptide and side chain structure of the naturally occurring form. Such changes include, but are not limited to: changes in one or a few amino acid side chains; changes in one or a few amino acids, including deletions (e.g., a truncated version of the peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. As used herein, a homologue or analogue has either enhanced or substantially similar functionality as the naturally occurring polypeptide. Typically, when optimally aligned, such as by the programs GAP or BESTFIT using default parameters, a naturally occurring polypeptide and a homologue thereof share at least a certain percentage of sequence identity. GAP uses the Needleman and Wunsch global alignment algorithm to align two sequences over their entire length, maximizing the number of matches and minimizes the number of gaps. Generally, the GAP default parameters are used, with a gap creation penalty=8 and gap extension penalty=2. For proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752, USA. Alternatively percent similarity or identity may be determined by searching against databases such as FASTA, BLAST, etc.

A homologue herein is understood to comprise an immunogenic polypeptide having at least 70%, preferably at least 80%, more preferably at least 90%, still more preferably at least 95%, still more preferably at least 98% and most preferably at least 99% amino acid sequence identity with the naturally occurring ZP polypeptides mentioned above and is still capable of eliciting at least the immune response obtainable thereby. A homologue or analogue may herein comprise substitutions, insertions, deletions, additional N- or C-terminal amino acids, and/or additional chemical moieties, such as carbohydrates, to increase stability, solubility and immunogenicity.

Expressly included in the invention is the use of an immunogenic polypeptide comprising an amino acid sequence that is a homologue of a wild-type hZP(3) protein, but differs therefrom as a result of tumor-specific mutations (which can be patient-specific or shared) that result in altered amino acid sequences, i.e. so-called neoantigens.

In accordance with the present invention, the immunogenic polypeptide that is administered to the human according to the present method, may be or comprise a protein or glycoprotein, a digest of the protein or glycoprotein and/or fragments thereof, which may be in a purified form or may be comprised within a crude composition, preferably of biological origin, such as lysates, sonicates or fixates of prokaryotic or eukaryotic cell lines. More preferably however, the immunogenic polypeptide is or comprises chemically synthesized (poly)peptides or (poly)peptides that have been produced enzymatically in vitro, which may be in a purified form or may be comprised within a crude composition.

The term "epitope" as used herein refers to a portion of an antigen, typically defined by a short peptide, which is capable of eliciting a cellular or humoral immune response when presented in a physiologically relevant context in vivo. A "T cell epitope" refers to a short peptide or portion thereof that binds to an MHC molecule and is recognized by certain T cells when presented in certain MHC molecules. A T cell epitope is capable of inducing a cell mediated immune response via direct or indirect presentation in heterodimeric membrane MHC molecules. Preferably, in the immunogenic polypeptide at least one MHC class II restricted epitope and at least one MHC class I restricted epitope are present within a contiguous amino sequence from the amino acid sequence of the hZP(3) protein, whereby preferably, the MHC class II restricted epitopes and at least one MHC class I restricted epitopes are selected from Tables 3, and 2 and 5, respectively. For the sake of clarity, the peptide of the invention preferably comprises at least one MHC class I presented epitope and preferably also at least one MHC class II presented epitope. Each of these epitopes are presentable and will bind to the corresponding specific MHC molecule present on the cells after having been processed as described herein. Each MHC restricted epitope may therefore also be named an MHC binding and/or presentable epitope. Preferably, a specific proteasomal cleavage site generating the C-terminus of such epitope is present exactly after the epitope's amino acid sequence in order to be liberated from the immunogenic polypeptide and presented on the MHC class I molecule. Length requirements are much less strict for MHC class II presented epitopes, therefore a need for precise enzymatic generation of the class II binding peptide is less absolute. Briefly, MHC molecules preferentially bind particular amino acid residues known as "anchor" residues (K. Falk et al., Nature 351:290-96 (1991)). This characterization permits class I and II MHC binding motifs to be recognized within any known peptide sequence (see e.g. Tables 2, 5 and 3).

In the present context, the term "MHC restricted epitope" is synonymous with T cell epitope. The term "class I MHC restricted epitope", as used herein, refers to peptide sequences recognized by cytotoxic T lymphocytes (also called CD8+ cells, TCD8 or CTLs) in association with class I MHC. The term "class II MHC restricted epitope", as used herein, refers to a peptide recognized by helper T cells (also called CD4+ cells, TCD4 or HTLs) in association with class II MHC. A "B cell epitope" is the portion of an antigen that is capable of binding to an antigen binding site of an immunoglobulin and therefore capable of stimulating a humoral response without presentation by an MHC molecule. As explained herein before the polypeptide useful in the present invention, or the nucleic acid encoding said polypeptide, comprises at least one T cell epitope. The use of polypeptides that also comprise a B cell epitope is however not excluded from the present invention. The present immunogenic polypeptides may also include multiple T cell epitopes and, optionally a B cell epitope. When multiple epitopes are present in a peptide, the epitopes may be oriented in tandem or in a nested or overlapping configuration wherein at least one amino acid residue may be shared by two or more epitopes.

The immunogenic polypeptide of the invention preferably includes one or more MHC class I restricted epitopes. As is generally known by the skilled person, an antigen comprising a single MHC restricted epitope will be useful only for treating a (small) subset of patients who express the MHC allele product that is capable of binding that specific peptide. It has been calculated that, in humans, vaccines containing CTL epitopes restricted by HLA-A1, -A2, -A3, -A24 and -B7 would offer coverage to approximately 80% of individuals of most ethnic backgrounds. Therefore, if the present method is used to treat a human, it is particularly preferred that the method comprises the administration of a composition comprising one or more different polypeptides comprising one, more preferably two, most preferably three MHC class I binding native ZP, preferably hZP3, epitopes selected from HLA-A1, HLA-A2, HLA-A3, HLA-A24 and HLA-B7 restricted epitopes; or homologues thereof.

According to another embodiment the immunogenic polypeptide of the invention preferably includes one or more MHC class II restricted epitopes. The most frequently found MHC class II allele products in humans include HLA-DR1, -DR3, -DR4 and -DR7. Accordingly, it is preferred that the method comprises the administration of a composition comprising one or more different polypeptides, said one or more different polypeptides comprising one, more preferably two and most preferably three MHC class II binding native ZP, preferably hZP3, epitopes selected from HLA-DR1, HLA-DR3, HLA-DR4 and HLA-DR7 restricted epitopes; or homologues thereof.

In still another embodiment, the method of the invention comprises the administration of a composition comprising one or more polypeptides, said one or more polypeptides comprising one or more MHC class I restricted epitopes and one or more MCH class II restricted epitopes, as described here above and/or in Tables 2, 5 and 3, respectively; or homologues thereof. Even, more preferably said composition comprises an effective amount of one or more different polypeptides that together include essentially all of the MHC class I and MHC class II binding epitopes comprised in one of the native ZP, preferably hZP3, glycoproteins; or homologues of said one or more polypeptides.

In one embodiment, the present method comprises the administration of a composition comprising one or more different immunogenic polypeptides. Preferably, said one or more different polypeptides together comprise at least 50%, more preferably at least 70%, still more preferably at least 80%, still more preferably at least 90% and most preferably at least 95% of the MHC class I and MHC class II restricted epitopes comprised in a native ZP, preferably hZP3 or hZP3(23-350) or homologues of said one or more polypeptides.

In a preferred embodiment, the present method comprises the administration of a composition comprising one or more immunogenic peptides selected from the peptides presented in FIG. 4, e.g. the immunogenic peptides comprising or consisting of an amino acid sequence of one or more of SEQ ID NO.'s 66-75. The composition can thus comprise one of the immunogenic peptides comprising or consisting of an amino acid sequence selected from SEQ ID NO.'s 66-75. Preferably, however, the composition comprises a combination of at least two of the immunogenic peptides comprising or consisting of an amino acid sequence selected from SEQ ID NO.'s 66-75. Specifically, the composition comprises a combination of the immunogenic peptides comprising or consisting of an amino acid sequence selected from the combinations of sequences listed in Table 4, or the combination of all 10 of SEQ ID NO.'s 66-75.

In a further preferred embodiment, the present method comprises the administration of a composition comprising one or more immunogenic peptides comprising or consisting of an epitope selected from the epitopes presented in Table 5, i.e. SEQ ID NO.'s 76-85. The composition can thus comprise one of the immunogenic peptides comprising or consisting of an amino acid sequence selected from SEQ ID NO.'s 76-85. Preferably, however, the composition comprises a combination of at least two of the immunogenic peptides comprising or consisting of an amino acid sequence selected from SEQ ID NO.'s 76-85. Specifically, the composition comprises a combination of the immunogenic peptides comprising or consisting of an amino acid sequence selected from the combinations of sequences listed in Table 6, or the combination of all 10 of SEQ ID NO.'s 76-85. A particularly preferred composition comprises one or more or all of the immunogenic peptides comprising or consisting of the amino acid sequences of SEQ ID NO.'s 79, 80, 81, 83 and 84.

In a preferred embodiment the present method comprises the administration of a source of an immunogenic polypeptide, which polypeptide comprises at least 50%, more preferably at least 70%, still more preferably at least 80%, still more preferably at least 90% and most preferably at least 95% of the complete amino acid backbone of a native ZP, preferably hZP3 or hZP3(23-350), glycoprotein; or a homologue of said polypeptide.

In a particularly preferred embodiment the present method comprises the administration of a composition comprising a source of an immunogenic polypeptide, which polypeptide comprises 90, 95, 97, 98, 99 or 100% of the complete amino acid backbone of the extracellular domain of a native ZP, preferably hZP3 or hZP3(23-350) or a homologue of said polypeptide. The present immunogenic polypeptides as defined herein before, can be glycosylated. Without wishing to be bound by theory it is hypothesized that by glycosylation of these polypeptides the immunogenicity thereof, at least in as far as they elicit a humoral (B cell response), is increased. Therefore, the immunogenic polypeptide as defined herein before, preferably is glycosylated, having a carbohydrate content varying from 10-80, 15-70 or 20-60 wt. %, based on the total weight of the glycoprotein or glycosylated polypeptide. Preferably, said glycosylated immunogenic polypeptide comprises a glycosylation pattern that is similar to that of the corresponding native zona ZP glycoprotein of a human.

In another particularly preferred embodiment, the method comprises administering a source of an immunogenic polypeptide that is a composition comprising an effective amount of a plurality of different overlapping polypeptide fragments of a native ZP, preferably hZP3 or hZP3(23-350), glycoprotein, which different overlapping polypeptide fragments are between 18-60 amino acids in length, and which together comprise at least 50%, more preferably at least 70%, still more preferably at least 80%, still more preferably at least 90% and most preferably at least 95% of the complete amino acid backbone of said native ZP or of the extracellular domain of said native ZP, preferably hZP3 or hZP3(23-350)

or homologues of said polypeptides. More preferably, the different overlapping polypeptide fragments 25-40 amino acids, even more preferably 25-35 and most preferably 25-30 amino acids in length. Typically, the amino acid sequence overlap between the different consecutive 18-60 amino acid polypeptide fragments is at least 7 amino acids, preferably at least 8, more preferably at least 9 and most preferably at least 10 amino acids.

The MHC binding motifs for most common MHC class I and II alleles have been described. These motifs itemize the amino acid residues that serve as MHC binding anchors for specific class I and class II MHC alleles. Sophisticated computer-based algorithms that take into account the MHC binding anchors as well as the amino acids sequence of a peptide are used to predict and quantify the binding affinity of the peptide/MHC interaction. Thus, from the input of the known amino acid sequence of Zona Pellucida proteins, these algorithms list all potential T-cell epitopes, each with its corresponding predictive binding score (see e.g. Tables 2, 5 and 3). Commonly known bio-informatics tools for these purposes include e.g. HLA_BIND (Parker et al., 1994, J. Immunol. 152:163), SYFPEITHI (Rammensee et al., 1995, Immunogenetics 41, 178-228; Rammensee et al., Landes Bioscience 1997, International distributor: Springer Verlag GmbH & Co. KG, Heidelberg, Germany; www.syfpeithi.de/), NetMHC (Buus et al., 2003, Tissue Antigens, 62:378-84; Nielsen et al., 2003, Protein Sci., 12:1007-17; Nielsen et al., 2004, Bioinformatics, 20(9):1388-97; www.cbs.dtu.dk/), TEPITOPE 2000 (Sturniolo et al., 1999, Nature Biotechnology 17, 555-562; www.vaccinome.com/), and the (continuously updated) IEDB analysis resources—T Cell epitope prediction tools: tools.iedb.org/.

Alternatively, the skilled artisan will be able to determine HTL and CTL binding epitopes experimentally using standard experimentation (Current Protocols in Immunology, Wiley Interscience 2004). In a preferred embodiment, the method comprises administering a composition comprising an effective amount of a plurality of different polypeptide fragments of between 18-100 amino acids in length, of a native ZP, preferably hZP3 or hZP3(23-350), glycoprotein, wherein each polypeptide fragments comprises one or more of said predicted potential MHC I or MHC II restricted epitopes. Preferably, the amino acid sequence of said predicted potential MHC I or MHC II restricted epitopes in the different polypeptide fragments do not overlap. Preferably, the plurality of different polypeptide fragments collectively comprise at least 50, 70, 80, 90 or 95% of the potential MHC I or MHC II epitopes predicted by one or more of the above-mentioned bio-informatics tools.

In some cases it has been observed that the same peptide may bind to several MHC I or II allele products (see e.g. Table 2, 5 and 3). In one embodiment, the use of such 'promiscuous' MHC binding peptides in the present method is particularly preferred.

The present method of immunization preferably comprises the administration of a source of immunogenic active polypeptide fragments, said polypeptide fragments being selected from Zona Pellucida protein fragments and/or homologues thereof as defined herein before, said polypeptide fragments comprising CTL and/or HTL epitopes restricted by a variety of HLA molecules and which fragments are between 18 and 45 amino acids in length. Peptides having a length between 18 and 45 amino acids have been observed to provide superior immunogenic properties as is described in WO 02/070006. Peptides may advantageously be chemically synthesized and may optionally be (partially) overlapping and/or may also be ligated to other molecules, peptides or proteins. It may also be advantageous to add to the amino- or carboxy-terminus of the peptide chemical moieties or additional (modified or D-) amino acids in order to increase the stability and/or decrease the biodegradability of the peptide. To improve the immunogenicity/immunostimulating properties, moieties may be attached, e.g. by lipidation, elongation and/or conjugation (see below). The peptide can e.g. be elongated by addition of charged or polar amino acids, in order to enhance its solubility and/or increase its stability in vivo.

For immunization purposes the aforementioned immunogenic polypeptides of the invention may also be fused with proteins such as, but not limited to, tetanus toxin/toxoid, diphtheria toxin/toxoid or other carrier molecules. The polypeptides of the invention may also be advantageously fused to heat shock proteins, such as recombinant endogenous (murine) gp96 (GRP94) as a carrier for immunodominant peptides as described in (references: Rapp U K and Kaufmann S H, Int Immunol. 2004 April; 16(4):597-605; Zugel U, Infect Immun. 2001; 69(6):4164-7) or fusion proteins with Hsp70 (Triebel et al; WO99/54464). The immunogenic polypeptides of the invention can also be conjugated with molecules having adjuvant activity as listed hereinbelow, in particular TLR ligands/agonists as listed hereinbelow.

The individual amino acid residues of the present immunogenic (poly)peptides of the invention can be incorporated in the peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone cross-links. See, generally, Spatola, Chemistry and Biochemistry of Amino Acids, Peptides and Proteins, Vol. VII (Weinstein ed., 1983). Several peptide backbone modifications are known, these include, $\psi$ [CH$_2$S], $\psi$ [CH$_2$NH], $\psi$ [CSNH$_2$], $\psi$ [NHCO], $\psi$ [COCH$_2$] and $\psi$ [(E) or (Z) CH=CH]. The nomenclature used above, follows that suggested by Spatola, above. In this context, $\psi$ indicates the absence of an amide bond. The structure that replaces the amide group is specified within the brackets.

Amino acid mimetics may also be incorporated in the polypeptides. An "amino acid mimetic" as used herein is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to elicit an immune response against the native ZP T cell epitopes. Amino acid mimetics may include non-protein amino acids, such as β-, γ-, δ-amino acids, β-, γ-, δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) Ann. Repts. Med. Chem. 24:243-252.

According to a preferred embodiment, the present method comprises the administration of a composition comprising one or more of the present immunogenic polypeptides as defined herein above, and at least one excipient. Excipients are well known in the art of pharmacy and may for instance be found in textbooks such as Remington's pharmaceutical sciences, Mack Publishing, 1995.

In another preferred embodiment, the source of the immunogenic polypeptide of the invention to be administered comprises a nucleic acid molecule encoding the immunogenic polypeptide. The source or composition comprising the nucleic acid molecule encoding the immunogenic polypeptide can comprise one or more different nucleic acid molecule encoding any one of the immunogenic polypeptides, polypeptide fragments, and/or peptides as herein defined above. In addition, the nucleic acid molecule can encode a larger part of a native ZP. The nucleic acid molecule can e.g. encode a polypeptide comprises at least 50, 70, 80, 90, 95 or 100% of the complete amino acid backbone of a ZP, preferably of hZP3, more preferably of hZP3(23-350) or a homologue of said polypeptide. Preferably the nucleic acid molecule encodes a contiguous stretch of at least 50, 70, 80, 90, 95 or 99% of the complete amino acid backbone. It is also possible that a nucleic acid molecule encodes more than one (T cell epitope containing) immunologically active fragments of contiguous amino sequences from an hZP(3) as defined hereinabove, whereby in the encoded amino acids sequences, the different immunologically active fragments can be separated by spacer or linker sequences as beads on a string.

The nucleic acid molecule encoding the immunogenic polypeptide of the invention can be a DNA molecule, preferably a genetic construct wherein the nucleotide sequence coding for the immunogenic polypeptide (cDNA) is operably linked to appropriate expression regulatory sequence that ensure functional expression of the immunogenic polypeptide in the target cells in the human subject, e.g. including at least a strong (e.g. viral) promoter. Genetic constructs for use as DNA vaccines, including e.g. plasmids or viral vectors, are inter alia described in WO2014/165291, WO2016/123285 and WO2017/136758. Alternatively, the nucleic acid molecule encoding the immunogenic polypeptide of the invention can be an RNA molecule, e.g. an mRNA, ssRNA, dsRNA or combinations thereof. The RNA molecule can e.g. be formulated in a particle comprising the molecule. Suitable embodiments for RNA-based vaccines are e.g. described in WO2013/087083.

Routes of administration for nucleic acid vaccines include, but are not limited to, intramuscular, intranasal, intraperitoneal, intradermal, subcutaneous, intravenous, intra-arterial, intraocular and oral as well as topically, transdermal, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "micro projectile bombardment gone guns".

The source of the immunogenic polypeptide of the invention can further be a live cell that expresses and/or presents the immunogenic polypeptide. The cell can be an autologous or allogeneic immune cell, e.g. a dendritic cell derived from the subject to treated, or the cell can be a microbial cell, more preferably a bacterium such as e.g. a live-attenuated *Listeria monocytogenes*. The expressed immunogenic polypeptide preferably is an immunogenic polypeptide as defined hereinabove. The immunogenic polypeptide can be expressed as part of a fusion protein, wherein preferably the immunogenic polypeptide is fused to a protein that is endogenous to the organism, e.g. an N-terminal fragment of an *L. monocytogenes* LLO or ActA protein. Suitable embodiments for *Listeria*-based vaccines are e.g. described in WO2015/164121. A bacterium expressing the immunogenic polypeptide of the invention can be administered orally or parenterally, preferably intravenously.

In another embodiment of the invention, the source of the immunogenic polypeptide of the invention is an autologous or allogeneic dendritic cell (DC) that presents at least one MHC restricted epitope of the immunogenic polypeptide in an HLA molecule on its surfaces. Such dendritic cells can e.g. be prepared ex vivo by contacting and/or loading DCs from the patient's blood, e.g. DCs isolated from mononuclear cells from the patient/subject, with a composition comprising the immunogenic polypeptide of the inventions. The immunogenic polypeptide contacted with mononuclear cells or DCs preferably is an immunogenic polypeptide as defined hereinabove. A pharmaceutical to facilitate harvesting of DC can be used, such as Progenipoietin™ (Monsanto, St. Louis, Mo.) or GM-CSF/IL-4. After pulsing the DCs with peptides and washing to remove unbound peptides, the DCs are reinfused into the patient. In this embodiment, a composition is provided comprising peptide-pulsed DC which present the pulsed peptide epitopes in HLA molecules on their surfaces. Alternatively, instead of using autologous cells derived from the subject, allogenic DCs can be used that are derived from a precursor human dendritic cell line and designed to deliver tumor associated antigens, such as e.g. described in WO2009/019320, WO2014/090795 and WO2014/006058. Methods of inducing an immune response employing ex vivo peptide-pulsed DC are well known to the skilled person.

The present method for immunization may further comprise the administration, preferably the co-administration, of at least one adjuvant. Adjuvants may comprise any adjuvant known in the art of vaccination and may be selected using textbooks like Current Protocols in Immunology, Wiley Interscience, 2004.

Adjuvants are herein intended to include any substance or compound that, when used in combination with an antigen to immunize a human or an animal, stimulates the immune system, thereby provoking, enhancing or facilitating the immune response against the antigen, preferably without generating a specific immune response to the adjuvant itself. Preferred adjuvants enhance the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the invention will usually be a compound that is foreign to a human, thereby excluding immunostimulatory compounds that are endogenous to humans, such as e.g. interleukins, interferons and other hormones.

A number of adjuvants are well known to one skilled in the art. Suitable adjuvants include e.g. Granulocyte-macrophage colony-stimulating factor (GM-CSF), incomplete Freund's adjuvant (IFA), Montanide™ ISA-51, Montanide™ ISA 720 (adjuvants produced by Seppic, France), alpha-galactosylceramide, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy-phosphoryloxy)-ethylamine (CGP 19835A, referred to as MTP-PE), DDA (2 dimethyldioctadecylammonium bromide), polyIC, Poly-A- poly-U, RIBI™, GERBU™, Pam3™, Carbopol™, Specol™, Titermax™, tetanus toxoid, diphtheria toxoid, meningococcal outer membrane proteins, diphtheria protein CRM197. Preferred adjuvants comprise a ligand that is recognised by a Toll-like-receptor (TLR) present on antigen presenting cells. Various ligands recognised by TLR's are known in the art and include e.g. lipopeptides (see e.g. WO 04/110486), lipopolysaccharides, peptidoglycans, lipoteichoic acids, lipoarabinomannans, lipoproteins (from mycoplasma or spirochetes), double-stranded RNA (poly I:C), poly ICLC (Hiltonol™, produced by Oncovir, Inc., USA), unmethylated DNA, flagellin, CpG-containing oligonucleotides, Pam3CysSK4 and imidazoquinolines, as well derivatives of these ligands having chemical modifications. The use of poly I:C is particularly preferred.

For therapeutic applications, the present immunogenic polypeptides, nucleic acid sequences encoding them, cells expressing or presenting them or the present compositions comprising these polypeptides, nucleic acid sequences or cells are administered to a patient suffering from lung cancer and possibly metastases thereof or to a patient that has received other methods of treating lung cancer, described herein before, in an amount sufficient to induce a primary autoimmune response directed against native ZP glycoproteins and tissue cells expressing ZP proteins. An amount sufficient to accomplish this is defined as a "therapeutically-" or "prophylactically-effective" dose. Such effective dosages will depend on a variety of factors including the condition and general state of health of the patient. Thus dosage regimens can be determined and adjusted by trained medical personnel to provide the optimum therapeutic or prophylactic effect.

In the present method the one or more immunogenic polypeptides are typically administered at a dosage of about 1, 2, 5, 10, 20, 50, 100, 200, 500 or 1000 µg per immunogenic polypeptide or nucleic acid molecule or more at least once. Preferably administration of the dosage is repeated one, two, three or more times at intervals of 2, 3 or 4 weeks.

According to one preferred embodiment typical dosage regimens comprise administering a dosage of 1-1000 µg per peptide per immunization, more preferably 10-500 µg per peptide per immunization, still more preferably 5-150 µg per peptide per immunization, at least once. Preferably administration of the dosage is repeated one, two, three or more times at intervals of 2, 3 or 4 weeks. According to a preferred embodiment 5-150 µg per peptide per immunization is administered and repeated within 2-3 weeks for one or more times per treatment.

The present method preferably comprises administration of the present immunogenic polypeptides and compositions comprising them via the parenteral or oral route, preferably the parenteral route. Preferred routes of administration include, but are not limited to, intratumoral, intramuscular, intranasal, intraperitoneal, intradermal, subcutaneous, intravenous, intra-arterial, intraocular and oral as well as topically, transdermal, by inhalation or suppository or to mucosal tissue such as by lavage to vaginal, rectal, urethral, buccal and sublingual tissue. Preferred routes of administration include intramuscular, intraperitoneal, intradermal and subcutaneous injection. In another embodiment, administration is into an anatomic site that drains into a lymph node basin. In another embodiment, the administration is into multiple lymph node basins.

Particularly preferred is a combination of an intradermal and a subcutaneous administration of a medicament according to the invention. DC in the epidermis are clearly different from DC in the dermis and in the subcutis. The intracutaneous (intradermal) immunization will cause antigen processing and activation of epidermal DC (Langerin-positive Langerhans cells) that through their dendritic network are in close contact with the keratinocytes. This will also optimally activate inflammatory pathways in the interactions between Langerhans cell and keratinocytes, followed by trafficking of antigen loaded and activated Langerhans cell to the skin-draining lymph nodes. The subcutaneous administration will activate other DC subsets that will also become loaded with antigen and travel independently to the skin-draining lymph nodes. Conceivably, the use of a medicament which may be administered both intradermally and subcutaneously may lead to a synergistic stimulation of T-cells in these draining nodes by the different DC subsets.

A medicament according to the invention has another advantage, which is that by intradermal administration of low amounts of a medicament, preferably a peptide as earlier herein defined, an immunogenic effect may still be achieved. The amount of each peptide used is preferably ranged from 0.3 and 1000 µg, more preferably from 1 and 500 µg, even more preferably from 5 and 150 µg. Another aspect of the invention relates to a pharmaceutical preparation comprising as the active ingredient the present source of a polypeptide as defined herein before. More particularly the pharmaceutical preparation comprises as the active ingredient one or more of the aforementioned immunogenic polypeptides selected from the group of ZP proteins, homologues thereof and fragments of said ZP proteins and homologues thereof, or, alternatively, a gene therapy vector as defined herein above.

According to a first embodiment a pharmaceutical preparation is provided comprising one or more of the immunogenic polypeptides of the invention. The concentration of said polypeptide in the pharmaceutical composition can vary widely, i.e., from less than about 0.1% by weight, usually being at least about 1% by weight to as much as 20% by weight or more.

The composition preferably at least comprises a pharmaceutically acceptable carrier in addition to the active ingredient. The pharmaceutical carrier can be any compatible, non-toxic substance suitable to deliver the immunogenic polypeptides or gene therapy vectors to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

According to a particularly preferred embodiment, the present pharmaceutical composition comprises an adjuvant, as defined in more detail herein before. Adjuvants for incorporation in the present composition are preferably selected from the group of ligands that are recognised by a Toll-like-receptor (TLR) present on antigen presenting cells, including lipopeptides (see e.g. WO 04/110486), lipopolysaccharides, peptidoglycans, lipoteichoic acids, lipoarabinomannans, lipoproteins (from mycoplasma or spirochetes), double-stranded RNA (poly I:C), unmethylated DNA, flagellin, CpG-containing DNA, Pam3cysSK4, and imidazoquinolines, as well derivatives of these ligands having chemical modifications. The skilled person will be able to determine the exact amounts of any one of these adjuvants to be incorporated in the present pharmaceutical preparations in order to render them sufficiently immunogenic. According to another preferred embodiment, the present pharmaceutical preparation may comprise one or more additional ingredients that are used to enhance CTL immunity as explained herein before.

Formulation of the medicaments of the invention, e.g. composition comprising a source of the immunogenic polypeptide, ways of administration and the use of pharmaceutically acceptable excipients are known and customary in the art and for instance described in "Remington: The Science and Practice of Pharmacy" (Ed. Allen, L. V. $22^{nd}$ edition, 2012, www.pharmpress.com).

The immunogenic polypeptides, nucleic acids encoding them or cells expressing them for use in the present invention can be prepared using recombinant techniques such as described in Ausubel et al., "Current Protocols in Molecular Biology", Greene Publishing and Wiley-Interscience, New York (1987) and in Sambrook and Russell (2001) "Molecular Cloning: A Laboratory Manual" ($3^{rd}$ edition), Cold Spring Harbor Laboratory, Cold Spring Harbor Laboratory Press, New York; both of which are incorporated herein by reference in their entirety. Also see, Kunkel (1985) Proc. Natl. Acad. Sci. 82:488 (describing site directed mutagenesis) and Roberts et al. (1987) Nature 328:731-734 or Wells, J. A., et al. (1985) Gene 34:315 (describing cassette mutagenesis). However, more preferably, immunogenic polypeptides of the invention or nucleic acids encoding them are prepared by chemical synthesis. Chemical synthesis of peptides or nucleic acids is routine practice and various suitable methods are known to the skilled person. Chemical synthesis of peptides or nucleic acids also overcomes the problems associated with recombinant production, which is more difficult to standardize and requires extensive purification and quality control measures.

In a yet a further aspect the inventions pertains to a T cell comprising a T cell receptor that binds an MHC-peptide complex, wherein the peptide preferably is a peptide comprising or consisting of an MHC class I and MHC class II restricted epitopes comprised in a native ZP, preferably hZP3 or hZP3(23-350), or a homologue of said one or more polypeptides. Such a T cell can e.g. be obtained in a method comprising contacting a T-cell with an antigen presenting cell expressing a polynucleotide encoding an immunogenic polypeptide of the invention and/or contacting a T-cell with an antigen presenting cell loaded with an immunogenic polypeptide of the invention; and, optionally, culturing said T-cell. The antigen presenting cell (APC), preferably is a dendritic cell (DC). The T-cell is preferably a $CD8^+$ cytotoxic T-cell or a $CD4^+$ T-helper cell. Introducing a polynucleotide encoding the immunogenic polypeptide into the APC or DC may be performed using any method known to the person skilled in the art, preferably a polynucleotide according to the invention is introduced into the APC or DC using transfection. Preferably the polynucleotide encoding the immunogenic polypeptide is provided with proper control sequences, or be comprised in a proper expression vector. Contacting a T-cell with an immunogenic polypeptide of the invention can be performed by any method known to the person skilled in the art. Preferably, the immunogenic polypeptide or an epitope comprised in the immunogenic polypeptide is presented to the $CD8^+$ cytotoxic T-cell or $CD4^+$ T-helper cell by an MHC class I or an MHC class II molecule on the surface of an APC, preferably a DC. The person skilled in the art knows how to load an APC or DC with a peptide. Culturing said T-cell may be performed using any method known by the person skilled in the art. Maintaining a T-cell under conditions to keep the cell alive is herein also to be construed to be culturing. Preferably, the T-cell according to this aspect of the invention is contacted with an immunogenic polypeptide according to the invention as defined in the first aspect of the invention. Ex vivo methods for obtaining and activating tumor antigen-specific T cells are described in more detail e.g. in WO2017/173321. In this aspect the invention also relates to a composition comprising an (activated) T cell according to the invention, as well as to methods of the inventions for therapeutic and/or prophylactic treatment of lung cancer and/or metastases, comprising administering to the subject a therapeutically effective amount of an (activated) tumor specific T cell described herein, or produced by a method described herein (see e.g. Examples 4). In embodiments, the administering comprises administering from about $10^6$ to $10^{12}$, from about $10^8$ to $10^{11}$ or from about $10^9$ to $10^{10}$ of the (activated) tumor specific T cells. The T cell or composition therewith is preferably administered via intravenous, intraperitoneal, intratumoral, intradermal, or subcutaneous administration. In another embodiment, the T cell or composition therewith is administered into an anatomic site that drains into a lymph node basin. In another embodiment, the administration is into multiple lymph node basins.

A further aspect of the invention relates to a method for treatment or diagnosis of lung cancer and metastases thereof in a subject by administering an antibody or fragment thereof that specifically binds to an epitope of human Zona Pellucida (hZP) protein, preferably the antibody or fragment thereof specifically binds to an epitope of hZP3 or hZP3 (23-350).

An antibody "which binds" an antigen of interest, e.g. a tumor-associated hZP protein antigen or epitope thereof, is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoassay (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labelled target. In this case, specific binding is indicated if the binding of the labelled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_d$ for the target (which may be determined as described below) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

A "$K_d$" or "$K_d$ value" can be measured by using surface plasmon resonance assays using a BIAcore™-2000 or a BIAcore™-3000 (BIAcore, Inc., Piscataway, NJ) at 25° C.

with immobilized antigen CM5 chips at ~10-50 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of the antibody or Fab (0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant ($K_d$) is calculated as the ratio $k_{off}/k_{on}$. See, e.g., Chen, Y., et al., (1999) J. Mol Biol 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophometer (ThermoSpectronic) with a stir red cuvette. An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, NJ) as described above.

The term "antibody" as used herein is meant in a broad sense and refers to any type of immunoglobulin molecule, including polyclonal antibodies, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

One embodiment of the invention concerns a method of treating method for treatment of lung cancer and metastases thereof in a subject, said method comprising administering to said subject a composition comprising an anti-ZP antibody, preferably an anti-hZP3 or anti-hZP3(23-350) antibody, wherein the antibody induces killing of lung cancer cells by antibody-dependent cell-mediated cytotoxicity (ADCC), antibody-dependent cellular phagocytosis (ADCP), complement dependent cytotoxicity (CDC) or apoptosis. As is generally understood by those of average skill in the art these antibody effector functions may be mediated by the Fc portion of the antibody, e.g. by binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components eventually result in inhibition and/or depletion of target cells, i.e. ZP-expressing cells. Human IgG isotypes IgG1, IgG2, IgG3 and IgG4 exhibit differential capacity for effector functions. ADCC may be mediated by IgG1 and IgG3, ADCP may be mediated by IgG1, IgG2, IgG3 and IgG4, and CDC may be mediated by IgG1 and IgG3. In the methods described herein the anti-hZP3 or anti-hZP3(23-350) antibody preferably is an IgG1, IgG2, IgG3 or IgG4 antibody.

In the methods described herein the anti-hZP3 or anti-hZP3(23-350) antibody induces in vitro and/or in vivo killing of lung cancer cells that express ZP3 protein by antibody-dependent cellular cytotoxicity (ADCC). In the methods described herein the anti-hZP3 or anti-hZP3(23-350) antibody induces in vitro and/or in vivo killing of lung cancer cells that express ZP protein by complement-dependent cytotoxicity (CDC). In the methods described herein the anti-hZP3 or anti-hZP3(23-350) antibody induces in vitro and/or in vivo killing of lung cancer cells that express ZP3 protein by antibody-dependent cellular phagocytosis (ADCP).

In the methods described herein the anti-hZP3 or anti-hZP3(23-350) antibody induces in vitro and/or in vivo killing of lung cancer cells that express ZP3 protein by apoptosis.

In the methods described herein the anti-ZP antibody can bind human ZP with a range of affinities ($K_D$). In one embodiment according to the invention the anti-ZP antibody binds to ZP with high affinity, for example, with a $K_D$ equal to or less than about $10^{-7}$ M, such as but not limited to, 1-9.9 (or any range or value therein, such as 1, 2, 3, 4, 5, 6, 7, 8, or 9)$\times 10^{-8}$, $10^{-9}$, $10^{-10}$, $10^{-11}$, $10^{-12}$, $10^{-13}$, $10^{-14}$, $10^{-15}$ or any range or value therein, as determined by surface plasmon resonance or the Kinexa method, as practiced by those of skill in the art. One exemplary affinity is equal to or less than $1\times 10^{-8}$ M. Another exemplary affinity is equal to or less than $1\times 10^{-9}$ M.

Preferred antibodies for use in the present invention are monoclonal antibodies. Suitable (monoclonal) antibodies can be generated, screened and produced by methods that are well known in the art and e.g. described in textbooks like "Antibodies: A Laboratory Manual, Second edition, Edited by E. A. Greenfield, 2014, Cold Spring Harbor Laboratory Press. More specifically, Ranking et al. (1998, Development 125, 2415-2424) describe the generation of a monoclonal antibody H3.1 against a C-terminal peptide of the hZP3 extracellular domain comprising amino acids 335-350 of SEQ ID NO: 3. More preferably, antibodies for use in the present invention are humanized, or even more preferably human monoclonal antibodies, as may be obtained by methods well known in the art, such as e.g. described resp. in Olimpieri et al. (Bioinformatics. 2015; 31(3): 434-435) and Sheehan and Marasco (Microbiol Spectr. 2015; 3(1):AID-0028-2014) and reference cited therein.

Any antibodies that bind to an extracellular domain of a ZP protein, such as the extracellular domain of hZP3, i.e. hZP3(23-350), which extracellular protein has the amino acid sequence of SEQ ID NO: 5, can be used for the present invention, Examples of suitable antibodies that can be used for the present invention include e.g. antibodies that have the ability to cross-block the binding of one or more of the reference antibodies that are known to bind to hZP3(23-350). One such reference antibody that is known to specifically bind to hZP3(23-350) is the H3.1 antibody described by Ranking et al. (1998, supra), for which the hybridoma is obtainable from ATCC under accession no.: ATCC CRL-2569.

Thus, a preferred antibody for use in the present invention has the ability to cross-block the binding of at least one antibody that is known to specifically bind to a ZP, preferably to hZP3, more preferably to hZP3(23-350) or a homologue of said polypeptide. More preferably, the antibody has the ability to cross-block the binding of the H3.1 antibody with accession no.: ATCC CRL-2569. The ability of an anti-ZP antibody to cross-block the binding of a reference antibody is herein defined as the ability to reduce the binding of the reference antibody to a suitable target molecule comprising a ZP, hZP3 or hZP3(23-350) amino acid sequences by at least 10, 20, 50, 75, 90, 95, 99, 99.9 or 99.99% when the target molecule has first been bound by the anti-ZP antibody, or vice versa (i.e. binding of the anti-ZP antibody is reduced when the target molecule is first bound by the reference antibody). The ability to cross-block may in principle be determined using any type of immunoassay, preferably a competitive immunoassay, including e.g. ELISA, solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et 20 al., J. Immunol. 137:3614-3619 (1986)); solid phase direct labeled assay, solid phase direct labeled sandwich assay (see "Antibodies, A Laboratory Manual," Second edition, 2014; supra); solid phase direct label RIA using $I^{125}$ label (see Morel et al., Molec. Immunol. 25(1):7-15 (1988)); solid phase direct biotinavidin EIA (Cheung et al, Virology 176:546-552 (1990)); and direct labeled RIA (Moldenhauer et al., Scand. J. Immunol. 32:77-82 (1990)). Typically, such an assay involves the use of a purified target molecule bound to a solid surface, an unlabeled test antibody and a labelled reference antibody. Competitive inhibition is measured by determining the amount of label bound to the solid surface in the presence of the test antigen-binding protein. Usually the test antibody is present in excess.

In the methods of the invention described herein the anti-ZP antibody may be provided in suitable pharmaceutical compositions comprising the anti-ZP antibody and a pharmaceutically acceptable carrier. Suitable vehicles and formulations, inclusive of other human proteins, e.g., human serum albumin, are described, for example, in e.g. Remington: The Science and Practice of Pharmacy, 21st Edition, Troy, D. B. ed., Lipincott Williams and Wilkins, Philadelphia, Pa. 2006, Part 5, Pharmaceutical Manufacturing pp 691-1092, see especially pp. 958-989.

The mode of administration of the anti-ZP antibody in the methods of the invention described herein may be any suitable route such as parenteral administration, e.g., intradermal, intramuscular, intraperitoneal, intravenous or subcutaneous, pulmonary, transmucosal (oral, intranasal, intravaginal or rectal) or other means appreciated by the skilled artisan, as well known in the art. The anti-ZP antibody in the methods of the invention described herein may be administered to a patient by any suitable route, for example parentally by intravenous (i.v.) infusion or bolus injection, intramuscularly or subcutaneously or intraperitoneally.

In the methods of the invention, the anti-ZP antibody is administered in a therapeutically effective amount. The term "therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics include, for example, improved well-being of the patient, reduction of a tumor burden, arrested or slowed growth of a tumor, and/or absence of metastasis of cancer cells to other locations in the body.

The dose given to a subject suffering from lung cancer is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

The present invention also relates to a method for treatment of lung cancer and metastases thereof in a subject by targeted therapy, typically by administering a composition comprising an antibody or fragment thereof capable of immunospecifically binding to an epitope of human Zona Pellucida (hZP) protein, preferably an antibody or fragment thereof capable of immunospecifically binding to an epitope of human Zona Pellucida 3 (hZP3) protein, wherein the antibody or fragment is part of an immunoconjugate, such as an immunotoxin, an antibody-drug conjugate or an antibody carrying radioisotope.

The term 'immunoconjugate' refers to conjugates in which an antibody or fragment thereof is chemically linked to another molecule. When the molecule linked to the antibody or fragment thereof is a toxin, the immunoconjugate is known as an immunotoxin. When the molecule linked to the antibody or fragment thereof is a (cytotoxic) drug, the immunoconjugate is often referred to as 'antibody-drug conjugate'. The use of immunoconjugates for the local delivery of cytotoxic or cytostatic agents, i.e. drugs to kill or inhibit tumor cells in the treatment of cancer may allow targeted delivery of the drug moiety to tumors, and intracellular accumulation therein, where systemic administration of these unconjugated drug agents may result in unacceptable levels of toxicity to normal cells as well as the tumor cells sought to be eliminated. Maximal efficacy with minimal toxicity is sought thereby. Efforts to design and refine antibody conjugates have focused on the selectivity of monoclonal antibodies (mAbs) as well as drug-linking and drug-releasing properties In some embodiments a radioisotope may be linked to the antibody, the resulting immunoconjugate is often referred to as immunoradioisotope.

As will be understood by those skilled in the art, the anti-ZP antibody portion can be an anti-ZP antibody having any or all of the characteristics described herein before in relation to the passive immunization embodiment. Immunoconjugates may also comprise an antibody or fragment thereof that is merely capable of immunospecifically binding to an epitope of human Zona Pellucida (hZP) protein, preferably an antibody or fragment thereof capable of immunospecifically binding to an epitope of human Zona Pellucida 3 (hZP3) protein, without inducing any effector mechanisms.

The present invention further contemplates immunoconjugates comprising an antibody or fragment thereof conjugated with a radioactive isotope or radionuclide or with or moiety (capable of) containing such a radionuclide. The skilled practitioner will realize that there are numerous radionuclides that can be coupled to tumor-specific antibodies by well-known techniques and delivered to a site to specifically damage tumor cells and tissue. For example, reagents that are suitable for use include $^{125}I$, $^{123}I$, $^{111}In$, $^{177}Lu$, $^{90}Y$, $^{213}Bi$, $^{225}Ac$ and $^{99m}Tc$. Among the radionuclides, Yttrium-90 ($^{90}Y$) may be particularly suitable for radioimmunotherapy, since Yttrium-90 ($^{90}Y$) provides advantages over Iodine-131 ($^{131}I$) because it delivers higher beta energy (2.3 MeV vs 0.61 MeV) to the tumor and has path length of 5 to 10 mm resulting in the improved ability to kill both targeted and neighboring cells, an advantage particularly in bulky or poorly vascularized tumor.

In a further embodiment, the invention pertains to a method for diagnosis and/or prognosis of a lung cancer and/or metastases thereof and/or a recurrence thereof in a human subject. The method is preferably applied to diagnosis and/or prognosis of non-small cell lung cancer and/or metastases thereof and/or a recurrence thereof. The method for diagnosis and/or prognosis preferably comprises the administration of an antibody or fragment thereof that specifically binds to an epitope of an hZP, preferably to an hZP3 or hZP3(23-350) as herein described above. The antibody of fragment thereof is preferably conjugated to an imaging agent or a detectable agent, preferably the agent is an in vivo imaging agent. Non-limiting examples of such agents include enzymes, radiolabels, haptens, fluorescent labels, phosphorescent molecules, chemiluminescent molecules, chromophores, luminescent molecules, photoaffinity molecules, colored particles or ligands, such as biotin, paramagnetic ions, radioactive isotopes, fluorochromes, NMR-detectable substances and X-ray imaging agents (see e.g. US20170240637 A1).

The phrase "in vivo imaging" as used herein refers to methods of detecting the presence of a detectably labeled antibody of the invention in whole, live mammal. Optically detectable proteins such as fluorescent antibodies and luciferases-conjugated antibodies may be detected by in vivo imaging. In vivo imaging may be used to provide 2-D as well as 3-D images of a mammal. Radiolabeled antibodies, for example, may be administered to a subject and the subject imaged with a gamma camera. Charge-coupled device cameras, CMOS, or 3D topographers may be used to carry out in vivo imaging. Methods of in vivo imaging using computed tomography, magnetic resonance imaging, ultrasonography, positron emission tomography, single-photon emission computed tomography (SPECT), and the like are well known in the art. The information from many in vivo imaging methods as those described above can provide information on cancer cells in the subject.

In the diagnostic and/or prognostic methods a detectably labelled antibody of the invention can be used to determine whether a subject has a lung cancer, and/or metastases thereof and/or a recurrence thereof, that is more or less amenable to a therapy described herein, as well as monitor the progress of treatment and/or response to therapy in a subject. It also may be used to assess the course of other (combination) therapies. Thus, the diagnostic/prognostic methods can inform selection of therapy and treatment regimen by a clinician.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention is further illustrated in the following examples, which are not intended to limit the scope of the invention in any manner.

DESCRIPTION OF THE FIGURES

FIG. 4: Selected hZP3 peptide sequences corresponding to SEQ ID Nos: 66-75. Boxes and ovals enclose predicted MHC class I and II binders as indicated in Tables 2 and 5, and 3, respectively. Asterisks indicate potential N-linked glycosylation sites, and the brackets above the sequences mark regions with cluster of O-linked glycans.

EXAMPLES

Example 1

Figure 1:
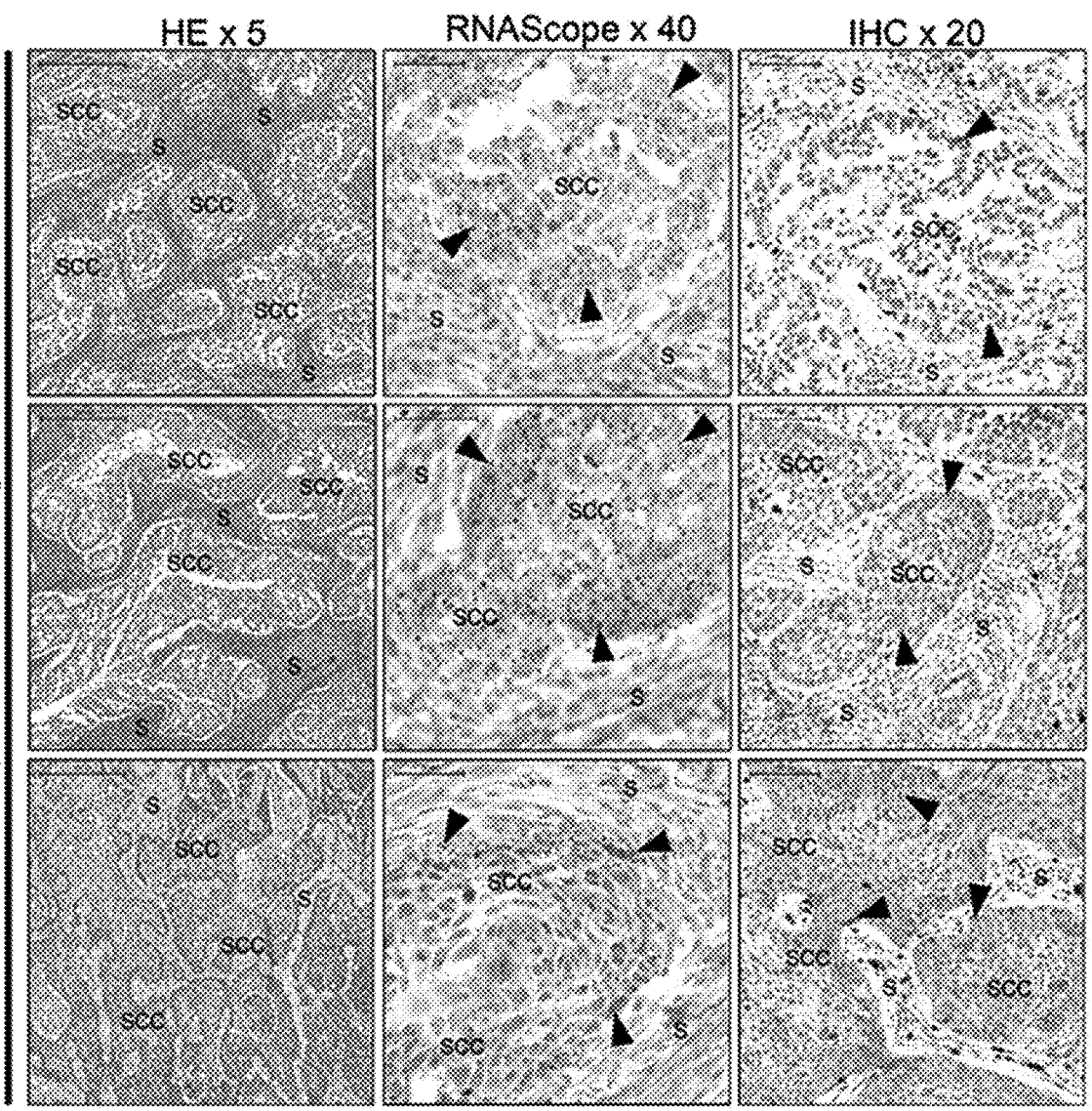
FIG. 1: ZP3 expression in squamous carcinoma cell lung cancers from three different patients. Each horizontal lane represents results from one single patient. From left to right, respectively, hematoxylin Eosin histopathology (HE×5); in situ hybridization of ZP3 mRNA expression (RNA Scope× 40); and, ZP3 protein expression by immunohistochemistry (IHX×20). Abundant ZP3 expression is detected exclusively in squamous carcinoma cells (SCC; arrows) and no expression of ZP3 can be seen in stromal cells (S) or healthy cells.

The expression of ZP3 in human lung cancer tissue is determined using immunohistochemistry (IHC). Tissue micro arrays (TMAs) from lung cancer tissues originating from different patients were obtained from a pathology institute in the Netherlands.

Immunohistochemical determinations were done with human ZP3 monoclonal antibodies H3.1 in two different concentrations; 1.0 μg/mL and 0.1 μg/mL.

Sections of human ovary containing oocytes were used as tissue positive controls. In addition, a sample of spleen tissue was used as a negative control.

The following IHC protocol was used for all samples:
Day 1
1. Deparaffinization and hydration:
   a) Xylen—3×3 min,
   b) Abs. EtOH—2×3 min,
   c) 96% EtOH—2×3 min,
   d) 70% EtOH—2×3 min
   e) dH$_2$O—1×10 min,
2. Antigen retrieval:
   a) 10 mM citric acid buffer with 0.05% Tween 20 (pH 6.0) in retriever for 2.5 h
   b) cool down
3. Wash sections in Tris-Buffered Saline (TBS) with 0.05% Tween 20 (TBST) 3 times for 5 minutes each.
4. Incubate sections in 3% H$_2$O$_2$ (diluted in TBS) for 15 minutes to quench endogenous peroxidase activity at room temperature (RT), in dark.
5. Wash sections in TBST (TBS with 0.05% Tween 20) 2 times for 5 minutes each.
6. Incubate sections in 1 mg/mL sodium borohydride solution (diluted in TBS) for 15 minutes to quench free aldehyde groups (RT, in dark, more important for IF staining, ZP3 co-localization).
7. Wash sections in TPBS (TBS with 0.05% Tween 20) 3 times for 5 minutes each.
8. Incubate sections in blocking solution—3% BSA in TBST (1 h; RT; humidified chamber).
9. Incubate sections with primary antibody against hZP3 (1.0, 0.125 or 0.1 µg/ml) diluted in blocking solution (3% BSA in TBST) overnight in humidified chamber in the cold room.
Day 2
10. Wash sections in TBST 3 times for 5 minutes each.
11. Incubate sections with anti-mouse DAKO polymer 30 min (EnVision #4001).
12. Wash sections in TBST 3 times for 5 minutes each.
13. Incubate sections with Chromogen System (DAKO, 1 drop for 1 ml of buffer #K3468) —10 min, stop the reaction by dipping slides in container with tap water.
14. Incubate sections in tap water for 2 min.
15. Rinse slides with ddH$_2$O before counterstaining
16. Counterstain sections in hematoxilin—20-30 s.
17. Incubate sections in tap water to remove excess of hematoxylin.
18. Dehydrate sections:
    a. 70% EtOH—2×3 min
    b. 96% EtOH—2×3 min
    c. Abs. EtOH—2×3 min
    d. Xylene—3×3 min
19. Mount with Pertex.

In the positive controls, antibodies detect proteins in the ZP surrounding the human oocyte. ZP3 proteins are also present in the oocyte cytoplasm. No positive staining is detected in sections of the lung cancer tissue samples when the primary antibody is omitted. No positive staining is observed, with the ZP monoclonal antibody, in spleen and liver tissue.

In the lung cancer samples (TMAs), presence of the ZP3 is confirmed by areas of the tissue staining positive for ZP3, with intensities varying among the samples obtained from different patients (see results of the squamous cell cancer TMAs in Table 1). Such tumors staining positive for ZP3 expression can be treated by immunization with ZP3-antigens in accordance with the present invention.

TABLE 1

| | Non-small cell lung cancer (NSCLC)-Squamous cell cancer, n = 42 (TMAs) | | | |
|---|---|---|---|---|
| Scoring | Result ZP3 antibody concentration (1.0 µg/mL) | Percentage ZP3 antibody concentration (1.0 µg/mL) | Result ZP3 antibody concentration (0.1 µg/mL) | Percentage ZP3 antibody concentration (0.1 µg/mL) |
| Negative | 1 | 2% | 4 | 33% |
| No Score | 4 | 10% | 6 | 14% |
| Positive | 37 | 88% | 22 | 52% |
| Details of positive score | | | | |
| Weak (>0-1) | 2 | 5% | 2 | 9% |
| Intermediate (>1-2) | 24 | 65% | 16 | 73% |
| Strong (>2-3) | 11 | 30% | 4 | 18% |

Example 2

The expression of ZP3 in human lung cancer tissue is determined using IHC (squamous cell cancer, n=10 and lung adenocarcinoma, n=10) and RNA scope in situ hybridization (squamous cell cancer, n=4 and lung adenocarcinoma, n=4). Tissue samples were from different patients were obtained from a pathology institute in Poland.

Immunohistochemical determinations were done with human ZP3 monoclonal antibodies in two different concentrations. The same IHC protocol was followed as described in Example 1.

Sections of human ovary was used as tissue positive control. In addition, a sample of spleen tissue was used as a negative control.

In situ hybridization of formalin fixed paraffin embedded (FFPE) human ovary and cancer samples were done with RNAscope FFPE 2.0 HD Detection Kit Brown [Advanced Cell Diagnostics (ACD), Hayward, California, USA, CAT #310033] according to manufacturer's protocol.

Deparaffinized FFPE Sections
1. In a fume hood, fill two clearing agent dishes with ~200 ml fresh xylene and 2 with 200 mL fresh 100% ethanol.
2. Place the slides in the first xylene-containing clearing agent dish and incubate for 5 min at RT. Agitate the slides by occasionally lifting the slide rack up and down in the clearing agent dish.
3. Remove the slide rack from the first xylene-containing dish and immediately place in the second xylene-containing clearing agent dish in the fume hood and repeat incubation.
4. Remove the slide rack from the second xylene-containing dish and immediately place in the staining dish containing 100% ethanol. Incubate the slides in 100% ethanol for 1 min at RT with agitation.
5. Repeat step 4 with fresh 100% ethanol.
6. Remove the slides from the rack, and place on absorbent paper with the section face-up. Air Dry for 5 min at RT.

Equilibrate Equipment
1. Turn on HybEZ™ OVEN and set temperature to 40° C.
2. Place a humidifying paper in the humidity control tray and wet completely with Distilled water.
3. Insert covered tray into oven and close the oven door. Warm the tray for 30 min at 40° C. before use.

Prepare 1× Pretreat 2
Prepare 700 mL of fresh 1× pretreat 2 by adding 630 mL distilled water to 1 bottle (70 mL) 10× pretreat 2 solution in a 1 L beaker. Mix well. Place the beaker containing 1× pretreat 2 on the hot plate. Cover the beaker with foil and turn the hot plate on high for 10-15 min. Once 1× pretreat 2 reaches boiling, turn the hot plate knob to 100-104° C. to maintain uniform boiling.

Pretreat 1 & 2

1. Apply pretreat to cover the entire section and incubate for 10 min at RT.
2. Remove pretreat 1 solution from one slide at a time by tapping the slide on absorbent paper, and/or flicking. Immediately insert the slide into a slide rack submerged in a staining dish filled with distilled water.
3. Wash the slides twice in the distilled water.
4. Apply pretreat 2. Ensure that 1× pretreat 2 solution is at mild boiling. With a pair of forceps very slowly submerge the slide rack containing the slides into the boiling 1× pretreat 2 solution. Cover the beaker with foil and boil the slides for 15 min. After pretreatment time is over, use the forceps to immediately transfer the hot slide rack from the 1× pretreat 2 to the staining dish containing distilled water. Do not let the slides cool in Pretreat 2.
5. Wash the slides twice in the distilled water.
6. Wash the slides in fresh 100% ethanol by moving the rack up and down 3-5 times. Air dry the slides. Create a hydrophobic barrier using hydrophobic barrier pen.
7. Place the dried slides on the slide rack, and add pretreat 3 to entirely cover each section. Remove the HybEZ™ humidity control tray from the HybEZ™ oven and place the HybEZ™ slide rack in the tray. Close the lid, and insert tray back into the oven.
8. Incubate the slides at 40° C. for 30 min.
9. Remove the HybEZ™ humidity control tray from the oven.
10. Wash the slides twice with distilled water.
11. Add appropriate probe to entirely cover each section. Human ZP3 probe (Cat No. 442631), positive control probes for low abundance transcripts Mm-Polr-2a, #312471) and negative control probe (DapB, ACD-310043) Place the HybEZ™ slide rack in the HybEZ™ humidity control tray, cover with lid and insert into the oven for 2 hr at 40° C.
12. Remove the HybEZ™ control tray from the oven and remove HybEZ™ slide rack.
13. Wash the slides in 1× wash buffer for 2 min at RT. Agitate slides by moving the slide rack up and down in the dish.
14. Repeat Step 13 with fresh 1× wash buffer.
15. Incubate the slides with Amp 1 entirely cover each section for 30 min at 40° C.
16. Wash the slides twice in 1× wash buffer for 2 min at RT with occasional agitation.
17. Incubate the slides with Amp 2 entirely cover each section for 15 min at 40° C.
18. Wash the slides twice in 1× wash buffer for 2 min at RT with occasional agitation.
19. Incubate the slides with Amp 3 entirely cover each section for 30 min at 40° C.
20. Wash the slides twice in 1× wash buffer for 2 min at RT with occasional agitation.
21. Incubate the slides with Amp 4 entirely cover each section for 15 min at 40° C.
22. Wash the slides twice in 1× wash buffer for 2 min at RT with occasional agitation.
23. Incubate the slides with Amp 5 entirely cover each section for 30 min at RT.
24. Wash the slides twice in 1× wash buffer for 2 min at RT with occasional agitation.
25. Incubate the slides with Amp 6 entirely cover each section for 15 min at RT.
26. Wash the slides twice in 1× wash buffer for 2 min at RT with occasional agitation.
27. Mix equal volumes of brown-A and brown-B (DAB substrate) in an appropriately sized tube by dispensing the same number of drops (2 drops of each reagent total of 4) for each solution. Pipette DAB onto each tissue section. Ensure sections are covered, and incubate for 10 min at RT.
28. Wash the slides in distilled water by moving the slide rack up and down 3-5 times. Replace with fresh distilled water.
29. Counterstain the slides in 50% hematoxylin staining solution for 2 min at RT.
30. Wash the slides in distilled water by moving the slide rack up and down 3-5 times. Keep repeating with fresh distilled water until the slides are clear, while sections remain purple.
31. Replace distilled water in the staining dish with 0.02% ammonia water. Move rack up and down 2-3 times. Section should turn blue. Replace ammonia water with distilled water. Wash the slides 3-5 times.
32. Dehydrate the slides (70% ethanol for 2 min, 100% 70% ethanol for 2 min, xylene for 5 min).
33. Mount the samples with Pertex.

Figure 3:
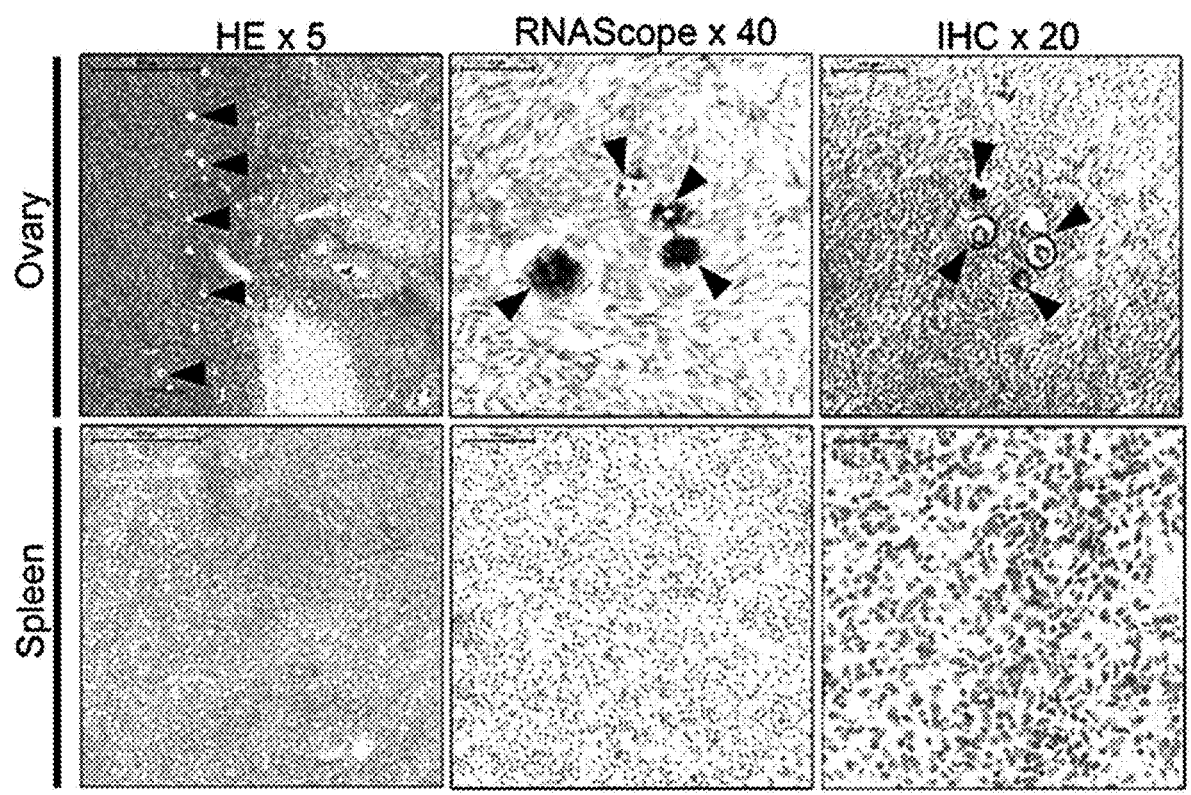
FIG. 3: ZP3 expression in ovary (top row) and in spleen (bottom row) as respectively positive and negative controls. From left to right, respectively, hematoxylin eosin histopathology (HE×5); in situ hybridization of ZP3 mRNA expression (RNA Scope×40); and, ZP3 protein expression by immunohistochemistry (IHC×20). Abundant ZP3 mRNA is detected in oocytes and ZP3 protein is detected in the ZP surrounding the human oocytes, as well as in the oocytes' cytoplasm. No expression of ZP3 mRNA or protein is detected in spleen.

In the positive controls, antibodies detect proteins in the ZP surrounding the human oocyte, as well as in the oocyte cytoplasm (FIG. 3, top row IHC×20). No positive staining is detected in sections of the lung cancer tissue samples when the primary antibody is omitted (not shown). No positive staining is observed, with the ZP monoclonal antibody, in spleen tissue (FIG. 3, bottom row IHC×20).

Figure 2:
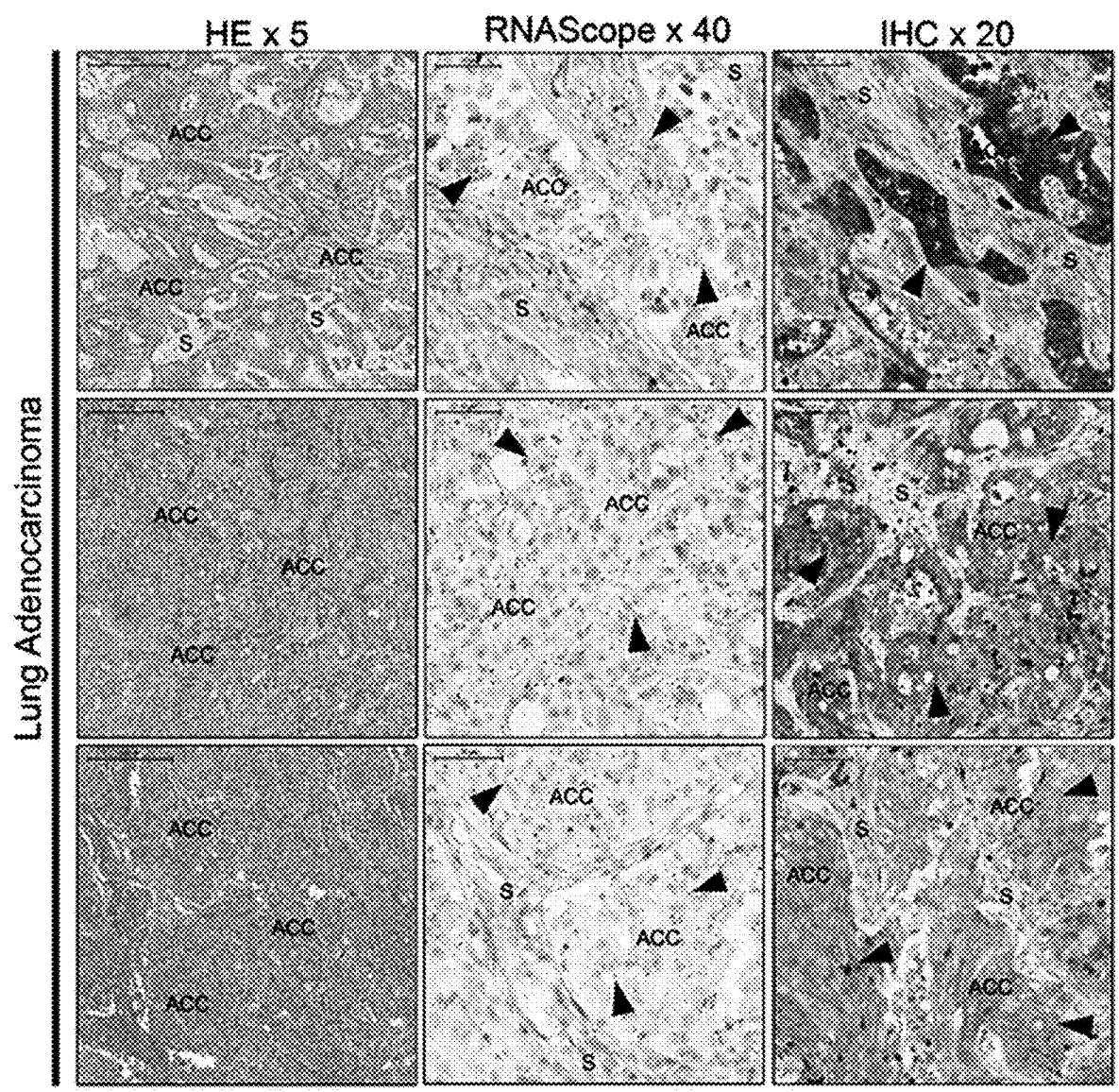
FIG. 2: ZP3 expression in adenocarcinoma cell lung cancers from three different patients. Each horizontal lane represents results from one single patient. From left to right, respectively, hematoxylin Eosin histopathology (HE×5); in situ hybridization of ZP3 mRNA expression (RNA Scope× 40); and, ZP3 protein expression by immunohistochemistry (IHX×20). Abundant ZP3 expression is detected exclusively in adenocarcinoma cells (ACC; arrows) and no expression of ZP3 can be seen in stromal cells (S) or healthy cells.

In the lung cancer samples, the subtypes squamous cell cancer (FIG. 1) and adenocarcinomas (FIG. 2), presence of the ZP3 is confirmed by areas of the tissue staining positive for ZP3 both by IHC and by RNA scope, with intensities varying among the samples obtained from different patients. Tumors such as these, which stain positive for ZP3 expression, can be treated by immunization with ZP3-antigens in accordance with the present invention.

Example 3

The sequence of hZP3 was analysed for HLA class I restricted cytotoxic T cell (CTL) epitopes and HLA class II restricted T helper epitopes using algorithms that predict HLA class I and II peptide binding.

The MHC class I binding predictions was performed using the NetCTLpan Server from the Center for Biological Sequence Analysis (CBS), Technical University of Denmark (www.cbs.dtu.dk/) (Xu et al., 2012, Clin Dev Immunol; 12:831010).

The MHC class II binding predictions were made using the IEDB analysis resource Consensus tool (tools.immuneepitope.org/) (Stranzl et al., 2010, Immunogenetics; 62:357-368; Wang et al., 2008, PLoS Comput Biol. 4(4): e1000048). This tool employs different methods to predict MHC Class II epitopes, including a consensus approach which combines NN-align, SMM-align and combinatorial library methods. A low percentile rank is equal to good binders.

The alelles submitted were those belonging to the HLA class I and II supertypes (Wang et al., 2010, BMC Bioinformatics. 11:568; Sidney et al., 2008, BMC Immunol.; 9:1. doi:10.1186/1471-2172-9-1). MHC molecules are extremely polymorphic but, despite this polymorphism HLA class I molecules can be clustered into groups, designated as supertypes, representing sets of molecules that share largely overlapping peptide binding specificity (Wang et al., 2010 BMC Bioinformatics. 11:568). In the same way, seven different supertypes (main DR, DR4, DRB3, main DQ, DQ7, main DP, and DP2) were defined for HLA class II (Greenbaum et al., 2011, Immunogenetics; 63(6):325-35).

The hZP3 peptide sequence was submitted without the signal peptide and transmembrane domain, i.e from aa 23 to aa 387. Results of the analysis are contained in Table 2 and 5 (MHC class I ligands) and in Table 3 (MHC class II ligands).

The MHC class I and class II ligands presented in Table 2 and 3 resp., serve as a guideline for designing immunogenic peptides of the invention, for example a composition comprising one or more polypeptides, wherein said one or more polypeptides comprise one or more MHC class I restricted epitopes selected from Table 2 and/or one or more MCH class II restricted epitopes selected from Table 3.

A series of hZP3 peptides covering the hZP3 sequences for use in a clinical setting are contained in FIG. 4. Predicted MHC class I and II binder sequences from Tables 2 and 3, as well as possible glycosylation sites have been taken into account for defining the peptides, each of which contains a number of predicted MHC class I and II binders with a low percentile rank, for inducing a good immune response. These hZP3 peptide fragments include hZP3$^{30-78}$ (SEQ ID NO: 66), hZP3$^{76-101}$ (SEQ ID NO: 67), hZP3$^{99-141}$ (SEQ ID NO: 68), hZP3$^{138-187}$ (SEQ ID NO: 69), hZP3$^{185-225}$ (SEQ ID NO: 70), hZP3$^{224-267}$ (SEQ ID NO: 71), hZP3$^{257-288}$ (SEQ ID NO: 72), hZP3$^{298-317}$ (SEQ ID NO: 73), hZP3$^{331-357}$ (SEQ ID NO: 74) and hZP3$^{358-383}$ (SEQ ID NO: 75). Combinations of these peptide fragments for composing composition comprising combinations of at least two of the peptide fragments are listed in Table 4.

TABLE 2

Predicted MHC class I ligands contained in the hZP3 protein.

| aa* | Ligand sequence | HLA allele (%Rank) | SEQ ID NO: |
|---|---|---|---|
| 34-42 | HPETSVQPV | HLA-B*07:02 (0.80) | 6 |
| 35-43 | PETSVQPVL | HLA-B*40:01 (0.80) | 7 |
| 47-55 | ***QEATLMVMV | HLA-B*40:01 (0.80) | 8 |
| 49-57 | ATLMVMVSK | HLA-A*03:01 (0.30) | 9 |
| 65-73 | LIRAADLTL | HLA-B*07:02 (0.80) | 10 |
| 86-94 | TEDVVRFEV | HLA-B*40:01 (0.40) | 11 |
| 104-112 | QVTDDALVY | HLA-A*01:01 (0.30); HLA-A*26:01 (0.40) | 12 |
| 109-117 | ALVYSTFLL | HLA-A*02:01 (0.80) | 13 |
| 115-123 | FLLHDPRPV | HLA-A*02:01 (0.80) | 14 |
| 121-129 | RPVGNLSIV¶ | HLA-B*07:02 (0.30) | 15 |
| 142-150 | YPRQGNVSS¶ | HLA-B*07:02 (0.80) | 16 |
| 149-157 | SSQAILPTW | HLA-B*58:01 (0.10) | 17 |
| 152-160 | AILPTWLPF | HLA-B*15:01 (0.80) | 18 |
| 157-165 | WLPFRTTVF | HLA-A*24:02 (0.80); HLA-3*08:01; HLA-3*15:01 (0.80) | 19 |
| 164-172 | VFSEEKLTF | HLA-A*24:02 (0.30) | 20 |
| 166-174 | SEEKLTFSL | HLA-3*40:01 (0.15) | 21 |
| 175-183 | RLMEENWNA | HLA-A*02:01 (0.20) | 22 |

TABLE 2-continued

Predicted MHC class I ligands contained in the hZP3 protein.

| aa* | Ligand sequence | HLA allele (%Rank) | SEQ ID NO: |
|---|---|---|---|
| 190-198 | FHLGDAAHL | HLA-3*39:01 (0.05) | 23 |
| 202-210 | IHTGSHVPL | HLA-3*39:01 (0.10) | 24 |
| 228-234 | SPYHTIVDF | HLA-3*07:02 (0.80) | 25 |
| 243-251 | GLTDASSAF | HLA-3*15:01 (0.20) | 26 |
| 244-252 | LTDASSAFK | HLA-A*03:01 (0.80) | 27 |
| 253-261 | VPRPGPDTL | HLA-3*07:02 (0.15) | 28 |
| 255-263 | RPGPDTLQF | HLA-3*07:02 (0.30) | 29 |
| 262-270 | QFTVDVFHF | HLA-A*24:02 (0.80) | 30 |
| 263-271 | FTVDVFHFA | HLA-A*02:01 (0.80); HLA-A*26:01 (0.80) | 31 |
| 271-279 | ANDSRNMIY¶ | HLA-A*01:01 (0.30) | 32 |
| 277-285 | MIYITCHLK | HLA-A*03:01 (0.10) | 33 |
| 278-286 | IYITCHLKV | HLA-A*24:02 (0.20) | 34 |
| 302-310 | FSKPSNSWF | HLA-3*15:01 (0.80) | 35 |
| 304-312 | KPSNSWFPV | HLA-3*07:02 (0.30) | 36 |
| 334-342 | RQPHVMSQW | HLA-A*24:02 (0.80) | 37 |
| 371-379 | RGDHEVEQW | HLA-3*58:01 (0.80) | 38 |

*Position is that of aa in complete hZP3 protein.
¶Ligand contains N-linked glycosylation site (position 125, 147 and 272, respectively).

TABLE 3

Predicted MHC class II ligands contained in the hZP3 protein.

| aa* | Core sequence | HLA allele (percentile rank)§ | SEQ ID NO: |
|---|---|---|---|
| 48-56 | EATLMVMVS | DQA1*01:02/DQB*06:02 (0.14) | 39 |
| 51-59 | LMVMVSKDL | DRB5*01:01 (0.88); DRB1*15:01 (2.37) | 40 |
| 52-60 | MVMVSKDLF | DRB1*03:01 (1.01) | 41 |
| 65-73 | LIRAADLTL | DRB1*08:02 (2.49) | 42 |
| 81-89 | LVMSDTEDV | DRB1*01:02 (1.31) | 43 |

TABLE 3-continued

Predicted MHC class II ligands contained in the hZP3 protein.

| aa* | Core sequence | HLA allele (percentile rank)§ | SEQ ID NO: |
|---|---|---|---|
| 82-90 | VSMDTEDVV | DRB1*03:01 (0.54) | 44 |
| 89-97 | VVRFEVGLH | DRB1*11:02 (0.52) | 45 |
| 104-112 | QVTDDALVY | DRB1*03:01 (1.91) | 46 |
| 109-117 | ALVYSTFLL | DPA1*01:03/DPB1*02:01 (0.01); DPA1*02:01/DPB1*01:01 (0.12) | 47 |
| 110-118 | LVYSTFLLH | DPA1*01/DPB1*04:01 (0.01); DPA1*0301/DPB1*04:02 (0.04) | 48 |
| 115-123 | FLLDPHRPV | DRB1*11:02 (0.39) | 49 |
| 116-124 | LLHDPRPVG | DRB1*03:01 (0.17) | 50 |
| 126-134 | *LSIVRTNRA† | DRB1*08:02 (1.55) | 51 |
| 128-136 | IVRTNRAEI | DRB1*03:01 (1.77) | 52 |
| 159-167 | PFRTTVFSE | DPA1*01:03/DPB1*02:01 (0.58); HLA-DPA1*02:01/DPB1*01:01 (0.69) | 53 |
| 160-168 | FRTTVFSEE | DPA1*01/DPB1*04:01 (0.35) | 54 |
| 171-179 | **TFSLRLMEE | DQA1*04:01/DQB1*04:02 (1.05) | 55 |
| 190-198 | FHLGDAAHL | DRB1*09:01 (0.49) | 56 |
| 210-218 | LRLFVDHCV | DQA1*01:01 (0.48) | 57 |
| 212-220 | LFVDHCVAT | DRB1*03:01 (2.05) | 58 |
| 262-270 | QFTVDVFHF | DRB3*01:01 (1.5) | 59 |
| 270-278 | FANDSNRMI¶ | DRB3*01:01 (0.35); DRB3*02:02 (1.37); DRB1*03:01 (1.77) | 60 |
| 278-286 | IYITCHLKV | DRB1*11:01 (1.16); DPA1*03:01/DPB1*04:02 (1.53) | 61 |
| 339-347 | VMSQWSRSA | DRB1*11:02 (0.79) | 62 |
| 343-351 | WSRSASRNR | DRB5*01:01 (1.4) | 63 |
| 365-373 | LIFLDRRGD | DRB1*11:02 (1.01) | 64 |
| 366-374 | IFLDRRGDH | DRB1*03:01 (0.08) | 65 |

*Position is that of aa in complete hZP3 protein.
§The percentile rank is given in parentheses after the corresponding HLA allele; only ligands with percentile ranks > 2.5 were considered.
†N-linked glycosylation site in preceding position 125.
¶Ligand contains N-linked glycosylation site (position 272).

Example 4

With in silico prediction software, potential HLA-A2 restricted T cell epitopes from rhZP3 protein has been identified. The software used was NETMHCPAN 3.0 in silico prediction software.

TABLE 5

HLA-A2 restricted T cell epitopes from rhZP3 protein.

| Number | Position | Peptide | Affinity (nM) | %Rank | SEQ ID NO |
|---|---|---|---|---|---|
| 1 | 115 | FLLHDPRPV | 5.1 | 0.04 | 76 |
| 2 | 175 | RLMEENWNA | 5.2 | 0.04 | 77 |
| 3 | 109 | ALVYSTFLL | 21.3 | 0.3 | 78 |
| 4 | 263 | FTVDVFHFA | 19.9 | 0.3 | 79 |
| 5 | 174 | LRLMEENWNA | 28.6 | 0.4 | 80 |
| 6 | 367 | FLDRRGDHEV | 53.2 | 0.7 | 81 |
| 7 | 239 | CLVDGLTDA | 79.1 | 0.9 | 82 |
| 8 | 276 | NMIYITCHL | 76.6 | 0.9 | 83 |
| 9 | 114 | TFLLHDPRPV | 101.9 | 1.1 | 84 |
| 10 | 64 | KLIRAADLTL | 129.9 | 1.2 | 85 |

An in vivo pre-clinical efficacy study has been conducted to assess the immune response and the anti-tumor response after immunization with rhZP3 polypeptide (aa 1-383 with his-tag) and 5 different ZP3 epitopes. The hZP3 epitopes were selected based on CD8+ T cell responses observed during previously performed immunogenicity experiments with rhZP3 polypeptide (aa 1-383) and with pools of peptides comprising hZP3 epitopes as indicated (see Table 5) combined with different adjuvants (data not shown). The peptides were synthesized by Pepscan (the Netherlands) at a purity >96%.

In this experiment in a therapeutic setting, HLA-A2 transgenic mice with a ZP3-expressing tumor were treated with the rhZP3 protein, pool of hZP3 peptides or PBS as control.

A HLA-A2 transgenic mice model was used for this study. To set up the tumor model, B16-HLA-A2 transgenic murine melanoma cell line was transfected with rhZP3 (see example in Tran et al., Clin Cancer Res, 2016; 22(16):4133-44).

Three groups of female HLA-A2 transgenic mice (n=6) with ZP3 expressing tumors were treated with:
1. PBS;
2. Pool of 5 hZP3 peptides (5 dominant peptides previously identified in HLA-A2/DR1 mice, including the epitopes identified as 4, 5, 6, 8 and 9 in Table 5; 0.5 nmol per peptide) plus GM-CSF/CpG as adjuvant (20 μg GM-CSF and 50 μg CpG); and,
3. rhZP3 protein (100 μg, s.c.) plus GM-CSF/CpG as adjuvant (20 μg GM-CSF and 50 μg CpG).

Figure 5:
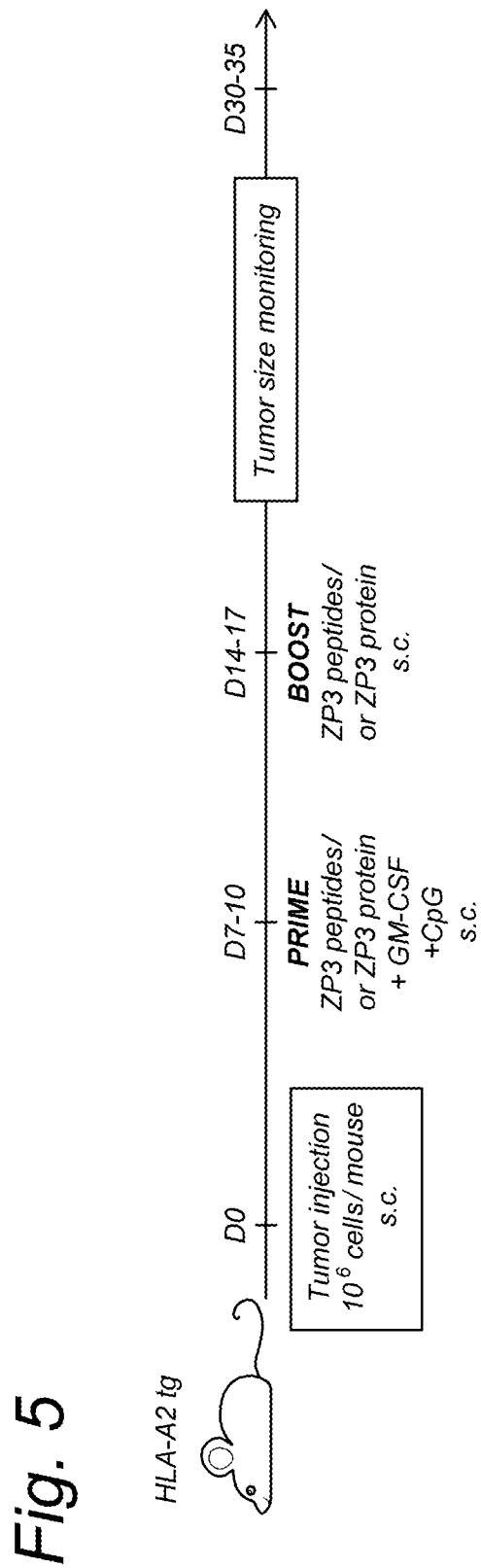
FIG. 5: Schedule for administration of hZP3-positive B16-HLA-A2 melanoma tumor cells and an hZP3 peptide-mixture (comprising peptides 4, 5, 6, 8 and 9 in Table 5), or rhZP3$^{1-383}$ protein to HLA-A2 transgenic mice. On Day 0 (D0), a tumor injection with $10^6$ cells/mouse was given subcutaneously (s.c.). Thereafter, the prime injection was administered 7 to 10 days (D7-10) and a boost injection on Day 14 to Day 17 (D14-17). Tumor size was monitored after treatment. At Day 30 to 35, mice were sacrificed to determine hZP3 specific CD8$^+$ responses (ELISpot).

On Day 0 (D0), a tumor injection with $10^6$ cells/mouse (s.c.) was given. Thereafter, the prime injection was administered 7 to 10 days (D7-10) and a boost injection on Day 14 to Day 17 (D14-17). Tumor size was monitored after treatment. At Day 30 to 35, mice were sacrificed to determine ZP3 specific TCD8+ response (ELISpot). See schedule in FIG. 5.

Figure 6:
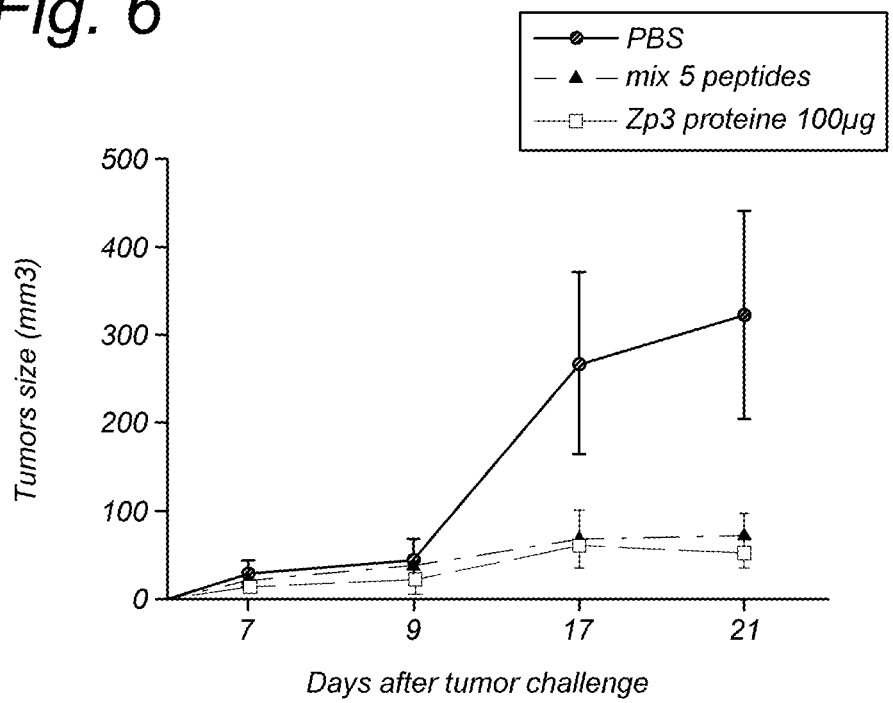
FIG. 6: Tumor size (in mm$^3$) as a function of days after tumor challenge in control mice receiving PBS, and in mice after 2 s.c. immunizations with either rhZP3$^{1-383}$ protein or the combination of the 5 hZP3 peptides (comprising peptides 4, 5, 6, 8 and 9 in Table 5).

After administration of PBS, tumor size did increase whereas after 2 s.c. immunizations with either rhZP3 protein or the combination of the 5 hZP3 peptides no growth of the tumor was observed (see FIG. 6).

Figure 7:
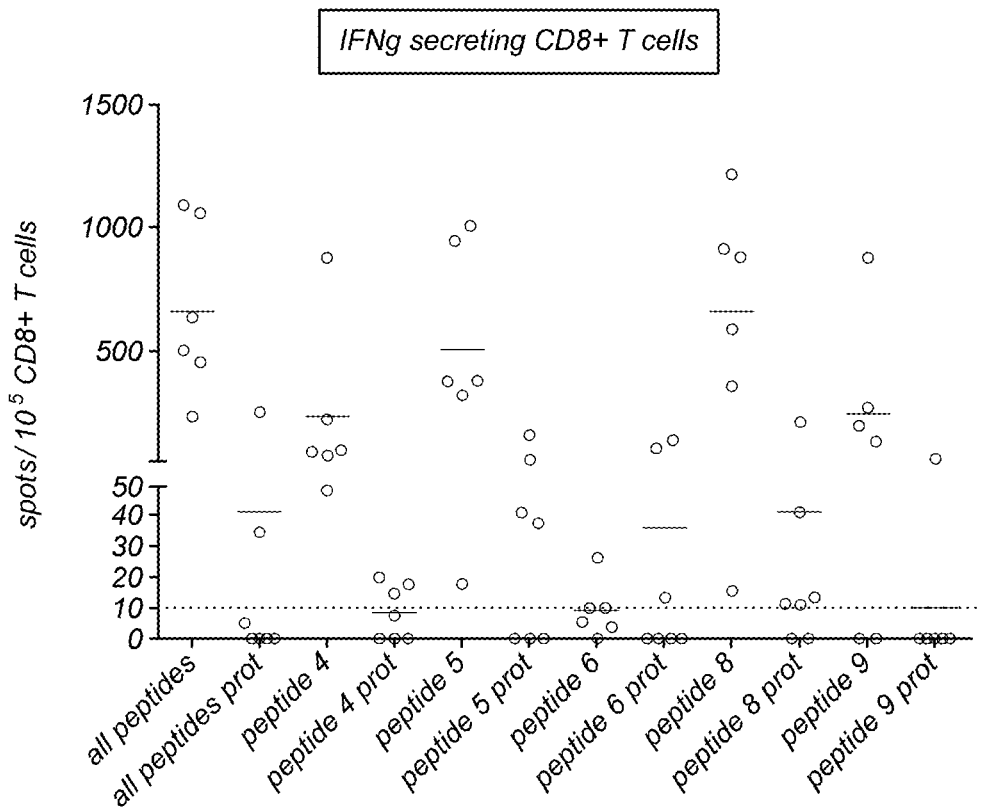
FIG. 7: CD8$^+$ T cell responses as determined by interferon-γ (IFNg) ELISpot as measured against the peptides (all 5 or peptides 4, 5, 6, 8 or 9 individually) after immunization with the mixture of the 5 hZP3 peptides (peptide), or after immunization with the rhZP3$^{1-383}$ protein ZP3 (prot).

Furthermore, as shown in FIG. 7 a strong CD8+ T cell response (IFNg) was measured against the peptides after immunization with the 5 hZP3 peptides. Also after immunization with the ZP3 protein a TCD8 response was observed (see FIG. 7).

TABLE 4

Combinations of amino acid sequences from FIG. 4, to be incorporated in immunogenic peptides for composing an composition of synthetic long peptides in accordance with the invention. The various combination are separated by semicolons.

Combination of 2 peptides

SEQ ID NO. 66, SEQ ID NO. 67; SEQ ID NO. 66, SEQ ID NO. 68; SEQ ID NO. 66, SEQ ID NO. 69; SEQ ID NO. 66, SEQ ID NO. 70; SEQ ID NO. 66, SEQ ID NO. 71; SEQ ID NO. 66, SEQ ID NO. 72; SEQ ID NO. 66, SEQ ID NO. 73; SEQ ID NO. 66, SEQ ID NO. 74; SEQ ID NO. 66, SEQ ID NO. 75; SEQ ID NO. 67, SEQ ID NO. 68; SEQ ID NO. 67, SEQ ID NO. 69; SEQ ID NO. 67, SEQ ID NO. 70; SEQ ID NO. 67, SEQ ID NO. 71; SEQ ID NO. 67, SEQ ID NO. 72; SEQ ID NO. 67, SEQ ID NO. 73; SEQ ID NO. 67, SEQ ID NO. 74; SEQ ID NO. 67, SEQ ID NO. 75; SEQ ID NO. 68, SEQ ID NO. 69; SEQ ID NO. 68, SEQ ID NO. 70; SEQ ID NO. 68, SEQ ID NO. 71; SEQ ID NO. 68, SEQ ID NO. 72; SEQ ID NO. 68, SEQ ID NO. 73; SEQ ID NO. 68, SEQ ID NO. 74; SEQ ID NO. 68, SEQ ID NO. 75; SEQ ID NO. 69, SEQ ID NO. 70; SEQ ID NO. 69, SEQ ID NO. 71; SEQ ID NO. 69, SEQ ID NO. 72; SEQ ID NO. 69, SEQ ID NO. 73; SEQ ID NO. 69, SEQ ID NO. 74; SEQ ID NO. 69, SEQ ID NO. 75; SEQ ID NO. 70, SEQ ID NO. 71; SEQ ID NO. 70, SEQ ID NO. 72; SEQ ID NO. 70, SEQ ID NO. 73; SEQ ID NO. 70, SEQ ID NO. 74; SEQ ID NO. 70, SEQ ID NO. 75; SEQ ID NO. 71, SEQ ID NO. 72; SEQ ID NO. 71, SEQ ID NO. 73; SEQ ID NO. 71, SEQ ID NO. 74; SEQ ID NO. 71, SEQ ID NO. 75; SEQ ID NO. 72, SEQ ID NO. 73; SEQ ID NO. 72, SEQ ID NO. 74; SEQ ID NO. 72, SEQ ID NO. 75; SEQ ID NO. 73, SEQ ID NO. 74; SEQ ID NO. 73, SEQ ID NO. 75; SEQ ID NO. 74, SEQ ID NO. 75;

Combination of 3 peptides

SEQ ID NO. 66, SEQ ID NO. 67, SEQ ID NO. 68; SEQ ID NO. 66, SEQ ID NO. 67, SEQ ID NO. 69; SEQ ID NO. 66, SEQ ID NO. 67, SEQ ID NO. 70; SEQ ID NO. 66, SEQ ID NO. 67, SEQ ID NO. 71; SEQ ID NO. 66, SEQ ID NO. 67, SEQ ID NO. 72; SEQ ID NO. 66, SEQ ID NO. 67, SEQ ID NO. 73; SEQ ID NO. 66, SEQ ID NO. 67, SEQ ID NO. 74; SEQ ID NO. 66, SEQ ID NO. 67, SEQ ID NO. 75; SEQ ID NO. 66, SEQ ID NO. 68, SEQ ID NO. 69; SEQ ID NO. 66, SEQ ID NO. 68, SEQ ID NO. 70; SEQ ID NO. 66, SEQ ID NO. 68, SEQ ID NO. 71; SEQ ID NO. 66, SEQ ID NO. 68, SEQ ID NO. 72; SEQ ID NO. 66, SEQ ID NO. 68, SEQ ID NO. 73; SEQ ID NO. 66, SEQ ID NO. 68, SEQ ID NO. 74; SEQ ID NO. 66, SEQ ID NO. 68, SEQ ID NO. 75; SEQ ID NO. 66, SEQ ID NO. 69, SEQ ID NO. 70; SEQ ID NO. 66, SEQ ID NO. 69, SEQ ID NO. 71; SEQ ID NO. 66, SEQ ID NO. 69, SEQ ID NO. 72; SEQ ID NO. 66, SEQ ID NO. 69, SEQ

TABLE 4-continued

Combinations of amino acid sequences from FIG. 4, to be incorporated in immunogenic peptides for composing an composition of synthetic long peptides in accordance with the invention. The various combination are separated by semicolons.

ID NO. 73; SEQ ID NO. 66, SEQ ID NO. 69, SEQ ID NO. 74; SEQ ID NO. 66, SEQ ID NO. 69, SEQ ID NO. 75; SEQ ID NO. 66, SEQ ID NO. 70, SEQ ID NO. 71; SEQ ID NO. 66, SEQ ID NO. 70, SEQ ID NO. 72; SEQ ID NO. 66, SEQ ID NO. 70, SEQ ID NO. 73; SEQ ID NO. 66, SEQ ID NO. 70, SEQ ID NO. 74; SEQ ID NO. 66, SEQ ID NO. 70, SEQ ID NO. 75; SEQ ID NO. 66, SEQ ID NO. 71, SEQ ID NO. 72; SEQ ID NO. 66, SEQ ID NO. 71, SEQ ID NO. 73; SEQ ID NO. 66, SEQ ID NO. 71, SEQ ID NO. 74; SEQ ID NO. 66, SEQ ID NO. 71, SEQ ID NO. 75; SEQ ID NO. 66, SEQ ID NO. 72, SEQ ID NO. 73; SEQ ID NO. 66, SEQ ID NO. 72, SEQ ID NO. 74; SEQ ID NO. 66, SEQ ID NO. 72, SEQ ID NO. 75; SEQ ID NO. 66, SEQ ID NO. 73, SEQ ID NO. 74; SEQ ID NO. 66, SEQ ID NO. 73, SEQ ID NO. 75; SEQ ID NO. 66, SEQ ID NO. 74, SEQ ID NO. 75; SEQ ID NO. 67, SEQ ID NO. 68, SEQ ID NO. 69; SEQ ID NO. 67, SEQ ID NO. 68, SEQ ID NO. 70; SEQ ID NO. 67, SEQ ID NO. 68, SEQ ID NO. 71; SEQ ID NO. 67, SEQ ID NO. 68, SEQ ID NO. 72; SEQ ID NO. 67, SEQ ID NO. 68, SEQ ID NO. 73; SEQ ID NO. 67, SEQ ID NO. 68, SEQ ID NO. 74; SEQ ID NO. 67, SEQ ID NO. 68, SEQ ID NO. 75; SEQ ID NO. 67, SEQ ID NO. 69, SEQ ID NO. 70; SEQ ID NO. 67, SEQ ID NO. 69, SEQ ID NO. 71; SEQ ID NO. 67, SEQ ID NO. 69, SEQ ID NO. 72; SEQ ID NO. 67, SEQ ID NO. 69, SEQ ID NO. 73; SEQ ID NO. 67, SEQ ID NO. 69, SEQ ID NO. 74; SEQ ID NO. 67, SEQ ID NO. 69, SEQ ID NO. 75; SEQ ID NO. 67, SEQ ID NO. 70, SEQ ID NO. 71; SEQ ID NO. 67, SEQ ID NO. 70, SEQ ID NO. 72; SEQ ID NO. 67, SEQ ID NO. 70, SEQ ID NO. 73; SEQ ID NO. 67, SEQ ID NO. 70, SEQ ID NO. 74; SEQ ID NO. 67, SEQ ID NO. 70, SEQ ID NO. 75; SEQ ID NO. 67, SEQ ID NO. 71, SEQ ID NO. 72; SEQ ID NO. 67, SEQ ID NO. 71, SEQ ID NO. 73; SEQ ID NO. 67, SEQ ID NO. 71, SEQ ID NO. 74; SEQ ID NO. 67, SEQ ID NO. 71, SEQ ID NO. 75; SEQ ID NO. 67, SEQ ID NO. 72, SEQ ID NO. 73; SEQ ID NO. 67, SEQ ID NO. 72, SEQ ID NO. 74; SEQ ID NO. 67, SEQ ID NO. 72, SEQ ID NO. 75; SEQ ID NO. 67, SEQ ID NO. 73, SEQ ID NO. 74; SEQ ID NO. 67, SEQ ID NO. 73, SEQ ID NO. 75; SEQ ID NO. 67, SEQ ID NO. 74, SEQ ID NO. 75; SEQ ID NO. 68, SEQ ID NO. 69, SEQ ID NO. 70; SEQ ID NO. 68, SEQ ID NO. 69, SEQ ID NO. 71; SEQ ID NO. 68, SEQ ID NO. 69, SEQ ID NO. 72; SEQ ID NO. 68, SEQ ID NO. 69, SEQ ID NO. 73; SEQ ID NO. 68, SEQ ID NO. 69, SEQ ID NO. 74; SEQ ID NO. 68, SEQ ID NO. 69, SEQ ID NO. 75; SEQ ID NO. 68, SEQ ID NO. 70, SEQ ID NO. 71; SEQ ID NO. 68, SEQ ID NO. 70, SEQ ID NO. 72; SEQ ID NO. 68, SEQ ID NO. 70, SEQ ID NO. 73; SEQ ID NO. 68, SEQ ID NO. 70, SEQ ID NO. 74; SEQ ID NO. 68, SEQ ID NO. 70, SEQ ID NO. 75; SEQ ID NO. 68, SEQ ID NO. 71, SEQ ID NO. 72; SEQ ID NO. 68, SEQ ID NO. 71, SEQ ID NO. 73; SEQ ID NO. 68, SEQ ID NO. 71, SEQ ID NO. 74; SEQ ID NO. 68, SEQ ID NO. 71, SEQ ID NO. 75; SEQ ID NO. 68, SEQ ID NO. 72, SEQ ID NO. 73; SEQ ID NO. 68, SEQ ID NO. 72, SEQ ID NO. 74; SEQ ID NO. 68, SEQ ID NO. 72, SEQ ID NO. 75; SEQ ID NO. 68, SEQ ID NO. 73, SEQ ID NO. 74; SEQ ID NO. 68, SEQ ID NO. 73, SEQ ID NO. 75; SEQ ID NO. 68, SEQ ID NO. 74, SEQ ID NO. 75; SEQ ID NO. 69, SEQ ID NO. 70, SEQ ID NO. 71; SEQ ID NO. 69, SEQ ID NO. 70, SEQ ID NO. 72; SEQ ID NO. 69, SEQ ID NO. 70, SEQ ID NO. 73; SEQ ID NO. 69, SEQ ID NO. 70, SEQ ID NO. 74; SEQ ID NO. 69, SEQ ID NO. 70, SEQ ID NO. 75; SEQ ID NO. 69, SEQ ID NO. 71, SEQ ID NO. 72; SEQ ID NO. 69, SEQ ID NO. 71, SEQ ID NO. 73; SEQ ID NO. 69, SEQ ID NO. 71, SEQ ID NO. 74; SEQ ID NO. 69, SEQ ID NO. 71, SEQ ID NO. 75; SEQ ID NO. 69, SEQ ID NO. 72, SEQ ID NO. 73; SEQ ID NO. 69, SEQ ID NO. 72, SEQ ID NO. 74; SEQ ID NO. 69, SEQ ID NO. 72, SEQ ID NO. 75; SEQ ID NO. 69, SEQ ID NO. 73, SEQ ID NO. 74; SEQ ID NO. 69, SEQ ID NO. 73, SEQ ID NO. 75; SEQ ID NO. 69, SEQ ID NO. 74, SEQ ID NO. 75; SEQ ID NO. 70, SEQ ID NO. 71, SEQ ID NO. 72; SEQ ID NO. 70, SEQ ID NO. 71, SEQ ID NO. 73; SEQ ID NO. 70, SEQ ID NO. 71, SEQ ID NO. 74; SEQ ID NO. 70, SEQ ID NO. 71, SEQ ID NO. 75; SEQ ID NO. 70, SEQ ID NO. 72, SEQ ID NO. 73; SEQ ID NO. 70, SEQ ID NO. 72, SEQ ID NO. 74; SEQ ID NO. 70, SEQ ID NO. 72, SEQ ID NO. 75; SEQ ID NO. 70, SEQ ID NO. 73, SEQ ID NO. 74; SEQ ID NO. 70, SEQ ID NO. 73, SEQ ID NO. 75; SEQ ID NO. 70, SEQ ID NO. 74, SEQ ID NO. 75; SEQ ID NO. 71, SEQ ID NO. 72, SEQ ID NO. 73; SEQ ID NO. 71, SEQ ID NO. 72, SEQ ID NO. 74; SEQ ID NO. 71, SEQ ID NO. 72, SEQ ID NO. 75; SEQ ID NO. 71, SEQ ID NO. 73, SEQ ID NO. 74; SEQ ID NO. 71, SEQ ID NO. 73, SEQ ID NO. 75; SEQ ID NO. 71, SEQ ID NO. 74, SEQ ID NO. 75; SEQ ID NO. 72, SEQ ID NO. 73, SEQ ID NO. 74; SEQ ID NO. 72, SEQ ID NO. 73, SEQ ID NO. 75; SEQ ID NO. 72, SEQ ID NO. 74, SEQ ID NO. 75; SEQ ID NO. 73, SEQ ID NO. 74, SEQ ID NO. 75;

Combination of 4 peptides

SEQ ID NO. 66, SEQ ID NO. 67, SEQ ID NO. 68, SEQ ID NO. 69; SEQ ID NO. 66, SEQ ID NO. 67, SEQ ID NO. 68, SEQ ID NO. 70; SEQ ID NO. 66, SEQ ID NO. 67, SEQ ID NO. 68, SEQ ID NO. 71; SEQ ID NO. 66, SEQ ID NO. 67, SEQ ID NO. 68, SEQ ID NO. 72; SEQ ID NO. 66, SEQ ID NO. 67, SEQ ID NO. 68, SEQ ID NO. 73; SEQ ID NO. 66, SEQ ID NO. 67, SEQ ID NO. 68, SEQ ID NO. 74; SEQ ID NO. 66, SEQ ID NO. 67, SEQ ID NO. 68, SEQ ID NO. 75; SEQ ID NO. 66, SEQ ID NO. 67, SEQ ID NO. 69, SEQ ID NO. 70; SEQ ID NO. 66, SEQ ID NO. 67, SEQ ID NO. 69, SEQ ID NO. 71; SEQ ID NO. 66, SEQ ID NO. 67, SEQ ID NO. 69, SEQ ID NO. 72; SEQ ID NO. 66, SEQ ID NO. 67, SEQ ID NO. 69, SEQ ID NO. 73; SEQ ID NO. 66, SEQ ID NO. 67, SEQ ID NO. 69, SEQ ID NO. 74; SEQ ID NO. 66, SEQ ID NO. 67, SEQ ID NO. 69, SEQ ID NO. 75; SEQ ID NO. 66, SEQ ID NO. 67, SEQ ID NO. 70, SEQ ID NO. 71; SEQ ID NO. 66, SEQ ID NO. 67, SEQ ID NO. 70, SEQ ID NO. 72; SEQ ID NO. 66, SEQ ID NO. 67, SEQ ID NO. 70, SEQ ID NO. 73; SEQ ID NO. 66, SEQ ID NO. 67, SEQ ID NO. 70, SEQ ID NO. 74; SEQ ID NO. 66, SEQ ID NO. 67, SEQ ID NO. 70, SEQ ID NO. 75; SEQ ID NO. 66, SEQ ID NO. 67, SEQ ID NO. 71, SEQ ID NO. 72; SEQ ID NO. 66, SEQ ID NO. 67, SEQ ID NO. 71, SEQ ID NO. 73; SEQ ID NO. 66, SEQ ID NO. 67, SEQ ID NO. 71, SEQ ID NO. 74; SEQ ID NO. 66, SEQ ID NO. 67, SEQ ID NO. 71, SEQ ID NO. 75; SEQ ID NO. 66, SEQ ID NO. 67, SEQ ID NO. 72, SEQ ID NO. 73; SEQ ID NO. 66, SEQ ID NO. 67, SEQ ID NO. 72, SEQ ID NO. 74; SEQ ID NO. 66, SEQ ID NO. 67, SEQ ID NO. 72, SEQ ID NO. 75; SEQ ID NO. 66, SEQ ID NO. 67, SEQ ID NO. 73, SEQ ID NO. 74; SEQ ID NO. 66, SEQ ID NO. 67, SEQ ID NO. 73, SEQ ID NO. 75; SEQ ID NO. 66, SEQ ID NO. 67, SEQ ID NO. 74, SEQ ID NO. 75; SEQ ID NO. 66, SEQ ID NO. 68, SEQ ID NO. 69, SEQ ID NO. 70; SEQ ID NO. 66, SEQ ID NO. 68, SEQ ID NO. 69, SEQ ID NO. 71; SEQ ID NO. 66, SEQ ID NO. 68, SEQ ID NO. 69, SEQ ID NO. 72; SEQ ID NO. 66, SEQ ID NO. 68, SEQ ID NO. 69, SEQ ID NO. 73; SEQ ID NO. 66, SEQ ID NO. 68, SEQ ID NO. 69, SEQ ID NO. 74; SEQ ID NO. 66, SEQ ID NO. 68, SEQ ID NO. 69, SEQ ID NO. 75; SEQ ID NO. 66, SEQ ID NO. 68, SEQ ID NO. 70, SEQ ID NO. 71; SEQ ID NO. 66, SEQ ID NO. 68, SEQ ID NO. 70, SEQ ID NO. 72; SEQ ID NO. 66, SEQ ID NO. 68, SEQ ID NO. 70, SEQ ID NO. 73; SEQ ID NO. 66, SEQ ID NO. 68, SEQ ID NO. 70, SEQ ID NO. 74; SEQ ID NO. 66, SEQ ID NO. 68, SEQ ID NO. 70, SEQ ID NO. 75; SEQ

TABLE 4-continued

Combinations of amino acid sequences from FIG. 4, to be incorporated in immunogenic peptides for composing an composition of synthetic long peptides in accordance with the invention. The various combination are separated by semicolons.

ID NO. 66, SEQ ID NO. 68, SEQ ID NO. 71, SEQ ID NO. 72; SEQ ID NO. 66, SEQ ID NO. 68, SEQ ID NO. 71, SEQ ID NO. 73; SEQ ID NO. 66, SEQ ID NO. 68, SEQ ID NO. 71, SEQ ID NO. 74; SEQ ID NO. 66, SEQ ID NO. 68, SEQ ID NO. 71, SEQ ID NO. 75; SEQ ID NO. 66, SEQ ID NO. 68, SEQ ID NO. 72, SEQ ID NO. 73; SEQ ID NO. 66, SEQ ID NO. 68, SEQ ID NO. 72, SEQ ID NO. 74; SEQ ID NO. 66, SEQ ID NO. 68, SEQ ID NO. 72, SEQ ID NO. 75; SEQ ID NO. 66, SEQ ID NO. 68, SEQ ID NO. 73, SEQ ID NO. 74; SEQ ID NO. 66, SEQ ID NO. 68, SEQ ID NO. 73, SEQ ID NO. 75; SEQ ID NO. 66, SEQ ID NO. 68, SEQ ID NO. 74, SEQ ID NO. 75; SEQ ID NO. 66, SEQ ID NO. 69, SEQ ID NO. 70, SEQ ID NO. 71; SEQ ID NO. 66, SEQ ID NO. 69, SEQ ID NO. 70, SEQ ID NO. 72; SEQ ID NO. 66, SEQ ID NO. 69, SEQ ID NO. 70, SEQ ID NO. 73; SEQ ID NO. 66, SEQ ID NO. 69, SEQ ID NO. 70, SEQ ID NO. 74; SEQ ID NO. 66, SEQ ID NO. 69, SEQ ID NO. 70, SEQ ID NO. 75; SEQ ID NO. 66, SEQ ID NO. 69, SEQ ID NO. 71, SEQ ID NO. 72; SEQ ID NO. 66, SEQ ID NO. 69, SEQ ID NO. 71, SEQ ID NO. 73; SEQ ID NO. 66, SEQ ID NO. 69, SEQ ID NO. 71, SEQ ID NO. 74; SEQ ID NO. 66, SEQ ID NO. 69, SEQ ID NO. 71, SEQ ID NO. 75; SEQ ID NO. 66, SEQ ID NO. 69, SEQ ID NO. 72, SEQ ID NO. 73; SEQ ID NO. 66, SEQ ID NO. 69, SEQ ID NO. 72, SEQ ID NO. 74; SEQ ID NO. 66, SEQ ID NO. 69, SEQ ID NO. 72, SEQ ID NO. 75; SEQ ID NO. 66, SEQ ID NO. 69, SEQ ID NO. 73, SEQ ID NO. 74; SEQ ID NO. 66, SEQ ID NO. 69, SEQ ID NO. 73, SEQ ID NO. 75; SEQ ID NO. 66, SEQ ID NO. 69, SEQ ID NO. 74, SEQ ID NO. 75; SEQ ID NO. 66, SEQ ID NO. 70, SEQ ID NO. 71, SEQ ID NO. 72; SEQ ID NO. 66, SEQ ID NO. 70, SEQ ID NO. 71, SEQ ID NO. 73; SEQ ID NO. 66, SEQ ID NO. 70, SEQ ID NO. 71, SEQ ID NO. 74; SEQ ID NO. 66, SEQ ID NO. 70, SEQ ID NO. 71, SEQ ID NO. 75; SEQ ID NO. 66, SEQ ID NO. 70, SEQ ID NO. 72, SEQ ID NO. 73; SEQ ID NO. 66, SEQ ID NO. 70, SEQ ID NO. 72, SEQ ID NO. 74; SEQ ID NO. 66, SEQ ID NO. 70, SEQ ID NO. 72, SEQ ID NO. 75; SEQ ID NO. 66, SEQ ID NO. 70, SEQ ID NO. 73, SEQ ID NO. 74; SEQ ID NO. 66, SEQ ID NO. 70, SEQ ID NO. 73, SEQ ID NO. 75; SEQ ID NO. 66, SEQ ID NO. 70, SEQ ID NO. 74, SEQ ID NO. 75; SEQ ID NO. 66, SEQ ID NO. 71, SEQ ID NO. 72, SEQ ID NO. 73; SEQ ID NO. 66, SEQ ID NO. 71, SEQ ID NO. 72, SEQ ID NO. 74; SEQ ID NO. 66, SEQ ID NO. 71, SEQ ID NO. 72, SEQ ID NO. 75; SEQ ID NO. 66, SEQ ID NO. 71, SEQ ID NO. 73, SEQ ID NO. 74; SEQ ID NO. 66, SEQ ID NO. 71, SEQ ID NO. 73, SEQ ID NO. 75; SEQ ID NO. 66, SEQ ID NO. 71, SEQ ID NO. 74, SEQ ID NO. 75; SEQ ID NO. 66, SEQ ID NO. 72, SEQ ID NO. 73, SEQ ID NO. 74; SEQ ID NO. 66, SEQ ID NO. 72, SEQ ID NO. 73, SEQ ID NO. 75; SEQ ID NO. 66, SEQ ID NO. 72, SEQ ID NO. 74, SEQ ID NO. 75; SEQ ID NO. 66, SEQ ID NO. 73, SEQ ID NO. 74, SEQ ID NO. 75; SEQ ID NO. 67, SEQ ID NO. 68, SEQ ID NO. 69, SEQ ID NO. 70; SEQ ID NO. 67, SEQ ID NO. 68, SEQ ID NO. 69, SEQ ID NO. 71; SEQ ID NO. 67, SEQ ID NO. 68, SEQ ID NO. 69, SEQ ID NO. 72; SEQ ID NO. 67, SEQ ID NO. 68, SEQ ID NO. 69, SEQ ID NO. 73; SEQ ID NO. 67, SEQ ID NO. 68, SEQ ID NO. 69, SEQ ID NO. 74; SEQ ID NO. 67, SEQ ID NO. 68, SEQ ID NO. 69, SEQ ID NO. 75; SEQ ID NO. 67, SEQ ID NO. 68, SEQ ID NO. 70, SEQ ID NO. 71; SEQ ID NO. 67, SEQ ID NO. 68, SEQ ID NO. 70, SEQ ID NO. 72; SEQ ID NO. 67, SEQ ID NO. 68, SEQ ID NO. 70, SEQ ID NO. 73; SEQ ID NO. 67, SEQ ID NO. 68, SEQ ID NO. 70, SEQ ID NO. 74; SEQ ID NO. 67, SEQ ID NO. 68, SEQ ID NO. 70, SEQ ID NO. 75; SEQ ID NO. 67, SEQ ID NO. 68, SEQ ID NO. 71, SEQ ID NO. 72; SEQ ID NO. 67, SEQ ID NO. 68, SEQ ID NO. 71, SEQ ID NO. 73; SEQ ID NO. 67, SEQ ID NO. 68, SEQ ID NO. 71, SEQ ID NO. 74; SEQ ID NO. 67, SEQ ID NO. 68, SEQ ID NO. 71, SEQ ID NO. 75; SEQ ID NO. 67, SEQ ID NO. 68, SEQ ID NO. 72, SEQ ID NO. 73; SEQ ID NO. 67, SEQ ID NO. 68, SEQ ID NO. 72, SEQ ID NO. 74; SEQ ID NO. 67, SEQ ID NO. 68, SEQ ID NO. 72, SEQ ID NO. 75; SEQ ID NO. 67, SEQ ID NO. 68, SEQ ID NO. 73, SEQ ID NO. 74; SEQ ID NO. 67, SEQ ID NO. 68, SEQ ID NO. 73, SEQ ID NO. 75; SEQ ID NO. 67, SEQ ID NO. 68, SEQ ID NO. 74, SEQ ID NO. 75; SEQ ID NO. 67, SEQ ID NO. 69, SEQ ID NO. 70, SEQ ID NO. 71; SEQ ID NO. 67, SEQ ID NO. 69, SEQ ID NO. 70, SEQ ID NO. 72; SEQ ID NO. 67, SEQ ID NO. 69, SEQ ID NO. 70, SEQ ID NO. 73; SEQ ID NO. 67, SEQ ID NO. 69, SEQ ID NO. 70, SEQ ID NO. 74; SEQ ID NO. 67, SEQ ID NO. 69, SEQ ID NO. 70, SEQ ID NO. 75; SEQ ID NO. 67, SEQ ID NO. 69, SEQ ID NO. 71, SEQ ID NO. 72; SEQ ID NO. 67, SEQ ID NO. 69, SEQ ID NO. 71, SEQ ID NO. 73; SEQ ID NO. 67, SEQ ID NO. 69, SEQ ID NO. 71, SEQ ID NO. 74; SEQ ID NO. 67, SEQ ID NO. 69, SEQ ID NO. 71, SEQ ID NO. 75; SEQ ID NO. 67, SEQ ID NO. 69, SEQ ID NO. 72, SEQ ID NO. 73; SEQ ID NO. 67, SEQ ID NO. 69, SEQ ID NO. 72, SEQ ID NO. 74; SEQ ID NO. 67, SEQ ID NO. 69, SEQ ID NO. 72, SEQ ID NO. 75; SEQ ID NO. 67, SEQ ID NO. 69, SEQ ID NO. 73, SEQ ID NO. 74; SEQ ID NO. 67, SEQ ID NO. 69, SEQ ID NO. 73, SEQ ID NO. 75; SEQ ID NO. 67, SEQ ID NO. 69, SEQ ID NO. 74, SEQ ID NO. 75; SEQ ID NO. 67, SEQ ID NO. 70, SEQ ID NO. 71, SEQ ID NO. 72; SEQ ID NO. 67, SEQ ID NO. 70, SEQ ID NO. 71, SEQ ID NO. 73; SEQ ID NO. 67, SEQ ID NO. 70, SEQ ID NO. 71, SEQ ID NO. 74; SEQ ID NO. 67, SEQ ID NO. 70, SEQ ID NO. 71, SEQ ID NO. 75; SEQ ID NO. 67, SEQ ID NO. 70, SEQ ID NO. 72, SEQ ID NO. 73; SEQ ID NO. 67, SEQ ID NO. 70, SEQ ID NO. 72, SEQ ID NO. 74; SEQ ID NO. 67, SEQ ID NO. 70, SEQ ID NO. 72, SEQ ID NO. 75; SEQ ID NO. 67, SEQ ID NO. 70, SEQ ID NO. 73, SEQ ID NO. 74; SEQ ID NO. 67, SEQ ID NO. 70, SEQ ID NO. 73, SEQ ID NO. 75; SEQ ID NO. 67, SEQ ID NO. 70, SEQ ID NO. 74, SEQ ID NO. 75; SEQ ID NO. 67, SEQ ID NO. 71, SEQ ID NO. 72, SEQ ID NO. 73; SEQ ID NO. 67, SEQ ID NO. 71, SEQ ID NO. 72, SEQ ID NO. 74; SEQ ID NO. 67, SEQ ID NO. 71, SEQ ID NO. 72, SEQ ID NO. 75; SEQ ID NO. 67, SEQ ID NO. 71, SEQ ID NO. 73, SEQ ID NO. 74; SEQ ID NO. 67, SEQ ID NO. 71, SEQ ID NO. 73, SEQ ID NO. 75; SEQ ID NO. 67, SEQ ID NO. 71, SEQ ID NO. 74, SEQ ID NO. 75; SEQ ID NO. 67, SEQ ID NO. 72, SEQ ID NO. 73, SEQ ID NO. 74; SEQ ID NO. 67, SEQ ID NO. 72, SEQ ID NO. 73, SEQ ID NO. 75; SEQ ID NO. 67, SEQ ID NO. 72, SEQ ID NO. 74, SEQ ID NO. 75; SEQ ID NO. 67, SEQ ID NO. 73, SEQ ID NO. 74, SEQ ID NO. 75; SEQ ID NO. 68, SEQ ID NO. 69, SEQ ID NO. 70, SEQ ID NO. 71; SEQ ID NO. 68, SEQ ID NO. 69, SEQ ID NO. 70, SEQ ID NO. 72; SEQ ID NO. 68, SEQ ID NO. 69, SEQ ID NO. 70, SEQ ID NO. 73; SEQ ID NO. 68, SEQ ID NO. 69, SEQ ID NO. 70, SEQ ID NO. 74; SEQ ID NO. 68, SEQ ID NO. 69, SEQ ID NO. 70, SEQ ID NO. 75; SEQ ID NO. 68, SEQ ID NO. 69, SEQ ID NO. 71, SEQ ID NO. 72; SEQ ID NO. 68, SEQ ID NO. 69, SEQ ID NO. 71, SEQ ID NO. 73; SEQ ID NO. 68, SEQ ID NO. 69, SEQ ID NO. 71, SEQ ID NO. 74; SEQ ID NO. 68, SEQ ID NO. 69, SEQ ID NO. 71, SEQ ID NO. 75; SEQ ID NO. 68, SEQ ID NO. 69, SEQ ID NO. 72, SEQ ID NO. 73; SEQ ID NO. 68, SEQ ID NO. 69, SEQ ID NO. 72, SEQ ID NO. 74; SEQ ID NO. 68, SEQ ID NO. 69, SEQ ID NO. 72, SEQ ID NO. 75; SEQ ID NO. 68, SEQ ID NO. 69, SEQ ID NO. 73, SEQ ID NO. 74; SEQ ID NO. 68, SEQ ID NO. 69, SEQ ID NO. 73, SEQ ID NO. 75; SEQ ID NO. 68, SEQ ID NO. 69, SEQ ID NO. 74, SEQ ID NO. 75; SEQ ID NO. 68, SEQ ID NO. 70, SEQ ID NO. 71, SEQ ID NO. 72; SEQ ID NO. 68, SEQ ID NO. 70, SEQ ID NO. 71, SEQ ID NO. 73; SEQ ID NO. 68, SEQ ID NO. 70, SEQ ID NO. 71, SEQ

TABLE 4-continued

Combinations of amino acid sequences from FIG. 4, to be incorporated in immunogenic peptides for composing an composition of synthetic long peptides in accordance with the invention. The various combination are separated by semicolons.

ID NO. 74; SEQ ID NO. 68, SEQ ID NO. 70, SEQ ID NO. 71, SEQ ID NO. 75; SEQ ID NO. 68, SEQ ID NO. 70, SEQ ID NO. 72, SEQ ID NO. 73; SEQ ID NO. 68, SEQ ID NO. 70, SEQ ID NO. 72, SEQ ID NO. 74; SEQ ID NO. 68, SEQ ID NO. 70, SEQ ID NO. 72, SEQ ID NO. 75; SEQ ID NO. 68, SEQ ID NO. 70, SEQ ID NO. 73, SEQ ID NO. 74; SEQ ID NO. 68, SEQ ID NO. 70, SEQ ID NO. 73, SEQ ID NO. 75; SEQ ID NO. 68, SEQ ID NO. 70, SEQ ID NO. 74, SEQ ID NO. 75; SEQ ID NO. 68, SEQ ID NO. 71, SEQ ID NO. 72, SEQ ID NO. 73; SEQ ID NO. 68, SEQ ID NO. 71, SEQ ID NO. 72, SEQ ID NO. 74; SEQ ID NO. 68, SEQ ID NO. 71, SEQ ID NO. 72, SEQ ID NO. 75; SEQ ID NO. 68, SEQ ID NO. 71, SEQ ID NO. 73, SEQ ID NO. 74; SEQ ID NO. 68, SEQ ID NO. 71, SEQ ID NO. 73, SEQ ID NO. 75; SEQ ID NO. 68, SEQ ID NO. 71, SEQ ID NO. 74, SEQ ID NO. 75; SEQ ID NO. 68, SEQ ID NO. 72, SEQ ID NO. 73, SEQ ID NO. 74; SEQ ID NO. 68, SEQ ID NO. 72, SEQ ID NO. 73, SEQ ID NO. 75; SEQ ID NO. 68, SEQ ID NO. 72, SEQ ID NO. 74, SEQ ID NO. 75; SEQ ID NO. 68, SEQ ID NO. 73, SEQ ID NO. 74, SEQ ID NO. 75; SEQ ID NO. 69, SEQ ID NO. 70, SEQ ID NO. 71, SEQ ID NO. 72; SEQ ID NO. 69, SEQ ID NO. 70, SEQ ID NO. 71, SEQ ID NO. 73; SEQ ID NO. 69, SEQ ID NO. 70, SEQ ID NO. 71, SEQ ID NO. 74; SEQ ID NO. 69, SEQ ID NO. 70, SEQ ID NO. 71, SEQ ID NO. 75; SEQ ID NO. 69, SEQ ID NO. 70, SEQ ID NO. 72, SEQ ID NO. 73; SEQ ID NO. 69, SEQ ID NO. 70, SEQ ID NO. 72, SEQ ID NO. 74; SEQ ID NO. 69, SEQ ID NO. 70, SEQ ID NO. 72, SEQ ID NO. 75; SEQ ID NO. 69, SEQ ID NO. 70, SEQ ID NO. 73, SEQ ID NO. 74; SEQ ID NO. 69, SEQ ID NO. 70, SEQ ID NO. 73, SEQ ID NO. 75; SEQ ID NO. 69, SEQ ID NO. 70, SEQ ID NO. 74, SEQ ID NO. 75; SEQ ID NO. 69, SEQ ID NO. 71, SEQ ID NO. 72, SEQ ID NO. 73; SEQ ID NO. 69, SEQ ID NO. 71, SEQ ID NO. 72, SEQ ID NO. 74; SEQ ID NO. 69, SEQ ID NO. 71, SEQ ID NO. 72, SEQ ID NO. 75; SEQ ID NO. 69, SEQ ID NO. 71, SEQ ID NO. 73, SEQ ID NO. 74; SEQ ID NO. 69, SEQ ID NO. 71, SEQ ID NO. 73, SEQ ID NO. 75; SEQ ID NO. 69, SEQ ID NO. 71, SEQ ID NO. 74, SEQ ID NO. 75; SEQ ID NO. 69, SEQ ID NO. 72, SEQ ID NO. 73, SEQ ID NO. 74; SEQ ID NO. 69, SEQ ID NO. 72, SEQ ID NO. 73, SEQ ID NO. 75; SEQ ID NO. 69, SEQ ID NO. 72, SEQ ID NO. 74, SEQ ID NO. 75; SEQ ID NO. 69, SEQ ID NO. 73, SEQ ID NO. 74, SEQ ID NO. 75; SEQ ID NO. 70, SEQ ID NO. 71, SEQ ID NO. 72, SEQ ID NO. 73; SEQ ID NO. 70, SEQ ID NO. 71, SEQ ID NO. 72, SEQ ID NO. 74; SEQ ID NO. 70, SEQ ID NO. 71, SEQ ID NO. 72, SEQ ID NO. 75; SEQ ID NO. 70, SEQ ID NO. 71, SEQ ID NO. 73, SEQ ID NO. 74; SEQ ID NO. 70, SEQ ID NO. 71, SEQ ID NO. 73, SEQ ID NO. 75; SEQ ID NO. 70, SEQ ID NO. 71, SEQ ID NO. 74, SEQ ID NO. 75; SEQ ID NO. 70, SEQ ID NO. 72, SEQ ID NO. 73, SEQ ID NO. 74; SEQ ID NO. 70, SEQ ID NO. 72, SEQ ID NO. 73, SEQ ID NO. 75; SEQ ID NO. 70, SEQ ID NO. 72, SEQ ID NO. 74, SEQ ID NO. 75; SEQ ID NO. 70, SEQ ID NO. 73, SEQ ID NO. 74, SEQ ID NO. 75; SEQ ID NO. 71, SEQ ID NO. 72, SEQ ID NO. 73, SEQ ID NO. 74; SEQ ID NO. 71, SEQ ID NO. 72, SEQ ID NO. 73, SEQ ID NO. 75; SEQ ID NO. 71, SEQ ID NO. 72, SEQ ID NO. 74, SEQ ID NO. 75; SEQ ID NO. 71, SEQ ID NO. 73, SEQ ID NO. 74, SEQ ID NO. 75; SEQ ID NO. 72, SEQ ID NO. 73, SEQ ID NO. 74, SEQ ID NO. 75;

Combination of 5 peptides

SEQ ID NO. 66, SEQ ID NO. 68, SEQ ID NO. 70, SEQ ID NO. 71, SEQ ID NO. 74; SEQ ID NO. 66, SEQ ID NO. 68, SEQ ID NO. 70, SEQ ID NO. 71, SEQ ID NO. 75; SEQ ID NO. 66, SEQ ID NO. 68, SEQ ID NO. 70, SEQ ID NO. 72, SEQ ID NO. 73; SEQ ID NO. 66, SEQ ID NO. 68, SEQ ID NO. 70, SEQ ID NO. 72, SEQ ID NO. 74; SEQ ID NO. 66, SEQ ID NO. 68, SEQ ID NO. 70, SEQ ID NO. 72, SEQ ID NO. 75; SEQ ID NO. 66, SEQ ID NO. 68, SEQ ID NO. 70, SEQ ID NO. 73, SEQ ID NO. 74; SEQ ID NO. 66, SEQ ID NO. 68, SEQ ID NO. 70, SEQ ID NO. 73, SEQ ID NO. 75; SEQ ID NO. 66, SEQ ID NO. 68, SEQ ID NO. 70, SEQ ID NO. 74, SEQ ID NO. 75; SEQ ID NO. 66, SEQ ID NO. 68, SEQ ID NO. 71, SEQ ID NO. 72, SEQ ID NO. 73; SEQ ID NO. 66, SEQ ID NO. 68, SEQ ID NO. 71, SEQ ID NO. 72, SEQ ID NO. 74; SEQ ID NO. 66, SEQ ID NO. 68, SEQ ID NO. 71, SEQ ID NO. 72, SEQ ID NO. 75; SEQ ID NO. 66, SEQ ID NO. 68, SEQ ID NO. 71, SEQ ID NO. 73, SEQ ID NO. 74; SEQ ID NO. 66, SEQ ID NO. 68, SEQ ID NO. 71, SEQ ID NO. 73, SEQ ID NO. 75; SEQ ID NO. 66, SEQ ID NO. 68, SEQ ID NO. 71, SEQ ID NO. 74, SEQ ID NO. 75; SEQ ID NO. 66, SEQ ID NO. 68, SEQ ID NO. 72, SEQ ID NO. 73, SEQ ID NO. 74; SEQ ID NO. 66, SEQ ID NO. 68, SEQ ID NO. 72, SEQ ID NO. 73, SEQ ID NO. 75; SEQ ID NO. 66, SEQ ID NO. 68, SEQ ID NO. 72, SEQ ID NO. 74, SEQ ID NO. 75; SEQ ID NO. 66, SEQ ID NO. 68, SEQ ID NO. 73, SEQ ID NO. 74, SEQ ID NO. 75; SEQ ID NO. 66, SEQ ID NO. 69, SEQ ID NO. 70, SEQ ID NO. 71, SEQ ID NO. 72; SEQ ID NO. 66, SEQ ID NO. 69, SEQ ID NO. 70, SEQ ID NO. 71, SEQ ID NO. 73; SEQ ID NO. 66, SEQ ID NO. 69, SEQ ID NO. 70, SEQ ID NO. 71, SEQ ID NO. 74; SEQ ID NO. 66, SEQ ID NO. 69, SEQ ID NO. 70, SEQ ID NO. 71, SEQ ID NO. 75; SEQ ID NO. 66, SEQ ID NO. 69, SEQ ID NO. 70, SEQ ID NO. 72, SEQ ID NO. 73; SEQ ID NO. 66, SEQ ID NO. 69, SEQ ID NO. 70, SEQ ID NO. 72, SEQ ID NO. 74; SEQ ID NO. 66, SEQ ID NO. 69, SEQ ID NO. 70, SEQ ID NO. 72, SEQ ID NO. 75; SEQ ID NO. 66, SEQ ID NO. 69, SEQ ID NO. 70, SEQ ID NO. 73, SEQ ID NO. 74; SEQ ID NO. 66, SEQ ID NO. 69, SEQ ID NO. 70, SEQ ID NO. 73, SEQ ID NO. 75; SEQ ID NO. 66, SEQ ID NO. 69, SEQ ID NO. 70, SEQ ID NO. 74, SEQ ID NO. 75; SEQ ID NO. 66, SEQ ID NO. 69, SEQ ID NO. 71, SEQ ID NO. 72, SEQ ID NO. 73; SEQ ID NO. 66, SEQ ID NO. 69, SEQ ID NO. 71, SEQ ID NO. 72, SEQ ID NO. 74; SEQ ID NO. 66, SEQ ID NO. 69, SEQ ID NO. 71, SEQ ID NO. 72, SEQ ID NO. 75; SEQ ID NO. 66, SEQ ID NO. 69, SEQ ID NO. 71, SEQ ID NO. 73, SEQ ID NO. 74; SEQ ID NO. 66, SEQ ID NO. 69, SEQ ID NO. 71, SEQ ID NO. 73, SEQ ID NO. 75; SEQ ID NO. 66, SEQ ID NO. 69, SEQ ID NO. 71, SEQ ID NO. 74, SEQ ID NO. 75; SEQ ID NO. 66, SEQ ID NO. 69, SEQ ID NO. 72, SEQ ID NO. 73, SEQ ID NO. 74; SEQ ID NO. 66, SEQ ID NO. 69, SEQ ID NO. 72, SEQ ID NO. 73, SEQ ID NO. 75; SEQ ID NO. 66, SEQ ID NO. 69, SEQ ID NO. 72, SEQ ID NO. 74, SEQ ID NO. 75; SEQ ID NO. 66, SEQ ID NO. 69, SEQ ID NO. 73, SEQ ID NO. 74, SEQ ID NO. 75; SEQ ID NO. 66, SEQ ID NO. 70, SEQ ID NO. 71, SEQ ID NO. 72, SEQ ID NO. 73; SEQ ID NO. 66, SEQ ID NO. 70, SEQ ID NO. 71, SEQ ID NO. 72, SEQ ID NO. 74; SEQ ID NO. 66, SEQ ID NO. 70, SEQ ID NO. 71, SEQ ID NO. 72, SEQ ID NO. 75; SEQ ID NO. 66, SEQ ID NO. 70, SEQ ID NO. 71, SEQ ID NO. 73, SEQ ID NO. 74; SEQ ID NO. 66, SEQ ID NO. 70, SEQ ID NO. 71, SEQ ID NO. 73, SEQ ID NO. 75; SEQ ID NO. 66, SEQ ID NO. 70, SEQ ID NO. 71, SEQ ID NO. 74, SEQ ID NO. 75; SEQ ID NO. 66, SEQ ID NO. 70, SEQ ID NO. 72, SEQ ID NO. 73, SEQ ID NO. 74; SEQ ID NO. 66, SEQ ID NO. 70, SEQ ID NO. 72, SEQ ID NO. 73, SEQ ID NO. 75; SEQ ID NO. 66, SEQ ID NO. 70, SEQ ID NO. 72, SEQ ID NO. 74, SEQ ID NO. 75; SEQ ID NO. 66, SEQ ID NO. 70, SEQ ID NO. 73, SEQ ID NO. 74, SEQ ID NO. 75; SEQ ID NO. 66, SEQ ID NO. 71, SEQ ID NO. 72, SEQ ID NO. 73, SEQ ID NO. 74; SEQ ID NO. 66, SEQ ID NO. 71, SEQ ID NO. 72, SEQ ID NO. 73, SEQ ID NO. 75;

TABLE 4-continued

Combinations of amino acid sequences from FIG. 4, to be incorporated in immunogenic peptides for composing an composition of synthetic long peptides in accordance with the invention. The various combination are separated by semicolons.

SEQ ID NO. 66, SEQ ID NO. 71, SEQ ID NO. 72, SEQ ID NO. 74, SEQ ID NO. 75; SEQ ID NO. 66, SEQ ID NO. 71, SEQ ID NO. 73, SEQ ID NO. 74, SEQ ID NO. 75; SEQ ID NO. 66, SEQ ID NO. 72, SEQ ID NO. 73, SEQ ID NO. 74, SEQ ID NO. 75; SEQ ID NO. 67, SEQ ID NO. 68, SEQ ID NO. 69, SEQ ID NO. 70, SEQ ID NO. 71; SEQ ID NO. 67, SEQ ID NO. 68, SEQ ID NO. 69, SEQ ID NO. 70, SEQ ID NO. 72; SEQ ID NO. 67, SEQ ID NO. 68, SEQ ID NO. 69, SEQ ID NO. 70, SEQ ID NO. 73; SEQ ID NO. 67, SEQ ID NO. 68, SEQ ID NO. 69, SEQ ID NO. 70, SEQ ID NO. 74; SEQ ID NO. 67, SEQ ID NO. 68, SEQ ID NO. 69, SEQ ID NO. 70, SEQ ID NO. 75; SEQ ID NO. 67, SEQ ID NO. 68, SEQ ID NO. 69, SEQ ID NO. 71, SEQ ID NO. 72; SEQ ID NO. 67, SEQ ID NO. 68, SEQ ID NO. 69, SEQ ID NO. 71, SEQ ID NO. 73; SEQ ID NO. 67, SEQ ID NO. 68, SEQ ID NO. 69, SEQ ID NO. 71, SEQ ID NO. 74; SEQ ID NO. 67, SEQ ID NO. 68, SEQ ID NO. 69, SEQ ID NO. 71, SEQ ID NO. 75; SEQ ID NO. 67, SEQ ID NO. 68, SEQ ID NO. 69, SEQ ID NO. 72, SEQ ID NO. 73; SEQ ID NO. 67, SEQ ID NO. 68, SEQ ID NO. 69, SEQ ID NO. 72, SEQ ID NO. 74; SEQ ID NO. 67, SEQ ID NO. 68, SEQ ID NO. 69, SEQ ID NO. 72, SEQ ID NO. 75; SEQ ID NO. 67, SEQ ID NO. 68, SEQ ID NO. 69, SEQ ID NO. 73, SEQ ID NO. 74; SEQ ID NO. 67, SEQ ID NO. 68, SEQ ID NO. 69, SEQ ID NO. 73, SEQ ID NO. 75; SEQ ID NO. 67, SEQ ID NO. 68, SEQ ID NO. 69, SEQ ID NO. 74, SEQ ID NO. 75; SEQ ID NO. 67, SEQ ID NO. 68, SEQ ID NO. 70, SEQ ID NO. 71, SEQ ID NO. 72; SEQ ID NO. 67, SEQ ID NO. 68, SEQ ID NO. 70, SEQ ID NO. 71, SEQ ID NO. 73; SEQ ID NO. 67, SEQ ID NO. 68, SEQ ID NO. 70, SEQ ID NO. 71, SEQ ID NO. 74; SEQ ID NO. 67, SEQ ID NO. 68, SEQ ID NO. 70, SEQ ID NO. 71, SEQ ID NO. 75; SEQ ID NO. 67, SEQ ID NO. 68, SEQ ID NO. 70, SEQ ID NO. 72, SEQ ID NO. 73; SEQ ID NO. 67, SEQ ID NO. 68, SEQ ID NO. 70, SEQ ID NO. 72, SEQ ID NO. 74; SEQ ID NO. 67, SEQ ID NO. 68, SEQ ID NO. 70, SEQ ID NO. 72, SEQ ID NO. 75; SEQ ID NO. 67, SEQ ID NO. 68, SEQ ID NO. 70, SEQ ID NO. 73, SEQ ID NO. 74; SEQ ID NO. 67, SEQ ID NO. 68, SEQ ID NO. 70, SEQ ID NO. 73, SEQ ID NO. 75; SEQ ID NO. 67, SEQ ID NO. 68, SEQ ID NO. 70, SEQ ID NO. 74, SEQ ID NO. 75; SEQ ID NO. 67, SEQ ID NO. 68, SEQ ID NO. 71, SEQ ID NO. 72, SEQ ID NO. 73; SEQ ID NO. 67, SEQ ID NO. 68, SEQ ID NO. 71, SEQ ID NO. 72, SEQ ID NO. 74; SEQ ID NO. 67, SEQ ID NO. 68, SEQ ID NO. 71, SEQ ID NO. 72, SEQ ID NO. 75; SEQ ID NO. 67, SEQ ID NO. 68, SEQ ID NO. 71, SEQ ID NO. 73, SEQ ID NO. 74; SEQ ID NO. 67, SEQ ID NO. 68, SEQ ID NO. 71, SEQ ID NO. 73, SEQ ID NO. 75; SEQ ID NO. 67, SEQ ID NO. 68, SEQ ID NO. 71, SEQ ID NO. 74, SEQ ID NO. 75; SEQ ID NO. 67, SEQ ID NO. 68, SEQ ID NO. 72, SEQ ID NO. 73, SEQ ID NO. 74; SEQ ID NO. 67, SEQ ID NO. 68, SEQ ID NO. 72, SEQ ID NO. 73, SEQ ID NO. 75; SEQ ID NO. 67, SEQ ID NO. 68, SEQ ID NO. 72, SEQ ID NO. 74, SEQ ID NO. 75; SEQ ID NO. 67, SEQ ID NO. 68, SEQ ID NO. 73, SEQ ID NO. 74, SEQ ID NO. 75; SEQ ID NO. 67, SEQ ID NO. 69, SEQ ID NO. 70, SEQ ID NO. 71, SEQ ID NO. 72; SEQ ID NO. 67, SEQ ID NO. 69, SEQ ID NO. 70, SEQ ID NO. 71, SEQ ID NO. 73; SEQ ID NO. 67, SEQ ID NO. 69, SEQ ID NO. 70, SEQ ID NO. 71, SEQ ID NO. 74; SEQ ID NO. 67, SEQ ID NO. 69, SEQ ID NO. 70, SEQ ID NO. 71, SEQ ID NO. 75; SEQ ID NO. 67, SEQ ID NO. 69, SEQ ID NO. 70, SEQ ID NO. 72, SEQ ID NO. 73; SEQ ID NO. 67, SEQ ID NO. 69, SEQ ID NO. 70, SEQ ID NO. 72, SEQ ID NO. 74; SEQ ID NO. 67, SEQ ID NO. 69, SEQ ID NO. 70, SEQ ID NO. 72, SEQ ID NO. 75; SEQ ID NO. 67, SEQ ID NO. 69, SEQ ID NO. 70, SEQ ID NO. 73, SEQ ID NO. 74; SEQ ID NO. 67, SEQ ID NO. 69, SEQ ID NO. 70, SEQ ID NO. 73, SEQ ID NO. 75; SEQ ID NO. 67, SEQ ID NO. 69, SEQ ID NO. 70, SEQ ID NO. 74, SEQ ID NO. 75; SEQ ID NO. 67, SEQ ID NO. 69, SEQ ID NO. 71, SEQ ID NO. 72, SEQ ID NO. 73; SEQ ID NO. 67, SEQ ID NO. 69, SEQ ID NO. 71, SEQ ID NO. 72, SEQ ID NO. 74; SEQ ID NO. 67, SEQ ID NO. 69, SEQ ID NO. 71, SEQ ID NO. 72, SEQ ID NO. 75; SEQ ID NO. 67, SEQ ID NO. 69, SEQ ID NO. 71, SEQ ID NO. 73, SEQ ID NO. 74; SEQ ID NO. 67, SEQ ID NO. 69, SEQ ID NO. 71, SEQ ID NO. 73, SEQ ID NO. 75; SEQ ID NO. 67, SEQ ID NO. 69, SEQ ID NO. 71, SEQ ID NO. 74, SEQ ID NO. 75; SEQ ID NO. 67, SEQ ID NO. 69, SEQ ID NO. 72, SEQ ID NO. 73, SEQ ID NO. 74; SEQ ID NO. 67, SEQ ID NO. 69, SEQ ID NO. 72, SEQ ID NO. 73, SEQ ID NO. 75; SEQ ID NO. 67, SEQ ID NO. 69, SEQ ID NO. 72, SEQ ID NO. 74, SEQ ID NO. 75; SEQ ID NO. 67, SEQ ID NO. 69, SEQ ID NO. 73, SEQ ID NO. 74, SEQ ID NO. 75; SEQ ID NO. 67, SEQ ID NO. 70, SEQ ID NO. 71, SEQ ID NO. 72, SEQ ID NO. 73; SEQ ID NO. 67, SEQ ID NO. 70, SEQ ID NO. 71, SEQ ID NO. 72, SEQ ID NO. 74; SEQ ID NO. 67, SEQ ID NO. 70, SEQ ID NO. 71, SEQ ID NO. 72, SEQ ID NO. 75; SEQ ID NO. 67, SEQ ID NO. 70, SEQ ID NO. 71, SEQ ID NO. 73, SEQ ID NO. 74; SEQ ID NO. 67, SEQ ID NO. 70, SEQ ID NO. 71, SEQ ID NO. 73, SEQ ID NO. 75; SEQ ID NO. 67, SEQ ID NO. 70, SEQ ID NO. 71, SEQ ID NO. 74, SEQ ID NO. 75; SEQ ID NO. 67, SEQ ID NO. 70, SEQ ID NO. 72, SEQ ID NO. 73, SEQ ID NO. 74; SEQ ID NO. 67, SEQ ID NO. 70, SEQ ID NO. 72, SEQ ID NO. 73, SEQ ID NO. 75; SEQ ID NO. 67, SEQ ID NO. 70, SEQ ID NO. 72, SEQ ID NO. 74, SEQ ID NO. 75; SEQ ID NO. 67, SEQ ID NO. 71, SEQ ID NO. 72, SEQ ID NO. 73, SEQ ID NO. 74; SEQ ID NO. 67, SEQ ID NO. 71, SEQ ID NO. 72, SEQ ID NO. 73, SEQ ID NO. 75; SEQ ID NO. 67, SEQ ID NO. 71, SEQ ID NO. 72, SEQ ID NO. 74, SEQ ID NO. 75; SEQ ID NO. 67, SEQ ID NO. 71, SEQ ID NO. 73, SEQ ID NO. 74, SEQ ID NO. 75; SEQ ID NO. 67, SEQ ID NO. 72, SEQ ID NO. 73, SEQ ID NO. 74, SEQ ID NO. 75; SEQ ID NO. 68, SEQ ID NO. 69, SEQ ID NO. 70, SEQ ID NO. 71, SEQ ID NO. 72; SEQ ID NO. 68, SEQ ID NO. 69, SEQ ID NO. 70, SEQ ID NO. 71, SEQ ID NO. 73; SEQ ID NO. 68, SEQ ID NO. 69, SEQ ID NO. 70, SEQ ID NO. 71, SEQ ID NO. 74; SEQ ID NO. 68, SEQ ID NO. 69, SEQ ID NO. 70, SEQ ID NO. 71, SEQ ID NO. 75; SEQ ID NO. 68, SEQ ID NO. 69, SEQ ID NO. 70, SEQ ID NO. 72, SEQ ID NO. 73; SEQ ID NO. 68, SEQ ID NO. 69, SEQ ID NO. 70, SEQ ID NO. 72, SEQ ID NO. 74; SEQ ID NO. 68, SEQ ID NO. 69, SEQ ID NO. 70, SEQ ID NO. 72, SEQ ID NO. 75; SEQ ID NO. 68, SEQ ID NO. 69, SEQ ID NO. 70, SEQ ID NO. 73, SEQ ID NO. 74; SEQ ID NO. 68, SEQ ID NO. 69, SEQ ID NO. 70, SEQ ID NO. 73, SEQ ID NO. 75; SEQ ID NO. 68, SEQ ID NO. 69, SEQ ID NO. 70, SEQ ID NO. 74, SEQ ID NO. 75; SEQ ID NO. 68, SEQ ID NO. 69, SEQ ID NO. 71, SEQ ID NO. 72, SEQ ID NO. 73; SEQ ID NO. 68, SEQ ID NO. 69, SEQ ID NO. 71, SEQ ID NO. 72, SEQ ID NO. 74; SEQ ID NO. 68, SEQ ID NO. 69, SEQ ID NO. 71, SEQ ID NO. 72, SEQ ID NO. 75; SEQ ID NO. 68, SEQ ID NO. 69, SEQ ID NO. 71, SEQ ID NO. 73, SEQ ID NO. 74; SEQ ID NO. 68, SEQ ID NO. 69, SEQ ID NO. 71, SEQ ID NO. 73, SEQ ID NO. 75; SEQ ID NO. 68, SEQ ID NO. 69, SEQ ID NO. 71, SEQ ID NO. 74, SEQ ID NO. 75; SEQ ID NO. 68, SEQ ID NO. 69, SEQ ID NO. 72, SEQ ID NO. 73, SEQ ID NO. 74; SEQ ID NO. 68, SEQ ID NO. 69, SEQ ID NO. 72, SEQ ID NO. 73, SEQ ID NO. 75; SEQ ID NO. 68, SEQ ID NO. 69, SEQ ID NO. 72, SEQ ID NO. 74, SEQ ID NO. 75; SEQ ID NO. 68, SEQ ID NO. 69, SEQ ID NO. 73, SEQ ID NO. 74, SEQ ID NO. 75; SEQ ID NO. 68, SEQ ID NO. 70, SEQ ID NO. 71, SEQ ID NO. 72, SEQ ID NO. 73; SEQ ID NO. 68, SEQ ID NO. 70, SEQ ID NO. 71, SEQ ID NO. 72, SEQ ID NO. 74;

TABLE 4-continued

Combinations of amino acid sequences from FIG. 4, to be incorporated in immunogenic peptides for composing an composition of synthetic long peptides in accordance with the invention. The various combination are separated by semicolons.

SEQ ID NO. 68, SEQ ID NO. 70, SEQ ID NO. 71, SEQ ID NO. 72, SEQ ID NO. 75; SEQ ID NO. 68, SEQ ID NO. 70, SEQ ID NO. 71, SEQ ID NO. 73, SEQ ID NO. 74; SEQ ID NO. 68, SEQ ID NO. 70, SEQ ID NO. 71, SEQ ID NO. 73, SEQ ID NO. 75; SEQ ID NO. 68, SEQ ID NO. 70, SEQ ID NO. 71, SEQ ID NO. 74, SEQ ID NO. 75; SEQ ID NO. 68, SEQ ID NO. 70, SEQ ID NO. 72, SEQ ID NO. 73, SEQ ID NO. 74; SEQ ID NO. 68, SEQ ID NO. 70, SEQ ID NO. 72, SEQ ID NO. 73, SEQ ID NO. 75; SEQ ID NO. 68, SEQ ID NO. 70, SEQ ID NO. 72, SEQ ID NO. 74, SEQ ID NO. 75; SEQ ID NO. 68, SEQ ID NO. 70, SEQ ID NO. 73, SEQ ID NO. 74, SEQ ID NO. 75; SEQ ID NO. 68, SEQ ID NO. 71, SEQ ID NO. 72, SEQ ID NO. 73, SEQ ID NO. 74; SEQ ID NO. 68, SEQ ID NO. 71, SEQ ID NO. 72, SEQ ID NO. 73, SEQ ID NO. 75; SEQ ID NO. 68, SEQ ID NO. 71, SEQ ID NO. 72, SEQ ID NO. 74, SEQ ID NO. 75; SEQ ID NO. 68, SEQ ID NO. 71, SEQ ID NO. 73, SEQ ID NO. 74, SEQ ID NO. 75; SEQ ID NO. 68, SEQ ID NO. 72, SEQ ID NO. 73, SEQ ID NO. 74, SEQ ID NO. 75; SEQ ID NO. 69, SEQ ID NO. 70, SEQ ID NO. 71, SEQ ID NO. 72, SEQ ID NO. 73; SEQ ID NO. 69, SEQ ID NO. 70, SEQ ID NO. 71, SEQ ID NO. 72, SEQ ID NO. 74; SEQ ID NO. 69, SEQ ID NO. 70, SEQ ID NO. 71, SEQ ID NO. 72, SEQ ID NO. 75; SEQ ID NO. 69, SEQ ID NO. 70, SEQ ID NO. 71, SEQ ID NO. 73, SEQ ID NO. 74; SEQ ID NO. 69, SEQ ID NO. 70, SEQ ID NO. 71, SEQ ID NO. 73, SEQ ID NO. 75; SEQ ID NO. 69, SEQ ID NO. 70, SEQ ID NO. 71, SEQ ID NO. 74, SEQ ID NO. 75; SEQ ID NO. 69, SEQ ID NO. 70, SEQ ID NO. 72, SEQ ID NO. 73, SEQ ID NO. 74; SEQ ID NO. 69, SEQ ID NO. 70, SEQ ID NO. 72, SEQ ID NO. 73, SEQ ID NO. 75; SEQ ID NO. 69, SEQ ID NO. 70, SEQ ID NO. 72, SEQ ID NO. 74, SEQ ID NO. 75; SEQ ID NO. 69, SEQ ID NO. 70, SEQ ID NO. 73, SEQ ID NO. 74, SEQ ID NO. 75; SEQ ID NO. 69, SEQ ID NO. 71, SEQ ID NO. 72, SEQ ID NO. 73, SEQ ID NO. 74; SEQ ID NO. 69, SEQ ID NO. 71, SEQ ID NO. 72, SEQ ID NO. 73, SEQ ID NO. 75; SEQ ID NO. 69, SEQ ID NO. 71, SEQ ID NO. 72, SEQ ID NO. 74, SEQ ID NO. 75; SEQ ID NO. 69, SEQ ID NO. 71, SEQ ID NO. 73, SEQ ID NO. 74, SEQ ID NO. 75; SEQ ID NO. 69, SEQ ID NO. 72, SEQ ID NO. 73, SEQ ID NO. 74, SEQ ID NO. 75; SEQ ID NO. 70, SEQ ID NO. 71, SEQ ID NO. 72, SEQ ID NO. 73, SEQ ID NO. 74; SEQ ID NO. 70, SEQ ID NO. 71, SEQ ID NO. 72, SEQ ID NO. 73, SEQ ID NO. 75; SEQ ID NO. 70, SEQ ID NO. 71, SEQ ID NO. 72, SEQ ID NO. 74, SEQ ID NO. 75; SEQ ID NO. 70, SEQ ID NO. 71, SEQ ID NO. 73, SEQ ID NO. 74, SEQ ID NO. 75; SEQ ID NO. 70, SEQ ID NO. 72, SEQ ID NO. 73, SEQ ID NO. 74, SEQ ID NO. 75; SEQ ID NO. 71, SEQ ID NO. 72, SEQ ID NO. 73, SEQ ID NO. 74, SEQ ID NO. 75;

Combination of 6 peptides

SEQ ID NO. 66, SEQ ID NO. 67, SEQ ID NO. 68, SEQ ID NO. 69, SEQ ID NO. 70, SEQ ID NO. 71; SEQ ID NO. 66, SEQ ID NO. 67, SEQ ID NO. 68, SEQ ID NO. 69, SEQ ID NO. 70, SEQ ID NO. 72; SEQ ID NO. 66, SEQ ID NO. 67, SEQ ID NO. 68, SEQ ID NO. 69, SEQ ID NO. 70, SEQ ID NO. 73; SEQ ID NO. 66, SEQ ID NO. 67, SEQ ID NO. 68, SEQ ID NO. 69, SEQ ID NO. 70, SEQ ID NO. 74; SEQ ID NO. 66, SEQ ID NO. 67, SEQ ID NO. 68, SEQ ID NO. 69, SEQ ID NO. 70, SEQ ID NO. 75; SEQ ID NO. 66, SEQ ID NO. 67, SEQ ID NO. 68, SEQ ID NO. 69, SEQ ID NO. 71, SEQ ID NO. 72; SEQ ID NO. 66, SEQ ID NO. 67, SEQ ID NO. 68, SEQ ID NO. 69, SEQ ID NO. 71, SEQ ID NO. 73; SEQ ID NO. 66, SEQ ID NO. 67, SEQ ID NO. 68, SEQ ID NO. 69, SEQ ID NO. 71, SEQ ID NO. 74; SEQ ID NO. 66, SEQ ID NO. 67, SEQ ID NO. 68, SEQ ID NO. 69, SEQ ID NO. 71, SEQ ID NO. 75; SEQ ID NO. 66, SEQ ID NO. 67, SEQ ID NO. 68, SEQ ID NO. 69, SEQ ID NO. 72, SEQ ID NO. 73; SEQ ID NO. 66, SEQ ID NO. 67, SEQ ID NO. 68, SEQ ID NO. 69, SEQ ID NO. 72, SEQ ID NO. 74; SEQ ID NO. 66, SEQ ID NO. 67, SEQ ID NO. 68, SEQ ID NO. 69, SEQ ID NO. 72, SEQ ID NO. 75; SEQ ID NO. 66, SEQ ID NO. 67, SEQ ID NO. 68, SEQ ID NO. 69, SEQ ID NO. 73, SEQ ID NO. 74; SEQ ID NO. 66, SEQ ID NO. 67, SEQ ID NO. 68, SEQ ID NO. 69, SEQ ID NO. 73, SEQ ID NO. 75; SEQ ID NO. 66, SEQ ID NO. 67, SEQ ID NO. 68, SEQ ID NO. 69, SEQ ID NO. 74, SEQ ID NO. 75; SEQ ID NO. 66, SEQ ID NO. 67, SEQ ID NO. 68, SEQ ID NO. 70, SEQ ID NO. 71, SEQ ID NO. 72; SEQ ID NO. 66, SEQ ID NO. 67, SEQ ID NO. 68, SEQ ID NO. 70, SEQ ID NO. 71, SEQ ID NO. 73; SEQ ID NO. 66, SEQ ID NO. 67, SEQ ID NO. 68, SEQ ID NO. 70, SEQ ID NO. 71, SEQ ID NO. 74; SEQ ID NO. 66, SEQ ID NO. 67, SEQ ID NO. 68, SEQ ID NO. 70, SEQ ID NO. 71, SEQ ID NO. 75; SEQ ID NO. 66, SEQ ID NO. 67, SEQ ID NO. 68, SEQ ID NO. 70, SEQ ID NO. 72, SEQ ID NO. 73; SEQ ID NO. 66, SEQ ID NO. 67, SEQ ID NO. 68, SEQ ID NO. 70, SEQ ID NO. 72, SEQ ID NO. 74; SEQ ID NO. 66, SEQ ID NO. 67, SEQ ID NO. 68, SEQ ID NO. 70, SEQ ID NO. 72, SEQ ID NO. 75; SEQ ID NO. 66, SEQ ID NO. 67, SEQ ID NO. 68, SEQ ID NO. 70, SEQ ID NO. 73, SEQ ID NO. 74; SEQ ID NO. 66, SEQ ID NO. 67, SEQ ID NO. 68, SEQ ID NO. 70, SEQ ID NO. 73, SEQ ID NO. 75; SEQ ID NO. 66, SEQ ID NO. 67, SEQ ID NO. 68, SEQ ID NO. 70, SEQ ID NO. 74, SEQ ID NO. 75; SEQ ID NO. 66, SEQ ID NO. 67, SEQ ID NO. 68, SEQ ID NO. 71, SEQ ID NO. 72, SEQ ID NO. 73; SEQ ID NO. 66, SEQ ID NO. 67, SEQ ID NO. 68, SEQ ID NO. 71, SEQ ID NO. 72, SEQ ID NO. 74; SEQ ID NO. 66, SEQ ID NO. 67, SEQ ID NO. 68, SEQ ID NO. 71, SEQ ID NO. 72, SEQ ID NO. 75; SEQ ID NO. 66, SEQ ID NO. 67, SEQ ID NO. 68, SEQ ID NO. 71, SEQ ID NO. 73, SEQ ID NO. 74; SEQ ID NO. 66, SEQ ID NO. 67, SEQ ID NO. 68, SEQ ID NO. 71, SEQ ID NO. 73, SEQ ID NO. 75; SEQ ID NO. 66, SEQ ID NO. 67, SEQ ID NO. 68, SEQ ID NO. 71, SEQ ID NO. 74, SEQ ID NO. 75; SEQ ID NO. 66, SEQ ID NO. 67, SEQ ID NO. 68, SEQ ID NO. 72, SEQ ID NO. 73, SEQ ID NO. 74; SEQ ID NO. 66, SEQ ID NO. 67, SEQ ID NO. 68, SEQ ID NO. 72, SEQ ID NO. 73, SEQ ID NO. 75; SEQ ID NO. 66, SEQ ID NO. 67, SEQ ID NO. 68, SEQ ID NO. 72, SEQ ID NO. 74, SEQ ID NO. 75; SEQ ID NO. 66, SEQ ID NO. 67, SEQ ID NO. 68, SEQ ID NO. 73, SEQ ID NO. 74, SEQ ID NO. 75; SEQ ID NO. 66, SEQ ID NO. 67, SEQ ID NO. 69, SEQ ID NO. 70, SEQ ID NO. 71, SEQ ID NO. 72; SEQ ID NO. 66, SEQ ID NO. 67, SEQ ID NO. 69, SEQ ID NO. 70, SEQ ID NO. 71, SEQ ID NO. 73; SEQ ID NO. 66, SEQ ID NO. 67, SEQ ID NO. 69, SEQ ID NO. 70, SEQ ID NO. 71, SEQ ID NO. 74; SEQ ID NO. 66, SEQ ID NO. 67, SEQ ID NO. 69, SEQ ID NO. 70, SEQ ID NO. 71, SEQ ID NO. 75; SEQ ID NO. 66, SEQ ID NO. 67, SEQ ID NO. 69, SEQ ID NO. 70, SEQ ID NO. 72, SEQ ID NO. 73; SEQ ID NO. 66, SEQ ID NO. 67, SEQ ID NO. 69, SEQ ID NO. 70, SEQ ID NO. 72, SEQ ID NO. 74; SEQ ID NO. 66, SEQ ID NO. 67, SEQ ID NO. 69, SEQ ID NO. 70, SEQ ID NO. 72, SEQ ID NO. 75; SEQ ID NO. 66, SEQ ID NO. 67, SEQ ID NO. 69, SEQ ID NO. 70, SEQ ID NO. 73, SEQ ID NO. 74; SEQ ID NO. 66, SEQ ID NO. 67, SEQ ID NO. 69, SEQ ID NO. 70, SEQ ID NO. 73, SEQ ID NO. 75; SEQ ID NO. 66, SEQ ID NO. 67, SEQ ID NO. 69, SEQ ID NO. 70, SEQ ID NO. 74, SEQ ID NO. 75; SEQ ID NO. 66, SEQ ID NO. 67, SEQ ID NO. 69, SEQ ID NO. 71, SEQ ID NO. 72, SEQ ID NO. 73; SEQ ID NO. 66, SEQ ID NO. 67, SEQ ID NO. 69, SEQ ID NO. 71, SEQ ID NO. 72, SEQ ID NO. 74; SEQ ID NO. 66, SEQ ID NO. 67, SEQ ID NO. 69, SEQ ID NO. 71, SEQ ID NO. 72, SEQ ID

TABLE 4-continued

Combinations of amino acid sequences from FIG. 4, to be incorporated in immunogenic peptides for composing an composition of synthetic long peptides in accordance with the invention. The various combination are separated by semicolons.

NO. 75; SEQ ID NO. 66, SEQ ID NO. 67, SEQ ID NO. 69, SEQ ID NO. 71, SEQ ID NO. 73, SEQ ID NO. 74; SEQ ID NO. 66, SEQ ID NO. 67, SEQ ID NO. 69, SEQ ID NO. 71, SEQ ID NO. 73, SEQ ID NO. 75; SEQ ID NO. 66, SEQ ID NO. 67, SEQ ID NO. 69, SEQ ID NO. 71, SEQ ID NO. 74, SEQ ID NO. 75; SEQ ID NO. 66, SEQ ID NO. 67, SEQ ID NO. 69, SEQ ID NO. 72, SEQ ID NO. 73, SEQ ID NO. 74; SEQ ID NO. 66, SEQ ID NO. 67, SEQ ID NO. 69, SEQ ID NO. 72, SEQ ID NO. 73, SEQ ID NO. 75; SEQ ID NO. 66, SEQ ID NO. 67, SEQ ID NO. 69, SEQ ID NO. 72, SEQ ID NO. 74, SEQ ID NO. 75; SEQ ID NO. 66, SEQ ID NO. 67, SEQ ID NO. 69, SEQ ID NO. 73, SEQ ID NO. 74, SEQ ID NO. 75; SEQ ID NO. 66, SEQ ID NO. 67, SEQ ID NO. 70, SEQ ID NO. 71, SEQ ID NO. 72, SEQ ID NO. 73; SEQ ID NO. 66, SEQ ID NO. 67, SEQ ID NO. 70, SEQ ID NO. 71, SEQ ID NO. 72, SEQ ID NO. 74; SEQ ID NO. 66, SEQ ID NO. 67, SEQ ID NO. 70, SEQ ID NO. 71, SEQ ID NO. 72, SEQ ID NO. 75; SEQ ID NO. 66, SEQ ID NO. 67, SEQ ID NO. 70, SEQ ID NO. 71, SEQ ID NO. 73, SEQ ID NO. 74; SEQ ID NO. 66, SEQ ID NO. 67, SEQ ID NO. 70, SEQ ID NO. 71, SEQ ID NO. 73, SEQ ID NO. 75; SEQ ID NO. 66, SEQ ID NO. 67, SEQ ID NO. 70, SEQ ID NO. 71, SEQ ID NO. 74, SEQ ID NO. 75; SEQ ID NO. 66, SEQ ID NO. 67, SEQ ID NO. 70, SEQ ID NO. 72, SEQ ID NO. 73, SEQ ID NO. 74; SEQ ID NO. 66, SEQ ID NO. 67, SEQ ID NO. 70, SEQ ID NO. 72, SEQ ID NO. 73, SEQ ID NO. 75; SEQ ID NO. 66, SEQ ID NO. 67, SEQ ID NO. 70, SEQ ID NO. 72, SEQ ID NO. 74, SEQ ID NO. 75; SEQ ID NO. 66, SEQ ID NO. 67, SEQ ID NO. 70, SEQ ID NO. 73, SEQ ID NO. 74, SEQ ID NO. 75; SEQ ID NO. 66, SEQ ID NO. 67, SEQ ID NO. 71, SEQ ID NO. 72, SEQ ID NO. 73, SEQ ID NO. 74; SEQ ID NO. 66, SEQ ID NO. 67, SEQ ID NO. 71, SEQ ID NO. 72, SEQ ID NO. 73, SEQ ID NO. 75; SEQ ID NO. 66, SEQ ID NO. 67, SEQ ID NO. 71, SEQ ID NO. 72, SEQ ID NO. 74, SEQ ID NO. 75; SEQ ID NO. 66, SEQ ID NO. 67, SEQ ID NO. 71, SEQ ID NO. 73, SEQ ID NO. 74, SEQ ID NO. 75; SEQ ID NO. 66, SEQ ID NO. 67, SEQ ID NO. 72, SEQ ID NO. 73, SEQ ID NO. 74, SEQ ID NO. 75; SEQ ID NO. 66, SEQ ID NO. 68, SEQ ID NO. 69, SEQ ID NO. 70, SEQ ID NO. 71, SEQ ID NO. 72; SEQ ID NO. 66, SEQ ID NO. 68, SEQ ID NO. 69, SEQ ID NO. 70, SEQ ID NO. 71, SEQ ID NO. 73; SEQ ID NO. 66, SEQ ID NO. 68, SEQ ID NO. 69, SEQ ID NO. 70, SEQ ID NO. 71, SEQ ID NO. 74; SEQ ID NO. 66, SEQ ID NO. 68, SEQ ID NO. 69, SEQ ID NO. 70, SEQ ID NO. 71, SEQ ID NO. 75; SEQ ID NO. 66, SEQ ID NO. 68, SEQ ID NO. 69, SEQ ID NO. 70, SEQ ID NO. 72, SEQ ID NO. 73; SEQ ID NO. 66, SEQ ID NO. 68, SEQ ID NO. 69, SEQ ID NO. 70, SEQ ID NO. 72, SEQ ID NO. 74; SEQ ID NO. 66, SEQ ID NO. 68, SEQ ID NO. 69, SEQ ID NO. 70, SEQ ID NO. 72, SEQ ID NO. 75; SEQ ID NO. 66, SEQ ID NO. 68, SEQ ID NO. 69, SEQ ID NO. 70, SEQ ID NO. 73, SEQ ID NO. 74; SEQ ID NO. 66, SEQ ID NO. 68, SEQ ID NO. 69, SEQ ID NO. 70, SEQ ID NO. 73, SEQ ID NO. 75; SEQ ID NO. 66, SEQ ID NO. 68, SEQ ID NO. 69, SEQ ID NO. 70, SEQ ID NO. 74, SEQ ID NO. 75; SEQ ID NO. 66, SEQ ID NO. 68, SEQ ID NO. 69, SEQ ID NO. 71, SEQ ID NO. 72, SEQ ID NO. 73; SEQ ID NO. 66, SEQ ID NO. 68, SEQ ID NO. 69, SEQ ID NO. 71, SEQ ID NO. 72, SEQ ID NO. 74; SEQ ID NO. 66, SEQ ID NO. 68, SEQ ID NO. 69, SEQ ID NO. 71, SEQ ID NO. 72, SEQ ID NO. 75; SEQ ID NO. 66, SEQ ID NO. 68, SEQ ID NO. 69, SEQ ID NO. 71, SEQ ID NO. 73, SEQ ID NO. 74; SEQ ID NO. 66, SEQ ID NO. 68, SEQ ID NO. 69, SEQ ID NO. 71, SEQ ID NO. 73, SEQ ID NO. 75; SEQ ID NO. 66, SEQ ID NO. 68, SEQ ID NO. 69, SEQ ID NO. 71, SEQ ID NO. 74, SEQ ID NO. 75; SEQ ID NO. 66, SEQ ID NO. 68, SEQ ID NO. 69, SEQ ID NO. 72, SEQ ID NO. 73, SEQ ID NO. 74; SEQ ID NO. 66, SEQ ID NO. 68, SEQ ID NO. 69, SEQ ID NO. 72, SEQ ID NO. 73, SEQ ID NO. 75; SEQ ID NO. 66, SEQ ID NO. 68, SEQ ID NO. 69, SEQ ID NO. 72, SEQ ID NO. 74, SEQ ID NO. 75; SEQ ID NO. 66, SEQ ID NO. 68, SEQ ID NO. 69, SEQ ID NO. 73, SEQ ID NO. 74, SEQ ID NO. 75; SEQ ID NO. 66, SEQ ID NO. 68, SEQ ID NO. 70, SEQ ID NO. 71, SEQ ID NO. 72, SEQ ID NO. 73; SEQ ID NO. 66, SEQ ID NO. 68, SEQ ID NO. 70, SEQ ID NO. 71, SEQ ID NO. 72, SEQ ID NO. 74; SEQ ID NO. 66, SEQ ID NO. 68, SEQ ID NO. 70, SEQ ID NO. 71, SEQ ID NO. 72, SEQ ID NO. 75; SEQ ID NO. 66, SEQ ID NO. 68, SEQ ID NO. 70, SEQ ID NO. 71, SEQ ID NO. 73, SEQ ID NO. 74; SEQ ID NO. 66, SEQ ID NO. 68, SEQ ID NO. 70, SEQ ID NO. 71, SEQ ID NO. 73, SEQ ID NO. 75; SEQ ID NO. 66, SEQ ID NO. 68, SEQ ID NO. 70, SEQ ID NO. 71, SEQ ID NO. 74, SEQ ID NO. 75; SEQ ID NO. 66, SEQ ID NO. 68, SEQ ID NO. 70, SEQ ID NO. 72, SEQ ID NO. 73, SEQ ID NO. 74; SEQ ID NO. 66, SEQ ID NO. 68, SEQ ID NO. 70, SEQ ID NO. 72, SEQ ID NO. 73, SEQ ID NO. 75; SEQ ID NO. 66, SEQ ID NO. 68, SEQ ID NO. 70, SEQ ID NO. 72, SEQ ID NO. 74, SEQ ID NO. 75; SEQ ID NO. 66, SEQ ID NO. 68, SEQ ID NO. 70, SEQ ID NO. 73, SEQ ID NO. 74, SEQ ID NO. 75; SEQ ID NO. 66, SEQ ID NO. 68, SEQ ID NO. 71, SEQ ID NO. 72, SEQ ID NO. 73, SEQ ID NO. 74; SEQ ID NO. 66, SEQ ID NO. 68, SEQ ID NO. 71, SEQ ID NO. 72, SEQ ID NO. 73, SEQ ID NO. 75; SEQ ID NO. 66, SEQ ID NO. 68, SEQ ID NO. 71, SEQ ID NO. 72, SEQ ID NO. 74, SEQ ID NO. 75; SEQ ID NO. 66, SEQ ID NO. 68, SEQ ID NO. 71, SEQ ID NO. 73, SEQ ID NO. 74, SEQ ID NO. 75; SEQ ID NO. 66, SEQ ID NO. 68, SEQ ID NO. 72, SEQ ID NO. 73, SEQ ID NO. 74, SEQ ID NO. 75; SEQ ID NO. 66, SEQ ID NO. 69, SEQ ID NO. 70, SEQ ID NO. 71, SEQ ID NO. 72, SEQ ID NO. 73; SEQ ID NO. 66, SEQ ID NO. 69, SEQ ID NO. 70, SEQ ID NO. 71, SEQ ID NO. 72, SEQ ID NO. 74; SEQ ID NO. 66, SEQ ID NO. 69, SEQ ID NO. 70, SEQ ID NO. 71, SEQ ID NO. 72, SEQ ID NO. 75; SEQ ID NO. 66, SEQ ID NO. 69, SEQ ID NO. 70, SEQ ID NO. 71, SEQ ID NO. 73, SEQ ID NO. 74; SEQ ID NO. 66, SEQ ID NO. 69, SEQ ID NO. 70, SEQ ID NO. 71, SEQ ID NO. 73, SEQ ID NO. 75; SEQ ID NO. 66, SEQ ID NO. 69, SEQ ID NO. 70, SEQ ID NO. 71, SEQ ID NO. 74, SEQ ID NO. 75; SEQ ID NO. 66, SEQ ID NO. 69, SEQ ID NO. 70, SEQ ID NO. 72, SEQ ID NO. 73, SEQ ID NO. 74; SEQ ID NO. 66, SEQ ID NO. 69, SEQ ID NO. 70, SEQ ID NO. 72, SEQ ID NO. 73, SEQ ID NO. 75; SEQ ID NO. 66, SEQ ID NO. 69, SEQ ID NO. 70, SEQ ID NO. 72, SEQ ID NO. 74, SEQ ID NO. 75; SEQ ID NO. 66, SEQ ID NO. 69, SEQ ID NO. 70, SEQ ID NO. 73, SEQ ID NO. 74, SEQ ID NO. 75; SEQ ID NO. 66, SEQ ID NO. 69, SEQ ID NO. 71, SEQ ID NO. 72, SEQ ID NO. 73, SEQ ID NO. 74; SEQ ID NO. 66, SEQ ID NO. 69, SEQ ID NO. 71, SEQ ID NO. 72, SEQ ID NO. 73, SEQ ID NO. 75; SEQ ID NO. 66, SEQ ID NO. 69, SEQ ID NO. 71, SEQ ID NO. 72, SEQ ID NO. 74, SEQ ID NO. 75; SEQ ID NO. 66, SEQ ID NO. 69, SEQ ID NO. 71, SEQ ID NO. 73, SEQ ID NO. 74, SEQ ID NO. 75; SEQ ID NO. 66, SEQ ID NO. 69, SEQ ID NO. 72, SEQ ID NO. 73, SEQ ID NO. 74, SEQ ID NO. 75; SEQ ID NO. 66, SEQ ID NO. 70, SEQ ID NO. 71, SEQ ID NO. 72, SEQ ID NO. 73, SEQ ID NO. 74; SEQ ID NO. 66, SEQ ID NO. 70, SEQ ID NO. 71, SEQ ID NO. 72, SEQ ID NO. 73, SEQ ID NO. 75; SEQ ID NO. 66, SEQ ID NO. 70, SEQ ID NO. 71, SEQ ID NO. 72, SEQ ID NO. 74, SEQ ID NO. 75; SEQ ID NO. 66, SEQ ID NO. 70, SEQ ID NO. 71, SEQ ID NO. 73, SEQ ID NO. 74, SEQ ID NO. 75; SEQ ID NO. 66, SEQ ID NO. 70, SEQ ID NO. 72, SEQ ID NO. 73, SEQ ID NO. 74, SEQ ID NO. 75; SEQ ID NO. 66, SEQ ID NO. 71, SEQ ID NO. 72, SEQ ID NO. 73, SEQ ID NO. 74, SEQ ID NO. 75; SEQ ID NO. 67, SEQ ID NO. 68, SEQ ID NO. 69, SEQ ID NO. 70, SEQ ID NO. 71, SEQ ID NO. 72; SEQ ID

TABLE 4-continued

Combinations of amino acid sequences from FIG. 4, to be incorporated in immunogenic peptides for composing an composition of synthetic long peptides in accordance with the invention. The various combination are separated by semicolons.

NO. 67, SEQ ID NO. 68, SEQ ID NO. 69, SEQ ID NO. 70, SEQ ID NO. 71, SEQ ID NO. 73; SEQ ID NO. 67, SEQ ID NO. 68, SEQ ID NO. 69, SEQ ID NO. 70, SEQ ID NO. 71, SEQ ID NO. 74; SEQ ID NO. 67, SEQ ID NO. 68, SEQ ID NO. 69, SEQ ID NO. 70, SEQ ID NO. 71, SEQ ID NO. 75; SEQ ID NO. 67, SEQ ID NO. 68, SEQ ID NO. 69, SEQ ID NO. 70, SEQ ID NO. 72, SEQ ID NO. 73; SEQ ID NO. 67, SEQ ID NO. 68, SEQ ID NO. 69, SEQ ID NO. 70, SEQ ID NO. 72, SEQ ID NO. 74; SEQ ID NO. 67, SEQ ID NO. 68, SEQ ID NO. 69, SEQ ID NO. 70, SEQ ID NO. 72, SEQ ID NO. 75; SEQ ID NO. 67, SEQ ID NO. 68, SEQ ID NO. 69, SEQ ID NO. 70, SEQ ID NO. 73, SEQ ID NO. 74; SEQ ID NO. 67, SEQ ID NO. 68, SEQ ID NO. 69, SEQ ID NO. 70, SEQ ID NO. 73, SEQ ID NO. 75; SEQ ID NO. 67, SEQ ID NO. 68, SEQ ID NO. 69, SEQ ID NO. 70, SEQ ID NO. 74, SEQ ID NO. 75; SEQ ID NO. 67, SEQ ID NO. 68, SEQ ID NO. 69, SEQ ID NO. 71, SEQ ID NO. 72, SEQ ID NO. 73; SEQ ID NO. 67, SEQ ID NO. 68, SEQ ID NO. 69, SEQ ID NO. 71, SEQ ID NO. 72, SEQ ID NO. 74; SEQ ID NO. 67, SEQ ID NO. 68, SEQ ID NO. 69, SEQ ID NO. 71, SEQ ID NO. 72, SEQ ID NO. 75; SEQ ID NO. 67, SEQ ID NO. 68, SEQ ID NO. 69, SEQ ID NO. 71, SEQ ID NO. 73, SEQ ID NO. 74; SEQ ID NO. 67, SEQ ID NO. 68, SEQ ID NO. 69, SEQ ID NO. 71, SEQ ID NO. 73, SEQ ID NO. 75; SEQ ID NO. 67, SEQ ID NO. 68, SEQ ID NO. 69, SEQ ID NO. 71, SEQ ID NO. 74, SEQ ID NO. 75; SEQ ID NO. 67, SEQ ID NO. 68, SEQ ID NO. 69, SEQ ID NO. 72, SEQ ID NO. 73, SEQ ID NO. 74; SEQ ID NO. 67, SEQ ID NO. 68, SEQ ID NO. 69, SEQ ID NO. 72, SEQ ID NO. 73, SEQ ID NO. 75; SEQ ID NO. 67, SEQ ID NO. 68, SEQ ID NO. 69, SEQ ID NO. 72, SEQ ID NO. 74, SEQ ID NO. 75; SEQ ID NO. 67, SEQ ID NO. 68, SEQ ID NO. 69, SEQ ID NO. 73, SEQ ID NO. 74, SEQ ID NO. 75; SEQ ID NO. 67, SEQ ID NO. 68, SEQ ID NO. 70, SEQ ID NO. 71, SEQ ID NO. 72, SEQ ID NO. 73; SEQ ID NO. 67, SEQ ID NO. 68, SEQ ID NO. 70, SEQ ID NO. 71, SEQ ID NO. 72, SEQ ID NO. 74; SEQ ID NO. 67, SEQ ID NO. 68, SEQ ID NO. 70, SEQ ID NO. 71, SEQ ID NO. 72, SEQ ID NO. 75; SEQ ID NO. 67, SEQ ID NO. 68, SEQ ID NO. 70, SEQ ID NO. 71, SEQ ID NO. 73, SEQ ID NO. 74; SEQ ID NO. 67, SEQ ID NO. 68, SEQ ID NO. 70, SEQ ID NO. 71, SEQ ID NO. 73, SEQ ID NO. 75; SEQ ID NO. 67, SEQ ID NO. 68, SEQ ID NO. 70, SEQ ID NO. 71, SEQ ID NO. 74, SEQ ID NO. 75; SEQ ID NO. 67, SEQ ID NO. 68, SEQ ID NO. 70, SEQ ID NO. 72, SEQ ID NO. 73, SEQ ID NO. 74; SEQ ID NO. 67, SEQ ID NO. 68, SEQ ID NO. 70, SEQ ID NO. 72, SEQ ID NO. 73, SEQ ID NO. 75; SEQ ID NO. 67, SEQ ID NO. 68, SEQ ID NO. 70, SEQ ID NO. 72, SEQ ID NO. 74, SEQ ID NO. 75; SEQ ID NO. 67, SEQ ID NO. 68, SEQ ID NO. 70, SEQ ID NO. 73, SEQ ID NO. 74, SEQ ID NO. 75; SEQ ID NO. 67, SEQ ID NO. 68, SEQ ID NO. 71, SEQ ID NO. 72, SEQ ID NO. 73, SEQ ID NO. 74; SEQ ID NO. 67, SEQ ID NO. 68, SEQ ID NO. 71, SEQ ID NO. 72, SEQ ID NO. 73, SEQ ID NO. 75; SEQ ID NO. 67, SEQ ID NO. 68, SEQ ID NO. 71, SEQ ID NO. 72, SEQ ID NO. 74, SEQ ID NO. 75; SEQ ID NO. 67, SEQ ID NO. 68, SEQ ID NO. 71, SEQ ID NO. 73, SEQ ID NO. 74, SEQ ID NO. 75; SEQ ID NO. 67, SEQ ID NO. 68, SEQ ID NO. 72, SEQ ID NO. 73, SEQ ID NO. 74, SEQ ID NO. 75; SEQ ID NO. 67, SEQ ID NO. 69, SEQ ID NO. 70, SEQ ID NO. 71, SEQ ID NO. 72, SEQ ID NO. 73; SEQ ID NO. 67, SEQ ID NO. 69, SEQ ID NO. 70, SEQ ID NO. 71, SEQ ID NO. 72, SEQ ID NO. 74; SEQ ID NO. 67, SEQ ID NO. 69, SEQ ID NO. 70, SEQ ID NO. 71, SEQ ID NO. 72, SEQ ID NO. 75; SEQ ID NO. 67, SEQ ID NO. 69, SEQ ID NO. 70, SEQ ID NO. 71, SEQ ID NO. 73, SEQ ID NO. 74; SEQ ID NO. 67, SEQ ID NO. 69, SEQ ID NO. 70, SEQ ID NO. 71, SEQ ID NO. 73, SEQ ID NO. 75; SEQ ID NO. 67, SEQ ID NO. 69, SEQ ID NO. 70, SEQ ID NO. 71, SEQ ID NO. 74, SEQ ID NO. 75; SEQ ID NO. 67, SEQ ID NO. 69, SEQ ID NO. 70, SEQ ID NO. 72, SEQ ID NO. 73, SEQ ID NO. 74; SEQ ID NO. 67, SEQ ID NO. 69, SEQ ID NO. 70, SEQ ID NO. 72, SEQ ID NO. 73, SEQ ID NO. 75; SEQ ID NO. 67, SEQ ID NO. 69, SEQ ID NO. 70, SEQ ID NO. 72, SEQ ID NO. 74, SEQ ID NO. 75; SEQ ID NO. 67, SEQ ID NO. 69, SEQ ID NO. 70, SEQ ID NO. 73, SEQ ID NO. 74, SEQ ID NO. 75; SEQ ID NO. 67, SEQ ID NO. 69, SEQ ID NO. 71, SEQ ID NO. 72, SEQ ID NO. 73, SEQ ID NO. 74; SEQ ID NO. 67, SEQ ID NO. 69, SEQ ID NO. 71, SEQ ID NO. 72, SEQ ID NO. 73, SEQ ID NO. 75; SEQ ID NO. 67, SEQ ID NO. 69, SEQ ID NO. 71, SEQ ID NO. 72, SEQ ID NO. 74, SEQ ID NO. 75; SEQ ID NO. 67, SEQ ID NO. 69, SEQ ID NO. 71, SEQ ID NO. 73, SEQ ID NO. 74, SEQ ID NO. 75; SEQ ID NO. 67, SEQ ID NO. 69, SEQ ID NO. 72, SEQ ID NO. 73, SEQ ID NO. 74, SEQ ID NO. 75; SEQ ID NO. 67, SEQ ID NO. 70, SEQ ID NO. 71, SEQ ID NO. 72, SEQ ID NO. 73, SEQ ID NO. 74; SEQ ID NO. 67, SEQ ID NO. 70, SEQ ID NO. 71, SEQ ID NO. 72, SEQ ID NO. 73, SEQ ID NO. 75; SEQ ID NO. 67, SEQ ID NO. 70, SEQ ID NO. 71, SEQ ID NO. 72, SEQ ID NO. 74, SEQ ID NO. 75; SEQ ID NO. 67, SEQ ID NO. 70, SEQ ID NO. 71, SEQ ID NO. 73, SEQ ID NO. 74, SEQ ID NO. 75; SEQ ID NO. 67, SEQ ID NO. 70, SEQ ID NO. 72, SEQ ID NO. 73, SEQ ID NO. 74, SEQ ID NO. 75; SEQ ID NO. 67, SEQ ID NO. 71, SEQ ID NO. 72, SEQ ID NO. 73, SEQ ID NO. 74, SEQ ID NO. 75; SEQ ID NO. 68, SEQ ID NO. 69, SEQ ID NO. 70, SEQ ID NO. 71, SEQ ID NO. 72, SEQ ID NO. 73; SEQ ID NO. 68, SEQ ID NO. 69, SEQ ID NO. 70, SEQ ID NO. 71, SEQ ID NO. 72, SEQ ID NO. 74; SEQ ID NO. 68, SEQ ID NO. 69, SEQ ID NO. 70, SEQ ID NO. 71, SEQ ID NO. 72, SEQ ID NO. 75; SEQ ID NO. 68, SEQ ID NO. 69, SEQ ID NO. 70, SEQ ID NO. 71, SEQ ID NO. 73, SEQ ID NO. 74; SEQ ID NO. 68, SEQ ID NO. 69, SEQ ID NO. 70, SEQ ID NO. 71, SEQ ID NO. 73, SEQ ID NO. 75; SEQ ID NO. 68, SEQ ID NO. 69, SEQ ID NO. 70, SEQ ID NO. 71, SEQ ID NO. 74, SEQ ID NO. 75; SEQ ID NO. 68, SEQ ID NO. 69, SEQ ID NO. 70, SEQ ID NO. 72, SEQ ID NO. 73, SEQ ID NO. 74; SEQ ID NO. 68, SEQ ID NO. 69, SEQ ID NO. 70, SEQ ID NO. 72, SEQ ID NO. 73, SEQ ID NO. 75; SEQ ID NO. 68, SEQ ID NO. 69, SEQ ID NO. 70, SEQ ID NO. 72, SEQ ID NO. 74, SEQ ID NO. 75; SEQ ID NO. 68, SEQ ID NO. 69, SEQ ID NO. 70, SEQ ID NO. 73, SEQ ID NO. 74, SEQ ID NO. 75; SEQ ID NO. 68, SEQ ID NO. 69, SEQ ID NO. 71, SEQ ID NO. 72, SEQ ID NO. 73, SEQ ID NO. 74; SEQ ID NO. 68, SEQ ID NO. 69, SEQ ID NO. 71, SEQ ID NO. 72, SEQ ID NO. 73, SEQ ID NO. 75; SEQ ID NO. 68, SEQ ID NO. 69, SEQ ID NO. 71, SEQ ID NO. 72, SEQ ID NO. 74, SEQ ID NO. 75; SEQ ID NO. 68, SEQ ID NO. 69, SEQ ID NO. 71, SEQ ID NO. 73, SEQ ID NO. 74, SEQ ID NO. 75; SEQ ID NO. 68, SEQ ID NO. 69, SEQ ID NO. 72, SEQ ID NO. 73, SEQ ID NO. 74, SEQ ID NO. 75; SEQ ID NO. 68, SEQ ID NO. 70, SEQ ID NO. 71, SEQ ID NO. 72, SEQ ID NO. 73, SEQ ID NO. 74; SEQ ID NO. 68, SEQ ID NO. 70, SEQ ID NO. 71, SEQ ID NO. 72, SEQ ID NO. 73, SEQ ID NO. 75; SEQ ID NO. 68, SEQ ID NO. 70, SEQ ID NO. 71, SEQ ID NO. 72, SEQ ID NO. 74, SEQ ID NO. 75; SEQ ID NO. 68, SEQ ID NO. 70, SEQ ID NO. 71, SEQ ID NO. 73, SEQ ID NO. 74, SEQ ID NO. 75; SEQ ID NO. 68, SEQ ID NO. 70, SEQ ID NO. 72, SEQ ID NO. 73, SEQ ID NO. 74, SEQ ID NO. 75; SEQ ID NO. 68, SEQ ID NO. 71, SEQ ID NO. 72, SEQ ID NO. 73, SEQ ID NO. 74, SEQ ID NO. 75; SEQ ID NO. 69, SEQ ID NO. 70, SEQ ID NO. 71, SEQ ID NO. 72, SEQ ID NO. 73, SEQ ID NO. 74; SEQ ID NO. 69, SEQ ID NO. 70, SEQ ID NO. 71, SEQ ID NO. 72, SEQ ID NO. 73, SEQ ID NO. 75; SEQ ID NO. 69, SEQ ID NO. 70, SEQ ID NO. 71, SEQ ID NO. 72, SEQ ID NO. 74, SEQ ID NO. 75; SEQ ID NO. 69, SEQ ID

TABLE 4-continued

Combinations of amino acid sequences from FIG. 4, to be incorporated in immunogenic peptides for composing an composition of synthetic long peptides in accordance with the invention. The various combination are separated by semicolons.

NO. 70, SEQ ID NO. 71, SEQ ID NO. 73, SEQ ID NO. 74, SEQ ID NO. 75; SEQ ID NO. 69, SEQ ID NO. 70, SEQ ID NO. 72, SEQ ID NO. 73, SEQ ID NO. 74, SEQ ID NO. 75; SEQ ID NO. 69, SEQ ID NO. 71, SEQ ID NO. 72, SEQ ID NO. 73, SEQ ID NO. 74, SEQ ID NO. 75; SEQ ID NO. 70, SEQ ID NO. 71, SEQ ID NO. 72, SEQ ID NO. 73, SEQ ID NO. 74, SEQ ID NO. 75;

Combination of 7 peptides

SEQ ID NO. 66, SEQ ID NO. 67, SEQ ID NO. 68, SEQ ID NO. 69, SEQ ID NO. 70, SEQ ID NO. 71, SEQ ID NO. 72; SEQ ID NO. 66, SEQ ID NO. 67, SEQ ID NO. 68, SEQ ID NO. 69, SEQ ID NO. 70, SEQ ID NO. 71, SEQ ID NO. 73; SEQ ID NO. 66, SEQ ID NO. 67, SEQ ID NO. 68, SEQ ID NO. 69, SEQ ID NO. 70, SEQ ID NO. 71, SEQ ID NO. 74; SEQ ID NO. 66, SEQ ID NO. 67, SEQ ID NO. 68, SEQ ID NO. 69, SEQ ID NO. 70, SEQ ID NO. 71, SEQ ID NO. 75; SEQ ID NO. 66, SEQ ID NO. 67, SEQ ID NO. 68, SEQ ID NO. 69, SEQ ID NO. 70, SEQ ID NO. 72, SEQ ID NO. 73; SEQ ID NO. 66, SEQ ID NO. 67, SEQ ID NO. 68, SEQ ID NO. 69, SEQ ID NO. 70, SEQ ID NO. 72, SEQ ID NO. 74; SEQ ID NO. 66, SEQ ID NO. 67, SEQ ID NO. 68, SEQ ID NO. 69, SEQ ID NO. 70, SEQ ID NO. 72, SEQ ID NO. 75; SEQ ID NO. 66, SEQ ID NO. 67, SEQ ID NO. 68, SEQ ID NO. 69, SEQ ID NO. 70, SEQ ID NO. 73, SEQ ID NO. 74; SEQ ID NO. 66, SEQ ID NO. 67, SEQ ID NO. 68, SEQ ID NO. 69, SEQ ID NO. 70, SEQ ID NO. 73, SEQ ID NO. 75; SEQ ID NO. 66, SEQ ID NO. 67, SEQ ID NO. 68, SEQ ID NO. 69, SEQ ID NO. 70, SEQ ID NO. 74, SEQ ID NO. 75; SEQ ID NO. 66, SEQ ID NO. 67, SEQ ID NO. 68, SEQ ID NO. 69, SEQ ID NO. 71, SEQ ID NO. 72, SEQ ID NO. 73; SEQ ID NO. 66, SEQ ID NO. 67, SEQ ID NO. 68, SEQ ID NO. 69, SEQ ID NO. 71, SEQ ID NO. 72, SEQ ID NO. 74; SEQ ID NO. 66, SEQ ID NO. 67, SEQ ID NO. 68, SEQ ID NO. 69, SEQ ID NO. 71, SEQ ID NO. 72, SEQ ID NO. 75; SEQ ID NO. 66, SEQ ID NO. 67, SEQ ID NO. 68, SEQ ID NO. 69, SEQ ID NO. 71, SEQ ID NO. 73, SEQ ID NO. 74; SEQ ID NO. 66, SEQ ID NO. 67, SEQ ID NO. 68, SEQ ID NO. 69, SEQ ID NO. 71, SEQ ID NO. 73, SEQ ID NO. 75; SEQ ID NO. 66, SEQ ID NO. 67, SEQ ID NO. 68, SEQ ID NO. 69, SEQ ID NO. 71, SEQ ID NO. 74, SEQ ID NO. 75; SEQ ID NO. 66, SEQ ID NO. 67, SEQ ID NO. 68, SEQ ID NO. 69, SEQ ID NO. 72, SEQ ID NO. 73, SEQ ID NO. 74; SEQ ID NO. 66, SEQ ID NO. 67, SEQ ID NO. 68, SEQ ID NO. 69, SEQ ID NO. 72, SEQ ID NO. 73, SEQ ID NO. 75; SEQ ID NO. 66, SEQ ID NO. 67, SEQ ID NO. 68, SEQ ID NO. 69, SEQ ID NO. 72, SEQ ID NO. 74, SEQ ID NO. 75; SEQ ID NO. 66, SEQ ID NO. 67, SEQ ID NO. 68, SEQ ID NO. 69, SEQ ID NO. 73, SEQ ID NO. 74, SEQ ID NO. 75; SEQ ID NO. 66, SEQ ID NO. 67, SEQ ID NO. 68, SEQ ID NO. 70, SEQ ID NO. 71, SEQ ID NO. 72, SEQ ID NO. 73; SEQ ID NO. 66, SEQ ID NO. 67, SEQ ID NO. 68, SEQ ID NO. 70, SEQ ID NO. 71, SEQ ID NO. 72, SEQ ID NO. 74; SEQ ID NO. 66, SEQ ID NO. 67, SEQ ID NO. 68, SEQ ID NO. 70, SEQ ID NO. 71, SEQ ID NO. 72, SEQ ID NO. 75; SEQ ID NO. 66, SEQ ID NO. 67, SEQ ID NO. 68, SEQ ID NO. 70, SEQ ID NO. 71, SEQ ID NO. 73, SEQ ID NO. 74; SEQ ID NO. 66, SEQ ID NO. 67, SEQ ID NO. 68, SEQ ID NO. 70, SEQ ID NO. 71, SEQ ID NO. 73, SEQ ID NO. 75; SEQ ID NO. 66, SEQ ID NO. 67, SEQ ID NO. 68, SEQ ID NO. 70, SEQ ID NO. 71, SEQ ID NO. 74, SEQ ID NO. 75; SEQ ID NO. 66, SEQ ID NO. 67, SEQ ID NO. 68, SEQ ID NO. 70, SEQ ID NO. 72, SEQ ID NO. 73, SEQ ID NO. 74; SEQ ID NO. 66, SEQ ID NO. 67, SEQ ID NO. 68, SEQ ID NO. 70, SEQ ID NO. 72, SEQ ID NO. 73, SEQ ID NO. 75; SEQ ID NO. 66, SEQ ID NO. 67, SEQ ID NO. 68, SEQ ID NO. 70, SEQ ID NO. 72, SEQ ID NO. 74, SEQ ID NO. 75; SEQ ID NO. 66, SEQ ID NO. 67, SEQ ID NO. 68, SEQ ID NO. 71, SEQ ID NO. 72, SEQ ID NO. 73, SEQ ID NO. 74; SEQ ID NO. 66, SEQ ID NO. 67, SEQ ID NO. 68, SEQ ID NO. 71, SEQ ID NO. 72, SEQ ID NO. 73, SEQ ID NO. 75; SEQ ID NO. 66, SEQ ID NO. 67, SEQ ID NO. 68, SEQ ID NO. 71, SEQ ID NO. 72, SEQ ID NO. 74, SEQ ID NO. 75; SEQ ID NO. 66, SEQ ID NO. 67, SEQ ID NO. 68, SEQ ID NO. 71, SEQ ID NO. 73, SEQ ID NO. 74, SEQ ID NO. 75; SEQ ID NO. 66, SEQ ID NO. 67, SEQ ID NO. 68, SEQ ID NO. 72, SEQ ID NO. 73, SEQ ID NO. 74, SEQ ID NO. 75; SEQ ID NO. 66, SEQ ID NO. 67, SEQ ID NO. 69, SEQ ID NO. 70, SEQ ID NO. 71, SEQ ID NO. 72, SEQ ID NO. 73; SEQ ID NO. 66, SEQ ID NO. 67, SEQ ID NO. 69, SEQ ID NO. 70, SEQ ID NO. 71, SEQ ID NO. 72, SEQ ID NO. 74; SEQ ID NO. 66, SEQ ID NO. 67, SEQ ID NO. 69, SEQ ID NO. 70, SEQ ID NO. 71, SEQ ID NO. 72, SEQ ID NO. 75; SEQ ID NO. 66, SEQ ID NO. 67, SEQ ID NO. 69, SEQ ID NO. 70, SEQ ID NO. 71, SEQ ID NO. 73, SEQ ID NO. 74; SEQ ID NO. 66, SEQ ID NO. 67, SEQ ID NO. 69, SEQ ID NO. 70, SEQ ID NO. 71, SEQ ID NO. 73, SEQ ID NO. 75; SEQ ID NO. 66, SEQ ID NO. 67, SEQ ID NO. 69, SEQ ID NO. 70, SEQ ID NO. 71, SEQ ID NO. 74, SEQ ID NO. 75; SEQ ID NO. 66, SEQ ID NO. 67, SEQ ID NO. 69, SEQ ID NO. 70, SEQ ID NO. 72, SEQ ID NO. 73, SEQ ID NO. 74; SEQ ID NO. 66, SEQ ID NO. 67, SEQ ID NO. 69, SEQ ID NO. 70, SEQ ID NO. 72, SEQ ID NO. 73, SEQ ID NO. 75; SEQ ID NO. 66, SEQ ID NO. 67, SEQ ID NO. 69, SEQ ID NO. 70, SEQ ID NO. 72, SEQ ID NO. 74, SEQ ID NO. 75; SEQ ID NO. 66, SEQ ID NO. 67, SEQ ID NO. 69, SEQ ID NO. 70, SEQ ID NO. 73, SEQ ID NO. 74, SEQ ID NO. 75; SEQ ID NO. 66, SEQ ID NO. 67, SEQ ID NO. 69, SEQ ID NO. 71, SEQ ID NO. 72, SEQ ID NO. 73, SEQ ID NO. 74; SEQ ID NO. 66, SEQ ID NO. 67, SEQ ID NO. 69, SEQ ID NO. 71, SEQ ID NO. 72, SEQ ID NO. 73, SEQ ID NO. 75; SEQ ID NO. 66, SEQ ID NO. 67, SEQ ID NO. 69, SEQ ID NO. 72, SEQ ID NO. 73, SEQ ID NO. 74, SEQ ID NO. 75; SEQ ID NO. 66, SEQ ID NO. 67, SEQ ID NO. 70, SEQ ID NO. 71, SEQ ID NO. 72, SEQ ID NO. 73, SEQ ID NO. 74; SEQ ID NO. 66, SEQ ID NO. 67, SEQ ID NO. 70, SEQ ID NO. 71, SEQ ID NO. 72, SEQ ID NO. 73, SEQ ID NO. 75; SEQ ID NO. 66, SEQ ID NO. 67, SEQ ID NO. 70, SEQ ID NO. 71, SEQ ID NO. 72, SEQ ID NO. 74, SEQ ID NO. 75; SEQ ID NO. 66, SEQ ID NO. 67, SEQ ID NO. 70, SEQ ID NO. 71, SEQ ID NO. 73, SEQ ID NO. 74, SEQ ID NO. 75; SEQ ID NO. 66, SEQ ID NO. 68, SEQ ID NO. 69, SEQ ID NO. 70, SEQ ID NO. 71, SEQ ID NO. 72, SEQ ID NO. 73; SEQ ID NO. 66, SEQ ID NO. 68, SEQ ID NO. 69, SEQ ID NO. 70, SEQ ID NO. 71, SEQ ID NO. 72, SEQ ID NO. 74; SEQ ID NO. 66, SEQ ID NO. 68, SEQ ID NO. 69, SEQ ID NO. 70, SEQ ID NO. 71, SEQ ID NO. 72, SEQ ID NO. 75; SEQ ID NO. 66, SEQ ID NO. 68, SEQ ID NO. 69, SEQ ID NO. 70, SEQ ID NO. 71, SEQ ID NO. 73, SEQ ID NO. 74; SEQ ID NO. 66, SEQ ID NO. 68, SEQ ID NO. 69, SEQ ID NO. 70, SEQ ID NO. 71, SEQ ID NO. 73, SEQ ID NO. 75; SEQ ID NO. 66, SEQ ID NO. 68, SEQ ID NO. 69, SEQ ID NO. 70, SEQ ID NO. 71, SEQ ID NO. 74, SEQ ID NO. 75; SEQ ID NO. 66, SEQ ID NO. 68, SEQ ID NO. 69, SEQ ID

TABLE 4-continued

Combinations of amino acid sequences from FIG. 4, to be incorporated in immunogenic peptides for composing an composition of synthetic long peptides in accordance with the invention. The various combination are separated by semicolons.

NO. 70, SEQ ID NO. 72, SEQ ID NO. 73, SEQ ID NO. 74; SEQ ID NO. 66, SEQ ID NO. 68, SEQ ID NO. 69, SEQ ID NO. 70, SEQ ID NO. 72, SEQ ID NO. 73, SEQ ID NO. 75; SEQ ID NO. 66, SEQ ID NO. 68, SEQ ID NO. 69, SEQ ID NO. 70, SEQ ID NO. 72, SEQ ID NO. 74, SEQ ID NO. 75; SEQ ID NO. 66, SEQ ID NO. 68, SEQ ID NO. 69, SEQ ID NO. 70, SEQ ID NO. 73, SEQ ID NO. 74, SEQ ID NO. 75; SEQ ID NO. 66, SEQ ID NO. 68, SEQ ID NO. 69, SEQ ID NO. 71, SEQ ID NO. 72, SEQ ID NO. 73, SEQ ID NO. 74; SEQ ID NO. 66, SEQ ID NO. 68, SEQ ID NO. 69, SEQ ID NO. 71, SEQ ID NO. 72, SEQ ID NO. 73, SEQ ID NO. 75; SEQ ID NO. 66, SEQ ID NO. 68, SEQ ID NO. 69, SEQ ID NO. 71, SEQ ID NO. 72, SEQ ID NO. 74, SEQ ID NO. 75; SEQ ID NO. 66, SEQ ID NO. 68, SEQ ID NO. 69, SEQ ID NO. 71, SEQ ID NO. 73, SEQ ID NO. 74, SEQ ID NO. 75; SEQ ID NO. 66, SEQ ID NO. 68, SEQ ID NO. 69, SEQ ID NO. 72, SEQ ID NO. 73, SEQ ID NO. 74, SEQ ID NO. 75; SEQ ID NO. 66, SEQ ID NO. 68, SEQ ID NO. 70, SEQ ID NO. 71, SEQ ID NO. 72, SEQ ID NO. 73, SEQ ID NO. 74; SEQ ID NO. 66, SEQ ID NO. 68, SEQ ID NO. 70, SEQ ID NO. 71, SEQ ID NO. 72, SEQ ID NO. 73, SEQ ID NO. 75; SEQ ID NO. 66, SEQ ID NO. 68, SEQ ID NO. 70, SEQ ID NO. 71, SEQ ID NO. 72, SEQ ID NO. 74, SEQ ID NO. 75; SEQ ID NO. 66, SEQ ID NO. 68, SEQ ID NO. 70, SEQ ID NO. 71, SEQ ID NO. 73, SEQ ID NO. 74, SEQ ID NO. 75; SEQ ID NO. 66, SEQ ID NO. 68, SEQ ID NO. 70, SEQ ID NO. 72, SEQ ID NO. 73, SEQ ID NO. 74, SEQ ID NO. 75; SEQ ID NO. 66, SEQ ID NO. 68, SEQ ID NO. 71, SEQ ID NO. 72, SEQ ID NO. 73, SEQ ID NO. 74, SEQ ID NO. 75; SEQ ID NO. 66, SEQ ID NO. 69, SEQ ID NO. 70, SEQ ID NO. 71, SEQ ID NO. 72, SEQ ID NO. 73, SEQ ID NO. 74; SEQ ID NO. 66, SEQ ID NO. 69, SEQ ID NO. 70, SEQ ID NO. 71, SEQ ID NO. 72, SEQ ID NO. 73, SEQ ID NO. 75; SEQ ID NO. 66, SEQ ID NO. 69, SEQ ID NO. 70, SEQ ID NO. 71, SEQ ID NO. 72, SEQ ID NO. 74, SEQ ID NO. 75; SEQ ID NO. 66, SEQ ID NO. 69, SEQ ID NO. 70, SEQ ID NO. 71, SEQ ID NO. 73, SEQ ID NO. 74, SEQ ID NO. 75; SEQ ID NO. 66, SEQ ID NO. 69, SEQ ID NO. 70, SEQ ID NO. 72, SEQ ID NO. 73, SEQ ID NO. 74, SEQ ID NO. 75; SEQ ID NO. 66, SEQ ID NO. 69, SEQ ID NO. 71, SEQ ID NO. 72, SEQ ID NO. 73, SEQ ID NO. 74, SEQ ID NO. 75; SEQ ID NO. 66, SEQ ID NO. 70, SEQ ID NO. 71, SEQ ID NO. 72, SEQ ID NO. 73, SEQ ID NO. 74, SEQ ID NO. 75; SEQ ID NO. 67, SEQ ID NO. 68, SEQ ID NO. 69, SEQ ID NO. 70, SEQ ID NO. 71, SEQ ID NO. 72, SEQ ID NO. 73; SEQ ID NO. 67, SEQ ID NO. 68, SEQ ID NO. 69, SEQ ID NO. 70, SEQ ID NO. 71, SEQ ID NO. 72, SEQ ID NO. 74; SEQ ID NO. 67, SEQ ID NO. 68, SEQ ID NO. 69, SEQ ID NO. 70, SEQ ID NO. 71, SEQ ID NO. 72, SEQ ID NO. 75; SEQ ID NO. 67, SEQ ID NO. 68, SEQ ID NO. 69, SEQ ID NO. 70, SEQ ID NO. 71, SEQ ID NO. 73, SEQ ID NO. 74; SEQ ID NO. 67, SEQ ID NO. 68, SEQ ID NO. 69, SEQ ID NO. 70, SEQ ID NO. 71, SEQ ID NO. 73, SEQ ID NO. 75; SEQ ID NO. 67, SEQ ID NO. 68, SEQ ID NO. 69, SEQ ID NO. 70, SEQ ID NO. 71, SEQ ID NO. 74, SEQ ID NO. 75; SEQ ID NO. 67, SEQ ID NO. 68, SEQ ID NO. 69, SEQ ID NO. 70, SEQ ID NO. 72, SEQ ID NO. 73, SEQ ID NO. 74; SEQ ID NO. 67, SEQ ID NO. 68, SEQ ID NO. 69, SEQ ID NO. 70, SEQ ID NO. 72, SEQ ID NO. 73, SEQ ID NO. 75; SEQ ID NO. 67, SEQ ID NO. 68, SEQ ID NO. 69, SEQ ID NO. 70, SEQ ID NO. 72, SEQ ID NO. 74, SEQ ID NO. 75; SEQ ID NO. 67, SEQ ID NO. 68, SEQ ID NO. 69, SEQ ID NO. 70, SEQ ID NO. 73, SEQ ID NO. 74, SEQ ID NO. 75; SEQ ID NO. 67, SEQ ID NO. 68, SEQ ID NO. 69, SEQ ID NO. 71, SEQ ID NO. 72, SEQ ID NO. 73, SEQ ID NO. 74; SEQ ID NO. 67, SEQ ID NO. 68, SEQ ID NO. 69, SEQ ID NO. 71, SEQ ID NO. 72, SEQ ID NO. 73, SEQ ID NO. 75; SEQ ID NO. 67, SEQ ID NO. 68, SEQ ID NO. 69, SEQ ID NO. 71, SEQ ID NO. 72, SEQ ID NO. 74, SEQ ID NO. 75; SEQ ID NO. 67, SEQ ID NO. 68, SEQ ID NO. 69, SEQ ID NO. 71, SEQ ID NO. 73, SEQ ID NO. 74, SEQ ID NO. 75; SEQ ID NO. 67, SEQ ID NO. 68, SEQ ID NO. 69, SEQ ID NO. 72, SEQ ID NO. 73, SEQ ID NO. 74, SEQ ID NO. 75; SEQ ID NO. 67, SEQ ID NO. 68, SEQ ID NO. 70, SEQ ID NO. 71, SEQ ID NO. 72, SEQ ID NO. 73, SEQ ID NO. 74; SEQ ID NO. 67, SEQ ID NO. 68, SEQ ID NO. 70, SEQ ID NO. 71, SEQ ID NO. 72, SEQ ID NO. 73, SEQ ID NO. 75; SEQ ID NO. 67, SEQ ID NO. 68, SEQ ID NO. 70, SEQ ID NO. 71, SEQ ID NO. 72, SEQ ID NO. 74, SEQ ID NO. 75; SEQ ID NO. 67, SEQ ID NO. 68, SEQ ID NO. 70, SEQ ID NO. 71, SEQ ID NO. 73, SEQ ID NO. 74, SEQ ID NO. 75; SEQ ID NO. 67, SEQ ID NO. 68, SEQ ID NO. 70, SEQ ID NO. 72, SEQ ID NO. 73, SEQ ID NO. 74, SEQ ID NO. 75; SEQ ID NO. 67, SEQ ID NO. 68, SEQ ID NO. 71, SEQ ID NO. 72, SEQ ID NO. 73, SEQ ID NO. 74, SEQ ID NO. 75; SEQ ID NO. 67, SEQ ID NO. 69, SEQ ID NO. 70, SEQ ID NO. 71, SEQ ID NO. 72, SEQ ID NO. 73, SEQ ID NO. 74; SEQ ID NO. 67, SEQ ID NO. 69, SEQ ID NO. 70, SEQ ID NO. 71, SEQ ID NO. 72, SEQ ID NO. 73, SEQ ID NO. 75; SEQ ID NO. 67, SEQ ID NO. 69, SEQ ID NO. 70, SEQ ID NO. 71, SEQ ID NO. 72, SEQ ID NO. 74, SEQ ID NO. 75; SEQ ID NO. 67, SEQ ID NO. 69, SEQ ID NO. 70, SEQ ID NO. 71, SEQ ID NO. 73, SEQ ID NO. 74, SEQ ID NO. 75; SEQ ID NO. 67, SEQ ID NO. 69, SEQ ID NO. 70, SEQ ID NO. 72, SEQ ID NO. 73, SEQ ID NO. 74, SEQ ID NO. 75; SEQ ID NO. 67, SEQ ID NO. 69, SEQ ID NO. 71, SEQ ID NO. 72, SEQ ID NO. 73, SEQ ID NO. 74, SEQ ID NO. 75; SEQ ID NO. 67, SEQ ID NO. 70, SEQ ID NO. 71, SEQ ID NO. 72, SEQ ID NO. 73, SEQ ID NO. 74, SEQ ID NO. 75; SEQ ID NO. 68, SEQ ID NO. 69, SEQ ID NO. 70, SEQ ID NO. 71, SEQ ID NO. 72, SEQ ID NO. 73, SEQ ID NO. 74; SEQ ID NO. 68, SEQ ID NO. 69, SEQ ID NO. 70, SEQ ID NO. 71, SEQ ID NO. 72, SEQ ID NO. 73, SEQ ID NO. 75; SEQ ID NO. 68, SEQ ID NO. 69, SEQ ID NO. 70, SEQ ID NO. 71, SEQ ID NO. 72, SEQ ID NO. 74, SEQ ID NO. 75; SEQ ID NO. 68, SEQ ID NO. 69, SEQ ID NO. 70, SEQ ID NO. 71, SEQ ID NO. 73, SEQ ID NO. 74, SEQ ID NO. 75; SEQ ID NO. 68, SEQ ID NO. 69, SEQ ID NO. 70, SEQ ID NO. 72, SEQ ID NO. 73, SEQ ID NO. 74, SEQ ID NO. 75; SEQ ID NO. 68, SEQ ID NO. 69, SEQ ID NO. 71, SEQ ID NO. 72, SEQ ID NO. 73, SEQ ID NO. 74, SEQ ID NO. 75; SEQ ID NO. 68, SEQ ID NO. 70, SEQ ID NO. 71, SEQ ID NO. 72, SEQ ID NO. 73, SEQ ID NO. 74, SEQ ID NO. 75; SEQ ID NO. 69, SEQ ID NO. 70, SEQ ID NO. 71, SEQ ID NO. 72, SEQ ID NO. 73, SEQ ID NO. 74, SEQ ID NO. 75;

Combination of 8 peptides

SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73; SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 74; SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 75; SEQ ID NO. 66, SEQ ID NO. 67, SEQ ID NO. 68, SEQ ID NO. 69, SEQ ID NO. 70, SEQ ID NO. 71, SEQ ID NO. 73, SEQ ID NO. 74; SEQ ID NO. 66, SEQ ID NO. 67, SEQ ID NO. 68, SEQ ID NO. 69, SEQ ID NO. 70, SEQ ID NO. 71, SEQ ID NO. 73, SEQ ID NO. 75; SEQ ID NO. 66, SEQ ID NO. 67, SEQ ID NO. 68, SEQ ID NO. 69, SEQ ID NO. 70, SEQ ID NO. 71, SEQ ID NO. 74, SEQ ID NO. 75; SEQ ID NO. 66, SEQ ID NO. 67, SEQ ID NO. 68, SEQ ID NO. 69, SEQ ID NO. 70, SEQ ID NO. 72, SEQ ID NO. 73, SEQ ID NO. 74; SEQ

TABLE 4-continued

Combinations of amino acid sequences from FIG. 4, to be incorporated in immunogenic peptides for composing an composition of synthetic long peptides in accordance with the invention. The various combination are separated by semicolons.

ID NO. 66, SEQ ID NO. 67, SEQ ID NO. 68, SEQ ID NO. 69, SEQ ID NO. 70, SEQ ID NO. 72, SEQ ID NO. 73, SEQ ID NO. 75; SEQ ID NO. 66, SEQ ID NO. 67, SEQ ID NO. 68, SEQ ID NO. 69, SEQ ID NO. 70, SEQ ID NO. 72, SEQ ID NO. 74, SEQ ID NO. 75; SEQ ID NO. 66, SEQ ID NO. 67, SEQ ID NO. 68, SEQ ID NO. 69, SEQ ID NO. 70, SEQ ID NO. 73, SEQ ID NO. 74, SEQ ID NO. 75; SEQ ID NO. 66, SEQ ID NO. 67, SEQ ID NO. 68, SEQ ID NO. 69, SEQ ID NO. 71, SEQ ID NO. 72, SEQ ID NO. 73, SEQ ID NO. 74; SEQ ID NO. 66, SEQ ID NO. 67, SEQ ID NO. 68, SEQ ID NO. 69, SEQ ID NO. 71, SEQ ID NO. 72, SEQ ID NO. 73, SEQ ID NO. 75; SEQ ID NO. 66, SEQ ID NO. 67, SEQ ID NO. 68, SEQ ID NO. 69, SEQ ID NO. 71, SEQ ID NO. 72, SEQ ID NO. 74, SEQ ID NO. 75; SEQ ID NO. 66, SEQ ID NO. 67, SEQ ID NO. 68, SEQ ID NO. 69, SEQ ID NO. 71, SEQ ID NO. 73, SEQ ID NO. 74, SEQ ID NO. 75; SEQ ID NO. 66, SEQ ID NO. 67, SEQ ID NO. 68, SEQ ID NO. 69, SEQ ID NO. 72, SEQ ID NO. 73, SEQ ID NO. 74, SEQ ID NO. 75; SEQ ID NO. 66, SEQ ID NO. 67, SEQ ID NO. 68, SEQ ID NO. 70, SEQ ID NO. 71, SEQ ID NO. 72, SEQ ID NO. 73, SEQ ID NO. 74; SEQ ID NO. 66, SEQ ID NO. 67, SEQ ID NO. 68, SEQ ID NO. 70, SEQ ID NO. 71, SEQ ID NO. 72, SEQ ID NO. 73, SEQ ID NO. 75; SEQ ID NO. 66, SEQ ID NO. 67, SEQ ID NO. 68, SEQ ID NO. 70, SEQ ID NO. 71, SEQ ID NO. 72, SEQ ID NO. 74, SEQ ID NO. 75; SEQ ID NO. 66, SEQ ID NO. 67, SEQ ID NO. 68, SEQ ID NO. 70, SEQ ID NO. 71, SEQ ID NO. 73, SEQ ID NO. 74, SEQ ID NO. 75; SEQ ID NO. 66, SEQ ID NO. 67, SEQ ID NO. 68, SEQ ID NO. 70, SEQ ID NO. 72, SEQ ID NO. 73, SEQ ID NO. 74, SEQ ID NO. 75; SEQ ID NO. 66, SEQ ID NO. 67, SEQ ID NO. 68, SEQ ID NO. 71, SEQ ID NO. 72, SEQ ID NO. 73, SEQ ID NO. 74, SEQ ID NO. 75; SEQ ID NO. 66, SEQ ID NO. 67, SEQ ID NO. 69, SEQ ID NO. 70, SEQ ID NO. 71, SEQ ID NO. 72, SEQ ID NO. 73, SEQ ID NO. 74; SEQ ID NO. 66, SEQ ID NO. 67, SEQ ID NO. 69, SEQ ID NO. 70, SEQ ID NO. 71, SEQ ID NO. 72, SEQ ID NO. 73, SEQ ID NO. 75; SEQ ID NO. 66, SEQ ID NO. 67, SEQ ID NO. 69, SEQ ID NO. 70, SEQ ID NO. 71, SEQ ID NO. 72, SEQ ID NO. 74, SEQ ID NO. 75; SEQ ID NO. 66, SEQ ID NO. 67, SEQ ID NO. 69, SEQ ID NO. 70, SEQ ID NO. 71, SEQ ID NO. 73, SEQ ID NO. 74, SEQ ID NO. 75; SEQ ID NO. 66, SEQ ID NO. 67, SEQ ID NO. 69, SEQ ID NO. 70, SEQ ID NO. 72, SEQ ID NO. 73, SEQ ID NO. 74, SEQ ID NO. 75; SEQ ID NO. 66, SEQ ID NO. 67, SEQ ID NO. 69, SEQ ID NO. 71, SEQ ID NO. 72, SEQ ID NO. 73, SEQ ID NO. 74, SEQ ID NO. 75; SEQ ID NO. 66, SEQ ID NO. 67, SEQ ID NO. 70, SEQ ID NO. 71, SEQ ID NO. 72, SEQ ID NO. 73, SEQ ID NO. 74, SEQ ID NO. 75; SEQ ID NO. 66, SEQ ID NO. 68, SEQ ID NO. 69, SEQ ID NO. 70, SEQ ID NO. 71, SEQ ID NO. 72, SEQ ID NO. 73, SEQ ID NO. 74; SEQ ID NO. 66, SEQ ID NO. 68, SEQ ID NO. 69, SEQ ID NO. 70, SEQ ID NO. 71, SEQ ID NO. 72, SEQ ID NO. 73, SEQ ID NO. 75; SEQ ID NO. 66, SEQ ID NO. 68, SEQ ID NO. 69, SEQ ID NO. 71, SEQ ID NO. 72, SEQ ID NO. 74, SEQ ID NO. 75; SEQ ID NO. 66, SEQ ID NO. 68, SEQ ID NO. 69, SEQ ID NO. 70, SEQ ID NO. 71, SEQ ID NO. 73, SEQ ID NO. 74, SEQ ID NO. 75; SEQ ID NO. 66, SEQ ID NO. 68, SEQ ID NO. 69, SEQ ID NO. 70, SEQ ID NO. 72, SEQ ID NO. 73, SEQ ID NO. 74, SEQ ID NO. 75; SEQ ID NO. 66, SEQ ID NO. 68, SEQ ID NO. 69, SEQ ID NO. 71, SEQ ID NO. 72, SEQ ID NO. 73, SEQ ID NO. 74, SEQ ID NO. 75; SEQ ID NO. 66, SEQ ID NO. 68, SEQ ID NO. 70, SEQ ID NO. 71, SEQ ID NO. 72, SEQ ID NO. 73, SEQ ID NO. 74, SEQ ID NO. 75; SEQ ID NO. 66, SEQ ID NO. 69, SEQ ID NO. 70, SEQ ID NO. 71, SEQ ID NO. 72, SEQ ID NO. 73, SEQ ID NO. 74, SEQ ID NO. 75; SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74; SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 75; SEQ ID NO. 67, SEQ ID NO. 68, SEQ ID NO. 69, SEQ ID NO. 70, SEQ ID NO. 71, SEQ ID NO. 72, SEQ ID NO. 74, SEQ ID NO. 75; SEQ ID NO. 67, SEQ ID NO. 68, SEQ ID NO. 69, SEQ ID NO. 70, SEQ ID NO. 71, SEQ ID NO. 73, SEQ ID NO. 74, SEQ ID NO. 75; SEQ ID NO. 67, SEQ ID NO. 68, SEQ ID NO. 69, SEQ ID NO. 70, SEQ ID NO. 72, SEQ ID NO. 73, SEQ ID NO. 74, SEQ ID NO. 75; SEQ ID NO. 67, SEQ ID NO. 68, SEQ ID NO. 69, SEQ ID NO. 71, SEQ ID NO. 72, SEQ ID NO. 73, SEQ ID NO. 74, SEQ ID NO. 75; SEQ ID NO. 67, SEQ ID NO. 68, SEQ ID NO. 70, SEQ ID NO. 71, SEQ ID NO. 72, SEQ ID NO. 73, SEQ ID NO. 74, SEQ ID NO. 75; SEQ ID NO. 67, SEQ ID NO. 69, SEQ ID NO. 70, SEQ ID NO. 71, SEQ ID NO. 72, SEQ ID NO. 73, SEQ ID NO. 74, SEQ ID NO. 75; SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75;

Combination of 9 peptides

SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74; SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 75; SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 74, SEQ ID NO. 75; SEQ ID NO. 66, SEQ ID NO. 67, SEQ ID NO. 68, SEQ ID NO. 69, SEQ ID NO. 70, SEQ ID NO. 71, SEQ ID NO. 73, SEQ ID NO. 74, SEQ ID NO. 75; SEQ ID NO. 66, SEQ ID NO. 67, SEQ ID NO. 68, SEQ ID NO. 69, SEQ ID NO. 70, SEQ ID NO. 72, SEQ ID NO. 73, SEQ ID NO. 74, SEQ ID NO. 75; SEQ ID NO. 66, SEQ ID NO. 67, SEQ ID NO. 68, SEQ ID NO. 69, SEQ ID NO. 71, SEQ ID NO. 72, SEQ ID NO. 73, SEQ ID NO. 74, SEQ ID NO. 75; SEQ ID NO. 66, SEQ ID NO. 67, SEQ ID NO. 68, SEQ ID NO. 70, SEQ ID NO. 71, SEQ ID NO. 72, SEQ ID NO. 73, SEQ ID NO. 74, SEQ ID NO. 75; SEQ ID NO. 66, SEQ ID NO. 67, SEQ ID NO. 69, SEQ ID NO. 70, SEQ ID NO. 71, SEQ ID NO. 72, SEQ ID NO. 73, SEQ ID NO. 74, SEQ ID NO. 75; SEQ ID NO. 66, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75; SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75;

TABLE 6

Combinations of amino acid sequences from Table 5, to be incorporated in immunogenic peptides for composing an composition of synthetic long peptides in accordance with the invention. The various combination are separated by semicolons.

Combination of 2 peptides

SEQ ID NO. 76, SEQ ID NO. 77; SEQ ID NO. 76, SEQ ID NO. 78; SEQ ID NO. 76, SEQ ID NO. 79; SEQ ID NO. 76, SEQ ID NO. 80; SEQ ID NO. 76, SEQ ID NO. 81; SEQ ID NO. 76, SEQ ID NO. 82; SEQ ID NO. 76, SEQ ID NO. 83; SEQ ID NO. 76, SEQ ID NO. 84; SEQ ID NO. 76, SEQ ID NO. 85; SEQ ID NO. 77, SEQ ID NO. 78; SEQ ID NO. 77, SEQ ID NO. 79; SEQ ID NO. 77, SEQ ID NO. 80; SEQ ID NO. 77, SEQ ID NO. 81; SEQ ID NO. 77, SEQ ID NO. 82; SEQ ID NO. 77, SEQ ID NO. 83; SEQ ID NO. 77, SEQ ID NO. 84; SEQ ID NO. 77, SEQ ID NO. 85; SEQ ID NO. 78, SEQ ID NO. 79; SEQ ID NO. 78, SEQ ID NO. 80; SEQ ID NO. 78, SEQ ID NO. 81; SEQ ID NO. 78, SEQ ID NO. 82; SEQ ID NO. 78, SEQ ID NO. 83; SEQ ID NO. 78, SEQ ID NO. 84; SEQ ID NO. 78, SEQ ID NO. 85; SEQ ID NO. 79, SEQ ID NO. 80; SEQ ID NO. 79, SEQ ID NO. 81; SEQ ID NO. 79, SEQ ID NO. 82; SEQ ID NO. 79, SEQ ID NO. 83; SEQ ID NO. 79, SEQ ID NO. 84; SEQ ID NO. 79, SEQ ID NO. 85; SEQ ID NO. 80, SEQ ID NO. 81; SEQ ID NO. 80, SEQ ID NO. 82; SEQ ID NO. 80, SEQ ID NO. 83; SEQ ID NO. 80, SEQ ID NO. 84; SEQ ID NO. 80, SEQ ID NO. 85; SEQ ID NO. 81, SEQ ID NO. 82; SEQ ID NO. 81, SEQ ID NO. 83; SEQ ID NO. 81, SEQ ID NO. 84; SEQ ID NO. 81, SEQ ID NO. 85; SEQ ID NO. 82, SEQ ID NO. 83; SEQ ID NO. 82, SEQ ID NO. 84; SEQ ID NO. 82, SEQ ID NO. 85; SEQ ID NO. 83, SEQ ID NO. 84; SEQ ID NO. 83, SEQ ID NO. 85; SEQ ID NO. 84, SEQ ID NO. 85;

Combination of 3 peptides

SEQ ID NO. 76, SEQ ID NO. 77, SEQ ID NO. 78; SEQ ID NO. 76, SEQ ID NO. 77, SEQ ID NO. 79; SEQ ID NO. 76, SEQ ID NO. 77, SEQ ID NO. 80; SEQ ID NO. 76, SEQ ID NO. 77, SEQ ID NO. 81; SEQ ID NO. 76, SEQ ID NO. 77, SEQ ID NO. 82; SEQ ID NO. 76, SEQ ID NO. 77, SEQ ID NO. 83; SEQ ID NO. 76, SEQ ID NO. 77, SEQ ID NO. 84; SEQ ID NO. 76, SEQ ID NO. 77, SEQ ID NO. 85; SEQ ID NO. 76, SEQ ID NO. 78, SEQ ID NO. 79; SEQ ID NO. 76, SEQ ID NO. 78, SEQ ID NO. 80; SEQ ID NO. 76, SEQ ID NO. 78, SEQ ID NO. 81; SEQ ID NO. 76, SEQ ID NO. 78, SEQ ID NO. 82; SEQ ID NO. 76, SEQ ID NO. 78, SEQ ID NO. 83; SEQ ID NO. 76, SEQ ID NO. 78, SEQ ID NO. 84; SEQ ID NO. 76, SEQ ID NO. 78, SEQ ID NO. 85; SEQ ID NO. 76, SEQ ID NO. 79, SEQ ID NO. 80; SEQ ID NO. 76, SEQ ID NO. 79, SEQ ID NO. 81; SEQ ID NO. 76, SEQ ID NO. 79, SEQ ID NO. 82; SEQ ID NO. 76, SEQ ID NO. 79, SEQ ID NO. 83; SEQ ID NO. 76, SEQ ID NO. 79, SEQ ID NO. 84; SEQ ID NO. 76, SEQ ID NO. 79, SEQ ID NO. 85; SEQ ID NO. 76, SEQ ID NO. 80, SEQ ID NO. 81; SEQ ID NO. 76, SEQ ID NO. 80, SEQ ID NO. 82; SEQ ID NO. 76, SEQ ID NO. 80, SEQ ID NO. 83; SEQ ID NO. 76, SEQ ID NO. 80, SEQ ID NO. 84; SEQ ID NO. 76, SEQ ID NO. 80, SEQ ID NO. 85; SEQ ID NO. 76, SEQ ID NO. 81, SEQ ID NO. 82; SEQ ID NO. 76, SEQ ID NO. 81, SEQ ID NO. 83; SEQ ID NO. 76, SEQ ID NO. 81, SEQ ID NO. 84; SEQ ID NO. 76, SEQ ID NO. 81, SEQ ID NO. 85; SEQ ID NO. 76, SEQ ID NO. 82, SEQ ID NO. 83; SEQ ID NO. 76, SEQ ID NO. 82, SEQ ID NO. 84; SEQ ID NO. 76, SEQ ID NO. 82, SEQ ID NO. 85; SEQ ID NO. 76, SEQ ID NO. 83, SEQ ID NO. 84; SEQ ID NO. 76, SEQ ID NO. 83, SEQ ID NO. 85; SEQ ID NO. 76, SEQ ID NO. 84, SEQ ID NO. 85; SEQ ID NO. 77, SEQ ID NO. 78, SEQ ID NO. 79; SEQ ID NO. 77, SEQ ID NO. 78, SEQ ID NO. 80; SEQ ID NO. 77, SEQ ID NO. 78, SEQ ID NO. 81; SEQ ID NO. 77, SEQ ID NO. 78, SEQ ID NO. 82; SEQ ID NO. 77, SEQ ID NO. 78, SEQ ID NO. 83; SEQ ID NO. 77, SEQ ID NO. 78, SEQ ID NO. 84; SEQ ID NO. 77, SEQ ID NO. 78, SEQ ID NO. 85; SEQ ID NO. 77, SEQ ID NO. 79, SEQ ID NO. 80; SEQ ID NO. 77, SEQ ID NO. 79, SEQ ID NO. 81; SEQ ID NO. 77, SEQ ID NO. 79, SEQ ID NO. 82; SEQ ID NO. 77, SEQ ID NO. 79, SEQ ID NO. 83; SEQ ID NO. 77, SEQ ID NO. 79, SEQ ID NO. 84; SEQ ID NO. 77, SEQ ID NO. 79, SEQ ID NO. 85; SEQ ID NO. 77, SEQ ID NO. 80, SEQ ID NO. 81; SEQ ID NO. 77, SEQ ID NO. 80, SEQ ID NO. 82; SEQ ID NO. 77, SEQ ID NO. 80, SEQ ID NO. 83; SEQ ID NO. 77, SEQ ID NO. 80, SEQ ID NO. 84; SEQ ID NO. 77, SEQ ID NO. 80, SEQ ID NO. 85; SEQ ID NO. 77, SEQ ID NO. 81, SEQ ID NO. 82; SEQ ID NO. 77, SEQ ID NO. 81, SEQ ID NO. 83; SEQ ID NO. 77, SEQ ID NO. 81, SEQ ID NO. 84; SEQ ID NO. 77, SEQ ID NO. 81, SEQ ID NO. 85; SEQ ID NO. 77, SEQ ID NO. 82, SEQ ID NO. 83; SEQ ID NO. 77, SEQ ID NO. 82, SEQ ID NO. 84; SEQ ID NO. 77, SEQ ID NO. 82, SEQ ID NO. 85; SEQ ID NO. 77, SEQ ID NO. 83, SEQ ID NO. 84; SEQ ID NO. 77, SEQ ID NO. 83, SEQ ID NO. 85; SEQ ID NO. 77, SEQ ID NO. 84, SEQ ID NO. 85; SEQ ID NO. 78, SEQ ID NO. 79, SEQ ID NO. 80; SEQ ID NO. 78, SEQ ID NO. 79, SEQ ID NO. 81; SEQ ID NO. 78, SEQ ID NO. 79, SEQ ID NO. 82; SEQ ID NO. 78, SEQ ID NO. 79, SEQ ID NO. 83; SEQ ID NO. 78, SEQ ID NO. 79, SEQ ID NO. 84; SEQ ID NO. 78, SEQ ID NO. 79, SEQ ID NO. 85; SEQ ID NO. 78, SEQ ID NO. 80, SEQ ID NO. 81; SEQ ID NO. 78, SEQ ID NO. 80, SEQ ID NO. 82; SEQ ID NO. 78, SEQ ID NO. 80, SEQ ID NO. 83; SEQ ID NO. 78, SEQ ID NO. 80, SEQ ID NO. 84; SEQ ID NO. 78, SEQ ID NO. 80, SEQ ID NO. 85; SEQ ID NO. 78, SEQ ID NO. 81, SEQ ID NO. 82; SEQ ID NO. 78, SEQ ID NO. 81, SEQ ID NO. 83; SEQ ID NO. 78, SEQ ID NO. 81, SEQ ID NO. 84; SEQ ID NO. 78, SEQ ID NO. 81, SEQ ID NO. 85; SEQ ID NO. 78, SEQ ID NO. 82, SEQ ID NO. 83; SEQ ID NO. 78, SEQ ID NO. 82, SEQ ID NO. 84; SEQ ID NO. 78, SEQ ID NO. 82, SEQ ID NO. 85; SEQ ID NO. 78, SEQ ID NO. 83, SEQ ID NO. 84; SEQ ID NO. 78, SEQ ID NO. 83, SEQ ID NO. 85; SEQ ID NO. 78, SEQ ID NO. 84, SEQ ID NO. 85; SEQ ID NO. 79, SEQ ID NO. 80, SEQ ID NO. 81; SEQ ID NO. 79, SEQ ID NO. 80, SEQ ID NO. 82; SEQ ID NO. 79, SEQ ID NO. 80, SEQ ID NO. 83; SEQ ID NO. 79, SEQ ID NO. 80, SEQ ID NO. 84; SEQ ID NO. 79, SEQ ID NO. 80, SEQ ID NO. 85; SEQ ID NO. 79, SEQ ID NO. 81, SEQ ID NO. 82; SEQ ID NO. 79, SEQ ID NO. 81, SEQ ID NO. 83; SEQ ID NO. 79, SEQ ID NO. 81, SEQ ID NO. 84; SEQ ID NO. 79, SEQ ID NO. 81, SEQ ID NO. 85; SEQ ID NO. 79, SEQ ID NO. 82, SEQ ID NO. 83; SEQ ID NO. 79, SEQ ID NO. 82, SEQ ID NO. 84; SEQ ID NO. 79, SEQ ID NO. 82, SEQ ID NO. 85; SEQ ID NO. 79, SEQ ID NO. 83, SEQ ID NO. 84; SEQ ID NO. 79, SEQ ID NO. 83, SEQ ID NO. 85; SEQ ID NO. 79, SEQ ID NO. 84, SEQ ID NO. 85; SEQ ID NO. 80, SEQ ID NO. 81, SEQ ID NO. 82; SEQ ID NO. 80, SEQ ID NO. 81, SEQ ID NO. 83; SEQ ID NO. 80, SEQ ID NO. 81, SEQ ID NO. 84; SEQ ID NO. 80, SEQ ID NO. 81, SEQ ID NO. 85; SEQ ID NO. 80, SEQ ID NO. 82, SEQ ID NO. 83; SEQ ID NO. 80, SEQ ID NO. 82, SEQ ID NO. 84; SEQ ID NO. 80, SEQ ID NO. 82, SEQ ID NO. 85; SEQ ID NO. 80, SEQ ID NO. 83, SEQ ID NO. 84; SEQ ID NO. 80, SEQ ID NO. 83, SEQ ID NO. 85; SEQ ID NO. 80, SEQ ID NO. 84, SEQ ID NO. 85; SEQ ID NO. 81, SEQ ID NO. 82, SEQ ID NO. 83; SEQ ID NO. 81, SEQ ID NO. 82, SEQ ID NO. 84; SEQ ID NO. 81, SEQ ID NO. 82, SEQ ID NO. 85; SEQ ID NO. 81, SEQ ID NO. 83, SEQ ID NO. 84; SEQ ID NO. 81, SEQ ID NO. 83, SEQ ID NO. 85; SEQ ID NO. 81, SEQ ID NO. 84, SEQ ID NO. 85; SEQ ID NO. 82, SEQ ID NO. 83,

TABLE 6-continued

Combinations of amino acid sequences from Table 5, to be incorporated in immunogenic peptides for composing an composition of synthetic long peptides in accordance with the invention. The various combination are separated by semicolons.

SEQ ID NO. 84; SEQ ID NO. 82, SEQ ID NO. 83, SEQ ID NO. 85; SEQ ID NO. 82, SEQ ID NO. 84, SEQ ID NO. 85; SEQ ID NO. 83, SEQ ID NO. 84, SEQ ID NO. 85;

Combination of 4 peptides

SEQ ID NO. 76, SEQ ID NO. 77, SEQ ID NO. 78, SEQ ID NO. 79; SEQ ID NO. 76, SEQ ID NO. 77, SEQ ID NO. 78, SEQ ID NO. 80; SEQ ID NO. 76, SEQ ID NO. 77, SEQ ID NO. 78, SEQ ID NO. 81; SEQ ID NO. 76, SEQ ID NO. 77, SEQ ID NO. 78, SEQ ID NO. 82; SEQ ID NO. 76, SEQ ID NO. 77, SEQ ID NO. 78, SEQ ID NO. 83; SEQ ID NO. 76, SEQ ID NO. 77, SEQ ID NO. 78, SEQ ID NO. 84; SEQ ID NO. 76, SEQ ID NO. 77, SEQ ID NO. 78, SEQ ID NO. 85; SEQ ID NO. 76, SEQ ID NO. 77, SEQ ID NO. 79, SEQ ID NO. 80; SEQ ID NO. 76, SEQ ID NO. 77, SEQ ID NO. 79, SEQ ID NO. 81; SEQ ID NO. 76, SEQ ID NO. 77, SEQ ID NO. 79, SEQ ID NO. 82; SEQ ID NO. 76, SEQ ID NO. 77, SEQ ID NO. 79, SEQ ID NO. 83; SEQ ID NO. 76, SEQ ID NO. 77, SEQ ID NO. 79, SEQ ID NO. 84; SEQ ID NO. 76, SEQ ID NO. 77, SEQ ID NO. 79, SEQ ID NO. 85; SEQ ID NO. 76, SEQ ID NO. 77, SEQ ID NO. 80, SEQ ID NO. 81; SEQ ID NO. 76, SEQ ID NO. 77, SEQ ID NO. 80, SEQ ID NO. 82; SEQ ID NO. 76, SEQ ID NO. 77, SEQ ID NO. 80, SEQ ID NO. 83; SEQ ID NO. 76, SEQ ID NO. 77, SEQ ID NO. 80, SEQ ID NO. 84; SEQ ID NO. 76, SEQ ID NO. 77, SEQ ID NO. 80, SEQ ID NO. 85; SEQ ID NO. 76, SEQ ID NO. 77, SEQ ID NO. 81, SEQ ID NO. 82; SEQ ID NO. 76, SEQ ID NO. 77, SEQ ID NO. 81, SEQ ID NO. 83; SEQ ID NO. 76, SEQ ID NO. 77, SEQ ID NO. 81, SEQ ID NO. 84; SEQ ID NO. 76, SEQ ID NO. 77, SEQ ID NO. 81, SEQ ID NO. 85; SEQ ID NO. 76, SEQ ID NO. 77, SEQ ID NO. 82, SEQ ID NO. 83; SEQ ID NO. 76, SEQ ID NO. 77, SEQ ID NO. 82, SEQ ID NO. 84; SEQ ID NO. 76, SEQ ID NO. 77, SEQ ID NO. 82, SEQ ID NO. 85; SEQ ID NO. 76, SEQ ID NO. 77, SEQ ID NO. 83, SEQ ID NO. 84; SEQ ID NO. 76, SEQ ID NO. 77, SEQ ID NO. 83, SEQ ID NO. 85; SEQ ID NO. 76, SEQ ID NO. 77, SEQ ID NO. 84, SEQ ID NO. 85; SEQ ID NO. 76, SEQ ID NO. 78, SEQ ID NO. 79, SEQ ID NO. 80; SEQ ID NO. 76, SEQ ID NO. 78, SEQ ID NO. 79, SEQ ID NO. 81; SEQ ID NO. 76, SEQ ID NO. 78, SEQ ID NO. 79, SEQ ID NO. 82; SEQ ID NO. 76, SEQ ID NO. 78, SEQ ID NO. 79, SEQ ID NO. 83; SEQ ID NO. 76, SEQ ID NO. 78, SEQ ID NO. 79, SEQ ID NO. 84; SEQ ID NO. 76, SEQ ID NO. 78, SEQ ID NO. 79, SEQ ID NO. 85; SEQ ID NO. 76, SEQ ID NO. 78, SEQ ID NO. 80, SEQ ID NO. 81; SEQ ID NO. 76, SEQ ID NO. 78, SEQ ID NO. 80, SEQ ID NO. 82; SEQ ID NO. 76, SEQ ID NO. 78, SEQ ID NO. 80, SEQ ID NO. 83; SEQ ID NO. 76, SEQ ID NO. 78, SEQ ID NO. 80, SEQ ID NO. 84; SEQ ID NO. 76, SEQ ID NO. 78, SEQ ID NO. 80, SEQ ID NO. 85; SEQ ID NO. 76, SEQ ID NO. 78, SEQ ID NO. 81, SEQ ID NO. 82; SEQ ID NO. 76, SEQ ID NO. 78, SEQ ID NO. 81, SEQ ID NO. 83; SEQ ID NO. 76, SEQ ID NO. 78, SEQ ID NO. 81, SEQ ID NO. 84; SEQ ID NO. 76, SEQ ID NO. 78, SEQ ID NO. 81, SEQ ID NO. 85; SEQ ID NO. 76, SEQ ID NO. 78, SEQ ID NO. 82, SEQ ID NO. 83; SEQ ID NO. 76, SEQ ID NO. 78, SEQ ID NO. 82, SEQ ID NO. 84; SEQ ID NO. 76, SEQ ID NO. 78, SEQ ID NO. 82, SEQ ID NO. 85; SEQ ID NO. 76, SEQ ID NO. 78, SEQ ID NO. 83, SEQ ID NO. 84; SEQ ID NO. 76, SEQ ID NO. 78, SEQ ID NO. 83, SEQ ID NO. 85; SEQ ID NO. 76, SEQ ID NO. 78, SEQ ID NO. 84, SEQ ID NO. 85; SEQ ID NO. 76, SEQ ID NO. 79, SEQ ID NO. 80, SEQ ID NO. 81; SEQ ID NO. 76, SEQ ID NO. 79, SEQ ID NO. 80, SEQ ID NO. 82; SEQ ID NO. 76, SEQ ID NO. 79, SEQ ID NO. 80, SEQ ID NO. 83; SEQ ID NO. 76, SEQ ID NO. 79, SEQ ID NO. 80, SEQ ID NO. 84; SEQ ID NO. 76, SEQ ID NO. 79, SEQ ID NO. 80, SEQ ID NO. 85; SEQ ID NO. 76, SEQ ID NO. 79, SEQ ID NO. 81, SEQ ID NO. 82; SEQ ID NO. 76, SEQ ID NO. 79, SEQ ID NO. 81, SEQ ID NO. 83; SEQ ID NO. 76, SEQ ID NO. 79, SEQ ID NO. 81, SEQ ID NO. 84; SEQ ID NO. 76, SEQ ID NO. 79, SEQ ID NO. 81, SEQ ID NO. 85; SEQ ID NO. 76, SEQ ID NO. 79, SEQ ID NO. 82, SEQ ID NO. 83; SEQ ID NO. 76, SEQ ID NO. 79, SEQ ID NO. 82, SEQ ID NO. 84; SEQ ID NO. 76, SEQ ID NO. 79, SEQ ID NO. 82, SEQ ID NO. 85; SEQ ID NO. 76, SEQ ID NO. 79, SEQ ID NO. 83, SEQ ID NO. 84; SEQ ID NO. 76, SEQ ID NO. 79, SEQ ID NO. 83, SEQ ID NO. 85; SEQ ID NO. 76, SEQ ID NO. 79, SEQ ID NO. 84, SEQ ID NO. 85; SEQ ID NO. 76, SEQ ID NO. 80, SEQ ID NO. 81, SEQ ID NO. 82; SEQ ID NO. 76, SEQ ID NO. 80, SEQ ID NO. 81, SEQ ID NO. 83; SEQ ID NO. 76, SEQ ID NO. 80, SEQ ID NO. 81, SEQ ID NO. 84; SEQ ID NO. 76, SEQ ID NO. 80, SEQ ID NO. 81, SEQ ID NO. 85; SEQ ID NO. 76, SEQ ID NO. 80, SEQ ID NO. 82, SEQ ID NO. 83; SEQ ID NO. 76, SEQ ID NO. 80, SEQ ID NO. 82, SEQ ID NO. 84; SEQ ID NO. 76, SEQ ID NO. 80, SEQ ID NO. 82, SEQ ID NO. 85; SEQ ID NO. 76, SEQ ID NO. 80, SEQ ID NO. 83, SEQ ID NO. 84; SEQ ID NO. 76, SEQ ID NO. 80, SEQ ID NO. 83, SEQ ID NO. 85; SEQ ID NO. 76, SEQ ID NO. 80, SEQ ID NO. 84, SEQ ID NO. 85; SEQ ID NO. 76, SEQ ID NO. 81, SEQ ID NO. 82, SEQ ID NO. 83; SEQ ID NO. 76, SEQ ID NO. 81, SEQ ID NO. 82, SEQ ID NO. 84; SEQ ID NO. 76, SEQ ID NO. 81, SEQ ID NO. 82, SEQ ID NO. 85; SEQ ID NO. 76, SEQ ID NO. 81, SEQ ID NO. 83, SEQ ID NO. 84; SEQ ID NO. 76, SEQ ID NO. 81, SEQ ID NO. 83, SEQ ID NO. 85; SEQ ID NO. 76, SEQ ID NO. 81, SEQ ID NO. 84, SEQ ID NO. 85; SEQ ID NO. 76, SEQ ID NO. 82, SEQ ID NO. 83, SEQ ID NO. 84; SEQ ID NO. 76, SEQ ID NO. 82, SEQ ID NO. 83, SEQ ID NO. 85; SEQ ID NO. 76, SEQ ID NO. 82, SEQ ID NO. 84, SEQ ID NO. 85; SEQ ID NO. 76, SEQ ID NO. 83, SEQ ID NO. 84, SEQ ID NO. 85; SEQ ID NO. 77, SEQ ID NO. 78, SEQ ID NO. 79, SEQ ID NO. 80; SEQ ID NO. 77, SEQ ID NO. 78, SEQ ID NO. 79, SEQ ID NO. 81; SEQ ID NO. 77, SEQ ID NO. 78, SEQ ID NO. 79, SEQ ID NO. 82; SEQ ID NO. 77, SEQ ID NO. 78, SEQ ID NO. 79, SEQ ID NO. 83; SEQ ID NO. 77, SEQ ID NO. 78, SEQ ID NO. 79, SEQ ID NO. 84; SEQ ID NO. 77, SEQ ID NO. 78, SEQ ID NO. 79, SEQ ID NO. 85; SEQ ID NO. 77, SEQ ID NO. 78, SEQ ID NO. 80, SEQ ID NO. 81; SEQ ID NO. 77, SEQ ID NO. 78, SEQ ID NO. 80, SEQ ID NO. 82; SEQ ID NO. 77, SEQ ID NO. 78, SEQ ID NO. 80, SEQ ID NO. 83; SEQ ID NO. 77, SEQ ID NO. 78, SEQ ID NO. 80, SEQ ID NO. 84; SEQ ID NO. 77, SEQ ID NO. 78, SEQ ID NO. 80, SEQ ID NO. 85; SEQ ID NO. 77, SEQ ID NO. 78, SEQ ID NO. 81, SEQ ID NO. 82; SEQ ID NO. 77, SEQ ID NO. 78, SEQ ID NO. 81, SEQ ID NO. 83; SEQ ID NO. 77, SEQ ID NO. 78, SEQ ID NO. 81, SEQ ID NO. 84; SEQ ID NO. 77, SEQ ID NO. 78, SEQ ID NO. 81, SEQ ID NO. 85; SEQ ID NO. 77, SEQ ID NO. 78, SEQ ID NO. 82, SEQ ID NO. 83; SEQ ID NO. 77, SEQ ID NO. 78, SEQ ID NO. 82, SEQ ID NO. 84; SEQ ID NO. 77, SEQ ID NO. 78, SEQ ID NO. 82, SEQ ID NO. 85; SEQ ID NO. 77, SEQ ID NO. 78, SEQ ID NO. 83, SEQ ID NO. 84; SEQ ID NO. 77, SEQ ID NO. 78, SEQ ID NO. 83, SEQ ID NO. 85; SEQ ID NO. 77, SEQ ID NO. 78, SEQ ID NO. 84, SEQ ID NO. 85; SEQ ID NO. 77, SEQ ID NO. 79, SEQ ID NO. 80, SEQ ID NO. 81; SEQ ID NO. 77, SEQ ID NO. 79, SEQ ID NO. 80, SEQ ID NO. 82; SEQ ID NO. 77, SEQ ID NO. 79, SEQ ID NO. 80, SEQ ID NO. 83; SEQ ID NO. 77, SEQ ID NO. 79, SEQ ID NO. 80, SEQ ID NO. 84; SEQ ID NO. 77, SEQ ID NO. 79, SEQ ID NO. 80, SEQ ID NO. 85; SEQ ID NO. 77, SEQ ID NO. 79, SEQ ID NO. 81, SEQ ID NO. 82; SEQ ID NO. 77, SEQ ID NO. 79, SEQ ID NO. 81, SEQ ID NO. 83; SEQ ID NO. 77, SEQ ID NO. 79,

TABLE 6-continued

Combinations of amino acid sequences from Table 5, to be incorporated in immunogenic peptides for composing an composition of synthetic long peptides in accordance with the invention. The various combination are separated by semicolons.

SEQ ID NO. 81, SEQ ID NO. 84; SEQ ID NO. 77, SEQ ID NO. 79, SEQ ID NO. 81, SEQ ID NO. 85; SEQ ID NO. 77, SEQ ID NO. 79, SEQ ID NO. 82, SEQ ID NO. 83; SEQ ID NO. 77, SEQ ID NO. 79, SEQ ID NO. 82, SEQ ID NO. 84; SEQ ID NO. 77, SEQ ID NO. 79, SEQ ID NO. 82, SEQ ID NO. 85; SEQ ID NO. 77, SEQ ID NO. 79, SEQ ID NO. 83, SEQ ID NO. 84; SEQ ID NO. 77, SEQ ID NO. 79, SEQ ID NO. 83, SEQ ID NO. 85; SEQ ID NO. 77, SEQ ID NO. 79, SEQ ID NO. 84, SEQ ID NO. 85; SEQ ID NO. 77, SEQ ID NO. 80, SEQ ID NO. 81, SEQ ID NO. 82; SEQ ID NO. 77, SEQ ID NO. 80, SEQ ID NO. 81, SEQ ID NO. 83; SEQ ID NO. 77, SEQ ID NO. 80, SEQ ID NO. 81, SEQ ID NO. 84; SEQ ID NO. 77, SEQ ID NO. 80, SEQ ID NO. 81, SEQ ID NO. 85; SEQ ID NO. 77, SEQ ID NO. 80, SEQ ID NO. 82, SEQ ID NO. 83; SEQ ID NO. 77, SEQ ID NO. 80, SEQ ID NO. 82, SEQ ID NO. 84; SEQ ID NO. 77, SEQ ID NO. 80, SEQ ID NO. 82, SEQ ID NO. 85; SEQ ID NO. 77, SEQ ID NO. 80, SEQ ID NO. 83, SEQ ID NO. 84; SEQ ID NO. 77, SEQ ID NO. 80, SEQ ID NO. 83, SEQ ID NO. 85; SEQ ID NO. 77, SEQ ID NO. 80, SEQ ID NO. 84, SEQ ID NO. 85; SEQ ID NO. 77, SEQ ID NO. 81, SEQ ID NO. 82, SEQ ID NO. 83; SEQ ID NO. 77, SEQ ID NO. 81, SEQ ID NO. 82, SEQ ID NO. 84; SEQ ID NO. 77, SEQ ID NO. 81, SEQ ID NO. 82, SEQ ID NO. 85; SEQ ID NO. 77, SEQ ID NO. 81, SEQ ID NO. 83, SEQ ID NO. 84; SEQ ID NO. 77, SEQ ID NO. 81, SEQ ID NO. 83, SEQ ID NO. 85; SEQ ID NO. 77, SEQ ID NO. 81, SEQ ID NO. 84, SEQ ID NO. 85; SEQ ID NO. 77, SEQ ID NO. 82, SEQ ID NO. 83, SEQ ID NO. 84; SEQ ID NO. 77, SEQ ID NO. 82, SEQ ID NO. 83, SEQ ID NO. 85; SEQ ID NO. 77, SEQ ID NO. 82, SEQ ID NO. 84, SEQ ID NO. 85; SEQ ID NO. 77, SEQ ID NO. 83, SEQ ID NO. 84, SEQ ID NO. 85; SEQ ID NO. 78, SEQ ID NO. 79, SEQ ID NO. 80, SEQ ID NO. 81; SEQ ID NO. 78, SEQ ID NO. 79, SEQ ID NO. 80, SEQ ID NO. 82; SEQ ID NO. 78, SEQ ID NO. 79, SEQ ID NO. 80, SEQ ID NO. 83; SEQ ID NO. 78, SEQ ID NO. 79, SEQ ID NO. 80, SEQ ID NO. 84; SEQ ID NO. 78, SEQ ID NO. 79, SEQ ID NO. 80, SEQ ID NO. 85; SEQ ID NO. 78, SEQ ID NO. 79, SEQ ID NO. 81, SEQ ID NO. 82; SEQ ID NO. 78, SEQ ID NO. 79, SEQ ID NO. 81, SEQ ID NO. 83; SEQ ID NO. 78, SEQ ID NO. 79, SEQ ID NO. 81, SEQ ID NO. 84; SEQ ID NO. 78, SEQ ID NO. 79, SEQ ID NO. 81, SEQ ID NO. 85; SEQ ID NO. 78, SEQ ID NO. 79, SEQ ID NO. 82, SEQ ID NO. 83; SEQ ID NO. 78, SEQ ID NO. 79, SEQ ID NO. 82, SEQ ID NO. 84; SEQ ID NO. 78, SEQ ID NO. 79, SEQ ID NO. 82, SEQ ID NO. 85; SEQ ID NO. 78, SEQ ID NO. 79, SEQ ID NO. 83, SEQ ID NO. 84; SEQ ID NO. 78, SEQ ID NO. 79, SEQ ID NO. 83, SEQ ID NO. 85; SEQ ID NO. 78, SEQ ID NO. 79, SEQ ID NO. 84, SEQ ID NO. 85; SEQ ID NO. 78, SEQ ID NO. 80, SEQ ID NO. 81, SEQ ID NO. 82; SEQ ID NO. 78, SEQ ID NO. 80, SEQ ID NO. 81, SEQ ID NO. 83; SEQ ID NO. 78, SEQ ID NO. 80, SEQ ID NO. 81, SEQ ID NO. 84; SEQ ID NO. 78, SEQ ID NO. 80, SEQ ID NO. 81, SEQ ID NO. 85; SEQ ID NO. 78, SEQ ID NO. 80, SEQ ID NO. 82, SEQ ID NO. 83; SEQ ID NO. 78, SEQ ID NO. 80, SEQ ID NO. 82, SEQ ID NO. 84; SEQ ID NO. 78, SEQ ID NO. 80, SEQ ID NO. 82, SEQ ID NO. 85; SEQ ID NO. 78, SEQ ID NO. 80, SEQ ID NO. 83, SEQ ID NO. 84; SEQ ID NO. 78, SEQ ID NO. 80, SEQ ID NO. 83, SEQ ID NO. 85; SEQ ID NO. 78, SEQ ID NO. 80, SEQ ID NO. 84, SEQ ID NO. 85; SEQ ID NO. 78, SEQ ID NO. 81, SEQ ID NO. 82, SEQ ID NO. 83; SEQ ID NO. 78, SEQ ID NO. 81, SEQ ID NO. 82, SEQ ID NO. 84; SEQ ID NO. 78, SEQ ID NO. 81, SEQ ID NO. 82, SEQ ID NO. 85; SEQ ID NO. 78, SEQ ID NO. 81, SEQ ID NO. 83, SEQ ID NO. 84; SEQ ID NO. 78, SEQ ID NO. 81, SEQ ID NO. 83, SEQ ID NO. 85; SEQ ID NO. 78, SEQ ID NO. 81, SEQ ID NO. 84, SEQ ID NO. 85; SEQ ID NO. 78, SEQ ID NO. 82, SEQ ID NO. 83, SEQ ID NO. 84; SEQ ID NO. 78, SEQ ID NO. 82, SEQ ID NO. 83, SEQ ID NO. 85; SEQ ID NO. 78, SEQ ID NO. 82, SEQ ID NO. 84, SEQ ID NO. 85; SEQ ID NO. 78, SEQ ID NO. 83, SEQ ID NO. 84, SEQ ID NO. 85; SEQ ID NO. 79, SEQ ID NO. 80, SEQ ID NO. 81, SEQ ID NO. 82; SEQ ID NO. 79, SEQ ID NO. 80, SEQ ID NO. 81, SEQ ID NO. 83; SEQ ID NO. 79, SEQ ID NO. 80, SEQ ID NO. 81, SEQ ID NO. 84; SEQ ID NO. 79, SEQ ID NO. 80, SEQ ID NO. 81, SEQ ID NO. 85; SEQ ID NO. 79, SEQ ID NO. 80, SEQ ID NO. 82, SEQ ID NO. 83; SEQ ID NO. 79, SEQ ID NO. 80, SEQ ID NO. 82, SEQ ID NO. 84; SEQ ID NO. 79, SEQ ID NO. 80, SEQ ID NO. 82, SEQ ID NO. 85; SEQ ID NO. 79, SEQ ID NO. 80, SEQ ID NO. 83, SEQ ID NO. 84; SEQ ID NO. 79, SEQ ID NO. 80, SEQ ID NO. 83, SEQ ID NO. 85; SEQ ID NO. 79, SEQ ID NO. 80, SEQ ID NO. 84, SEQ ID NO. 85; SEQ ID NO. 79, SEQ ID NO. 81, SEQ ID NO. 82, SEQ ID NO. 83; SEQ ID NO. 79, SEQ ID NO. 81, SEQ ID NO. 82, SEQ ID NO. 84; SEQ ID NO. 79, SEQ ID NO. 81, SEQ ID NO. 82, SEQ ID NO. 85; SEQ ID NO. 79, SEQ ID NO. 81, SEQ ID NO. 83, SEQ ID NO. 84; SEQ ID NO. 79, SEQ ID NO. 81, SEQ ID NO. 83, SEQ ID NO. 85; SEQ ID NO. 79, SEQ ID NO. 81, SEQ ID NO. 84, SEQ ID NO. 85; SEQ ID NO. 79, SEQ ID NO. 82, SEQ ID NO. 83, SEQ ID NO. 84; SEQ ID NO. 79, SEQ ID NO. 82, SEQ ID NO. 83, SEQ ID NO. 85; SEQ ID NO. 79, SEQ ID NO. 82, SEQ ID NO. 84, SEQ ID NO. 85; SEQ ID NO. 79, SEQ ID NO. 83, SEQ ID NO. 84, SEQ ID NO. 85; SEQ ID NO. 80, SEQ ID NO. 81, SEQ ID NO. 82, SEQ ID NO. 83; SEQ ID NO. 80, SEQ ID NO. 81, SEQ ID NO. 82, SEQ ID NO. 84; SEQ ID NO. 80, SEQ ID NO. 81, SEQ ID NO. 82, SEQ ID NO. 85; SEQ ID NO. 80, SEQ ID NO. 81, SEQ ID NO. 83, SEQ ID NO. 84; SEQ ID NO. 80, SEQ ID NO. 81, SEQ ID NO. 83, SEQ ID NO. 85; SEQ ID NO. 80, SEQ ID NO. 81, SEQ ID NO. 84, SEQ ID NO. 85; SEQ ID NO. 80, SEQ ID NO. 82, SEQ ID NO. 83, SEQ ID NO. 84; SEQ ID NO. 80, SEQ ID NO. 82, SEQ ID NO. 83, SEQ ID NO. 85; SEQ ID NO. 80, SEQ ID NO. 82, SEQ ID NO. 84, SEQ ID NO. 85; SEQ ID NO. 80, SEQ ID NO. 83, SEQ ID NO. 84, SEQ ID NO. 85; SEQ ID NO. 81, SEQ ID NO. 82, SEQ ID NO. 83, SEQ ID NO. 84; SEQ ID NO. 81, SEQ ID NO. 82, SEQ ID NO. 83, SEQ ID NO. 85; SEQ ID NO. 81, SEQ ID NO. 82, SEQ ID NO. 84, SEQ ID NO. 85; SEQ ID NO. 81, SEQ ID NO. 83, SEQ ID NO. 84, SEQ ID NO. 85; SEQ ID NO. 82, SEQ ID NO. 83, SEQ ID NO. 84, SEQ ID NO. 85;

Combination of 5 peptides

SEQ ID NO. 76, SEQ ID NO. 78, SEQ ID NO. 80, SEQ ID NO. 81, SEQ ID NO. 84; SEQ ID NO. 76, SEQ ID NO. 78, SEQ ID NO. 80, SEQ ID NO. 81, SEQ ID NO. 85; SEQ ID NO. 76, SEQ ID NO. 78, SEQ ID NO. 80, SEQ ID NO. 82, SEQ ID NO. 83; SEQ ID NO. 76, SEQ ID NO. 78, SEQ ID NO. 80, SEQ ID NO. 82, SEQ ID NO. 84; SEQ ID NO. 76, SEQ ID NO. 78, SEQ ID NO. 80, SEQ ID NO. 82, SEQ ID NO. 85; SEQ ID NO. 76, SEQ ID NO. 78, SEQ ID NO. 80, SEQ ID NO. 83, SEQ ID NO. 84; SEQ ID NO. 76, SEQ ID NO. 78, SEQ ID NO. 80, SEQ ID NO. 83, SEQ ID NO. 85; SEQ ID NO. 76, SEQ ID NO. 78, SEQ ID NO. 80, SEQ ID NO. 84, SEQ ID NO. 85; SEQ ID NO. 76, SEQ ID NO. 78, SEQ ID NO. 81, SEQ ID NO. 82, SEQ ID NO. 83; SEQ ID NO. 76, SEQ ID NO. 78, SEQ ID NO. 81, SEQ ID NO. 82, SEQ ID NO. 84; SEQ ID NO. 76, SEQ ID NO. 78, SEQ ID NO. 81, SEQ ID NO. 82, SEQ ID NO. 85; SEQ ID NO. 76, SEQ ID NO. 78, SEQ ID NO. 81, SEQ ID NO. 83, SEQ ID NO. 84; SEQ ID NO. 76, SEQ ID NO. 78, SEQ ID NO. 81, SEQ ID NO. 83, SEQ ID NO. 85; SEQ ID NO. 76, SEQ ID NO. 78, SEQ ID NO. 81, SEQ ID NO.

TABLE 6-continued

Combinations of amino acid sequences from Table 5, to be incorporated in immunogenic peptides for composing an composition of synthetic long peptides in accordance with the invention. The various combination are separated by semicolons.

84, SEQ ID NO. 85; SEQ ID NO. 76, SEQ ID NO. 78, SEQ ID NO. 82, SEQ ID NO. 83, SEQ ID NO. 84; SEQ ID NO. 76, SEQ ID NO. 78, SEQ ID NO. 82, SEQ ID NO. 83, SEQ ID NO. 85; SEQ ID NO. 76, SEQ ID NO. 78, SEQ ID NO. 82, SEQ ID NO. 84, SEQ ID NO. 85; SEQ ID NO. 76, SEQ ID NO. 78, SEQ ID NO. 83, SEQ ID NO. 84, SEQ ID NO. 85; SEQ ID NO. 76, SEQ ID NO. 79, SEQ ID NO. 80, SEQ ID NO. 81, SEQ ID NO. 82; SEQ ID NO. 76, SEQ ID NO. 79, SEQ ID NO. 80, SEQ ID NO. 81, SEQ ID NO. 83; SEQ ID NO. 76, SEQ ID NO. 79, SEQ ID NO. 80, SEQ ID NO. 81, SEQ ID NO. 84; SEQ ID NO. 76, SEQ ID NO. 79, SEQ ID NO. 80, SEQ ID NO. 81, SEQ ID NO. 85; SEQ ID NO. 76, SEQ ID NO. 79, SEQ ID NO. 80, SEQ ID NO. 82, SEQ ID NO. 83; SEQ ID NO. 76, SEQ ID NO. 79, SEQ ID NO. 80, SEQ ID NO. 82, SEQ ID NO. 84; SEQ ID NO. 76, SEQ ID NO. 79, SEQ ID NO. 80, SEQ ID NO. 82, SEQ ID NO. 85; SEQ ID NO. 76, SEQ ID NO. 79, SEQ ID NO. 80, SEQ ID NO. 83, SEQ ID NO. 84; SEQ ID NO. 76, SEQ ID NO. 79, SEQ ID NO. 80, SEQ ID NO. 83, SEQ ID NO. 85; SEQ ID NO. 76, SEQ ID NO. 79, SEQ ID NO. 80, SEQ ID NO. 84, SEQ ID NO. 85; SEQ ID NO. 76, SEQ ID NO. 79, SEQ ID NO. 81, SEQ ID NO. 82, SEQ ID NO. 83; SEQ ID NO. 76, SEQ ID NO. 79, SEQ ID NO. 81, SEQ ID NO. 82, SEQ ID NO. 84; SEQ ID NO. 76, SEQ ID NO. 79, SEQ ID NO. 81, SEQ ID NO. 82, SEQ ID NO. 85; SEQ ID NO. 76, SEQ ID NO. 79, SEQ ID NO. 81, SEQ ID NO. 83, SEQ ID NO. 84; SEQ ID NO. 76, SEQ ID NO. 79, SEQ ID NO. 81, SEQ ID NO. 83, SEQ ID NO. 85; SEQ ID NO. 76, SEQ ID NO. 79, SEQ ID NO. 81, SEQ ID NO. 84, SEQ ID NO. 85; SEQ ID NO. 76, SEQ ID NO. 79, SEQ ID NO. 82, SEQ ID NO. 83, SEQ ID NO. 84; SEQ ID NO. 76, SEQ ID NO. 79, SEQ ID NO. 82, SEQ ID NO. 83, SEQ ID NO. 85; SEQ ID NO. 76, SEQ ID NO. 79, SEQ ID NO. 82, SEQ ID NO. 84, SEQ ID NO. 85; SEQ ID NO. 76, SEQ ID NO. 79, SEQ ID NO. 83, SEQ ID NO. 84, SEQ ID NO. 85; SEQ ID NO. 76, SEQ ID NO. 80, SEQ ID NO. 81, SEQ ID NO. 82, SEQ ID NO. 83; SEQ ID NO. 76, SEQ ID NO. 80, SEQ ID NO. 81, SEQ ID NO. 82, SEQ ID NO. 84; SEQ ID NO. 76, SEQ ID NO. 80, SEQ ID NO. 81, SEQ ID NO. 82, SEQ ID NO. 85; SEQ ID NO. 76, SEQ ID NO. 80, SEQ ID NO. 81, SEQ ID NO. 83, SEQ ID NO. 84; SEQ ID NO. 76, SEQ ID NO. 80, SEQ ID NO. 81, SEQ ID NO. 83, SEQ ID NO. 85; SEQ ID NO. 76, SEQ ID NO. 80, SEQ ID NO. 81, SEQ ID NO. 84, SEQ ID NO. 85; SEQ ID NO. 76, SEQ ID NO. 80, SEQ ID NO. 82, SEQ ID NO. 83, SEQ ID NO. 84; SEQ ID NO. 76, SEQ ID NO. 80, SEQ ID NO. 82, SEQ ID NO. 83, SEQ ID NO. 85; SEQ ID NO. 76, SEQ ID NO. 80, SEQ ID NO. 82, SEQ ID NO. 84, SEQ ID NO. 85; SEQ ID NO. 76, SEQ ID NO. 80, SEQ ID NO. 83, SEQ ID NO. 84, SEQ ID NO. 85; SEQ ID NO. 76, SEQ ID NO. 81, SEQ ID NO. 82, SEQ ID NO. 83, SEQ ID NO. 84; SEQ ID NO. 76, SEQ ID NO. 81, SEQ ID NO. 82, SEQ ID NO. 83, SEQ ID NO. 85; SEQ ID NO. 76, SEQ ID NO. 81, SEQ ID NO. 82, SEQ ID NO. 84, SEQ ID NO. 85; SEQ ID NO. 76, SEQ ID NO. 81, SEQ ID NO. 83, SEQ ID NO. 84, SEQ ID NO. 85; SEQ ID NO. 76, SEQ ID NO. 82, SEQ ID NO. 83, SEQ ID NO. 84, SEQ ID NO. 85; SEQ ID NO. 77, SEQ ID NO. 78, SEQ ID NO. 79, SEQ ID NO. 80, SEQ ID NO. 81; SEQ ID NO. 77, SEQ ID NO. 78, SEQ ID NO. 79, SEQ ID NO. 80, SEQ ID NO. 82; SEQ ID NO. 77, SEQ ID NO. 78, SEQ ID NO. 79, SEQ ID NO. 80, SEQ ID NO. 83; SEQ ID NO. 77, SEQ ID NO. 78, SEQ ID NO. 79, SEQ ID NO. 80, SEQ ID NO. 84; SEQ ID NO. 77, SEQ ID NO. 78, SEQ ID NO. 79, SEQ ID NO. 80, SEQ ID NO. 85; SEQ ID NO. 77, SEQ ID NO. 78, SEQ ID NO. 79, SEQ ID NO. 81, SEQ ID NO. 82; SEQ ID NO. 77, SEQ ID NO. 78, SEQ ID NO. 79, SEQ ID NO. 81, SEQ ID NO. 83; SEQ ID NO. 77, SEQ ID NO. 78, SEQ ID NO. 79, SEQ ID NO. 81, SEQ ID NO. 84; SEQ ID NO. 77, SEQ ID NO. 78, SEQ ID NO. 79, SEQ ID NO. 81, SEQ ID NO. 85; SEQ ID NO. 77, SEQ ID NO. 78, SEQ ID NO. 79, SEQ ID NO. 82, SEQ ID NO. 83; SEQ ID NO. 77, SEQ ID NO. 78, SEQ ID NO. 79, SEQ ID NO. 82, SEQ ID NO. 84; SEQ ID NO. 77, SEQ ID NO. 78, SEQ ID NO. 79, SEQ ID NO. 82, SEQ ID NO. 85; SEQ ID NO. 77, SEQ ID NO. 78, SEQ ID NO. 79, SEQ ID NO. 83, SEQ ID NO. 84; SEQ ID NO. 77, SEQ ID NO. 78, SEQ ID NO. 79, SEQ ID NO. 83, SEQ ID NO. 85; SEQ ID NO. 77, SEQ ID NO. 78, SEQ ID NO. 79, SEQ ID NO. 84, SEQ ID NO. 85; SEQ ID NO. 77, SEQ ID NO. 78, SEQ ID NO. 80, SEQ ID NO. 81, SEQ ID NO. 82; SEQ ID NO. 77, SEQ ID NO. 78, SEQ ID NO. 80, SEQ ID NO. 81, SEQ ID NO. 83; SEQ ID NO. 77, SEQ ID NO. 78, SEQ ID NO. 80, SEQ ID NO. 81, SEQ ID NO. 84; SEQ ID NO. 77, SEQ ID NO. 78, SEQ ID NO. 80, SEQ ID NO. 81, SEQ ID NO. 85; SEQ ID NO. 77, SEQ ID NO. 78, SEQ ID NO. 80, SEQ ID NO. 82, SEQ ID NO. 83; SEQ ID NO. 77, SEQ ID NO. 78, SEQ ID NO. 80, SEQ ID NO. 82, SEQ ID NO. 84; SEQ ID NO. 77, SEQ ID NO. 78, SEQ ID NO. 80, SEQ ID NO. 82, SEQ ID NO. 85; SEQ ID NO. 77, SEQ ID NO. 78, SEQ ID NO. 80, SEQ ID NO. 83, SEQ ID NO. 84; SEQ ID NO. 77, SEQ ID NO. 78, SEQ ID NO. 80, SEQ ID NO. 83, SEQ ID NO. 85; SEQ ID NO. 77, SEQ ID NO. 78, SEQ ID NO. 80, SEQ ID NO. 84, SEQ ID NO. 85; SEQ ID NO. 77, SEQ ID NO. 78, SEQ ID NO. 81, SEQ ID NO. 82, SEQ ID NO. 83; SEQ ID NO. 77, SEQ ID NO. 78, SEQ ID NO. 81, SEQ ID NO. 82, SEQ ID NO. 84; SEQ ID NO. 77, SEQ ID NO. 78, SEQ ID NO. 81, SEQ ID NO. 82, SEQ ID NO. 85; SEQ ID NO. 77, SEQ ID NO. 78, SEQ ID NO. 81, SEQ ID NO. 83, SEQ ID NO. 84; SEQ ID NO. 77, SEQ ID NO. 78, SEQ ID NO. 81, SEQ ID NO. 83, SEQ ID NO. 85; SEQ ID NO. 77, SEQ ID NO. 78, SEQ ID NO. 81, SEQ ID NO. 84, SEQ ID NO. 85; SEQ ID NO. 77, SEQ ID NO. 78, SEQ ID NO. 82, SEQ ID NO. 83, SEQ ID NO. 84; SEQ ID NO. 77, SEQ ID NO. 78, SEQ ID NO. 82, SEQ ID NO. 83, SEQ ID NO. 85; SEQ ID NO. 77, SEQ ID NO. 78, SEQ ID NO. 82, SEQ ID NO. 84, SEQ ID NO. 85; SEQ ID NO. 77, SEQ ID NO. 78, SEQ ID NO. 83, SEQ ID NO. 84, SEQ ID NO. 85; SEQ ID NO. 77, SEQ ID NO. 79, SEQ ID NO. 80, SEQ ID NO. 81, SEQ ID NO. 82; SEQ ID NO. 77, SEQ ID NO. 79, SEQ ID NO. 80, SEQ ID NO. 81, SEQ ID NO. 83; SEQ ID NO. 77, SEQ ID NO. 79, SEQ ID NO. 80, SEQ ID NO. 81, SEQ ID NO. 84; SEQ ID NO. 77, SEQ ID NO. 79, SEQ ID NO. 80, SEQ ID NO. 81, SEQ ID NO. 85; SEQ ID NO. 77, SEQ ID NO. 79, SEQ ID NO. 80, SEQ ID NO. 82, SEQ ID NO. 83; SEQ ID NO. 77, SEQ ID NO. 79, SEQ ID NO. 80, SEQ ID NO. 82, SEQ ID NO. 84; SEQ ID NO. 77, SEQ ID NO. 79, SEQ ID NO. 80, SEQ ID NO. 82, SEQ ID NO. 85; SEQ ID NO. 77, SEQ ID NO. 79, SEQ ID NO. 80, SEQ ID NO. 83, SEQ ID NO. 84; SEQ ID NO. 77, SEQ ID NO. 79, SEQ ID NO. 80, SEQ ID NO. 83, SEQ ID NO. 85; SEQ ID NO. 77, SEQ ID NO. 79, SEQ ID NO. 80, SEQ ID NO. 84, SEQ ID NO. 85; SEQ ID NO. 77, SEQ ID NO. 79, SEQ ID NO. 81, SEQ ID NO. 82, SEQ ID NO. 83; SEQ ID NO. 77, SEQ ID NO. 79, SEQ ID NO. 81, SEQ ID NO. 82, SEQ ID NO. 84; SEQ ID NO. 77, SEQ ID NO. 79, SEQ ID NO. 81, SEQ ID NO. 82, SEQ ID NO. 85; SEQ ID NO. 77, SEQ ID NO. 79, SEQ ID NO. 81, SEQ ID NO. 83, SEQ ID NO. 84; SEQ ID NO. 77, SEQ ID NO. 79, SEQ ID NO. 81, SEQ ID NO. 83, SEQ ID NO. 85; SEQ ID NO. 77, SEQ ID NO. 79, SEQ ID NO. 81, SEQ ID NO. 84, SEQ ID NO. 85; SEQ ID NO. 77, SEQ ID NO. 79, SEQ ID NO. 82, SEQ ID NO. 83, SEQ ID NO. 84; SEQ ID NO. 77, SEQ ID NO. 79, SEQ ID NO. 82, SEQ ID NO. 83, SEQ ID NO. 85; SEQ ID NO. 77, SEQ ID NO. 79, SEQ ID NO. 82, SEQ ID NO. 84, SEQ ID NO. 85; SEQ ID NO. 77, SEQ ID NO. 79, SEQ ID NO. 83, SEQ ID NO. 84, SEQ ID NO. 85; SEQ ID NO. 77, SEQ ID NO. 80, SEQ ID NO. 81, SEQ ID NO.

TABLE 6-continued

Combinations of amino acid sequences from Table 5, to be incorporated in immunogenic peptides for composing an composition of synthetic long peptides in accordance with the invention. The various combination are separated by semicolons.

82, SEQ ID NO. 83; SEQ ID NO. 77, SEQ ID NO. 80, SEQ ID NO. 81, SEQ ID NO. 82, SEQ ID NO. 84; SEQ ID NO. 77, SEQ ID NO. 80, SEQ ID NO. 81, SEQ ID NO. 82, SEQ ID NO. 85; SEQ ID NO. 77, SEQ ID NO. 80, SEQ ID NO. 81, SEQ ID NO. 83, SEQ ID NO. 84; SEQ ID NO. 77, SEQ ID NO. 80, SEQ ID NO. 81, SEQ ID NO. 83, SEQ ID NO. 85; SEQ ID NO. 77, SEQ ID NO. 80, SEQ ID NO. 81, SEQ ID NO. 84, SEQ ID NO. 85; SEQ ID NO. 77, SEQ ID NO. 80, SEQ ID NO. 82, SEQ ID NO. 83, SEQ ID NO. 84; SEQ ID NO. 77, SEQ ID NO. 80, SEQ ID NO. 82, SEQ ID NO. 83, SEQ ID NO. 85; SEQ ID NO. 77, SEQ ID NO. 80, SEQ ID NO. 82, SEQ ID NO. 84, SEQ ID NO. 85; SEQ ID NO. 77, SEQ ID NO. 80, SEQ ID NO. 83, SEQ ID NO. 84, SEQ ID NO. 85; SEQ ID NO. 77, SEQ ID NO. 81, SEQ ID NO. 82, SEQ ID NO. 83, SEQ ID NO. 84; SEQ ID NO. 77, SEQ ID NO. 81, SEQ ID NO. 82, SEQ ID NO. 83, SEQ ID NO. 85; SEQ ID NO. 77, SEQ ID NO. 81, SEQ ID NO. 82, SEQ ID NO. 84, SEQ ID NO. 85; SEQ ID NO. 77, SEQ ID NO. 81, SEQ ID NO. 83, SEQ ID NO. 84, SEQ ID NO. 85; SEQ ID NO. 77, SEQ ID NO. 82, SEQ ID NO. 83, SEQ ID NO. 84, SEQ ID NO. 85; SEQ ID NO. 78, SEQ ID NO. 79, SEQ ID NO. 80, SEQ ID NO. 81, SEQ ID NO. 82; SEQ ID NO. 78, SEQ ID NO. 79, SEQ ID NO. 80, SEQ ID NO. 81, SEQ ID NO. 83; SEQ ID NO. 78, SEQ ID NO. 79, SEQ ID NO. 80, SEQ ID NO. 81, SEQ ID NO. 84; SEQ ID NO. 78, SEQ ID NO. 79, SEQ ID NO. 80, SEQ ID NO. 81, SEQ ID NO. 85; SEQ ID NO. 78, SEQ ID NO. 79, SEQ ID NO. 80, SEQ ID NO. 82, SEQ ID NO. 83; SEQ ID NO. 78, SEQ ID NO. 79, SEQ ID NO. 80, SEQ ID NO. 82, SEQ ID NO. 84; SEQ ID NO. 78, SEQ ID NO. 79, SEQ ID NO. 80, SEQ ID NO. 82, SEQ ID NO. 85; SEQ ID NO. 78, SEQ ID NO. 79, SEQ ID NO. 80, SEQ ID NO. 83, SEQ ID NO. 84; SEQ ID NO. 78, SEQ ID NO. 79, SEQ ID NO. 80, SEQ ID NO. 83, SEQ ID NO. 85; SEQ ID NO. 78, SEQ ID NO. 79, SEQ ID NO. 80, SEQ ID NO. 84, SEQ ID NO. 85; SEQ ID NO. 78, SEQ ID NO. 79, SEQ ID NO. 81, SEQ ID NO. 82, SEQ ID NO. 83; SEQ ID NO. 78, SEQ ID NO. 79, SEQ ID NO. 81, SEQ ID NO. 82, SEQ ID NO. 84; SEQ ID NO. 78, SEQ ID NO. 79, SEQ ID NO. 81, SEQ ID NO. 82, SEQ ID NO. 85; SEQ ID NO. 78, SEQ ID NO. 79, SEQ ID NO. 81, SEQ ID NO. 83, SEQ ID NO. 84; SEQ ID NO. 78, SEQ ID NO. 79, SEQ ID NO. 81, SEQ ID NO. 83, SEQ ID NO. 85; SEQ ID NO. 78, SEQ ID NO. 79, SEQ ID NO. 81, SEQ ID NO. 84, SEQ ID NO. 85; SEQ ID NO. 78, SEQ ID NO. 79, SEQ ID NO. 82, SEQ ID NO. 83, SEQ ID NO. 84; SEQ ID NO. 78, SEQ ID NO. 79, SEQ ID NO. 82, SEQ ID NO. 83, SEQ ID NO. 85; SEQ ID NO. 78, SEQ ID NO. 79, SEQ ID NO. 82, SEQ ID NO. 84, SEQ ID NO. 85; SEQ ID NO. 78, SEQ ID NO. 79, SEQ ID NO. 83, SEQ ID NO. 84, SEQ ID NO. 85; SEQ ID NO. 78, SEQ ID NO. 80, SEQ ID NO. 81, SEQ ID NO. 82, SEQ ID NO. 83; SEQ ID NO. 78, SEQ ID NO. 80, SEQ ID NO. 81, SEQ ID NO. 82, SEQ ID NO. 84; SEQ ID NO. 78, SEQ ID NO. 80, SEQ ID NO. 81, SEQ ID NO. 82, SEQ ID NO. 85; SEQ ID NO. 78, SEQ ID NO. 80, SEQ ID NO. 81, SEQ ID NO. 83, SEQ ID NO. 84; SEQ ID NO. 78, SEQ ID NO. 80, SEQ ID NO. 81, SEQ ID NO. 83, SEQ ID NO. 85; SEQ ID NO. 78, SEQ ID NO. 80, SEQ ID NO. 81, SEQ ID NO. 84, SEQ ID NO. 85; SEQ ID NO. 78, SEQ ID NO. 80, SEQ ID NO. 82, SEQ ID NO. 83, SEQ ID NO. 84; SEQ ID NO. 78, SEQ ID NO. 80, SEQ ID NO. 82, SEQ ID NO. 83, SEQ ID NO. 85; SEQ ID NO. 78, SEQ ID NO. 80, SEQ ID NO. 82, SEQ ID NO. 84, SEQ ID NO. 85; SEQ ID NO. 78, SEQ ID NO. 80, SEQ ID NO. 83, SEQ ID NO. 84, SEQ ID NO. 85; SEQ ID NO. 78, SEQ ID NO. 81, SEQ ID NO. 82, SEQ ID NO. 83, SEQ ID NO. 84; SEQ ID NO. 78, SEQ ID NO. 81, SEQ ID NO. 82, SEQ ID NO. 83, SEQ ID NO. 85; SEQ ID NO. 78, SEQ ID NO. 81, SEQ ID NO. 82, SEQ ID NO. 84, SEQ ID NO. 85; SEQ ID NO. 78, SEQ ID NO. 81, SEQ ID NO. 83, SEQ ID NO. 84, SEQ ID NO. 85; SEQ ID NO. 78, SEQ ID NO. 82, SEQ ID NO. 83, SEQ ID NO. 84, SEQ ID NO. 85; SEQ ID NO. 79, SEQ ID NO. 80, SEQ ID NO. 81, SEQ ID NO. 82, SEQ ID NO. 83; SEQ ID NO. 79, SEQ ID NO. 80, SEQ ID NO. 81, SEQ ID NO. 82, SEQ ID NO. 84; SEQ ID NO. 79, SEQ ID NO. 80, SEQ ID NO. 81, SEQ ID NO. 82, SEQ ID NO. 85; SEQ ID NO. 79, SEQ ID NO. 80, SEQ ID NO. 81, SEQ ID NO. 83, SEQ ID NO. 84; SEQ ID NO. 79, SEQ ID NO. 80, SEQ ID NO. 81, SEQ ID NO. 83, SEQ ID NO. 85; SEQ ID NO. 79, SEQ ID NO. 80, SEQ ID NO. 81, SEQ ID NO. 84, SEQ ID NO. 85; SEQ ID NO. 79, SEQ ID NO. 80, SEQ ID NO. 82, SEQ ID NO. 83, SEQ ID NO. 84; SEQ ID NO. 79, SEQ ID NO. 80, SEQ ID NO. 82, SEQ ID NO. 83, SEQ ID NO. 85; SEQ ID NO. 79, SEQ ID NO. 80, SEQ ID NO. 82, SEQ ID NO. 84, SEQ ID NO. 85; SEQ ID NO. 79, SEQ ID NO. 80, SEQ ID NO. 83, SEQ ID NO. 84, SEQ ID NO. 85; SEQ ID NO. 79, SEQ ID NO. 81, SEQ ID NO. 82, SEQ ID NO. 83, SEQ ID NO. 84; SEQ ID NO. 79, SEQ ID NO. 81, SEQ ID NO. 82, SEQ ID NO. 83, SEQ ID NO. 85; SEQ ID NO. 79, SEQ ID NO. 81, SEQ ID NO. 82, SEQ ID NO. 84, SEQ ID NO. 85; SEQ ID NO. 79, SEQ ID NO. 81, SEQ ID NO. 83, SEQ ID NO. 84, SEQ ID NO. 85; SEQ ID NO. 79, SEQ ID NO. 82, SEQ ID NO. 83, SEQ ID NO. 84, SEQ ID NO. 85; SEQ ID NO. 80, SEQ ID NO. 81, SEQ ID NO. 82, SEQ ID NO. 83, SEQ ID NO. 84; SEQ ID NO. 80, SEQ ID NO. 81, SEQ ID NO. 82, SEQ ID NO. 83, SEQ ID NO. 85; SEQ ID NO. 80, SEQ ID NO. 81, SEQ ID NO. 82, SEQ ID NO. 84, SEQ ID NO. 85; SEQ ID NO. 80, SEQ ID NO. 81, SEQ ID NO. 83, SEQ ID NO. 84, SEQ ID NO. 85; SEQ ID NO. 80, SEQ ID NO. 82, SEQ ID NO. 83, SEQ ID NO. 84, SEQ ID NO. 85; SEQ ID NO. 81, SEQ ID NO. 82, SEQ ID NO. 83, SEQ ID NO. 84, SEQ ID NO. 85;

Combination of 6 peptides

SEQ ID NO. 76, SEQ ID NO. 77, SEQ ID NO. 78, SEQ ID NO. 79, SEQ ID NO. 80, SEQ ID NO. 81; SEQ ID NO. 76, SEQ ID NO. 77, SEQ ID NO. 78, SEQ ID NO. 79, SEQ ID NO. 80, SEQ ID NO. 82; SEQ ID NO. 76, SEQ ID NO. 77, SEQ ID NO. 78, SEQ ID NO. 79, SEQ ID NO. 80, SEQ ID NO. 83; SEQ ID NO. 76, SEQ ID NO. 77, SEQ ID NO. 78, SEQ ID NO. 79, SEQ ID NO. 80, SEQ ID NO. 84; SEQ ID NO. 76, SEQ ID NO. 77, SEQ ID NO. 78, SEQ ID NO. 79, SEQ ID NO. 80, SEQ ID NO. 85; SEQ ID NO. 76, SEQ ID NO. 77, SEQ ID NO. 78, SEQ ID NO. 79, SEQ ID NO. 81, SEQ ID NO. 82; SEQ ID NO. 76, SEQ ID NO. 77, SEQ ID NO. 78, SEQ ID NO. 79, SEQ ID NO. 81, SEQ ID NO. 83; SEQ ID NO. 76, SEQ ID NO. 77, SEQ ID NO. 78, SEQ ID NO. 79, SEQ ID NO. 81, SEQ ID NO. 84; SEQ ID NO. 76, SEQ ID NO. 77, SEQ ID NO. 78, SEQ ID NO. 79, SEQ ID NO. 81, SEQ ID NO. 85; SEQ ID NO. 76, SEQ ID NO. 77, SEQ ID NO. 78, SEQ ID NO. 79, SEQ ID NO. 82, SEQ ID NO. 83; SEQ ID NO. 76, SEQ ID NO. 77, SEQ ID NO. 78, SEQ ID NO. 79, SEQ ID NO. 82, SEQ ID NO. 84; SEQ ID NO. 76, SEQ ID NO. 77, SEQ ID NO. 78, SEQ ID NO. 79, SEQ ID NO. 82, SEQ ID NO. 85; SEQ ID NO. 76, SEQ ID NO. 77, SEQ ID NO. 78, SEQ ID NO. 79, SEQ ID NO. 83, SEQ ID NO. 84; SEQ ID NO. 76, SEQ ID NO. 77, SEQ ID NO. 78, SEQ ID NO. 79, SEQ ID NO. 83, SEQ ID NO. 85; SEQ ID NO. 76, SEQ ID NO. 77, SEQ ID NO. 78, SEQ ID NO. 79, SEQ ID NO. 84, SEQ ID NO. 85; SEQ ID NO. 76, SEQ ID NO. 77, SEQ ID NO. 78, SEQ ID NO. 80, SEQ ID NO. 81, SEQ ID NO. 82; SEQ ID NO. 76, SEQ ID NO. 77, SEQ ID NO. 78, SEQ ID NO. 80, SEQ ID NO. 81, SEQ ID NO. 83; SEQ ID NO. 76, SEQ ID NO. 77, SEQ ID NO. 78, SEQ ID NO. 80, SEQ

TABLE 6-continued

Combinations of amino acid sequences from Table 5, to be incorporated in immunogenic peptides for composing an composition of synthetic long peptides in accordance with the invention. The various combination are separated by semicolons.

ID NO. 81, SEQ ID NO. 84; SEQ ID NO. 76, SEQ ID NO. 77, SEQ ID NO. 78, SEQ ID NO. 80, SEQ ID NO. 81, SEQ ID NO. 85; SEQ ID NO. 76, SEQ ID NO. 77, SEQ ID NO. 78, SEQ ID NO. 80, SEQ ID NO. 82, SEQ ID NO. 83; SEQ ID NO. 76, SEQ ID NO. 77, SEQ ID NO. 78, SEQ ID NO. 80, SEQ ID NO. 82, SEQ ID NO. 84; SEQ ID NO. 76, SEQ ID NO. 77, SEQ ID NO. 78, SEQ ID NO. 80, SEQ ID NO. 82, SEQ ID NO. 85; SEQ ID NO. 76, SEQ ID NO. 77, SEQ ID NO. 78, SEQ ID NO. 80, SEQ ID NO. 83, SEQ ID NO. 84; SEQ ID NO. 76, SEQ ID NO. 77, SEQ ID NO. 78, SEQ ID NO. 80, SEQ ID NO. 83, SEQ ID NO. 85; SEQ ID NO. 76, SEQ ID NO. 77, SEQ ID NO. 78, SEQ ID NO. 80, SEQ ID NO. 84, SEQ ID NO. 85; SEQ ID NO. 76, SEQ ID NO. 77, SEQ ID NO. 78, SEQ ID NO. 81, SEQ ID NO. 82, SEQ ID NO. 83; SEQ ID NO. 76, SEQ ID NO. 77, SEQ ID NO. 78, SEQ ID NO. 81, SEQ ID NO. 82, SEQ ID NO. 84; SEQ ID NO. 76, SEQ ID NO. 77, SEQ ID NO. 78, SEQ ID NO. 81, SEQ ID NO. 82, SEQ ID NO. 85; SEQ ID NO. 76, SEQ ID NO. 77, SEQ ID NO. 78, SEQ ID NO. 81, SEQ ID NO. 83, SEQ ID NO. 84; SEQ ID NO. 76, SEQ ID NO. 77, SEQ ID NO. 78, SEQ ID NO. 81, SEQ ID NO. 83, SEQ ID NO. 85; SEQ ID NO. 76, SEQ ID NO. 77, SEQ ID NO. 78, SEQ ID NO. 81, SEQ ID NO. 84, SEQ ID NO. 85; SEQ ID NO. 76, SEQ ID NO. 77, SEQ ID NO. 78, SEQ ID NO. 82, SEQ ID NO. 83, SEQ ID NO. 84; SEQ ID NO. 76, SEQ ID NO. 77, SEQ ID NO. 78, SEQ ID NO. 82, SEQ ID NO. 83, SEQ ID NO. 85; SEQ ID NO. 76, SEQ ID NO. 77, SEQ ID NO. 78, SEQ ID NO. 82, SEQ ID NO. 84, SEQ ID NO. 85; SEQ ID NO. 76, SEQ ID NO. 77, SEQ ID NO. 78, SEQ ID NO. 83, SEQ ID NO. 84, SEQ ID NO. 85; SEQ ID NO. 76, SEQ ID NO. 77, SEQ ID NO. 79, SEQ ID NO. 80, SEQ ID NO. 81, SEQ ID NO. 82; SEQ ID NO. 76, SEQ ID NO. 77, SEQ ID NO. 79, SEQ ID NO. 80, SEQ ID NO. 81, SEQ ID NO. 83; SEQ ID NO. 76, SEQ ID NO. 77, SEQ ID NO. 79, SEQ ID NO. 80, SEQ ID NO. 81, SEQ ID NO. 84; SEQ ID NO. 76, SEQ ID NO. 77, SEQ ID NO. 79, SEQ ID NO. 80, SEQ ID NO. 81, SEQ ID NO. 85; SEQ ID NO. 76, SEQ ID NO. 77, SEQ ID NO. 79, SEQ ID NO. 80, SEQ ID NO. 82, SEQ ID NO. 83; SEQ ID NO. 76, SEQ ID NO. 77, SEQ ID NO. 79, SEQ ID NO. 80, SEQ ID NO. 82, SEQ ID NO. 84; SEQ ID NO. 76, SEQ ID NO. 77, SEQ ID NO. 79, SEQ ID NO. 80, SEQ ID NO. 82, SEQ ID NO. 85; SEQ ID NO. 76, SEQ ID NO. 77, SEQ ID NO. 79, SEQ ID NO. 80, SEQ ID NO. 83, SEQ ID NO. 84; SEQ ID NO. 76, SEQ ID NO. 77, SEQ ID NO. 79, SEQ ID NO. 80, SEQ ID NO. 83, SEQ ID NO. 85; SEQ ID NO. 76, SEQ ID NO. 77, SEQ ID NO. 79, SEQ ID NO. 80, SEQ ID NO. 84, SEQ ID NO. 85; SEQ ID NO. 76, SEQ ID NO. 77, SEQ ID NO. 79, SEQ ID NO. 81, SEQ ID NO. 82, SEQ ID NO. 83; SEQ ID NO. 76, SEQ ID NO. 77, SEQ ID NO. 79, SEQ ID NO. 81, SEQ ID NO. 82, SEQ ID NO. 84; SEQ ID NO. 76, SEQ ID NO. 77, SEQ ID NO. 79, SEQ ID NO. 81, SEQ ID NO. 82, SEQ ID NO. 85; SEQ ID NO. 76, SEQ ID NO. 77, SEQ ID NO. 79, SEQ ID NO. 81, SEQ ID NO. 83, SEQ ID NO. 84; SEQ ID NO. 76, SEQ ID NO. 77, SEQ ID NO. 79, SEQ ID NO. 81, SEQ ID NO. 83, SEQ ID NO. 85; SEQ ID NO. 76, SEQ ID NO. 77, SEQ ID NO. 79, SEQ ID NO. 81, SEQ ID NO. 84, SEQ ID NO. 85; SEQ ID NO. 76, SEQ ID NO. 77, SEQ ID NO. 79, SEQ ID NO. 82, SEQ ID NO. 83, SEQ ID NO. 84; SEQ ID NO. 76, SEQ ID NO. 77, SEQ ID NO. 79, SEQ ID NO. 82, SEQ ID NO. 83, SEQ ID NO. 85; SEQ ID NO. 76, SEQ ID NO. 77, SEQ ID NO. 79, SEQ ID NO. 82, SEQ ID NO. 84, SEQ ID NO. 85; SEQ ID NO. 76, SEQ ID NO. 77, SEQ ID NO. 79, SEQ ID NO. 83, SEQ ID NO. 84, SEQ ID NO. 85; SEQ ID NO. 76, SEQ ID NO. 77, SEQ ID NO. 80, SEQ ID NO. 81, SEQ ID NO. 82, SEQ ID NO. 83; SEQ ID NO. 76, SEQ ID NO. 77, SEQ ID NO. 80, SEQ ID NO. 81, SEQ ID NO. 82, SEQ ID NO. 84; SEQ ID NO. 76, SEQ ID NO. 77, SEQ ID NO. 80, SEQ ID NO. 81, SEQ ID NO. 82, SEQ ID NO. 85; SEQ ID NO. 76, SEQ ID NO. 77, SEQ ID NO. 80, SEQ ID NO. 81, SEQ ID NO. 83, SEQ ID NO. 84; SEQ ID NO. 76, SEQ ID NO. 77, SEQ ID NO. 80, SEQ ID NO. 81, SEQ ID NO. 83, SEQ ID NO. 85; SEQ ID NO. 76, SEQ ID NO. 77, SEQ ID NO. 80, SEQ ID NO. 81, SEQ ID NO. 84, SEQ ID NO. 85; SEQ ID NO. 76, SEQ ID NO. 77, SEQ ID NO. 80, SEQ ID NO. 82, SEQ ID NO. 83, SEQ ID NO. 84; SEQ ID NO. 76, SEQ ID NO. 77, SEQ ID NO. 80, SEQ ID NO. 82, SEQ ID NO. 83, SEQ ID NO. 85; SEQ ID NO. 76, SEQ ID NO. 77, SEQ ID NO. 80, SEQ ID NO. 82, SEQ ID NO. 84, SEQ ID NO. 85; SEQ ID NO. 76, SEQ ID NO. 77, SEQ ID NO. 80, SEQ ID NO. 83, SEQ ID NO. 84, SEQ ID NO. 85; SEQ ID NO. 76, SEQ ID NO. 77, SEQ ID NO. 81, SEQ ID NO. 82, SEQ ID NO. 83, SEQ ID NO. 84; SEQ ID NO. 76, SEQ ID NO. 77, SEQ ID NO. 81, SEQ ID NO. 82, SEQ ID NO. 83, SEQ ID NO. 85; SEQ ID NO. 76, SEQ ID NO. 77, SEQ ID NO. 81, SEQ ID NO. 82, SEQ ID NO. 84, SEQ ID NO. 85; SEQ ID NO. 76, SEQ ID NO. 77, SEQ ID NO. 81, SEQ ID NO. 83, SEQ ID NO. 84, SEQ ID NO. 85; SEQ ID NO. 76, SEQ ID NO. 77, SEQ ID NO. 82, SEQ ID NO. 83, SEQ ID NO. 84, SEQ ID NO. 85; SEQ ID NO. 76, SEQ ID NO. 78, SEQ ID NO. 79, SEQ ID NO. 80, SEQ ID NO. 81, SEQ ID NO. 82; SEQ ID NO. 76, SEQ ID NO. 78, SEQ ID NO. 79, SEQ ID NO. 80, SEQ ID NO. 81, SEQ ID NO. 83; SEQ ID NO. 76, SEQ ID NO. 78, SEQ ID NO. 79, SEQ ID NO. 80, SEQ ID NO. 81, SEQ ID NO. 84; SEQ ID NO. 76, SEQ ID NO. 78, SEQ ID NO. 79, SEQ ID NO. 80, SEQ ID NO. 81, SEQ ID NO. 85; SEQ ID NO. 76, SEQ ID NO. 78, SEQ ID NO. 79, SEQ ID NO. 80, SEQ ID NO. 82, SEQ ID NO. 83; SEQ ID NO. 76, SEQ ID NO. 78, SEQ ID NO. 79, SEQ ID NO. 80, SEQ ID NO. 82, SEQ ID NO. 84; SEQ ID NO. 76, SEQ ID NO. 78, SEQ ID NO. 79, SEQ ID NO. 80, SEQ ID NO. 82, SEQ ID NO. 85; SEQ ID NO. 76, SEQ ID NO. 78, SEQ ID NO. 79, SEQ ID NO. 80, SEQ ID NO. 83, SEQ ID NO. 84; SEQ ID NO. 76, SEQ ID NO. 78, SEQ ID NO. 79, SEQ ID NO. 80, SEQ ID NO. 83, SEQ ID NO. 85; SEQ ID NO. 76, SEQ ID NO. 78, SEQ ID NO. 79, SEQ ID NO. 80, SEQ ID NO. 84, SEQ ID NO. 85; SEQ ID NO. 76, SEQ ID NO. 78, SEQ ID NO. 79, SEQ ID NO. 81, SEQ ID NO. 82, SEQ ID NO. 83; SEQ ID NO. 76, SEQ ID NO. 78, SEQ ID NO. 79, SEQ ID NO. 81, SEQ ID NO. 82, SEQ ID NO. 84; SEQ ID NO. 76, SEQ ID NO. 78, SEQ ID NO. 79, SEQ ID NO. 81, SEQ ID NO. 82, SEQ ID NO. 85; SEQ ID NO. 76, SEQ ID NO. 78, SEQ ID NO. 79, SEQ ID NO. 81, SEQ ID NO. 83, SEQ ID NO. 84; SEQ ID NO. 76, SEQ ID NO. 78, SEQ ID NO. 79, SEQ ID NO. 81, SEQ ID NO. 83, SEQ ID NO. 85; SEQ ID NO. 76, SEQ ID NO. 78, SEQ ID NO. 79, SEQ ID NO. 81, SEQ ID NO. 84, SEQ ID NO. 85; SEQ ID NO. 76, SEQ ID NO. 78, SEQ ID NO. 79, SEQ ID NO. 82, SEQ ID NO. 83, SEQ ID NO. 84; SEQ ID NO. 76, SEQ ID NO. 78, SEQ ID NO. 79, SEQ ID NO. 82, SEQ ID NO. 83, SEQ ID NO. 85; SEQ ID NO. 76, SEQ ID NO. 78, SEQ ID NO. 79, SEQ ID NO. 82, SEQ ID NO. 84, SEQ ID NO. 85; SEQ ID NO. 76, SEQ ID NO. 78, SEQ ID NO. 79, SEQ ID NO. 83, SEQ ID NO. 84, SEQ ID NO. 85; SEQ ID NO. 76, SEQ ID NO. 78, SEQ ID NO. 80, SEQ ID NO. 81, SEQ ID NO. 82, SEQ ID NO. 83; SEQ ID NO. 76, SEQ ID NO. 78, SEQ ID NO. 80, SEQ ID NO. 81, SEQ ID NO. 82, SEQ ID NO. 84; SEQ ID NO. 76, SEQ ID NO. 78, SEQ ID NO. 80, SEQ ID NO. 81, SEQ ID NO. 82, SEQ ID NO. 85; SEQ ID NO. 76, SEQ ID NO. 78, SEQ ID NO. 80, SEQ ID NO. 81, SEQ ID NO. 83, SEQ ID NO. 84; SEQ ID NO. 76, SEQ ID NO. 78, SEQ ID NO. 80, SEQ ID NO. 81, SEQ ID NO. 83, SEQ ID NO. 85; SEQ ID NO. 76, SEQ ID NO. 78, SEQ ID NO. 80, SEQ ID NO. 81, SEQ ID NO. 84, SEQ ID NO. 85; SEQ ID NO. 76, SEQ ID NO. 78, SEQ ID NO. 80, SEQ ID NO. 82, SEQ ID NO. 83, SEQ

TABLE 6-continued

Combinations of amino acid sequences from Table 5, to be incorporated in immunogenic peptides for composing an composition of synthetic long peptides in accordance with the invention. The various combination are separated by semicolons.

ID NO. 84; SEQ ID NO. 76, SEQ ID NO. 78, SEQ ID NO. 80, SEQ ID NO. 82, SEQ ID NO. 83, SEQ ID NO. 85; SEQ ID NO. 76, SEQ ID NO. 78, SEQ ID NO. 80, SEQ ID NO. 82, SEQ ID NO. 84, SEQ ID NO. 85; SEQ ID NO. 76, SEQ ID NO. 78, SEQ ID NO. 80, SEQ ID NO. 83, SEQ ID NO. 84, SEQ ID NO. 85; SEQ ID NO. 76, SEQ ID NO. 78, SEQ ID NO. 81, SEQ ID NO. 82, SEQ ID NO. 83, SEQ ID NO. 84; SEQ ID NO. 76, SEQ ID NO. 78, SEQ ID NO. 81, SEQ ID NO. 82, SEQ ID NO. 83, SEQ ID NO. 85; SEQ ID NO. 76, SEQ ID NO. 78, SEQ ID NO. 81, SEQ ID NO. 82, SEQ ID NO. 84, SEQ ID NO. 85; SEQ ID NO. 76, SEQ ID NO. 78, SEQ ID NO. 81, SEQ ID NO. 83, SEQ ID NO. 84, SEQ ID NO. 85; SEQ ID NO. 76, SEQ ID NO. 78, SEQ ID NO. 82, SEQ ID NO. 83, SEQ ID NO. 84, SEQ ID NO. 85; SEQ ID NO. 76, SEQ ID NO. 79, SEQ ID NO. 80, SEQ ID NO. 81, SEQ ID NO. 82, SEQ ID NO. 83; SEQ ID NO. 76, SEQ ID NO. 79, SEQ ID NO. 80, SEQ ID NO. 81, SEQ ID NO. 82, SEQ ID NO. 84; SEQ ID NO. 76, SEQ ID NO. 79, SEQ ID NO. 80, SEQ ID NO. 81, SEQ ID NO. 82, SEQ ID NO. 85; SEQ ID NO. 76, SEQ ID NO. 79, SEQ ID NO. 80, SEQ ID NO. 81, SEQ ID NO. 83, SEQ ID NO. 84; SEQ ID NO. 76, SEQ ID NO. 79, SEQ ID NO. 80, SEQ ID NO. 81, SEQ ID NO. 83, SEQ ID NO. 85; SEQ ID NO. 76, SEQ ID NO. 79, SEQ ID NO. 80, SEQ ID NO. 81, SEQ ID NO. 84, SEQ ID NO. 85; SEQ ID NO. 76, SEQ ID NO. 79, SEQ ID NO. 80, SEQ ID NO. 82, SEQ ID NO. 83, SEQ ID NO. 84; SEQ ID NO. 76, SEQ ID NO. 79, SEQ ID NO. 80, SEQ ID NO. 82, SEQ ID NO. 83, SEQ ID NO. 85; SEQ ID NO. 76, SEQ ID NO. 79, SEQ ID NO. 80, SEQ ID NO. 82, SEQ ID NO. 84, SEQ ID NO. 85; SEQ ID NO. 76, SEQ ID NO. 79, SEQ ID NO. 80, SEQ ID NO. 83, SEQ ID NO. 84, SEQ ID NO. 85; SEQ ID NO. 76, SEQ ID NO. 79, SEQ ID NO. 81, SEQ ID NO. 82, SEQ ID NO. 83, SEQ ID NO. 84; SEQ ID NO. 76, SEQ ID NO. 79, SEQ ID NO. 81, SEQ ID NO. 82, SEQ ID NO. 83, SEQ ID NO. 85; SEQ ID NO. 76, SEQ ID NO. 79, SEQ ID NO. 81, SEQ ID NO. 82, SEQ ID NO. 84, SEQ ID NO. 85; SEQ ID NO. 76, SEQ ID NO. 79, SEQ ID NO. 81, SEQ ID NO. 83, SEQ ID NO. 84, SEQ ID NO. 85; SEQ ID NO. 76, SEQ ID NO. 79, SEQ ID NO. 82, SEQ ID NO. 83, SEQ ID NO. 84, SEQ ID NO. 85; SEQ ID NO. 76, SEQ ID NO. 80, SEQ ID NO. 81, SEQ ID NO. 82, SEQ ID NO. 83, SEQ ID NO. 84; SEQ ID NO. 76, SEQ ID NO. 80, SEQ ID NO. 81, SEQ ID NO. 82, SEQ ID NO. 83, SEQ ID NO. 85; SEQ ID NO. 76, SEQ ID NO. 80, SEQ ID NO. 81, SEQ ID NO. 82, SEQ ID NO. 84, SEQ ID NO. 85; SEQ ID NO. 76, SEQ ID NO. 80, SEQ ID NO. 81, SEQ ID NO. 83, SEQ ID NO. 84, SEQ ID NO. 85; SEQ ID NO. 76, SEQ ID NO. 80, SEQ ID NO. 82, SEQ ID NO. 83, SEQ ID NO. 84, SEQ ID NO. 85; SEQ ID NO. 76, SEQ ID NO. 81, SEQ ID NO. 82, SEQ ID NO. 83, SEQ ID NO. 84, SEQ ID NO. 85; SEQ ID NO. 77, SEQ ID NO. 78, SEQ ID NO. 79, SEQ ID NO. 80, SEQ ID NO. 81, SEQ ID NO. 82; SEQ ID NO. 77, SEQ ID NO. 78, SEQ ID NO. 79, SEQ ID NO. 80, SEQ ID NO. 81, SEQ ID NO. 83; SEQ ID NO. 77, SEQ ID NO. 78, SEQ ID NO. 79, SEQ ID NO. 80, SEQ ID NO. 81, SEQ ID NO. 84; SEQ ID NO. 77, SEQ ID NO. 78, SEQ ID NO. 79, SEQ ID NO. 80, SEQ ID NO. 81, SEQ ID NO. 85; SEQ ID NO. 77, SEQ ID NO. 78, SEQ ID NO. 79, SEQ ID NO. 80, SEQ ID NO. 82, SEQ ID NO. 83; SEQ ID NO. 77, SEQ ID NO. 78, SEQ ID NO. 79, SEQ ID NO. 80, SEQ ID NO. 82, SEQ ID NO. 84; SEQ ID NO. 77, SEQ ID NO. 78, SEQ ID NO. 79, SEQ ID NO. 80, SEQ ID NO. 82, SEQ ID NO. 85; SEQ ID NO. 77, SEQ ID NO. 78, SEQ ID NO. 79, SEQ ID NO. 80, SEQ ID NO. 83, SEQ ID NO. 84; SEQ ID NO. 77, SEQ ID NO. 78, SEQ ID NO. 79, SEQ ID NO. 80, SEQ ID NO. 83, SEQ ID NO. 85; SEQ ID NO. 77, SEQ ID NO. 78, SEQ ID NO. 79, SEQ ID NO. 80, SEQ ID NO. 84, SEQ ID NO. 85; SEQ ID NO. 77, SEQ ID NO. 78, SEQ ID NO. 79, SEQ ID NO. 81, SEQ ID NO. 82, SEQ ID NO. 83; SEQ ID NO. 77, SEQ ID NO. 78, SEQ ID NO. 79, SEQ ID NO. 81, SEQ ID NO. 82, SEQ ID NO. 84; SEQ ID NO. 77, SEQ ID NO. 78, SEQ ID NO. 79, SEQ ID NO. 81, SEQ ID NO. 82, SEQ ID NO. 85; SEQ ID NO. 77, SEQ ID NO. 78, SEQ ID NO. 79, SEQ ID NO. 81, SEQ ID NO. 83, SEQ ID NO. 84; SEQ ID NO. 77, SEQ ID NO. 78, SEQ ID NO. 79, SEQ ID NO. 81, SEQ ID NO. 83, SEQ ID NO. 85; SEQ ID NO. 77, SEQ ID NO. 78, SEQ ID NO. 79, SEQ ID NO. 81, SEQ ID NO. 84, SEQ ID NO. 85; SEQ ID NO. 77, SEQ ID NO. 78, SEQ ID NO. 79, SEQ ID NO. 82, SEQ ID NO. 83, SEQ ID NO. 84; SEQ ID NO. 77, SEQ ID NO. 78, SEQ ID NO. 79, SEQ ID NO. 82, SEQ ID NO. 83, SEQ ID NO. 85; SEQ ID NO. 77, SEQ ID NO. 78, SEQ ID NO. 79, SEQ ID NO. 82, SEQ ID NO. 84, SEQ ID NO. 85; SEQ ID NO. 77, SEQ ID NO. 78, SEQ ID NO. 79, SEQ ID NO. 83, SEQ ID NO. 84, SEQ ID NO. 85; SEQ ID NO. 77, SEQ ID NO. 78, SEQ ID NO. 80, SEQ ID NO. 81, SEQ ID NO. 82, SEQ ID NO. 83; SEQ ID NO. 77, SEQ ID NO. 78, SEQ ID NO. 80, SEQ ID NO. 81, SEQ ID NO. 82, SEQ ID NO. 84; SEQ ID NO. 77, SEQ ID NO. 78, SEQ ID NO. 80, SEQ ID NO. 81, SEQ ID NO. 82, SEQ ID NO. 85; SEQ ID NO. 77, SEQ ID NO. 78, SEQ ID NO. 80, SEQ ID NO. 81, SEQ ID NO. 83, SEQ ID NO. 84; SEQ ID NO. 77, SEQ ID NO. 78, SEQ ID NO. 80, SEQ ID NO. 81, SEQ ID NO. 83, SEQ ID NO. 85; SEQ ID NO. 77, SEQ ID NO. 78, SEQ ID NO. 80, SEQ ID NO. 81, SEQ ID NO. 84, SEQ ID NO. 85; SEQ ID NO. 77, SEQ ID NO. 78, SEQ ID NO. 80, SEQ ID NO. 82, SEQ ID NO. 83, SEQ ID NO. 84; SEQ ID NO. 77, SEQ ID NO. 78, SEQ ID NO. 80, SEQ ID NO. 82, SEQ ID NO. 83, SEQ ID NO. 85; SEQ ID NO. 77, SEQ ID NO. 78, SEQ ID NO. 80, SEQ ID NO. 82, SEQ ID NO. 84, SEQ ID NO. 85; SEQ ID NO. 77, SEQ ID NO. 78, SEQ ID NO. 80, SEQ ID NO. 83, SEQ ID NO. 84, SEQ ID NO. 85; SEQ ID NO. 77, SEQ ID NO. 78, SEQ ID NO. 81, SEQ ID NO. 82, SEQ ID NO. 83, SEQ ID NO. 84; SEQ ID NO. 77, SEQ ID NO. 78, SEQ ID NO. 81, SEQ ID NO. 82, SEQ ID NO. 83, SEQ ID NO. 85; SEQ ID NO. 77, SEQ ID NO. 78, SEQ ID NO. 81, SEQ ID NO. 82, SEQ ID NO. 84, SEQ ID NO. 85; SEQ ID NO. 77, SEQ ID NO. 78, SEQ ID NO. 81, SEQ ID NO. 83, SEQ ID NO. 84, SEQ ID NO. 85; SEQ ID NO. 77, SEQ ID NO. 78, SEQ ID NO. 82, SEQ ID NO. 83, SEQ ID NO. 84, SEQ ID NO. 85; SEQ ID NO. 77, SEQ ID NO. 79, SEQ ID NO. 80, SEQ ID NO. 81, SEQ ID NO. 82, SEQ ID NO. 83; SEQ ID NO. 77, SEQ ID NO. 79, SEQ ID NO. 80, SEQ ID NO. 81, SEQ ID NO. 82, SEQ ID NO. 84; SEQ ID NO. 77, SEQ ID NO. 79, SEQ ID NO. 80, SEQ ID NO. 81, SEQ ID NO. 82, SEQ ID NO. 85; SEQ ID NO. 77, SEQ ID NO. 79, SEQ ID NO. 80, SEQ ID NO. 81, SEQ ID NO. 83, SEQ ID NO. 84; SEQ ID NO. 77, SEQ ID NO. 79, SEQ ID NO. 80, SEQ ID NO. 81, SEQ ID NO. 83, SEQ ID NO. 85; SEQ ID NO. 77, SEQ ID NO. 79, SEQ ID NO. 80, SEQ ID NO. 81, SEQ ID NO. 84, SEQ ID NO. 85; SEQ ID NO. 77, SEQ ID NO. 79, SEQ ID NO. 80, SEQ ID NO. 82, SEQ ID NO. 83, SEQ ID NO. 84; SEQ ID NO. 77, SEQ ID NO. 79, SEQ ID NO. 80, SEQ ID NO. 82, SEQ ID NO. 83, SEQ ID NO. 85; SEQ ID NO. 77, SEQ ID NO. 79, SEQ ID NO. 80, SEQ ID NO. 82, SEQ ID NO. 84, SEQ ID NO. 85; SEQ ID NO. 77, SEQ ID NO. 79, SEQ ID NO. 80, SEQ ID NO. 83, SEQ ID NO. 84, SEQ ID NO. 85; SEQ ID NO. 77, SEQ ID NO. 79, SEQ ID NO. 81, SEQ ID NO. 82, SEQ ID NO. 83, SEQ ID NO. 84; SEQ ID NO. 77, SEQ ID NO. 79, SEQ ID NO. 81, SEQ ID NO. 82, SEQ ID NO. 83, SEQ ID NO. 85; SEQ ID NO. 77, SEQ ID NO. 79, SEQ ID NO. 81, SEQ ID NO. 82, SEQ ID NO. 84, SEQ ID NO. 85; SEQ ID NO. 77, SEQ ID NO. 79, SEQ ID NO. 81, SEQ ID NO. 83, SEQ ID NO. 84, SEQ ID NO. 85; SEQ ID NO. 77, SEQ ID NO. 79, SEQ ID NO. 82, SEQ ID NO. 83, SEQ ID NO. 84, SEQ ID NO. 85; SEQ

TABLE 6-continued

Combinations of amino acid sequences from Table 5, to be incorporated in immunogenic peptides for composing an composition of synthetic long peptides in accordance with the invention. The various combination are separated by semicolons.

ID NO. 77, SEQ ID NO. 80, SEQ ID NO. 81, SEQ ID NO. 82, SEQ ID NO. 83, SEQ ID NO. 84; SEQ ID NO. 77, SEQ ID NO. 80, SEQ ID NO. 81, SEQ ID NO. 82, SEQ ID NO. 83, SEQ ID NO. 85; SEQ ID NO. 77, SEQ ID NO. 80, SEQ ID NO. 81, SEQ ID NO. 82, SEQ ID NO. 84, SEQ ID NO. 85; SEQ ID NO. 77, SEQ ID NO. 80, SEQ ID NO. 81, SEQ ID NO. 83, SEQ ID NO. 84, SEQ ID NO. 85; SEQ ID NO. 77, SEQ ID NO. 80, SEQ ID NO. 82, SEQ ID NO. 83, SEQ ID NO. 84, SEQ ID NO. 85; SEQ ID NO. 77, SEQ ID NO. 81, SEQ ID NO. 82, SEQ ID NO. 83, SEQ ID NO. 84, SEQ ID NO. 85; SEQ ID NO. 78, SEQ ID NO. 79, SEQ ID NO. 80, SEQ ID NO. 81, SEQ ID NO. 82, SEQ ID NO. 83; SEQ ID NO. 78, SEQ ID NO. 79, SEQ ID NO. 80, SEQ ID NO. 81, SEQ ID NO. 82, SEQ ID NO. 84; SEQ ID NO. 78, SEQ ID NO. 79, SEQ ID NO. 80, SEQ ID NO. 81, SEQ ID NO. 82, SEQ ID NO. 85; SEQ ID NO. 78, SEQ ID NO. 79, SEQ ID NO. 80, SEQ ID NO. 81, SEQ ID NO. 83, SEQ ID NO. 84; SEQ ID NO. 78, SEQ ID NO. 79, SEQ ID NO. 80, SEQ ID NO. 81, SEQ ID NO. 83, SEQ ID NO. 85; SEQ ID NO. 78, SEQ ID NO. 79, SEQ ID NO. 80, SEQ ID NO. 81, SEQ ID NO. 84, SEQ ID NO. 85; SEQ ID NO. 78, SEQ ID NO. 79, SEQ ID NO. 80, SEQ ID NO. 82, SEQ ID NO. 83, SEQ ID NO. 84; SEQ ID NO. 78, SEQ ID NO. 79, SEQ ID NO. 80, SEQ ID NO. 82, SEQ ID NO. 83, SEQ ID NO. 85; SEQ ID NO. 78, SEQ ID NO. 79, SEQ ID NO. 80, SEQ ID NO. 82, SEQ ID NO. 84, SEQ ID NO. 85; SEQ ID NO. 78, SEQ ID NO. 79, SEQ ID NO. 80, SEQ ID NO. 83, SEQ ID NO. 84, SEQ ID NO. 85; SEQ ID NO. 78, SEQ ID NO. 79, SEQ ID NO. 81, SEQ ID NO. 82, SEQ ID NO. 83, SEQ ID NO. 84; SEQ ID NO. 78, SEQ ID NO. 79, SEQ ID NO. 81, SEQ ID NO. 82, SEQ ID NO. 83, SEQ ID NO. 85; SEQ ID NO. 78, SEQ ID NO. 79, SEQ ID NO. 81, SEQ ID NO. 82, SEQ ID NO. 84, SEQ ID NO. 85; SEQ ID NO. 78, SEQ ID NO. 79, SEQ ID NO. 81, SEQ ID NO. 83, SEQ ID NO. 84, SEQ ID NO. 85; SEQ ID NO. 78, SEQ ID NO. 79, SEQ ID NO. 82, SEQ ID NO. 83, SEQ ID NO. 84, SEQ ID NO. 85; SEQ ID NO. 78, SEQ ID NO. 80, SEQ ID NO. 81, SEQ ID NO. 82, SEQ ID NO. 83, SEQ ID NO. 84; SEQ ID NO. 78, SEQ ID NO. 80, SEQ ID NO. 81, SEQ ID NO. 82, SEQ ID NO. 83, SEQ ID NO. 85; SEQ ID NO. 78, SEQ ID NO. 80, SEQ ID NO. 81, SEQ ID NO. 82, SEQ ID NO. 84, SEQ ID NO. 85; SEQ ID NO. 78, SEQ ID NO. 80, SEQ ID NO. 81, SEQ ID NO. 83, SEQ ID NO. 84, SEQ ID NO. 85; SEQ ID NO. 78, SEQ ID NO. 80, SEQ ID NO. 82, SEQ ID NO. 83, SEQ ID NO. 84, SEQ ID NO. 85; SEQ ID NO. 78, SEQ ID NO. 81, SEQ ID NO. 82, SEQ ID NO. 83, SEQ ID NO. 84, SEQ ID NO. 85; SEQ ID NO. 79, SEQ ID NO. 80, SEQ ID NO. 81, SEQ ID NO. 82, SEQ ID NO. 83, SEQ ID NO. 84; SEQ ID NO. 79, SEQ ID NO. 80, SEQ ID NO. 81, SEQ ID NO. 82, SEQ ID NO. 83, SEQ ID NO. 85; SEQ ID NO. 79, SEQ ID NO. 80, SEQ ID NO. 81, SEQ ID NO. 82, SEQ ID NO. 84, SEQ ID NO. 85; SEQ ID NO. 79, SEQ ID NO. 80, SEQ ID NO. 81, SEQ ID NO. 83, SEQ ID NO. 84, SEQ ID NO. 85; SEQ ID NO. 79, SEQ ID NO. 80, SEQ ID NO. 82, SEQ ID NO. 83, SEQ ID NO. 84, SEQ ID NO. 85; SEQ ID NO. 79, SEQ ID NO. 81, SEQ ID NO. 82, SEQ ID NO. 83, SEQ ID NO. 84, SEQ ID NO. 85; SEQ ID NO. 80, SEQ ID NO. 81, SEQ ID NO. 82, SEQ ID NO. 83, SEQ ID NO. 84, SEQ ID NO. 85;

Combination of 7 peptides

SEQ ID NO. 76, SEQ ID NO. 77, SEQ ID NO. 78, SEQ ID NO. 79, SEQ ID NO. 80, SEQ ID NO. 81, SEQ ID NO. 82; SEQ ID NO. 76, SEQ ID NO. 77, SEQ ID NO. 78, SEQ ID NO. 79, SEQ ID NO. 80, SEQ ID NO. 81, SEQ ID NO. 83; SEQ ID NO. 76, SEQ ID NO. 77, SEQ ID NO. 78, SEQ ID NO. 79, SEQ ID NO. 80, SEQ ID NO. 81, SEQ ID NO. 84; SEQ ID NO. 76, SEQ ID NO. 77, SEQ ID NO. 78, SEQ ID NO. 79, SEQ ID NO. 80, SEQ ID NO. 81, SEQ ID NO. 85; SEQ ID NO. 76, SEQ ID NO. 77, SEQ ID NO. 78, SEQ ID NO. 79, SEQ ID NO. 80, SEQ ID NO. 82, SEQ ID NO. 83; SEQ ID NO. 76, SEQ ID NO. 77, SEQ ID NO. 78, SEQ ID NO. 79, SEQ ID NO. 80, SEQ ID NO. 82, SEQ ID NO. 84; SEQ ID NO. 76, SEQ ID NO. 77, SEQ ID NO. 78, SEQ ID NO. 79, SEQ ID NO. 80, SEQ ID NO. 82, SEQ ID NO. 85; SEQ ID NO. 76, SEQ ID NO. 77, SEQ ID NO. 78, SEQ ID NO. 79, SEQ ID NO. 80, SEQ ID NO. 83, SEQ ID NO. 84; SEQ ID NO. 76, SEQ ID NO. 77, SEQ ID NO. 78, SEQ ID NO. 79, SEQ ID NO. 80, SEQ ID NO. 83, SEQ ID NO. 85; SEQ ID NO. 76, SEQ ID NO. 77, SEQ ID NO. 78, SEQ ID NO. 79, SEQ ID NO. 80, SEQ ID NO. 84, SEQ ID NO. 85; SEQ ID NO. 76, SEQ ID NO. 77, SEQ ID NO. 78, SEQ ID NO. 79, SEQ ID NO. 81, SEQ ID NO. 82, SEQ ID NO. 83; SEQ ID NO. 76, SEQ ID NO. 77, SEQ ID NO. 78, SEQ ID NO. 79, SEQ ID NO. 81, SEQ ID NO. 82, SEQ ID NO. 84; SEQ ID NO. 76, SEQ ID NO. 77, SEQ ID NO. 78, SEQ ID NO. 79, SEQ ID NO. 81, SEQ ID NO. 82, SEQ ID NO. 85; SEQ ID NO. 76, SEQ ID NO. 77, SEQ ID NO. 78, SEQ ID NO. 79, SEQ ID NO. 81, SEQ ID NO. 83, SEQ ID NO. 84; SEQ ID NO. 76, SEQ ID NO. 77, SEQ ID NO. 78, SEQ ID NO. 79, SEQ ID NO. 81, SEQ ID NO. 83, SEQ ID NO. 85; SEQ ID NO. 76, SEQ ID NO. 77, SEQ ID NO. 78, SEQ ID NO. 79, SEQ ID NO. 81, SEQ ID NO. 84, SEQ ID NO. 85; SEQ ID NO. 76, SEQ ID NO. 77, SEQ ID NO. 78, SEQ ID NO. 79, SEQ ID NO. 82, SEQ ID NO. 83, SEQ ID NO. 84; SEQ ID NO. 76, SEQ ID NO. 77, SEQ ID NO. 78, SEQ ID NO. 79, SEQ ID NO. 82, SEQ ID NO. 83, SEQ ID NO. 85; SEQ ID NO. 76, SEQ ID NO. 77, SEQ ID NO. 78, SEQ ID NO. 79, SEQ ID NO. 82, SEQ ID NO. 84, SEQ ID NO. 85; SEQ ID NO. 76, SEQ ID NO. 77, SEQ ID NO. 78, SEQ ID NO. 79, SEQ ID NO. 83, SEQ ID NO. 84, SEQ ID NO. 85; SEQ ID NO. 76, SEQ ID NO. 77, SEQ ID NO. 78, SEQ ID NO. 80, SEQ ID NO. 81, SEQ ID NO. 82, SEQ ID NO. 83; SEQ ID NO. 76, SEQ ID NO. 77, SEQ ID NO. 78, SEQ ID NO. 80, SEQ ID NO. 81, SEQ ID NO. 82, SEQ ID NO. 84; SEQ ID NO. 76, SEQ ID NO. 77, SEQ ID NO. 78, SEQ ID NO. 80, SEQ ID NO. 81, SEQ ID NO. 82, SEQ ID NO. 85; SEQ ID NO. 76, SEQ ID NO. 77, SEQ ID NO. 78, SEQ ID NO. 80, SEQ ID NO. 81, SEQ ID NO. 83, SEQ ID NO. 84; SEQ ID NO. 76, SEQ ID NO. 77, SEQ ID NO. 78, SEQ ID NO. 80, SEQ ID NO. 81, SEQ ID NO. 83, SEQ ID NO. 85; SEQ ID NO. 76, SEQ ID NO. 77, SEQ ID NO. 78, SEQ ID NO. 80, SEQ ID NO. 81, SEQ ID NO. 84, SEQ ID NO. 85; SEQ ID NO. 76, SEQ ID NO. 77, SEQ ID NO. 78, SEQ ID NO. 80, SEQ ID NO. 82, SEQ ID NO. 83, SEQ ID NO. 84; SEQ ID NO. 76, SEQ ID NO. 77, SEQ ID NO. 78, SEQ ID NO. 80, SEQ ID NO. 82, SEQ ID NO. 83, SEQ ID NO. 85; SEQ ID NO. 76, SEQ ID NO. 77, SEQ ID NO. 78, SEQ ID NO. 80, SEQ ID NO. 82, SEQ ID NO. 84, SEQ ID NO. 85; SEQ ID NO. 76, SEQ ID NO. 77, SEQ ID NO. 78, SEQ ID NO. 80, SEQ ID NO. 83, SEQ ID NO. 84, SEQ ID NO. 85; SEQ ID NO. 76, SEQ ID NO. 77, SEQ ID NO. 78, SEQ ID NO. 81, SEQ ID NO. 82, SEQ ID NO. 83, SEQ ID NO. 84; SEQ ID NO. 76, SEQ ID NO. 77, SEQ ID NO. 78, SEQ ID NO. 81, SEQ ID NO. 82, SEQ ID NO. 83, SEQ ID NO. 85; SEQ ID NO. 76, SEQ ID NO. 77, SEQ ID NO. 78, SEQ ID NO. 81, SEQ ID NO. 82, SEQ ID NO. 84, SEQ ID NO. 85; SEQ ID NO. 76, SEQ ID NO. 77, SEQ ID NO. 78, SEQ ID NO. 81, SEQ ID NO. 83, SEQ ID NO. 84, SEQ ID NO. 85; SEQ ID NO. 76, SEQ ID NO. 77, SEQ ID NO. 78, SEQ ID NO. 82, SEQ ID NO. 83, SEQ ID NO. 84, SEQ ID NO. 85; SEQ ID NO. 76, SEQ ID NO. 77, SEQ ID NO. 79, SEQ ID NO. 80, SEQ ID NO. 81, SEQ ID NO. 82, SEQ ID NO. 83; SEQ ID NO. 76, SEQ ID NO. 77, SEQ ID NO. 79, SEQ ID NO. 80, SEQ

TABLE 6-continued

Combinations of amino acid sequences from Table 5, to be incorporated in immunogenic peptides for composing an composition of synthetic long peptides in accordance with the invention. The various combination are separated by semicolons.

ID NO. 81, SEQ ID NO. 82, SEQ ID NO. 84; SEQ ID NO. 76, SEQ ID NO. 77, SEQ ID NO. 79, SEQ ID NO. 80, SEQ ID NO. 81, SEQ ID NO. 82, SEQ ID NO. 85; SEQ ID NO. 76, SEQ ID NO. 77, SEQ ID NO. 79, SEQ ID NO. 80, SEQ ID NO. 81, SEQ ID NO. 83, SEQ ID NO. 84; SEQ ID NO. 76, SEQ ID NO. 77, SEQ ID NO. 79, SEQ ID NO. 80, SEQ ID NO. 81, SEQ ID NO. 83, SEQ ID NO. 85; SEQ ID NO. 76, SEQ ID NO. 77, SEQ ID NO. 79, SEQ ID NO. 80, SEQ ID NO. 81, SEQ ID NO. 84, SEQ ID NO. 85; SEQ ID NO. 76, SEQ ID NO. 77, SEQ ID NO. 79, SEQ ID NO. 80, SEQ ID NO. 82, SEQ ID NO. 83, SEQ ID NO. 84; SEQ ID NO. 76, SEQ ID NO. 77, SEQ ID NO. 79, SEQ ID NO. 80, SEQ ID NO. 82, SEQ ID NO. 83, SEQ ID NO. 85; SEQ ID NO. 76, SEQ ID NO. 77, SEQ ID NO. 79, SEQ ID NO. 80, SEQ ID NO. 82, SEQ ID NO. 84, SEQ ID NO. 85; SEQ ID NO. 76, SEQ ID NO. 77, SEQ ID NO. 79, SEQ ID NO. 80, SEQ ID NO. 83, SEQ ID NO. 84, SEQ ID NO. 85; SEQ ID NO. 76, SEQ ID NO. 77, SEQ ID NO. 79, SEQ ID NO. 81, SEQ ID NO. 82, SEQ ID NO. 83, SEQ ID NO. 84; SEQ ID NO. 76, SEQ ID NO. 77, SEQ ID NO. 79, SEQ ID NO. 81, SEQ ID NO. 82, SEQ ID NO. 83, SEQ ID NO. 85; SEQ ID NO. 76, SEQ ID NO. 77, SEQ ID NO. 79, SEQ ID NO. 81, SEQ ID NO. 82, SEQ ID NO. 84, SEQ ID NO. 85; SEQ ID NO. 76, SEQ ID NO. 77, SEQ ID NO. 79, SEQ ID NO. 81, SEQ ID NO. 83, SEQ ID NO. 84, SEQ ID NO. 85; SEQ ID NO. 76, SEQ ID NO. 77, SEQ ID NO. 79, SEQ ID NO. 82, SEQ ID NO. 83, SEQ ID NO. 84, SEQ ID NO. 85; SEQ ID NO. 76, SEQ ID NO. 77, SEQ ID NO. 80, SEQ ID NO. 81, SEQ ID NO. 82, SEQ ID NO. 83, SEQ ID NO. 84; SEQ ID NO. 76, SEQ ID NO. 77, SEQ ID NO. 80, SEQ ID NO. 81, SEQ ID NO. 82, SEQ ID NO. 83, SEQ ID NO. 85; SEQ ID NO. 76, SEQ ID NO. 77, SEQ ID NO. 80, SEQ ID NO. 81, SEQ ID NO. 82, SEQ ID NO. 84, SEQ ID NO. 85; SEQ ID NO. 76, SEQ ID NO. 77, SEQ ID NO. 80, SEQ ID NO. 81, SEQ ID NO. 83, SEQ ID NO. 84, SEQ ID NO. 85; SEQ ID NO. 76, SEQ ID NO. 77, SEQ ID NO. 80, SEQ ID NO. 82, SEQ ID NO. 83, SEQ ID NO. 84, SEQ ID NO. 85; SEQ ID NO. 76, SEQ ID NO. 77, SEQ ID NO. 81, SEQ ID NO. 82, SEQ ID NO. 83, SEQ ID NO. 84, SEQ ID NO. 85; SEQ ID NO. 76, SEQ ID NO. 78, SEQ ID NO. 79, SEQ ID NO. 80, SEQ ID NO. 81, SEQ ID NO. 82, SEQ ID NO. 83; SEQ ID NO. 76, SEQ ID NO. 78, SEQ ID NO. 79, SEQ ID NO. 80, SEQ ID NO. 81, SEQ ID NO. 82, SEQ ID NO. 84; SEQ ID NO. 76, SEQ ID NO. 78, SEQ ID NO. 79, SEQ ID NO. 80, SEQ ID NO. 81, SEQ ID NO. 82, SEQ ID NO. 85; SEQ ID NO. 76, SEQ ID NO. 78, SEQ ID NO. 79, SEQ ID NO. 80, SEQ ID NO. 81, SEQ ID NO. 83, SEQ ID NO. 84; SEQ ID NO. 76, SEQ ID NO. 78, SEQ ID NO. 79, SEQ ID NO. 80, SEQ ID NO. 81, SEQ ID NO. 83, SEQ ID NO. 85; SEQ ID NO. 76, SEQ ID NO. 78, SEQ ID NO. 79, SEQ ID NO. 80, SEQ ID NO. 81, SEQ ID NO. 84, SEQ ID NO. 85; SEQ ID NO. 76, SEQ ID NO. 78, SEQ ID NO. 79, SEQ ID NO. 80, SEQ ID NO. 82, SEQ ID NO. 83, SEQ ID NO. 84; SEQ ID NO. 76, SEQ ID NO. 78, SEQ ID NO. 79, SEQ ID NO. 80, SEQ ID NO. 82, SEQ ID NO. 83, SEQ ID NO. 85; SEQ ID NO. 76, SEQ ID NO. 78, SEQ ID NO. 79, SEQ ID NO. 80, SEQ ID NO. 82, SEQ ID NO. 84, SEQ ID NO. 85; SEQ ID NO. 76, SEQ ID NO. 78, SEQ ID NO. 79, SEQ ID NO. 80, SEQ ID NO. 83, SEQ ID NO. 84, SEQ ID NO. 85; SEQ ID NO. 76, SEQ ID NO. 78, SEQ ID NO. 79, SEQ ID NO. 81, SEQ ID NO. 82, SEQ ID NO. 83, SEQ ID NO. 84; SEQ ID NO. 76, SEQ ID NO. 78, SEQ ID NO. 79, SEQ ID NO. 81, SEQ ID NO. 82, SEQ ID NO. 83, SEQ ID NO. 85; SEQ ID NO. 76, SEQ ID NO. 78, SEQ ID NO. 79, SEQ ID NO. 81, SEQ ID NO. 82, SEQ ID NO. 84, SEQ ID NO. 85; SEQ ID NO. 76, SEQ ID NO. 78, SEQ ID NO. 79, SEQ ID NO. 81, SEQ ID NO. 83, SEQ ID NO. 84, SEQ ID NO. 85; SEQ ID NO. 76, SEQ ID NO. 78, SEQ ID NO. 79, SEQ ID NO. 82, SEQ ID NO. 83, SEQ ID NO. 84, SEQ ID NO. 85; SEQ ID NO. 76, SEQ ID NO. 78, SEQ ID NO. 80, SEQ ID NO. 81, SEQ ID NO. 82, SEQ ID NO. 83, SEQ ID NO. 84; SEQ ID NO. 76, SEQ ID NO. 78, SEQ ID NO. 80, SEQ ID NO. 81, SEQ ID NO. 82, SEQ ID NO. 83, SEQ ID NO. 85; SEQ ID NO. 76, SEQ ID NO. 78, SEQ ID NO. 80, SEQ ID NO. 81, SEQ ID NO. 82, SEQ ID NO. 84, SEQ ID NO. 85; SEQ ID NO. 76, SEQ ID NO. 78, SEQ ID NO. 80, SEQ ID NO. 81, SEQ ID NO. 83, SEQ ID NO. 84, SEQ ID NO. 85; SEQ ID NO. 76, SEQ ID NO. 78, SEQ ID NO. 80, SEQ ID NO. 82, SEQ ID NO. 83, SEQ ID NO. 84, SEQ ID NO. 85; SEQ ID NO. 76, SEQ ID NO. 78, SEQ ID NO. 81, SEQ ID NO. 82, SEQ ID NO. 83, SEQ ID NO. 84, SEQ ID NO. 85; SEQ ID NO. 76, SEQ ID NO. 79, SEQ ID NO. 80, SEQ ID NO. 81, SEQ ID NO. 82, SEQ ID NO. 83, SEQ ID NO. 85; SEQ ID NO. 76, SEQ ID NO. 79, SEQ ID NO. 80, SEQ ID NO. 81, SEQ ID NO. 82, SEQ ID NO. 84, SEQ ID NO. 85; SEQ ID NO. 76, SEQ ID NO. 79, SEQ ID NO. 80, SEQ ID NO. 81, SEQ ID NO. 83, SEQ ID NO. 84, SEQ ID NO. 85; SEQ ID NO. 76, SEQ ID NO. 79, SEQ ID NO. 80, SEQ ID NO. 82, SEQ ID NO. 83, SEQ ID NO. 84, SEQ ID NO. 85; SEQ ID NO. 76, SEQ ID NO. 79, SEQ ID NO. 81, SEQ ID NO. 82, SEQ ID NO. 83, SEQ ID NO. 84, SEQ ID NO. 85; SEQ ID NO. 76, SEQ ID NO. 80, SEQ ID NO. 81, SEQ ID NO. 82, SEQ ID NO. 83, SEQ ID NO. 84, SEQ ID NO. 85; SEQ ID NO. 77, SEQ ID NO. 78, SEQ ID NO. 79, SEQ ID NO. 80, SEQ ID NO. 81, SEQ ID NO. 82, SEQ ID NO. 83; SEQ ID NO. 77, SEQ ID NO. 78, SEQ ID NO. 79, SEQ ID NO. 80, SEQ ID NO. 81, SEQ ID NO. 82, SEQ ID NO. 84; SEQ ID NO. 77, SEQ ID NO. 78, SEQ ID NO. 79, SEQ ID NO. 80, SEQ ID NO. 81, SEQ ID NO. 82, SEQ ID NO. 85; SEQ ID NO. 77, SEQ ID NO. 78, SEQ ID NO. 79, SEQ ID NO. 80, SEQ ID NO. 81, SEQ ID NO. 83, SEQ ID NO. 84; SEQ ID NO. 77, SEQ ID NO. 78, SEQ ID NO. 79, SEQ ID NO. 80, SEQ ID NO. 81, SEQ ID NO. 83, SEQ ID NO. 85; SEQ ID NO. 77, SEQ ID NO. 78, SEQ ID NO. 79, SEQ ID NO. 80, SEQ ID NO. 81, SEQ ID NO. 84, SEQ ID NO. 85; SEQ ID NO. 77, SEQ ID NO. 78, SEQ ID NO. 79, SEQ ID NO. 80, SEQ ID NO. 82, SEQ ID NO. 83, SEQ ID NO. 84; SEQ ID NO. 77, SEQ ID NO. 78, SEQ ID NO. 79, SEQ ID NO. 80, SEQ ID NO. 82, SEQ ID NO. 83, SEQ ID NO. 85; SEQ ID NO. 77, SEQ ID NO. 78, SEQ ID NO. 79, SEQ ID NO. 80, SEQ ID NO. 82, SEQ ID NO. 84, SEQ ID NO. 85; SEQ ID NO. 77, SEQ ID NO. 78, SEQ ID NO. 79, SEQ ID NO. 80, SEQ ID NO. 83, SEQ ID NO. 84, SEQ ID NO. 85; SEQ ID NO. 77, SEQ ID NO. 78, SEQ ID NO. 79, SEQ ID NO. 81, SEQ ID NO. 82, SEQ ID NO. 83, SEQ ID NO. 84; SEQ ID NO. 77, SEQ ID NO. 78, SEQ ID NO. 79, SEQ ID NO. 81, SEQ ID NO. 82, SEQ ID NO. 83, SEQ ID NO. 85; SEQ ID NO. 77, SEQ ID NO. 78, SEQ ID NO. 79, SEQ ID NO. 81, SEQ ID NO. 82, SEQ ID NO. 84, SEQ ID NO. 85; SEQ ID NO. 77, SEQ ID NO. 78, SEQ ID NO. 79, SEQ ID NO. 81, SEQ ID NO. 83, SEQ ID NO. 84, SEQ ID NO. 85; SEQ ID NO. 77, SEQ ID NO. 78, SEQ ID NO. 79, SEQ ID NO. 82, SEQ ID NO. 83, SEQ ID NO. 84, SEQ ID NO. 85; SEQ ID NO. 77, SEQ ID NO. 78, SEQ ID NO. 80, SEQ ID NO. 81, SEQ ID NO. 82, SEQ ID NO. 83, SEQ ID NO. 84; SEQ ID NO. 77, SEQ ID NO. 78, SEQ ID NO. 80, SEQ ID NO. 81, SEQ ID NO. 82, SEQ ID NO. 83, SEQ ID NO. 85; SEQ ID NO. 77, SEQ ID NO. 78, SEQ ID NO. 80, SEQ ID NO. 81, SEQ ID NO. 82, SEQ ID NO. 84, SEQ ID NO. 85; SEQ ID NO. 77, SEQ ID NO. 78, SEQ ID NO. 80, SEQ ID NO. 81, SEQ ID NO. 83, SEQ ID NO. 84, SEQ ID NO. 85; SEQ ID NO. 77, SEQ ID NO. 78, SEQ ID NO. 80, SEQ ID NO. 82, SEQ ID NO. 83, SEQ ID NO. 84, SEQ ID NO. 85; SEQ ID NO. 77, SEQ ID NO. 78, SEQ ID NO. 81, SEQ

TABLE 6-continued

Combinations of amino acid sequences from Table 5, to be incorporated in immunogenic peptides for composing an composition of synthetic long peptides in accordance with the invention. The various combination are separated by semicolons.

ID NO. 82, SEQ ID NO. 83, SEQ ID NO. 84, SEQ ID NO. 85; SEQ ID NO. 77, SEQ ID NO. 79, SEQ ID NO. 80, SEQ ID NO. 81, SEQ ID NO. 82, SEQ ID NO. 83, SEQ ID NO. 84; SEQ ID NO. 77, SEQ ID NO. 79, SEQ ID NO. 80, SEQ ID NO. 81, SEQ ID NO. 82, SEQ ID NO. 83, SEQ ID NO. 85; SEQ ID NO. 77, SEQ ID NO. 79, SEQ ID NO. 80, SEQ ID NO. 81, SEQ ID NO. 82, SEQ ID NO. 84, SEQ ID NO. 85; SEQ ID NO. 77, SEQ ID NO. 79, SEQ ID NO. 80, SEQ ID NO. 81, SEQ ID NO. 83, SEQ ID NO. 84, SEQ ID NO. 85; SEQ ID NO. 77, SEQ ID NO. 79, SEQ ID NO. 80, SEQ ID NO. 82, SEQ ID NO. 83, SEQ ID NO. 84, SEQ ID NO. 85; SEQ ID NO. 77, SEQ ID NO. 79, SEQ ID NO. 81, SEQ ID NO. 82, SEQ ID NO. 83, SEQ ID NO. 84, SEQ ID NO. 85; SEQ ID NO. 77, SEQ ID NO. 80, SEQ ID NO. 81, SEQ ID NO. 82, SEQ ID NO. 83, SEQ ID NO. 84, SEQ ID NO. 85; SEQ ID NO. 78, SEQ ID NO. 79, SEQ ID NO. 80, SEQ ID NO. 81, SEQ ID NO. 82, SEQ ID NO. 83, SEQ ID NO. 84; SEQ ID NO. 78, SEQ ID NO. 79, SEQ ID NO. 80, SEQ ID NO. 81, SEQ ID NO. 82, SEQ ID NO. 83, SEQ ID NO. 85; SEQ ID NO. 78, SEQ ID NO. 79, SEQ ID NO. 80, SEQ ID NO. 81, SEQ ID NO. 82, SEQ ID NO. 84, SEQ ID NO. 85; SEQ ID NO. 78, SEQ ID NO. 79, SEQ ID NO. 80, SEQ ID NO. 81, SEQ ID NO. 83, SEQ ID NO. 84, SEQ ID NO. 85; SEQ ID NO. 78, SEQ ID NO. 79, SEQ ID NO. 80, SEQ ID NO. 82, SEQ ID NO. 83, SEQ ID NO. 84, SEQ ID NO. 85; SEQ ID NO. 78, SEQ ID NO. 79, SEQ ID NO. 81, SEQ ID NO. 82, SEQ ID NO. 83, SEQ ID NO. 84, SEQ ID NO. 85; SEQ ID NO. 78, SEQ ID NO. 80, SEQ ID NO. 81, SEQ ID NO. 82, SEQ ID NO. 83, SEQ ID NO. 84, SEQ ID NO. 85; SEQ ID NO. 79, SEQ ID NO. 80, SEQ ID NO. 81, SEQ ID NO. 82, SEQ ID NO. 83, SEQ ID NO. 84, SEQ ID NO. 85;

Combination of 8 peptides

SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83; SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 84; SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 85; SEQ ID NO. 76, SEQ ID NO. 77, SEQ ID NO. 78, SEQ ID NO. 79, SEQ ID NO. 80, SEQ ID NO. 81, SEQ ID NO. 83, SEQ ID NO. 84; SEQ ID NO. 76, SEQ ID NO. 77, SEQ ID NO. 78, SEQ ID NO. 79, SEQ ID NO. 80, SEQ ID NO. 81, SEQ ID NO. 83, SEQ ID NO. 85; SEQ ID NO. 76, SEQ ID NO. 77, SEQ ID NO. 78, SEQ ID NO. 79, SEQ ID NO. 80, SEQ ID NO. 81, SEQ ID NO. 84, SEQ ID NO. 85; SEQ ID NO. 76, SEQ ID NO. 77, SEQ ID NO. 78, SEQ ID NO. 79, SEQ ID NO. 80, SEQ ID NO. 82, SEQ ID NO. 83, SEQ ID NO. 84; SEQ ID NO. 76, SEQ ID NO. 77, SEQ ID NO. 78, SEQ ID NO. 79, SEQ ID NO. 80, SEQ ID NO. 82, SEQ ID NO. 83, SEQ ID NO. 85; SEQ ID NO. 76, SEQ ID NO. 77, SEQ ID NO. 78, SEQ ID NO. 79, SEQ ID NO. 80, SEQ ID NO. 82, SEQ ID NO. 84, SEQ ID NO. 85; SEQ ID NO. 76, SEQ ID NO. 77, SEQ ID NO. 78, SEQ ID NO. 79, SEQ ID NO. 80, SEQ ID NO. 83, SEQ ID NO. 84, SEQ ID NO. 85; SEQ ID NO. 76, SEQ ID NO. 77, SEQ ID NO. 78, SEQ ID NO. 79, SEQ ID NO. 81, SEQ ID NO. 82, SEQ ID NO. 83, SEQ ID NO. 84; SEQ ID NO. 76, SEQ ID NO. 77, SEQ ID NO. 78, SEQ ID NO. 79, SEQ ID NO. 81, SEQ ID NO. 82, SEQ ID NO. 83, SEQ ID NO. 85; SEQ ID NO. 76, SEQ ID NO. 77, SEQ ID NO. 78, SEQ ID NO. 79, SEQ ID NO. 81, SEQ ID NO. 82, SEQ ID NO. 84, SEQ ID NO. 85; SEQ ID NO. 76, SEQ ID NO. 77, SEQ ID NO. 78, SEQ ID NO. 79, SEQ ID NO. 81, SEQ ID NO. 83, SEQ ID NO. 84, SEQ ID NO. 85; SEQ ID NO. 76, SEQ ID NO. 77, SEQ ID NO. 78, SEQ ID NO. 79, SEQ ID NO. 82, SEQ ID NO. 83, SEQ ID NO. 84, SEQ ID NO. 85; SEQ ID NO. 76, SEQ ID NO. 77, SEQ ID NO. 78, SEQ ID NO. 80, SEQ ID NO. 81, SEQ ID NO. 82, SEQ ID NO. 83, SEQ ID NO. 84; SEQ ID NO. 76, SEQ ID NO. 77, SEQ ID NO. 78, SEQ ID NO. 80, SEQ ID NO. 81, SEQ ID NO. 82, SEQ ID NO. 83, SEQ ID NO. 85; SEQ ID NO. 76, SEQ ID NO. 77, SEQ ID NO. 78, SEQ ID NO. 80, SEQ ID NO. 81, SEQ ID NO. 82, SEQ ID NO. 84, SEQ ID NO. 85; SEQ ID NO. 76, SEQ ID NO. 77, SEQ ID NO. 78, SEQ ID NO. 80, SEQ ID NO. 81, SEQ ID NO. 83, SEQ ID NO. 84, SEQ ID NO. 85; SEQ ID NO. 76, SEQ ID NO. 77, SEQ ID NO. 78, SEQ ID NO. 80, SEQ ID NO. 82, SEQ ID NO. 83, SEQ ID NO. 84, SEQ ID NO. 85; SEQ ID NO. 76, SEQ ID NO. 77, SEQ ID NO. 78, SEQ ID NO. 81, SEQ ID NO. 82, SEQ ID NO. 83, SEQ ID NO. 84, SEQ ID NO. 85; SEQ ID NO. 76, SEQ ID NO. 77, SEQ ID NO. 79, SEQ ID NO. 80, SEQ ID NO. 81, SEQ ID NO. 82, SEQ ID NO. 83, SEQ ID NO. 84; SEQ ID NO. 76, SEQ ID NO. 77, SEQ ID NO. 79, SEQ ID NO. 80, SEQ ID NO. 81, SEQ ID NO. 82, SEQ ID NO. 83, SEQ ID NO. 85; SEQ ID NO. 76, SEQ ID NO. 77, SEQ ID NO. 79, SEQ ID NO. 80, SEQ ID NO. 81, SEQ ID NO. 82, SEQ ID NO. 84, SEQ ID NO. 85; SEQ ID NO. 76, SEQ ID NO. 77, SEQ ID NO. 79, SEQ ID NO. 80, SEQ ID NO. 81, SEQ ID NO. 83, SEQ ID NO. 84, SEQ ID NO. 85; SEQ ID NO. 76, SEQ ID NO. 77, SEQ ID NO. 79, SEQ ID NO. 80, SEQ ID NO. 82, SEQ ID NO. 83, SEQ ID NO. 84, SEQ ID NO. 85; SEQ ID NO. 76, SEQ ID NO. 77, SEQ ID NO. 79, SEQ ID NO. 81, SEQ ID NO. 82, SEQ ID NO. 83, SEQ ID NO. 84, SEQ ID NO. 85; SEQ ID NO. 76, SEQ ID NO. 77, SEQ ID NO. 80, SEQ ID NO. 81, SEQ ID NO. 82, SEQ ID NO. 83, SEQ ID NO. 84, SEQ ID NO. 85; SEQ ID NO. 76, SEQ ID NO. 78, SEQ ID NO. 79, SEQ ID NO. 80, SEQ ID NO. 81, SEQ ID NO. 82, SEQ ID NO. 83, SEQ ID NO. 84; SEQ ID NO. 76, SEQ ID NO. 78, SEQ ID NO. 79, SEQ ID NO. 80, SEQ ID NO. 81, SEQ ID NO. 82, SEQ ID NO. 83, SEQ ID NO. 85; SEQ ID NO. 76, SEQ ID NO. 78, SEQ ID NO. 79, SEQ ID NO. 80, SEQ ID NO. 81, SEQ ID NO. 82, SEQ ID NO. 84, SEQ ID NO. 85; SEQ ID NO. 76, SEQ ID NO. 78, SEQ ID NO. 79, SEQ ID NO. 80, SEQ ID NO. 81, SEQ ID NO. 83, SEQ ID NO. 84, SEQ ID NO. 85; SEQ ID NO. 76, SEQ ID NO. 78, SEQ ID NO. 79, SEQ ID NO. 80, SEQ ID NO. 82, SEQ ID NO. 83, SEQ ID NO. 84, SEQ ID NO. 85; SEQ ID NO. 76, SEQ ID NO. 78, SEQ ID NO. 80, SEQ ID NO. 81, SEQ ID NO. 82, SEQ ID NO. 83, SEQ ID NO. 84, SEQ ID NO. 85; SEQ ID NO. 76, SEQ ID NO. 79, SEQ ID NO. 80, SEQ ID NO. 81, SEQ ID NO. 82, SEQ ID NO. 83, SEQ ID NO. 84, SEQ ID NO. 85; SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84; SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 85; SEQ ID NO. 77, SEQ ID NO. 78, SEQ ID NO. 79, SEQ ID NO. 80, SEQ ID NO. 81, SEQ ID NO. 82, SEQ ID NO. 84, SEQ ID NO. 85; SEQ ID NO. 77, SEQ ID NO. 78, SEQ ID NO. 79, SEQ ID NO. 80, SEQ ID NO. 81, SEQ ID NO. 83, SEQ ID NO. 84, SEQ ID NO. 85; SEQ ID NO. 77, SEQ ID NO. 78, SEQ ID NO. 79, SEQ ID NO. 80, SEQ ID NO. 82, SEQ ID NO. 83, SEQ ID NO. 84, SEQ ID NO. 85; SEQ ID NO. 77, SEQ ID NO. 78, SEQ ID NO. 79, SEQ ID NO. 81, SEQ ID NO. 82, SEQ ID NO. 83, SEQ ID NO. 84, SEQ ID NO. 85; SEQ ID NO. 77, SEQ ID NO. 78, SEQ ID NO. 80, SEQ ID NO. 81, SEQ ID NO. 82, SEQ ID NO. 83, SEQ ID NO. 84, SEQ ID NO. 85; SEQ ID NO. 77, SEQ ID NO. 79, SEQ ID NO. 80, SEQ ID NO. 81, SEQ ID NO. 82, SEQ ID NO. 83,

TABLE 6-continued

Combinations of amino acid sequences from Table 5, to be incorporated in immunogenic peptides for composing an composition of synthetic long peptides in accordance with the invention. The various combination are separated by semicolons.

SEQ ID NO. 84, SEQ ID NO. 85; SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85;
Combination of 9 peptides SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84; SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 85; SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 84, SEQ ID NO. 85; SEQ ID NO. 76, SEQ ID NO. 77, SEQ ID NO. 78, SEQ ID NO. 79, SEQ ID NO. 80, SEQ ID NO. 81, SEQ ID NO. 83, SEQ ID NO. 84, SEQ ID NO. 85; SEQ ID NO. 76, SEQ ID NO. 77, SEQ ID NO. 78, SEQ ID NO. 79, SEQ ID NO. 80, SEQ ID NO. 82, SEQ ID NO. 83, SEQ ID NO. 84, SEQ ID NO. 85; SEQ ID NO. 76, SEQ ID NO. 77, SEQ ID NO. 78, SEQ ID NO. 79, SEQ ID NO. 81, SEQ ID NO. 82, SEQ ID NO. 83, SEQ ID NO. 84, SEQ ID NO. 85; SEQ ID NO. 76, SEQ ID NO. 77, SEQ ID NO. 78, SEQ ID NO. 80, SEQ ID NO. 81, SEQ ID NO. 82, SEQ ID NO. 83, SEQ ID NO. 84, SEQ ID NO. 85; SEQ ID NO. 76, SEQ ID NO. 77, SEQ ID NO. 79, SEQ ID NO. 80, SEQ ID NO. 81, SEQ ID NO. 82, SEQ ID NO. 83, SEQ ID NO. 84, SEQ ID NO. 85; SEQ ID NO. 76, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85; SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 85;

The invention claimed is:

1. A method for the therapeutic and/or prophylactic treatment of lung cancer expressing human Zona Pellucida protein 3 (hZP3) and/or metastases thereof in a human, the method comprising administering an effective amount of a pharmaceutical composition to the human, wherein the pharmaceutical composition comprises a source of an immunogenic polypeptide comprising at least one of a class I and a class II major histocompatibility complex (MHC)-restricted epitope from the amino acid sequence of SEQ ID NO:3.

2. The method of claim 1, wherein the source of an immunogenic polypeptide is a composition comprising:
   a) one or more immunogenic peptides comprising or consisting of an amino acid sequence selected from SEQ ID NO.'s 66-72, 74 and 75; and/or,
   b) one or more immunogenic peptides comprising or consisting of an amino acid sequence selected from SEQ ID NO.'s 76-85.

3. The method of claim 1, wherein the method of treatment is a method of preventing metastases and/or recurrence of lung cancer, wherein optionally, the lung cancer is non-small cell lung cancer.

4. The method of claim 1, wherein the method of treatment is combined with an immunomodulating therapy, surgery, radiation therapy, chemotherapy, targeted therapy or a combination thereof.

5. The method of claim 4, wherein the immunomodulating therapy comprises the use of at least one of a checkpoint inhibitor, an antibody targeting a tumor necrosis factor (TNF) receptor family member, an immunosuppressive cytokine, a γC cytokine, a Toll-like receptor (TLR) agonist and an agonist of invariant natural killer T (iNKT) cells.

6. The method of claim 1, wherein the source of the immunogenic polypeptide comprises a proteinaceous composition comprising at least one source of an immunogenic polypeptide comprising at least one of a class I MHC- and a class II MHC-restricted epitope from the amino acid sequence of SEQ ID NO:3.

7. The method of claim 6, wherein the proteinaceous composition comprises at least one immunogenic polypeptide comprising a contiguous amino acid sequence of at least 18 amino acids selected from the amino acid sequence of SEQ ID NO:3 and wherein the contiguous amino acid sequence comprises at least one of a class I MHC- and a class II MHC-restricted T cell epitope.

8. The method of claim 7, wherein the proteinaceous composition comprises more than one different immunogenic polypeptide, each comprising a contiguous amino acid sequence of at least 18 amino acids selected from the amino acid sequence of SEQ ID NO:3 and having a length in the range of 18-100 amino acids, optionally a length in the range of 18-60 amino acids.

9. The method of claim 1, wherein the source of the immunogenic peptide collectively comprises at least one of:
   a) at least 50, 70, 80, 90 or 95% of the complete amino acid sequence of SEQ ID NO: 3; and,
   b) at least 50, 70, 80, 90 or 95% of the potential MHC I and/or MHC II epitopes predicted by a computer-based algorithm bio-informatics tool.

10. The method of claim 1, wherein the method further comprises administering, optionally co-administering, at least one adjuvant.

11. The method of claim 1, wherein the composition is administered by at least one of intratumoral, intramuscular, intraperitoneal, intradermal, subcutaneous, transdermal administration, and administration into an anatomic site that drains into at least one lymph node basin.

12. The method of claim 8, wherein the more than one different immunogenic polypeptide collectively comprises at least one of:
   a) at least 50, 70, 80, 90 or 95% of the complete amino acid sequence of SEQ ID NO:3; and,
   b) at least 50, 70, 80, 90 or 95% of the potential WIC I and/or WIC II epitopes predicted by a computer-based algorithm bio-informatics tool.

* * * * *

```
                         SEQUENCE LISTING

<160> NUMBER OF SEQ ID NOS: 85

<210> SEQ ID NO 1
<211> LENGTH: 638
<212> TYPE: PRT
<213> ORGANISM: Homo sapiens

<400> SEQUENCE: 1

Met Ala Gly Gly Ser Ala Thr Thr Trp Gly Tyr Pro Val Ala Leu Leu
1               5                   10                  15

Leu Leu Val Ala Thr Leu Gly Leu Gly Arg Trp Leu Gln Pro Asp Pro
                20                  25                  30

Gly Leu Pro Gly Leu Arg His Ser Tyr Asp Cys Gly Ile Lys Gly Met
            35                  40                  45

Gln Leu Leu Val Phe Pro Arg Pro Gly Gln Thr Leu Arg Phe Lys Val
        50                  55                  60

Val Asp Glu Phe Gly Asn Arg Phe Asp Val Asn Asn Cys Ser Ile Cys
65                  70                  75                  80

Tyr His Trp Val Thr Ser Arg Pro Gln Glu Pro Ala Val Phe Ser Ala
                85                  90                  95

Asp Tyr Arg Gly Cys His Val Leu Glu Lys Asp Gly Arg Phe His Leu
            100                 105                 110

Arg Val Phe Met Glu Ala Val Leu Pro Asn Gly Arg Val Asp Val Ala
        115                 120                 125

Gln Asp Ala Thr Leu Ile Cys Pro Lys Pro Asp Pro Ser Arg Thr Leu
    130                 135                 140

Asp Ser Gln Leu Ala Pro Pro Ala Met Phe Ser Val Ser Thr Pro Gln
145                 150                 155                 160

Thr Leu Ser Phe Leu Pro Thr Ser Gly His Thr Ser Gln Gly Ser Gly
                165                 170                 175

His Ala Phe Pro Ser Pro Leu Asp Pro Gly His Ser Ser Val His Pro
            180                 185                 190

Thr Pro Ala Leu Pro Ser Pro Gly Pro Gly Pro Thr Leu Ala Thr Leu
        195                 200                 205

Ala Gln Pro His Trp Gly Thr Leu Glu His Trp Asp Val Asn Lys Arg
```

```
                210                 215                 220
Asp Tyr Ile Gly Thr His Leu Ser Gln Glu Gln Cys Gln Val Ala Ser
225                 230                 235                 240

Gly His Leu Pro Cys Ile Val Arg Arg Thr Ser Lys Glu Ala Cys Gln
                245                 250                 255

Gln Ala Gly Cys Cys Tyr Asp Asn Thr Arg Glu Val Pro Cys Tyr Tyr
                260                 265                 270

Gly Asn Thr Ala Thr Val Gln Cys Phe Arg Asp Gly Tyr Phe Val Leu
            275                 280                 285

Val Val Ser Gln Glu Met Ala Leu Thr His Arg Ile Thr Leu Ala Asn
        290                 295                 300

Ile His Leu Ala Tyr Ala Pro Thr Ser Cys Ser Pro Thr Gln His Thr
305                 310                 315                 320

Glu Ala Phe Val Val Phe Tyr Phe Pro Leu Thr His Cys Gly Thr Thr
                325                 330                 335

Met Gln Val Ala Gly Asp Gln Leu Ile Tyr Glu Asn Trp Leu Val Ser
                340                 345                 350

Gly Ile His Ile Gln Lys Gly Pro Gln Gly Ser Ile Thr Arg Asp Ser
            355                 360                 365

Thr Phe Gln Leu His Val Arg Cys Val Phe Asn Ala Ser Asp Phe Leu
370                 375                 380

Pro Ile Gln Ala Ser Ile Phe Pro Pro Ser Pro Ala Pro Met Thr
385                 390                 395                 400

Gln Pro Gly Pro Leu Arg Leu Glu Leu Arg Ile Ala Lys Asp Glu Thr
                405                 410                 415

Phe Ser Ser Tyr Tyr Gly Glu Asp Tyr Pro Ile Val Arg Leu Leu
                420                 425                 430

Arg Glu Pro Val His Val Glu Val Arg Leu Leu Gln Arg Thr Asp Pro
            435                 440                 445

Asn Leu Val Leu Leu Leu His Gln Cys Trp Gly Ala Pro Ser Ala Asn
450                 455                 460

Pro Phe Gln Gln Pro Gln Trp Pro Ile Leu Ser Asp Gly Cys Pro Phe
465                 470                 475                 480

Lys Gly Asp Ser Tyr Arg Thr Gln Met Val Ala Leu Asp Gly Ala Thr
                485                 490                 495

Pro Phe Gln Ser His Tyr Gln Arg Phe Thr Val Ala Thr Phe Ala Leu
                500                 505                 510

Leu Asp Ser Gly Ser Gln Arg Ala Leu Arg Gly Leu Val Tyr Leu Phe
            515                 520                 525

Cys Ser Thr Ser Ala Cys His Thr Ser Gly Leu Glu Thr Cys Ser Thr
        530                 535                 540

Ala Cys Ser Thr Gly Thr Thr Arg Gln Arg Ser Ser Gly His Arg
545                 550                 555                 560

Asn Asp Thr Ala Arg Pro Gln Asp Ile Val Ser Ser Pro Gly Val
                565                 570                 575

Gly Phe Glu Asp Ser Tyr Gly Gln Glu Pro Thr Leu Gly Pro Thr Asp
            580                 585                 590

Ser Asn Gly Asn Ser Ser Leu Arg Pro Leu Leu Trp Ala Val Leu Leu
        595                 600                 605

Leu Pro Ala Val Ala Leu Val Leu Gly Phe Gly Val Phe Val Gly Leu
    610                 615                 620

Ser Gln Thr Trp Ala Gln Lys Leu Trp Glu Ser Asn Arg Gln
625                 630                 635
```

<210> SEQ ID NO 2
<211> LENGTH: 745
<212> TYPE: PRT
<213> ORGANISM: Homo sapiens

<400> SEQUENCE: 2

```
Met Ala Cys Arg Gln Arg Gly Gly Ser Trp Ser Pro Ser Gly Trp Phe
1               5                   10                  15

Asn Ala Gly Trp Ser Thr Tyr Arg Ser Ile Ser Leu Phe Phe Ala Leu
            20                  25                  30

Val Thr Ser Gly Asn Ser Ile Asp Val Ser Gln Leu Val Asn Pro Ala
        35                  40                  45

Phe Pro Gly Thr Val Thr Cys Asp Glu Arg Glu Ile Thr Val Glu Phe
    50                  55                  60

Pro Ser Ser Pro Gly Thr Lys Lys Trp His Ala Ser Val Val Asp Pro
65                  70                  75                  80

Leu Gly Leu Asp Met Pro Asn Cys Thr Tyr Ile Leu Asp Pro Glu Lys
                85                  90                  95

Leu Thr Leu Arg Ala Thr Tyr Asp Asn Cys Thr Arg Arg Val His Gly
            100                 105                 110

Gly His Gln Met Thr Ile Arg Val Met Asn Asn Ser Ala Ala Leu Arg
        115                 120                 125

His Gly Ala Val Met Tyr Gln Phe Phe Cys Pro Ala Met Gln Val Glu
    130                 135                 140

Glu Thr Gln Gly Leu Ser Ala Ser Thr Ile Cys Gln Lys Asp Phe Met
145                 150                 155                 160

Ser Phe Ser Leu Pro Arg Val Phe Ser Gly Leu Ala Asp Asp Ser Lys
                165                 170                 175

Gly Thr Lys Val Gln Met Gly Trp Ser Ile Glu Val Gly Asp Gly Ala
            180                 185                 190

Arg Ala Lys Thr Leu Thr Leu Pro Glu Ala Met Lys Glu Gly Phe Ser
        195                 200                 205

Leu Leu Ile Asp Asn His Arg Met Thr Phe His Val Pro Phe Asn Ala
    210                 215                 220

Thr Gly Val Thr His Tyr Val Gln Gly Asn Ser His Leu Tyr Met Val
225                 230                 235                 240

Ser Leu Lys Leu Thr Phe Ile Ser Pro Gly Gln Lys Val Ile Phe Ser
                245                 250                 255

Ser Gln Ala Ile Cys Ala Pro Asp Pro Val Thr Cys Asn Ala Thr His
            260                 265                 270

Met Thr Leu Thr Ile Pro Glu Phe Pro Gly Lys Leu Lys Ser Val Ser
        275                 280                 285

Phe Glu Asn Gln Asn Ile Asp Val Ser Gln Leu His Asp Asn Gly Ile
    290                 295                 300

Asp Leu Glu Ala Thr Asn Gly Met Lys Leu His Phe Ser Lys Thr Leu
305                 310                 315                 320

Leu Lys Thr Lys Leu Ser Glu Lys Cys Leu Leu His Gln Phe Tyr Leu
                325                 330                 335

Ala Ser Leu Lys Leu Thr Phe Leu Leu Arg Pro Glu Thr Val Ser Met
            340                 345                 350

Val Ile Tyr Pro Glu Cys Leu Cys Glu Ser Pro Val Ser Ile Val Thr
        355                 360                 365

Gly Glu Leu Cys Thr Gln Asp Gly Phe Met Asp Val Glu Val Tyr Ser
```

```
                    370                 375                 380
Tyr Gln Thr Gln Pro Ala Leu Asp Leu Gly Thr Leu Arg Val Gly Asn
385                 390                 395                 400

Ser Ser Cys Gln Pro Val Phe Glu Ala Gln Ser Gln Gly Leu Val Arg
                405                 410                 415

Phe His Ile Pro Leu Asn Gly Cys Gly Thr Arg Tyr Lys Phe Glu Asp
                420                 425                 430

Asp Lys Val Val Tyr Glu Asn Glu Ile His Ala Leu Trp Thr Asp Phe
                435                 440                 445

Pro Pro Ser Lys Ile Ser Arg Asp Ser Glu Phe Arg Met Thr Val Lys
450                 455                 460

Cys Ser Tyr Ser Arg Asn Asp Met Leu Leu Asn Ile Asn Val Glu Ser
465                 470                 475                 480

Leu Thr Pro Pro Val Ala Ser Val Lys Leu Gly Pro Phe Thr Leu Ile
                485                 490                 495

Leu Gln Ser Tyr Pro Asp Asn Ser Tyr Gln Gln Pro Tyr Gly Glu Asn
                500                 505                 510

Glu Tyr Pro Leu Val Arg Phe Leu Arg Gln Pro Ile Tyr Met Glu Val
                515                 520                 525

Arg Val Leu Asn Arg Asp Asp Pro Asn Ile Lys Leu Val Leu Asp Asp
530                 535                 540

Cys Trp Ala Thr Ser Thr Met Asp Pro Asp Ser Phe Pro Gln Trp Asn
545                 550                 555                 560

Val Val Val Asp Gly Cys Ala Tyr Asp Leu Asp Asn Tyr Gln Thr Thr
                565                 570                 575

Phe His Pro Val Gly Ser Ser Val Thr His Pro Asp His Tyr Gln Arg
                580                 585                 590

Phe Asp Met Lys Ala Phe Ala Phe Val Ser Glu Ala His Val Leu Ser
                595                 600                 605

Ser Leu Val Tyr Phe His Cys Ser Ala Leu Ile Cys Asn Arg Leu Ser
                610                 615                 620

Pro Asp Ser Pro Leu Cys Ser Val Thr Cys Pro Val Ser Ser Arg His
625                 630                 635                 640

Arg Arg Ala Thr Gly Ala Thr Glu Ala Glu Lys Met Thr Val Ser Leu
                645                 650                 655

Pro Gly Pro Ile Leu Leu Leu Ser Asp Asp Ser Ser Phe Arg Gly Val
                660                 665                 670

Gly Ser Ser Asp Leu Lys Ala Ser Gly Ser Gly Glu Lys Ser Arg
                675                 680                 685

Ser Glu Thr Gly Glu Glu Val Gly Ser Arg Gly Ala Met Asp Thr Lys
690                 695                 700

Gly His Lys Thr Ala Gly Asp Val Gly Ser Lys Ala Val Ala Ala Val
705                 710                 715                 720

Ala Ala Phe Ala Gly Val Val Ala Thr Leu Gly Phe Ile Tyr Tyr Leu
                725                 730                 735

Tyr Glu Lys Arg Thr Val Ser Asn His
                740                 745

<210> SEQ ID NO 3
<211> LENGTH: 424
<212> TYPE: PRT
<213> ORGANISM: Homo sapiens

<400> SEQUENCE: 3
```

```
Met Glu Leu Ser Tyr Arg Leu Phe Ile Cys Leu Leu Leu Trp Gly Ser
1               5                   10                  15

Thr Glu Leu Cys Tyr Pro Gln Pro Leu Trp Leu Leu Gln Gly Gly Ala
            20                  25                  30

Ser His Pro Glu Thr Ser Val Gln Pro Val Leu Val Glu Cys Gln Glu
        35                  40                  45

Ala Thr Leu Met Val Met Val Ser Lys Asp Leu Phe Gly Thr Gly Lys
50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Arg Phe Glu Val Gly Leu
            85                  90                  95

His Glu Cys Gly Asn Ser Met Gln Val Thr Asp Asp Ala Leu Val Tyr
            100                 105                 110

Ser Thr Phe Leu Leu His Asp Pro Arg Pro Val Gly Asn Leu Ser Ile
            115                 120                 125

Val Arg Thr Asn Arg Ala Glu Ile Pro Ile Glu Cys Arg Tyr Pro Arg
            130                 135                 140

Gln Gly Asn Val Ser Ser Gln Ala Ile Leu Pro Thr Trp Leu Pro Phe
145                 150                 155                 160

Arg Thr Thr Val Phe Ser Glu Glu Lys Leu Thr Phe Ser Leu Arg Leu
                165                 170                 175

Met Glu Glu Asn Trp Asn Ala Glu Lys Arg Ser Pro Thr Phe His Leu
            180                 185                 190

Gly Asp Ala Ala His Leu Gln Ala Glu Ile His Thr Gly Ser His Val
            195                 200                 205

Pro Leu Arg Leu Phe Val Asp His Cys Val Ala Thr Pro Thr Pro Asp
            210                 215                 220

Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
            260                 265                 270

Asp Ser Arg Asn Met Ile Tyr Ile Thr Cys His Leu Lys Val Thr Leu
            275                 280                 285

Ala Glu Gln Asp Pro Asp Glu Leu Asn Lys Ala Cys Ser Phe Ser Lys
            290                 295                 300

Pro Ser Asn Ser Trp Phe Pro Val Glu Gly Ser Ala Asp Ile Cys Gln
305                 310                 315                 320

Cys Cys Asn Lys Gly Asp Cys Gly Thr Pro Ser His Ser Arg Arg Gln
                325                 330                 335

Pro His Val Met Ser Gln Trp Ser Arg Ser Ala Ser Arg Asn Arg Arg
            340                 345                 350

His Val Thr Glu Glu Ala Asp Val Thr Val Gly Pro Leu Ile Phe Leu
            355                 360                 365

Asp Arg Arg Gly Asp His Glu Val Glu Gln Trp Ala Leu Pro Ser Asp
            370                 375                 380

Thr Ser Val Val Leu Gly Val Gly Leu Ala Val Val Val Ser Leu
385                 390                 395                 400

Thr Leu Thr Ala Val Ile Leu Val Leu Thr Arg Arg Cys Arg Thr Ala
                405                 410                 415

Ser His Pro Val Ser Ala Ser Glu
```

420

<210> SEQ ID NO 4
<211> LENGTH: 540
<212> TYPE: PRT
<213> ORGANISM: Homo sapiens

<400> SEQUENCE: 4

Met Trp Leu Leu Arg Cys Val Leu Cys Val Ser Leu Ser Leu Ala
1               5                   10                  15

Val Ser Gly Gln His Lys Pro Glu Ala Pro Asp Tyr Ser Ser Val Leu
            20                  25                  30

His Cys Gly Pro Trp Ser Phe Gln Phe Ala Val Asn Leu Asn Gln Glu
        35                  40                  45

Ala Thr Ser Pro Pro Val Leu Ile Ala Trp Asp Asn Gln Gly Leu Leu
    50                  55                  60

His Glu Leu Gln Asn Asp Ser Asp Cys Gly Thr Trp Ile Arg Lys Gly
65                  70                  75                  80

Pro Gly Ser Ser Val Val Leu Glu Ala Thr Tyr Ser Ser Cys Tyr Val
                85                  90                  95

Thr Glu Trp Asp Ser His Tyr Ile Met Pro Val Gly Val Glu Gly Ala
            100                 105                 110

Gly Ala Ala Glu His Lys Val Val Thr Glu Arg Lys Leu Leu Lys Cys
        115                 120                 125

Pro Met Asp Leu Leu Ala Arg Asp Ala Pro Thr Asp Trp Cys Asp
    130                 135                 140

Ser Ile Pro Ala Arg Asp Arg Leu Pro Cys Ala Pro Ser Pro Ile Ser
145                 150                 155                 160

Arg Gly Asp Cys Glu Gly Leu Gly Cys Cys Tyr Ser Ser Glu Glu Val
                165                 170                 175

Asn Ser Cys Tyr Tyr Gly Asn Thr Val Thr Leu His Cys Thr Arg Glu
            180                 185                 190

Gly His Phe Ser Ile Ala Val Ser Arg Asn Val Thr Ser Pro Pro Leu
        195                 200                 205

Leu Leu Asp Ser Val Arg Leu Ala Leu Arg Asn Asp Ser Ala Cys Asn
    210                 215                 220

Pro Val Met Ala Thr Gln Ala Phe Val Leu Phe Gln Phe Pro Phe Thr
225                 230                 235                 240

Ser Cys Gly Thr Thr Arg Gln Ile Thr Gly Asp Arg Ala Val Tyr Glu
                245                 250                 255

Asn Glu Leu Val Ala Thr Arg Asp Val Lys Asn Gly Ser Arg Gly Ser
            260                 265                 270

Val Thr Arg Asp Ser Ile Phe Arg Leu His Val Ser Cys Ser Tyr Ser
        275                 280                 285

Val Ser Ser Asn Ser Leu Pro Ile Asn Val Gln Val Phe Thr Leu Pro
    290                 295                 300

Pro Pro Phe Pro Glu Thr Gln Pro Gly Pro Leu Thr Leu Glu Leu Gln
305                 310                 315                 320

Ile Ala Lys Asp Lys Asn Tyr Gly Ser Tyr Tyr Gly Val Gly Asp Tyr
                325                 330                 335

Pro Val Val Lys Leu Leu Arg Asp Pro Ile Tyr Val Glu Val Ser Ile
            340                 345                 350

Leu His Arg Thr Asp Pro Tyr Leu Gly Leu Leu Leu Gln Gln Cys Trp
        355                 360                 365

```
Ala Thr Pro Ser Thr Asp Pro Leu Ser Gln Pro Gln Trp Pro Ile Leu
    370             375                 380
Val Lys Gly Cys Pro Tyr Ile Gly Asp Asn Tyr Gln Thr Gln Leu Ile
385                 390                 395                 400
Pro Val Gln Lys Ala Leu Asp Leu Pro Phe Pro Ser His His Gln Arg
                405                 410                 415
Phe Ser Ile Phe Thr Phe Ser Phe Val Asn Pro Thr Val Glu Lys Gln
                420                 425                 430
Ala Leu Arg Gly Pro Val His Leu His Cys Ser Val Ser Val Cys Gln
            435                 440                 445
Pro Ala Glu Thr Pro Ser Cys Val Val Thr Cys Pro Asp Leu Ser Arg
    450                 455                 460
Arg Arg Asn Phe Asp Asn Ser Ser Gln Asn Thr Thr Ala Ser Val Ser
465                 470                 475                 480
Ser Lys Gly Pro Met Ile Leu Leu Gln Ala Thr Lys Asp Pro Pro Glu
                485                 490                 495
Lys Leu Arg Val Pro Val Asp Ser Lys Val Leu Trp Val Ala Gly Leu
            500                 505                 510
Ser Gly Thr Leu Ile Leu Gly Ala Leu Leu Val Ser Tyr Leu Ala Val
            515                 520                 525
Lys Lys Gln Lys Ser Cys Pro Asp Gln Met Cys Gln
530                 535                 540

<210> SEQ ID NO 5
<211> LENGTH: 328
<212> TYPE: PRT
<213> ORGANISM: Homo sapiens

<400> SEQUENCE: 5

Gln Pro Leu Trp Leu Leu Gln Gly Gly Ala Ser His Pro Glu Thr Ser
1               5                   10                  15
Val Gln Pro Val Leu Val Glu Cys Gln Glu Ala Thr Leu Met Val Met
                20                  25                  30
Val Ser Lys Asp Leu Phe Gly Thr Gly Lys Leu Ile Arg Ala Ala Asp
            35                  40                  45
Leu Thr Leu Gly Pro Glu Ala Cys Glu Pro Leu Val Ser Met Asp Thr
    50                  55                  60
Glu Asp Val Val Arg Phe Glu Val Gly Leu His Glu Cys Gly Asn Ser
65                  70                  75                  80
Met Gln Val Thr Asp Asp Ala Leu Val Tyr Ser Thr Phe Leu Leu His
                85                  90                  95
Asp Pro Arg Pro Val Gly Asn Leu Ser Ile Val Arg Thr Asn Arg Ala
                100                 105                 110
Glu Ile Pro Ile Glu Cys Arg Tyr Pro Arg Gln Gly Asn Val Ser Ser
            115                 120                 125
Gln Ala Ile Leu Pro Thr Trp Leu Pro Phe Arg Thr Thr Val Phe Ser
    130                 135                 140
Glu Glu Lys Leu Thr Phe Ser Leu Arg Leu Met Glu Glu Asn Trp Asn
145                 150                 155                 160
Ala Glu Lys Arg Ser Pro Thr Phe His Leu Gly Asp Ala Ala His Leu
                165                 170                 175
Gln Ala Glu Ile His Thr Gly Ser His Val Pro Leu Arg Leu Phe Val
            180                 185                 190
Asp His Cys Val Ala Thr Pro Thr Pro Asp Gln Asn Ala Ser Pro Tyr
            195                 200                 205
```

His Thr Ile Val Asp Phe His Gly Cys Leu Val Asp Gly Leu Thr Asp
    210                 215                 220

Ala Ser Ser Ala Phe Lys Val Pro Arg Pro Gly Pro Asp Thr Leu Gln
225                 230                 235                 240

Phe Thr Val Asp Val Phe His Phe Ala Asn Asp Ser Arg Asn Met Ile
                245                 250                 255

Tyr Ile Thr Cys His Leu Lys Val Thr Leu Ala Glu Gln Asp Pro Asp
            260                 265                 270

Glu Leu Asn Lys Ala Cys Ser Phe Ser Lys Pro Ser Asn Ser Trp Phe
        275                 280                 285

Pro Val Glu Gly Ser Ala Asp Ile Cys Gln Cys Asn Lys Gly Asp
    290                 295                 300

Cys Gly Thr Pro Ser His Ser Arg Arg Gln Pro His Val Met Ser Gln
305                 310                 315                 320

Trp Ser Arg Ser Ala Ser Arg Asn
                325

<210> SEQ ID NO 6
<211> LENGTH: 9
<212> TYPE: PRT
<213> ORGANISM: Homo sapiens

<400> SEQUENCE: 6

His Pro Glu Thr Ser Val Gln Pro Val
1               5

<210> SEQ ID NO 7
<211> LENGTH: 9
<212> TYPE: PRT
<213> ORGANISM: Homo sapiens

<400> SEQUENCE: 7

Pro Glu Thr Ser Val Gln Pro Val Leu
1               5

<210> SEQ ID NO 8
<211> LENGTH: 9
<212> TYPE: PRT
<213> ORGANISM: Homo sapiens

<400> SEQUENCE: 8

Gln Glu Ala Thr Leu Met Val Met Val
1               5

<210> SEQ ID NO 9
<211> LENGTH: 9
<212> TYPE: PRT
<213> ORGANISM: Homo sapiens

<400> SEQUENCE: 9

Ala Thr Leu Met Val Met Val Ser Lys
1               5

<210> SEQ ID NO 10
<211> LENGTH: 9
<212> TYPE: PRT
<213> ORGANISM: Homo sapiens

<400> SEQUENCE: 10

Leu Ile Arg Ala Ala Asp Leu Thr Leu
1               5

```
<210> SEQ ID NO 11
<211> LENGTH: 9
<212> TYPE: PRT
<213> ORGANISM: Homo sapiens

<400> SEQUENCE: 11

Thr Glu Asp Val Val Arg Phe Glu Val
1               5

<210> SEQ ID NO 12
<211> LENGTH: 9
<212> TYPE: PRT
<213> ORGANISM: Homo sapiens

<400> SEQUENCE: 12

Gln Val Thr Asp Asp Ala Leu Val Tyr
1               5

<210> SEQ ID NO 13
<211> LENGTH: 9
<212> TYPE: PRT
<213> ORGANISM: Homo sapiens

<400> SEQUENCE: 13

Ala Leu Val Tyr Ser Thr Phe Leu Leu
1               5

<210> SEQ ID NO 14
<211> LENGTH: 9
<212> TYPE: PRT
<213> ORGANISM: Homo sapiens

<400> SEQUENCE: 14

Phe Leu Leu His Asp Pro Arg Pro Val
1               5

<210> SEQ ID NO 15
<211> LENGTH: 9
<212> TYPE: PRT
<213> ORGANISM: Homo sapiens

<400> SEQUENCE: 15

Arg Pro Val Gly Asn Leu Ser Ile Val
1               5

<210> SEQ ID NO 16
<211> LENGTH: 9
<212> TYPE: PRT
<213> ORGANISM: Homo sapiens

<400> SEQUENCE: 16

Tyr Pro Arg Gln Gly Asn Val Ser Ser
1               5

<210> SEQ ID NO 17
<211> LENGTH: 9
<212> TYPE: PRT
<213> ORGANISM: Homo sapiens

<400> SEQUENCE: 17

Ser Ser Gln Ala Ile Leu Pro Thr Trp
1               5
```

```
<210> SEQ ID NO 18
<211> LENGTH: 9
<212> TYPE: PRT
<213> ORGANISM: Homo sapiens

<400> SEQUENCE: 18

Ala Ile Leu Pro Thr Trp Leu Pro Phe
1               5

<210> SEQ ID NO 19
<211> LENGTH: 9
<212> TYPE: PRT
<213> ORGANISM: Homo sapiens

<400> SEQUENCE: 19

Trp Leu Pro Phe Arg Thr Thr Val Phe
1               5

<210> SEQ ID NO 20
<211> LENGTH: 9
<212> TYPE: PRT
<213> ORGANISM: Homo sapiens

<400> SEQUENCE: 20

Val Phe Ser Glu Glu Lys Leu Thr Phe
1               5

<210> SEQ ID NO 21
<211> LENGTH: 9
<212> TYPE: PRT
<213> ORGANISM: Homo sapiens

<400> SEQUENCE: 21

Ser Glu Glu Lys Leu Thr Phe Ser Leu
1               5

<210> SEQ ID NO 22
<211> LENGTH: 9
<212> TYPE: PRT
<213> ORGANISM: Homo sapiens

<400> SEQUENCE: 22

Arg Leu Met Glu Glu Asn Trp Asn Ala
1               5

<210> SEQ ID NO 23
<211> LENGTH: 9
<212> TYPE: PRT
<213> ORGANISM: Homo sapiens

<400> SEQUENCE: 23

Phe His Leu Gly Asp Ala Ala His Leu
1               5

<210> SEQ ID NO 24
<211> LENGTH: 9
<212> TYPE: PRT
<213> ORGANISM: Homo sapiens

<400> SEQUENCE: 24

Ile His Thr Gly Ser His Val Pro Leu
1               5

<210> SEQ ID NO 25
<211> LENGTH: 9
```

<212> TYPE: PRT
<213> ORGANISM: Homo sapiens

<400> SEQUENCE: 25

Ser Pro Tyr His Thr Ile Val Asp Phe
1               5

<210> SEQ ID NO 26
<211> LENGTH: 9
<212> TYPE: PRT
<213> ORGANISM: Homo sapiens

<400> SEQUENCE: 26

Gly Leu Thr Asp Ala Ser Ser Ala Phe
1               5

<210> SEQ ID NO 27
<211> LENGTH: 9
<212> TYPE: PRT
<213> ORGANISM: Homo sapiens

<400> SEQUENCE: 27

Leu Thr Asp Ala Ser Ser Ala Phe Lys
1               5

<210> SEQ ID NO 28
<211> LENGTH: 9
<212> TYPE: PRT
<213> ORGANISM: Homo sapiens

<400> SEQUENCE: 28

Val Pro Arg Pro Gly Pro Asp Thr Leu
1               5

<210> SEQ ID NO 29
<211> LENGTH: 9
<212> TYPE: PRT
<213> ORGANISM: Homo sapiens

<400> SEQUENCE: 29

Arg Pro Gly Pro Asp Thr Leu Gln Phe
1               5

<210> SEQ ID NO 30
<211> LENGTH: 9
<212> TYPE: PRT
<213> ORGANISM: Homo sapiens

<400> SEQUENCE: 30

Gln Phe Thr Val Asp Val Phe His Phe
1               5

<210> SEQ ID NO 31
<211> LENGTH: 9
<212> TYPE: PRT
<213> ORGANISM: Homo sapiens

<400> SEQUENCE: 31

Phe Thr Val Asp Val Phe His Phe Ala
1               5

<210> SEQ ID NO 32
<211> LENGTH: 9
<212> TYPE: PRT
<213> ORGANISM: Homo sapiens

<400> SEQUENCE: 32

Ala Asn Asp Ser Arg Asn Met Ile Tyr
1               5

<210> SEQ ID NO 33
<211> LENGTH: 9
<212> TYPE: PRT
<213> ORGANISM: Homo sapiens

<400> SEQUENCE: 33

Met Ile Tyr Ile Thr Cys His Leu Lys
1               5

<210> SEQ ID NO 34
<211> LENGTH: 9
<212> TYPE: PRT
<213> ORGANISM: Homo sapiens

<400> SEQUENCE: 34

Ile Tyr Ile Thr Cys His Leu Lys Val
1               5

<210> SEQ ID NO 35
<211> LENGTH: 9
<212> TYPE: PRT
<213> ORGANISM: Homo sapiens

<400> SEQUENCE: 35

Phe Ser Lys Pro Ser Asn Ser Trp Phe
1               5

<210> SEQ ID NO 36
<211> LENGTH: 9
<212> TYPE: PRT
<213> ORGANISM: Homo sapiens

<400> SEQUENCE: 36

Lys Pro Ser Asn Ser Trp Phe Pro Val
1               5

<210> SEQ ID NO 37
<211> LENGTH: 9
<212> TYPE: PRT
<213> ORGANISM: Homo sapiens

<400> SEQUENCE: 37

Arg Gln Pro His Val Met Ser Gln Trp
1               5

<210> SEQ ID NO 38
<211> LENGTH: 9
<212> TYPE: PRT
<213> ORGANISM: Homo sapiens

<400> SEQUENCE: 38

Arg Gly Asp His Glu Val Glu Gln Trp
1               5

<210> SEQ ID NO 39
<211> LENGTH: 9
<212> TYPE: PRT
<213> ORGANISM: Homo sapiens

<400> SEQUENCE: 39

```
Glu Ala Thr Leu Met Val Met Val Ser
1               5
```

<210> SEQ ID NO 40
<211> LENGTH: 9
<212> TYPE: PRT
<213> ORGANISM: Homo sapiens

<400> SEQUENCE: 40

```
Leu Met Val Met Val Ser Lys Asp Leu
1               5
```

<210> SEQ ID NO 41
<211> LENGTH: 9
<212> TYPE: PRT
<213> ORGANISM: Homo sapiens

<400> SEQUENCE: 41

```
Met Val Met Val Ser Lys Asp Leu Phe
1               5
```

<210> SEQ ID NO 42
<211> LENGTH: 9
<212> TYPE: PRT
<213> ORGANISM: Homo sapiens

<400> SEQUENCE: 42

```
Leu Ile Arg Ala Ala Asp Leu Thr Leu
1               5
```

<210> SEQ ID NO 43
<211> LENGTH: 9
<212> TYPE: PRT
<213> ORGANISM: Homo sapiens

<400> SEQUENCE: 43

```
Leu Val Met Ser Asp Thr Glu Asp Val
1               5
```

<210> SEQ ID NO 44
<211> LENGTH: 9
<212> TYPE: PRT
<213> ORGANISM: Homo sapiens

<400> SEQUENCE: 44

```
Val Ser Met Asp Thr Glu Asp Val Val
1               5
```

<210> SEQ ID NO 45
<211> LENGTH: 9
<212> TYPE: PRT
<213> ORGANISM: Homo sapiens

<400> SEQUENCE: 45

```
Val Val Arg Phe Glu Val Gly Leu His
1               5
```

<210> SEQ ID NO 46
<211> LENGTH: 9
<212> TYPE: PRT
<213> ORGANISM: Homo sapiens

<400> SEQUENCE: 46

```
Gln Val Thr Asp Asp Ala Leu Val Tyr
```

```
1               5

<210> SEQ ID NO 47
<211> LENGTH: 9
<212> TYPE: PRT
<213> ORGANISM: Homo sapiens

<400> SEQUENCE: 47

Ala Leu Val Tyr Ser Thr Phe Leu Leu
1               5

<210> SEQ ID NO 48
<211> LENGTH: 9
<212> TYPE: PRT
<213> ORGANISM: Homo sapiens

<400> SEQUENCE: 48

Leu Val Tyr Ser Thr Phe Leu Leu His
1               5

<210> SEQ ID NO 49
<211> LENGTH: 9
<212> TYPE: PRT
<213> ORGANISM: Homo sapiens

<400> SEQUENCE: 49

Phe Leu Leu Asp Pro His Arg Pro Val
1               5

<210> SEQ ID NO 50
<211> LENGTH: 9
<212> TYPE: PRT
<213> ORGANISM: Homo sapiens

<400> SEQUENCE: 50

Leu Leu His Asp Pro Arg Pro Val Gly
1               5

<210> SEQ ID NO 51
<211> LENGTH: 9
<212> TYPE: PRT
<213> ORGANISM: Homo sapiens

<400> SEQUENCE: 51

Leu Ser Ile Val Arg Thr Asn Arg Ala
1               5

<210> SEQ ID NO 52
<211> LENGTH: 9
<212> TYPE: PRT
<213> ORGANISM: Homo sapiens

<400> SEQUENCE: 52

Ile Val Arg Thr Asn Arg Ala Glu Ile
1               5

<210> SEQ ID NO 53
<211> LENGTH: 9
<212> TYPE: PRT
<213> ORGANISM: Homo sapiens

<400> SEQUENCE: 53

Pro Phe Arg Thr Thr Val Phe Ser Glu
1               5
```

```
<210> SEQ ID NO 54
<211> LENGTH: 9
<212> TYPE: PRT
<213> ORGANISM: Homo sapiens

<400> SEQUENCE: 54

Phe Arg Thr Thr Val Phe Ser Glu Glu
1               5

<210> SEQ ID NO 55
<211> LENGTH: 9
<212> TYPE: PRT
<213> ORGANISM: Homo sapiens

<400> SEQUENCE: 55

Thr Phe Ser Leu Arg Leu Met Glu Glu
1               5

<210> SEQ ID NO 56
<211> LENGTH: 9
<212> TYPE: PRT
<213> ORGANISM: Homo sapiens

<400> SEQUENCE: 56

Phe His Leu Gly Asp Ala Ala His Leu
1               5

<210> SEQ ID NO 57
<211> LENGTH: 9
<212> TYPE: PRT
<213> ORGANISM: Homo sapiens

<400> SEQUENCE: 57

Leu Arg Leu Phe Val Asp His Cys Val
1               5

<210> SEQ ID NO 58
<211> LENGTH: 9
<212> TYPE: PRT
<213> ORGANISM: Homo sapiens

<400> SEQUENCE: 58

Leu Phe Val Asp His Cys Val Ala Thr
1               5

<210> SEQ ID NO 59
<211> LENGTH: 9
<212> TYPE: PRT
<213> ORGANISM: Homo sapiens

<400> SEQUENCE: 59

Gln Phe Thr Val Asp Val Phe His Phe
1               5

<210> SEQ ID NO 60
<211> LENGTH: 9
<212> TYPE: PRT
<213> ORGANISM: Homo sapiens

<400> SEQUENCE: 60

Phe Ala Asn Asp Ser Asn Arg Met Ile
1               5

<210> SEQ ID NO 61
```

```
<211> LENGTH: 9
<212> TYPE: PRT
<213> ORGANISM: Homo sapiens

<400> SEQUENCE: 61

Ile Tyr Ile Thr Cys His Leu Lys Val
1               5

<210> SEQ ID NO 62
<211> LENGTH: 9
<212> TYPE: PRT
<213> ORGANISM: Homo sapiens

<400> SEQUENCE: 62

Val Met Ser Gln Trp Ser Arg Ser Ala
1               5

<210> SEQ ID NO 63
<211> LENGTH: 9
<212> TYPE: PRT
<213> ORGANISM: Homo sapiens

<400> SEQUENCE: 63

Trp Ser Arg Ser Ala Ser Arg Asn Arg
1               5

<210> SEQ ID NO 64
<211> LENGTH: 9
<212> TYPE: PRT
<213> ORGANISM: Homo sapiens

<400> SEQUENCE: 64

Leu Ile Phe Leu Asp Arg Arg Gly Asp
1               5

<210> SEQ ID NO 65
<211> LENGTH: 9
<212> TYPE: PRT
<213> ORGANISM: Homo sapiens

<400> SEQUENCE: 65

Ile Phe Leu Asp Arg Arg Gly Asp His
1               5

<210> SEQ ID NO 66
<211> LENGTH: 49
<212> TYPE: PRT
<213> ORGANISM: Homo sapiens

<400> SEQUENCE: 66

Gly Gly Ala Ser His Pro Glu Thr Ser Val Gln Pro Val Leu Val Glu
1               5                   10                  15

Cys Gln Glu Ala Thr Leu Met Val Met Val Ser Lys Asp Leu Phe Gly
            20                  25                  30

Thr Gly Lys Leu Ile Arg Ala Ala Asp Leu Thr Leu Gly Pro Glu Ala
        35                  40                  45

Cys

<210> SEQ ID NO 67
<211> LENGTH: 26
<212> TYPE: PRT
<213> ORGANISM: Homo sapiens

<400> SEQUENCE: 67
```

```
Glu Ala Cys Glu Pro Leu Val Ser Met Asp Thr Asp Val Val Arg
1               5                   10                  15

Phe Glu Val Gly Leu His Glu Cys Gly Asn
            20                  25
```

<210> SEQ ID NO 68
<211> LENGTH: 43
<212> TYPE: PRT
<213> ORGANISM: Homo sapiens

<400> SEQUENCE: 68

```
Cys Gly Asn Ser Met Gln Val Thr Asp Asp Ala Leu Val Tyr Ser Thr
1               5                   10                  15

Phe Leu Leu His Asp Pro Arg Pro Val Gly Asn Leu Ser Ile Val Arg
            20                  25                  30

Thr Asn Arg Ala Glu Ile Pro Ile Glu Cys Arg
            35                  40
```

<210> SEQ ID NO 69
<211> LENGTH: 50
<212> TYPE: PRT
<213> ORGANISM: Homo sapiens

<400> SEQUENCE: 69

```
Ile Glu Cys Arg Tyr Pro Arg Gln Gly Asn Val Ser Ser Gln Ala Ile
1               5                   10                  15

Leu Pro Thr Trp Leu Pro Phe Arg Thr Val Phe Ser Glu Glu Lys
            20                  25                  30

Leu Thr Phe Ser Leu Arg Leu Met Glu Glu Asn Trp Asn Ala Glu Lys
            35                  40                  45

Arg Ser
    50
```

<210> SEQ ID NO 70
<211> LENGTH: 41
<212> TYPE: PRT
<213> ORGANISM: Homo sapiens

<400> SEQUENCE: 70

```
Lys Arg Ser Pro Thr Phe His Leu Gly Asp Ala Ala His Leu Gln Ala
1               5                   10                  15

Glu Ile His Thr Gly Ser His Val Pro Leu Arg Leu Phe Val Asp His
            20                  25                  30

Cys Val Ala Thr Pro Thr Pro Asp Gln
            35                  40
```

<210> SEQ ID NO 71
<211> LENGTH: 44
<212> TYPE: PRT
<213> ORGANISM: Homo sapiens

<400> SEQUENCE: 71

```
Asp Gln Asn Ala Ser Pro Tyr His Thr Ile Val Asp Phe His Gly Cys
1               5                   10                  15

Leu Val Asp Gly Leu Thr Asp Ala Ser Ser Ala Phe Lys Val Pro Arg
            20                  25                  30

Pro Gly Pro Asp Thr Leu Gln Phe Thr Val Asp Val
            35                  40
```

```
<210> SEQ ID NO 72
<211> LENGTH: 34
<212> TYPE: PRT
<213> ORGANISM: Homo sapiens

<400> SEQUENCE: 72

Gly Pro Asp Thr Leu Gln Phe Thr Val Asp Val Phe His Phe Ala Asn
1               5                   10                  15

Asp Ser Arg Asn Met Ile Tyr Ile Thr Cys His Leu Lys Val Thr Leu
            20                  25                  30

Ala Glu

<210> SEQ ID NO 73
<211> LENGTH: 20
<212> TYPE: PRT
<213> ORGANISM: Homo sapiens

<400> SEQUENCE: 73

Lys Ala Cys Ser Phe Ser Lys Pro Ser Asn Ser Trp Phe Pro Val Glu
1               5                   10                  15

Gly Pro Ala Asp
            20

<210> SEQ ID NO 74
<211> LENGTH: 27
<212> TYPE: PRT
<213> ORGANISM: Homo sapiens

<400> SEQUENCE: 74

Ser His Ser Arg Arg Gln Pro His Val Met Ser Gln Trp Ser Arg Ser
1               5                   10                  15

Ala Ser Arg Asn Arg Arg His Val Thr Glu Glu
            20                  25

<210> SEQ ID NO 75
<211> LENGTH: 26
<212> TYPE: PRT
<213> ORGANISM: Homo sapiens

<400> SEQUENCE: 75

Ala Asp Val Thr Val Gly Pro Leu Ile Phe Leu Asp Arg Arg Gly Asp
1               5                   10                  15

His Glu Val Glu Gln Trp Ala Leu Pro Ser
            20                  25

<210> SEQ ID NO 76
<211> LENGTH: 9
<212> TYPE: PRT
<213> ORGANISM: Homo sapiens

<400> SEQUENCE: 76

Phe Leu Leu His Asp Pro Arg Pro Val
1               5

<210> SEQ ID NO 77
<211> LENGTH: 9
<212> TYPE: PRT
<213> ORGANISM: Homo sapiens

<400> SEQUENCE: 77

Arg Leu Met Glu Glu Asn Trp Asn Ala
1               5
```

```
<210> SEQ ID NO 78
<211> LENGTH: 9
<212> TYPE: PRT
<213> ORGANISM: Homo sapiens

<400> SEQUENCE: 78

Ala Leu Val Tyr Ser Thr Phe Leu Leu
1               5

<210> SEQ ID NO 79
<211> LENGTH: 9
<212> TYPE: PRT
<213> ORGANISM: Homo sapiens

<400> SEQUENCE: 79

Phe Thr Val Asp Val Phe His Phe Ala
1               5

<210> SEQ ID NO 80
<211> LENGTH: 10
<212> TYPE: PRT
<213> ORGANISM: Homo sapiens

<400> SEQUENCE: 80

Leu Arg Leu Met Glu Glu Asn Trp Asn Ala
1               5                   10

<210> SEQ ID NO 81
<211> LENGTH: 10
<212> TYPE: PRT
<213> ORGANISM: Homo sapiens

<400> SEQUENCE: 81

Phe Leu Asp Arg Arg Gly Asp His Glu Val
1               5                   10

<210> SEQ ID NO 82
<211> LENGTH: 9
<212> TYPE: PRT
<213> ORGANISM: Homo sapiens

<400> SEQUENCE: 82

Cys Leu Val Asp Gly Leu Thr Asp Ala
1               5

<210> SEQ ID NO 83
<211> LENGTH: 9
<212> TYPE: PRT
<213> ORGANISM: Homo sapiens

<400> SEQUENCE: 83

Asn Met Ile Tyr Ile Thr Cys His Leu
1               5

<210> SEQ ID NO 84
<211> LENGTH: 10
<212> TYPE: PRT
<213> ORGANISM: Homo sapiens

<400> SEQUENCE: 84

Thr Phe Leu Leu His Asp Pro Arg Pro Val
1               5                   10

<210> SEQ ID NO 85
```

```
<211> LENGTH: 10
<212> TYPE: PRT
<213> ORGANISM: Homo sapiens

<400> SEQUENCE: 85

Lys Leu Ile Arg Ala Ala Asp Leu Thr Leu
1               5                   10
```